(12) United States Patent
McBride et al.

(10) Patent No.: US 11,168,315 B2
(45) Date of Patent: Nov. 9, 2021

(54) EXPRESSION OF BETA-GLUCOSIDASES FOR HYDROLYSIS OF LIGNOCELLULOSE AND ASSOCIATED OLIGOMERS

(71) Applicant: Lallemand Hungary Liquidity Management LLC, Budapest (HU)

(72) Inventors: John McBride, Lyme, NH (US); Erin Wiswall, Danbury, NH (US)

(73) Assignee: Lallemand Hungary Liquidity Management LLC, Budapest (HU)

( * ) Notice: Subject to any disclaimer, the term of this patent is extended or adjusted under 35 U.S.C. 154(b) by 0 days.

(21) Appl. No.: 16/790,315

(22) Filed: Feb. 13, 2020

(65) Prior Publication Data

US 2020/0248221 A1 Aug. 6, 2020

Related U.S. Application Data

(62) Division of application No. 14/772,100, filed as application No. PCT/US2014/026476 on Mar. 13, 2014, now Pat. No. 10,612,061.

(60) Provisional application No. 61/799,336, filed on Mar. 15, 2013.

(51) Int. Cl.
| | |
|---|---|
| *C12N 9/30* | (2006.01) |
| *C12N 15/00* | (2006.01) |
| *C12N 1/20* | (2006.01) |
| *C12N 9/42* | (2006.01) |
| *C12N 15/81* | (2006.01) |
| *C12P 7/10* | (2006.01) |
| *C12P 19/14* | (2006.01) |
| *C07C 29/86* | (2006.01) |
| *C12P 19/02* | (2006.01) |

(52) U.S. Cl.
CPC .......... *C12N 9/2445* (2013.01); *C12N 15/81* (2013.01); *C12Y 302/01021* (2013.01); *C07C 29/86* (2013.01); *C12P 7/10* (2013.01); *C12P 19/02* (2013.01); *C12P 19/14* (2013.01); *Y02E 50/10* (2013.01)

(58) Field of Classification Search
CPC .................................................. C12N 9/2445
See application file for complete search history.

(56) References Cited

U.S. PATENT DOCUMENTS

| | | |
|---|---|---|
| 4,683,202 A | 7/1987 | Mullis |
| 2012/0149081 A1 | 6/2012 | Shisa et al. |
| 2012/0252068 A1 | 10/2012 | Lopez de Leon et al. |
| 2016/0002692 A1 | 1/2016 | McBride et al. |

FOREIGN PATENT DOCUMENTS

| | | |
|---|---|---|
| JP | 2008/086310 A | 4/2008 |
| WO | 1992/03560 A1 | 3/1992 |
| WO | 1993/24631 A1 | 12/1993 |
| WO | 2004/111228 A1 | 12/2004 |
| WO | 2008/155665 A2 | 12/2008 |
| WO | 2009/073723 A1 | 6/2009 |
| WO | 2009/138877 A2 | 11/2009 |
| WO | 2009/139839 A1 | 11/2009 |
| WO | 2010/005553 A1 | 1/2010 |
| WO | 2010/060056 A2 | 5/2010 |
| WO | 2011/051806 A2 | 5/2011 |
| WO | 2011/153516 A2 | 12/2011 |
| WO | 2013/089890 A2 | 6/2013 |
| WO | 2014/035458 A1 | 3/2014 |

OTHER PUBLICATIONS

\*\*Benoliel, B., et al., Expression of a glucose-tolerant beta-glucosidase from *Humicola grisea* var. thermoidea in *Saccharomyces cerevisiae*. Appl Biochem Biotechnol. Apr. 2010;160(7):2036-44. doi: 10.1007/s12010-009-8732-7. Epub Aug. 12, 2009.
\*\*Bhatia, Y., et al., Microbial beta-glucosidases: cloning, properties, and applications. Crit Rev Biotechnol. 2002;22 (4):375-407.
\*\*Bowie, J.U., et al., Deciphering the Message in Protein Sequences: Tolerance to Amino Acid Substitutions. Science, 1990;247:1306-1310, Science, United States.
\*\*Brutlag, D.L., et al., Improved Sensitivity of Biological Sequence Database Searches. Comp. App. Biosci. 1990;6:237-245, Oxford Univ. Press, United Kingdom.
\*\*Casey, G.P., et al., A Convenient Dominant Selection Marker for Gene Transfer in Industrial Strains of *Saccharomyces cerevisicte*: SMRI Encoded Resistance to the Herbicide Sulfometuron Methyl. J Inst. Brew, 1988;94 (2):93-97.
\*\*Chinese Office Action for Application No. 201480028274 X, dated Jul. 25, 2017 (24 pages).
\*\*Cho, K.M., et at., Alpha-Integration of endo/exo-glucanase and Beta-glucosidase genes into the yeast chromosomes for direct conversion of cellulose to ethanol. Enzyme and Microbial Technology, 1999;25:23-30, Elsevier, Netherlands.
\*\*Cunningham, B.C., et al., High-Resolution Epitope Mapping of hGH-Receptor Interactions by Alanine-Scanning Mutagenesis. Science, 1989;244:1081-1085, American Association for the Advancement of Science, United States.
\*\*Den Haan, R., et al., Functional expression of cellobiohydrolases in *Saccharomyces cerevisiae* towards one-step conversion of cellulose to ethanol. Enzyme and Microbial Technology, Apr. 2007;40:1291-99, Elsevier Inc., United States (Apr. 2007).

(Continued)

*Primary Examiner* — Yong D Pak
(74) *Attorney, Agent, or Firm* — Nutter McClennen & Fish LLP

(57) ABSTRACT

The present invention provides for heterologous expression of beta-glucosidase (BGL) polypeptides encoded by *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* in host cells, such as the yeast *Saccharomyces cerevisiae*. The expression in such host cells of the corresponding genes, and variants and combinations thereof, result in improved specific activity of the expressed BGL. Thus, such genes and expression systems are useful for efficient and cost-effective consolidated bioprocessing systems.

14 Claims, 21 Drawing Sheets

Figure 1:
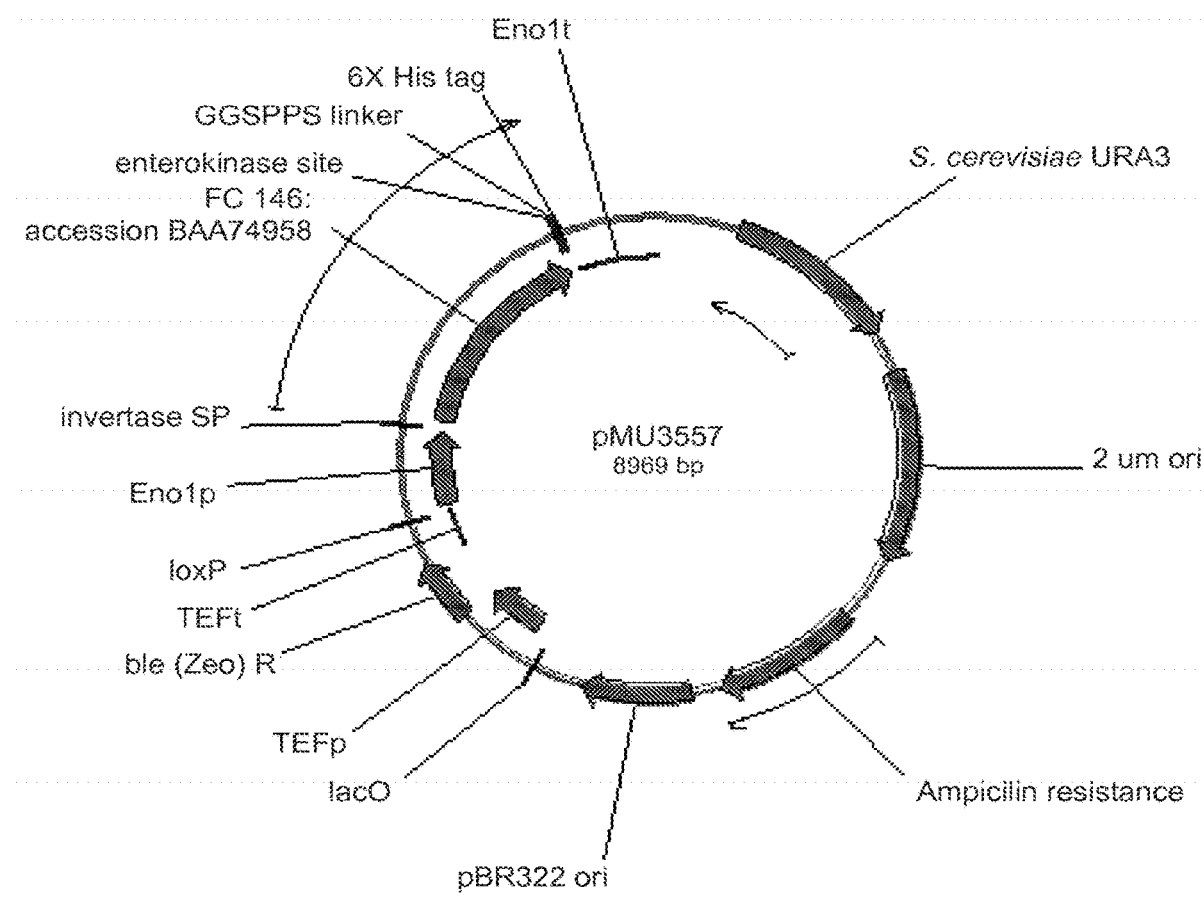

Specification includes a Sequence Listing.

(56) References Cited

OTHER PUBLICATIONS

\*\*Edelhoch, H., Spectroscopic determination of tryptophan and tyrosine in proteins. Biochemistry. Jul. 1967;6 (7): 1948-54.
\*\*European Office Action dated May 19, 2017, for Application No. 14722436.1 (6 pages).
\*\*Frohman, M.A., et al., Rapid production of full-length cDNAs from rare transcripts: amplification using a single gene-specific oligonucleotide primer. Proc Natl Acad Sci U S A. Dec. 1988;85(23):8998-9002.
\*\*Fujita, Y., et al., Synergistic Saccharification, and Direct Fermentation to Ethanol, of Amorphous Cellulose by Use of an Engineered Yeast Strain Codisplaying Three Types of Cellulolytic Etrzyme. Applied and Environmental Microbiology, 2004;70:1207-1212, American Society for Microbiology, United States.
\*\*Grassick, A., et al., Three-dimensional structure of a thermostable native cellobiohydrolase, CBH IB, and molecular characterization of the cel7 gene from the filamentous fungus, Talaromyces emersonii. Eur J Biochem. Nov. 2004;271(22):4495-506.
\*\*International Search Report and Written Opinion for Application No. PCT/US2014/026476, dated Nov. 14, 2014 (22 pages).
\*\*Invitation to Pay Additional Fees for Application No. PCT/US2014/026476, dated Jul. 30, 2014 (9 pages).
\*\*Kim, S., et al., Cellulosic ethanol production using a yeast consortium displaying a minicellulosome and Beta-glucosidase. Microb Cell Fact. Feb. 5, 2013;12:14. doi: 10.1186/1475-2859-12-14.
\*\*Kotaka, A., et al., Direct ethanol production from barley beta-glucan by sake yeast displaying Aspergillus oryzae beta-glucosidase and endoglucanase. J Biosci Bioeng Jun. 2008;105(6):622-7. doi: 10.1263/jbb.105.622.
\*\*Laemmli, U.K., et al., Cleavage of structural proteins during the assembly of the head of bacteriophage T4. Nature. Aug. 15, 1970;227(5259):680-5.
\*\*Loh, E.Y., et al., Polymerase chain reaction with single-sided specificity: analysis of T cell receptor delta chain. Science Jan. 13, 1989;243(4888):217-20.
\*\*Machida, M. et al., Genome Sequencing and Analysis of Aspergillus Oryzae, Nature, Dec. 22, 2005; vol. 438 (7071), pp. 1157-1161.
\*\*McBride, J.E., et al., Utilization of Cellobiose by Recombinant ?-Glucosidase-Expressing Strains of *Saccharomyces cerevisiae*: Characterization and Evaluation of the Sufficiency of Expression. Enzyme and Microbial Technology, 2005;37:93-101, Elsevier, Holland.
\*\*Murai, T., et al., Assimilation of cellooligosaccharides by a cell surface-engineered yeast expressing beta-glucosidase and carboxymethylcellulase from aspergillus aculeatus. Appl Environ Microbiol. Dec. 1998;64 (12):4857-61.
\*\*Nakamura, Y., et al., Codon Usage Tabulated from International DNA Sequence Databases: Status for the Year 2000. Nucl. Acids Res., 2000;28:292, Oxford University Press, United Kingdom.

\*\*Office Action for Brazilian App. No. BR112015023451-8, Published in Brazilian Industrial Property Journal No. 2544 dated Oct. 8, 2019.
\*\*Ohara, O., et al., One-sided polymerase chain reaction: the amplification of cDNA. Proc Natl Acad Sci U S A. Aug. 1989;86(15):5673-7.
\*\*Ostergaard, H., et al., Monitoring disulfide bond formation in the eukaryotic cytosol. J Cell Biol. Aug. 2, 2004;166 (3):337-45. Epub Jul. 26, 2004.
\*\*Sharp, P.M., et al., "The Codon Adaptation Index: A Measure of Directional Synonymous Codon Usage Bias, and Its Potential Applications" Nucleic Acids Res. 1987;15(3):1281-1295, IRL Press Limited, Oxford, England.
\*\*Smith, D.B., Single-step purification of polypeptides expressed in *Escherichia coli* as fusions with glutathione S-transferase. Gene. Jul. 15, 1988;67(1)31-40.
\*\*Tabor, S., et al., A bacteriophage T7 RNA polymerase/promoter system for controlled exclusive expression of specific genes Proc Natl Acad Sci U S A Feb. 1985;82(4):1074-8.
\*\*Takada, G et al., Expression of Aspergillus aculeatus No. F-50 cellobiohydrolase I (cbhl) and beta-glucosidase 1 (bgl1) genes by *Saccharomyces cerevisiae*, Biosci Biotechnol Biochem Aug. 1998; v. 62, pp. 1615-1618.
\*\*Takashima, S., et al., Molecular cloning and expression of the novel fungal beta-glucosidase genes from Humicola grisea and Trichoderma reesei. J Biochem. Apr. 1999; 125(4):728-36.
\*\*Van Rensburg, P., et al., Engineering Yeast for Efficient Cellulose Degradation. Yeast, 1998;14:67-76, Jon Wiley & Sons, Ltd., United States.
\*\*Van Rooyen, R., et al., Construction of Cellobiose-Growing and Fermenting *Saccharomyces cerevisiae* Strains. J. Biotechnol., 2005;120:284-295, Elsevier, Holland.
\*\*Van Zyl, W.H., et al., Consolidated Bioprocessing for Bioethanol Production using *Saccharomyces cereviside*. Advances in Biochemical Engineering Biotechnology, 2007;108:205-235, Springer-Verlag, Germany.
\*\*Viikari, L., et al., Thermostable enzymes in lignocellulose hydrolysis. Adv Biochem Eng Biotechnol. 2007;108:121-45.
\*\*Walker, G.T., et al., Isothermal in vitro amplification of DNA by a restriction enzyme/DNA polymerase system. Proc Natl Acad Sci USA Jan. 1, 1992;89(1):392-6.
\*\*Yang, F., et al., [Development and application of *Saccharomyces cerevisiae* cell-surface display for bioethanol production. Chin J Biotech, 2012, 28(8): 901-911. Chinese-language article, English abstract only.
\*\*Yao, S., et al., [Study on the display and enzymatic properties of beta-glucosidase on the surface of.] Journal of Qufu Normal University (Natural Science Edition), Jul. 2011, vol. 37, issue 3, pp. 81-86. Chinese-language article, English abstract only. 5 pages.
Chinese Office Action for Application No. 201480028274.X dated Dec. 10, 2019. 11 pages.
Examination Report for Canadian Patent Application No. 2,905,033 dated May 27, 2020. 7 pages.
Examination Report for Indian Patent Application No. 8099/DELNP/2015 dated Dec. 16, 2019. 9 pages.
Examination Report for Canadian Patent Application No. 2,905,033 dated Apr. 14, 2021. 6 pages.

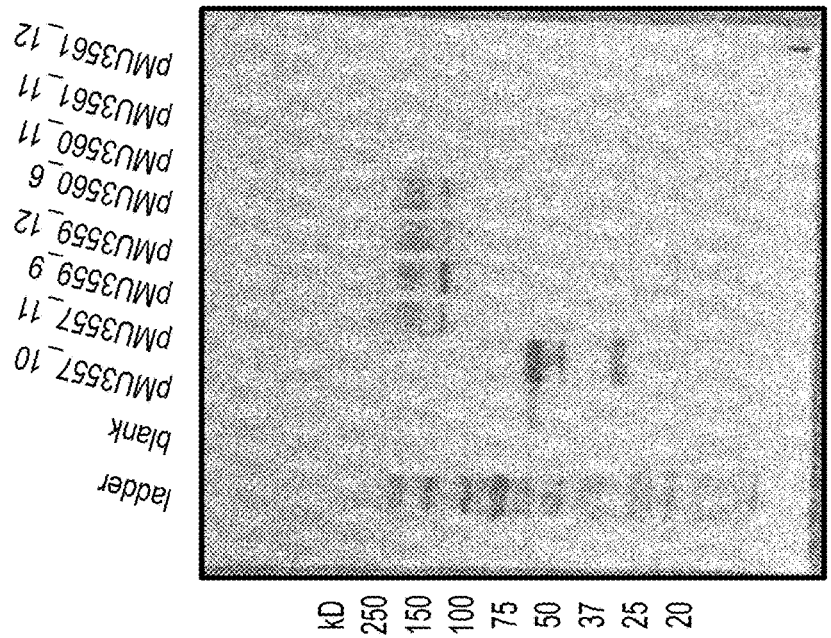
FIG. 12A
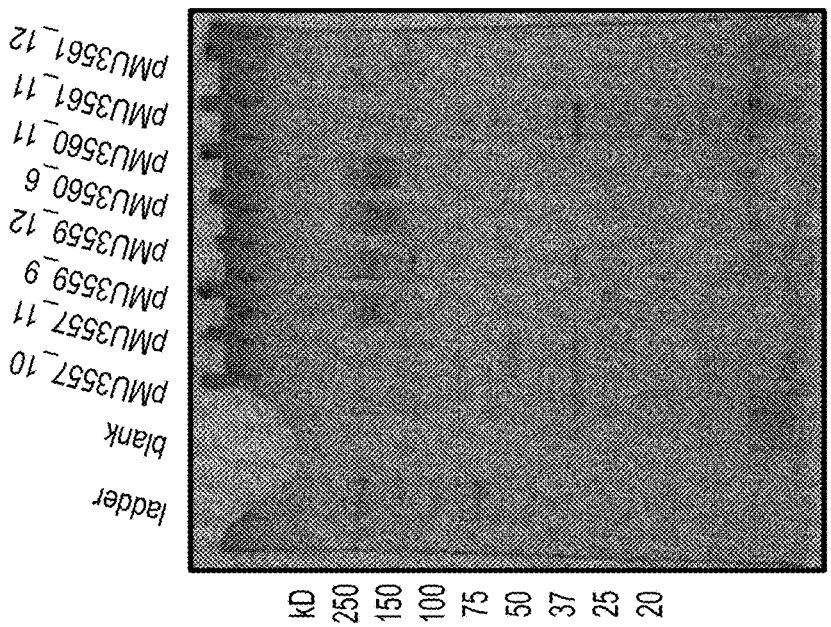

EXPRESSION OF BETA-GLUCOSIDASES FOR HYDROLYSIS OF LIGNOCELLULOSE AND ASSOCIATED OLIGOMERS

CROSS REFERENCE TO RELATED APPLICATIONS

The present application is a divisional application of U.S. Ser. No. 14/772,100 filed on Sep. 2, 2015 which is a 371 U.S. national phase application of PCT/US2014/026476, filed Mar. 13, 2014, entitled "EXPRESSION OF BETA-GLUCOSIDASES FOR HYDROLYSIS OF LIGNOCELLULOSE AND ASSOCIATED OLIGOMERS," which claims priority to U.S. Provisional Application No. 61/799,336, filed Mar. 15, 2013, each application of which is hereby incorporated by reference in its entirety.

REFERENCE TO SEQUENCE LISTING SUBMITTED ELECTRONICALLY VIA EFS-WEB

The content of the electronically submitted sequence listing (Name: 115235-270_SegList.txt; Size: 234,160 bytes; Date of Creation: Feb. 13, 2020) is in accordance with 37 C.F.R. § 1.821-1.825, and is incorporated by reference in its entirety.

BACKGROUND OF THE INVENTION

Lignocellulosic biomass is widely recognized as a promising source of raw material for production of renewable fuels and chemicals. The primary obstacle impeding the more widespread production of energy from biomass feedstocks is the general absence of low-cost technology for overcoming the recalcitrance of these materials to conversion into useful fuels. Lignocellulosic biomass contains carbohydrate fractions (e.g., cellulose and hemicellulose) that can be converted into ethanol. In order to convert these fractions, the cellulose and hemicellulose must ultimately be converted or hydrolyzed into monosaccharides; it is the hydrolysis that has historically proven to be problematic.

Biologically mediated processes are promising for energy conversion, in particular, for the conversion of lignocellulosic biomass into fuels. Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose and galactose); and (4) the fermentation of pentose sugars (e.g., xylose and arabinose). These four transformations occur in a single step in a process configuration called consolidated bioprocessing (CBP), which is distinguished from other less highly integrated configurations in that it does not involve a dedicated process step for cellulase and/or hemicellulase production. CBP offers the potential for lower cost and higher efficiency than processes featuring dedicated cellulase production. The benefits result in part from avoided capital costs, substrate and other raw materials, and utilities associated with cellulase production.

Bakers' yeast (*Saccharomyces cerevisiae* or *S. cerevisiae*) remains the preferred microorganism for the production of ethanol (Van Zyl et al., *Adv. Biochem. Eng. Biotechnol.* 108:205-235, 2007). Attributes in favor of this microbe are (i) high productivity at close to theoretical yields (0.51 gram of ethanol produced/gram glucose used), (ii) high osmo- and ethanol-tolerance, (iii) natural robustness in industrial processes, (iv) being generally regarded as safe (GRAS) due to its long association with wine and bread making and beer brewing. Furthermore, *S. cerevisiae* exhibits tolerance to inhibitors commonly found in hydrolyzates resulting from biomass pretreatment. The major shortcoming of *S. cerevisiae* is its inability to utilize complex polysaccharides such as cellulose, or its break-down products, such as cellobiose and cellodextrins. One strategy for developing CBP-enabling microorganisms such as *S. cerevisiae* is by engineering them to express a heterologous cellulase and/or a hemicellulase system.

Three major types of enzymatic activities are required for native cellulose degradation. One type is endoglucanases (1,4-β-D-glucan 4-glucanohydrolases; Enzyme Commission (EC) 3.2.1.4). Endoglucanases (Eg or EG) cut at random in the cellulose polysaccharide chain of amorphous cellulose, generating oligosaccharides of varying lengths and consequently new chain ends. Another type is exoglucanases. Exogluconases include cellodextrinases (1,4-β-D-glucan glucanohydrolases; EC 3.2.1.74) and cellobiohydrolases (1,4-β-D-glucan cellobiohydrolases; EC 3.2.1.91). Exoglucanases act in a processive manner on the reducing or non-reducing ends of cellulose polysaccharide chains, liberating either glucose (glucanohydrolases) or cellobiose (cellobiohydrolase) as major products. Exoglucanases can also act on microcrystalline cellulose, presumably peeling cellulose chains from the microcrystalline structure. Classically, exoglucanases such as the cellobiohydrolases (CBHs) possess tunnel-like active sites, which can only accept a substrate chain via its terminal regions. These exo-acting CBH enzymes act by threading the cellulose chain through the tunnel, where successive cellobiose units are removed in a sequential manner. Sequential hydrolysis of a cellulose chain is termed "processivity."

Yet another type is beta-glucosidases (beta glucoside glucohydrolases, β-glucosidases or BGLs; EC 3.2.1.21). BGLs play an important role in the hydrolysis of materials containing cellulose or soluble oligomers of glucose. There have been reports of the role and importance of BGLs during hydrolysis (see, e.g., Viikari et al., *Adv. Biochem. Eng. Biotechnol.*, 108:121-145, 2007; and Bhatia et al., *Crit. Rev. Biotechnol.*, 22:375-407, 2002). These enzymes typically act on soluble oligomers of glucose which are linked via beta 1-4 type bonds, including dimers (cellobiose) where they usually have highest activity, as well as longer chain oligomers where they are typically less active. Examples of BGL domains have been described and include, for example, a glycosyl hydrolase family 3 n-terminal domain, a glycosyl hydrolase family 3 c-terminal domain, and a fibronectin type III like domain.

Structurally, cellulases generally consist of a catalytic domain joined to a cellulose-binding module (CBM) via a linker region that is rich in proline and/or hydroxy-amino acids. In type I exoglucanases, the CBM domain is found at the C-terminal extremity of these enzyme (this short domain forms a hairpin loop structure stabilized by 2 disulfide bridges). In type 2 CBHs, the CBM is found at the N-terminus. In some cases, however, cellulases do not contain a CBM, and only contain a catalytic domain. Examples of such CBM-lacking cellulases include CBHs from *Humicola grisea*, *Phanerochaete chrysosporium* and *Aspergillus niger*. Grassick et al., *Eur. J Biochem.*, 271:4495-4506, 2004.

With the aid of recombinant DNA technology, several of these heterologous cellulases from bacterial and fungal sources have been transferred to *S. cerevisiae*, enabling the degradation of cellulosic derivatives (Van Rensburg et al., *Yeast*, 14:67-76, 1998), or growth on cellobiose (Van Rooyen et al., *J. Biotech.*, 120:284-295, 2005; and McBride et al., *Enzyme Microb. Techol.* 37:93-101, 2005).

Related work was described by Fujita et al., (*Appl. Environ. Microbiol.*, 70:1207-1212, 2004) where cellulases immobilized on the yeast cell surface had significant limitations. First, Fujita et al. were unable to achieve fermentation of amorphous cellulose using yeast expressing only recombinant Bgl1 and EgII. A second limitation of the Fujita et al. approach was that cells had to be pre-grown to high cell density on standard carbon sources before the cells were useful for ethanol production using amorphous cellulose (e.g., Fujita et al. uses high biomass loadings of ~15 g/L to accomplish ethanol production).

As noted above, ethanol producing yeast such as *S. cerevisiae* require addition of external cellulases when cultivated on cellulosic substrates, such as pre-treated wood, because this yeast does not produce endogenous cellulases. Expression of fungal cellulases such as *Trichoderma reesei* (*T. reesei*) Cbh1 and Cbh2 in yeast *S. cerevisiae* have been shown to be functional. Den Haan et al., *Enzyme and Microbial Technology*, 40:1291-1299, 2007. However, current levels of expression and specific activity of cellulases heterologously expressed in yeast are still not sufficient to enable growth and ethanol production by yeast on cellulosic substrates without externally added enzymes. While studies have shown that perhaps certain cellulases, such as *T. reesei* Cbh1, have some activity when heterologously expressed, there remains a significant need for improvement in the specific activity of heterologously expressed cellulases in order to attain the goal of achieving a CBP system capable of efficiently and cost-effectively converting cellulosic substrates to ethanol.

Currently, there is no reliable way to predict which cellulases will be efficiently expressed in heterologous organisms. For example, despite the fact that *T. reesei* Cbh1 and *T. emersonii* Cbh1 are both endogenously expressed at high levels, heterologous expression of these proteins in yeast yielded disparate results. Also, *Talaromyces emersonii* (*T. emersonii*) Cbh1 expression in yeast was significantly greater in yeast than *T. reesei* Cbh1 under similar conditions. See Int'l Pub. No. WO 2009/138877. Efficient expression may depend, for example, on chaperone proteins that differ in the heterologous organisms and in the cellulase's native organism. Furthermore, even cellulases which are expressed at high levels may not be particularly active in a heterologous organism. For example, a cellulase may be subject to different post-translational modifications in the heterologous host organism than in the native organism from which the cellulase is derived. Protein folding and secretion can also be a barrier to heterologous cellulase expression.

Therefore, in order to address the limitations of heterologous cellulase expression in CBP systems, the present invention provides the expression of several BGLs in host cells, such as the yeast *S. cerevisiae*. The expression level and secreted activity level of the BGLs was characterized. In addition, the BGLs were purified and their specific activity on hardwood derived pretreated solids (C6 solids) and hardwood derived hemicellulose liquor (C5 liquor) was determined. The corresponding BGL genes, or variants and combinations thereof, in such host cells were well expressed and resulted in improved specific activity of the expressed BGLs. Also, the combination of purified BGLs with one or more other cellulases, or host cells expressing the BGLs and one or more other cellulases, also resulted in improved specific activity of the expressed BGLs. Thus, such genes and expression systems are useful for efficient and cost-effective CBP systems.

BRIEF SUMMARY OF THE INVENTION

The present invention provides for the heterologous expression of *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* beta-glucosidases (BGLs), or fragments thereof, in host cells. The host cell can comprise one or more polynucleotides encoding a BGL that is (i) at least about 90% identical to any one of SEQ ID NOs:3, 6, 9, 12, 15, 18, 21, 24, 27, 30 or 31-40, (ii) at least about 95% identical to any one of SEQ ID NOs:3, 6, 9, 12, 15, 18, 21, 24, 27, 30 or 31-40, or (iii) identical to any one of SEQ ID NOs:3, 6, 9, 12, 15, 18, 21, 24, 27, 30 or 31-40. The host cell can comprise one or more polynucleotides encoding a BGL having (i) an amino acid sequence at least about 90% identical to any one of SEQ ID NOs:1, 4, 7, 10, 13, 16, 19, 22, 25 or 28, (ii) an amino acid sequence at least about 90% identical to any one of SEQ ID NOs:1, 4, 7, 10, 13, 16, 19, 22, 25 or 28 without the signal peptide sequence, (iii) an amino acid sequence at least about 95% identical to any one of SEQ ID NOs:1, 4, 7, 10, 13, 16, 19, 22, 25 or 28, or (iv) an amino acid sequence at least about 95% identical to any one of SEQ ID NOs:1, 4, 7, 10, 13, 16, 19, 22, 25 or 28 without the signal peptide sequence.

In some embodiments of the invention, the fragment of the BGL can be a BGL signal peptide. The signal peptide can comprise an amino acid sequence that is (i) at least about 90% identical to any one of SEQ ID NOs:2, 5, 11, 14, 17, 20, 23, 26 or 29, (ii) at least about 95% identical to any one of SEQ ID NOs:2, 5, 11, 14, 17, 20, 23, 26 or 29, or (iii) identical to any one of SEQ ID NOs:2, 5, 11, 14, 17, 20, 23, 26 or 29.

In some embodiments of the invention, the host cell further comprises one or more additional polynucleotides encoding a heterologous cellulase. The heterologous cellulase can be a xylanase, xylosidase, acetylxylanesterase (AXE), endoglucanase, alpha-galactosidase, glucosidase, mannanase, alpha-glucuronidase, acetyl esterase, beta-mannosidase, glucuronyl esterase, or cellobiohydrolase (CBH). The endogluconase can be *A. fumigatus* endoglucanase I, *N. fischeri* endoglucanase III, *T. reesei* endogluconase I, or *C. formosanus* endoglucanase I. The CBH can be CBH1 or CBH2. The CBH can also be *T. emersonii* cellobiohydrolase I, *C. lucknowense* cellobiohydrolase IIb, or *T. reesei* cellobiohydrolase II. The host cell can further comprise a polynucleotide encoding *S. fibuligera* BGL. The host cell can also further comprise one or more polynucleotides encoding *T. emersonii* CBH1, *T. reesei* CBD, *C. lucknowense* CBH2, *A. fumigatus* EG1, *N. fischeri* EG3, *S. fibuligera* BGL, or *A. niger* xylanase. The host cell can further comprise one or more polynucleotides encoding *A. niger* xylanase, P.t.r. xylosidase, *N. fischeri* AXE, *A. fumigatus* EG1, *T. reesei* AGL1, *T. reesei* beta-mannanase, *A. fumigatus* alpha-glucuronidase (FC110), *A. fumigatus* acetyl esterase (FC136), *N. fischeri* beta-mannosidase (FC124), or *S. fibuligera* BGL.

In some embodiments of the invention, the host cell can saccharify and/or ferment crystalline cellulose. In other embodiments, the host cell can hydrolyze hardwood solids or C5 liquor derived from hardwoods.

In some embodiments of the invention, the yeast is selected from *Saccharomyces cerevisiae, Saccharomyces*

*pastorianus, Saccharomyces bayanus, Kluyveromyces lactis, Kluyveromyces marxianus, Schizosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe, Schwanniomyces occidentalis,* or derivatives thereof. In some embodiments, the yeast is *Saccharomyces cerevisiae*.

Other embodiments of the invention are directed to a BGL peptide isolated from a host cell of the invention, or a purified BGL peptide isolated from a host cell of the invention. Other embodiments of the invention include a co-culture comprising (i) a host cell of the invention and (ii) a second host cell comprising one or more polynucleotides encoding a xylanase, xylosidase, AXE, endoglucanase, alpha-galactosidase, glucosidase, mannanase, alpha-glucuronidase, acetyl esterase, beta-mannosidase, glucuronyl esterase or CBH. In other embodiments, the invention is directed to a composition comprising (i) a peptide or purified peptide of the invention and (ii) a host cell comprising one or more polynucleotides encoding a xylanase, xylosidase, AXE, endoglucanase, alpha-galactosidase, glucosidase, mannanase, alpha-glucuronidase, acetyl esterase, beta-mannosidase, glucuronyl esterase or CBH.

The present invention also provides a method for hydrolyzing a cellulosic substrate, comprising contacting the cellulosic substrate with a host cell, co-culture, composition, peptide or purified peptide of the invention. The cellulosic substrate can comprise a lignocellulosic biomass. The lignocellulosic biomass can be grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, or combinations thereof. The cellulosic substrate can be hydrolyzed to xylose, glucose, mannose, galactose, arabinose, or combinations thereof. In some embodiments, the cellulose substrate is hydrolyzed to xylose, glucose, mannose, galactose or arabinose at a rate at least about 10% greater than the rate of a host cell comprising a polynucleotide encoding a BGL from *S. fibuligera*. In some embodiments of the method, the BGL is present in an amount of about 0.2 mg or less per gram of xylose.

The present invention also provides a method of fermenting cellulose, comprising culturing a host cell, co-culture, composition, peptide or purified peptide of the invention in medium that contains crystalline cellulose under suitable conditions for a period sufficient to allow saccharification and fermentation of the cellulose. In some embodiments, the host cell produces ethanol.

The present invention also provides yeast strains M4860, M4861, M4862, M4863, M4864, and M4865, and expression vectors pMU3557, pMU3558, pMU3559, pMU3560, pMU3561, pMU3562, pMU3563, pMU3564, pMU3565, and pMU3566.

The present invention also provides a fermentation product produced by a host cell, co-culture or yeast strain of the invention. The fermentation product can be ethanol.

BRIEF DESCRIPTION OF THE DRAWINGS/FIGURES

Figure 2:
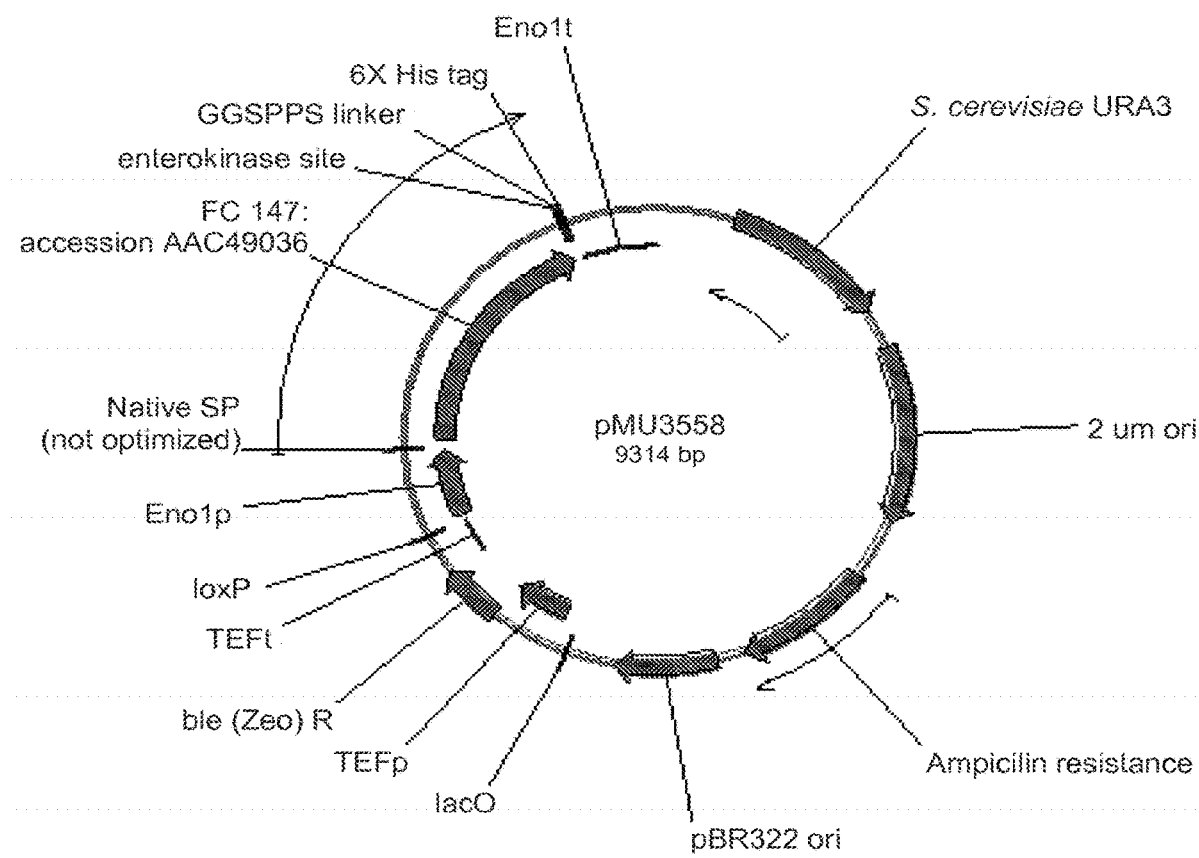
Figure 3:
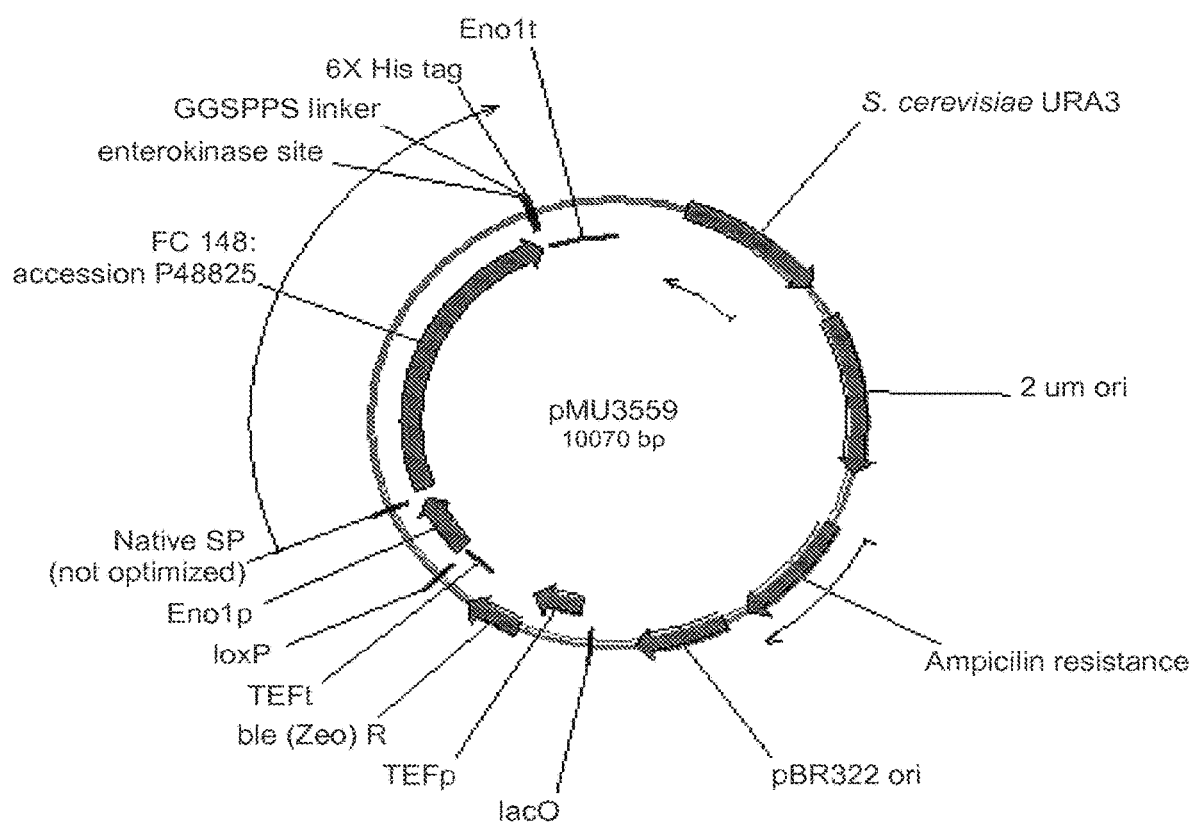
Figure 4:
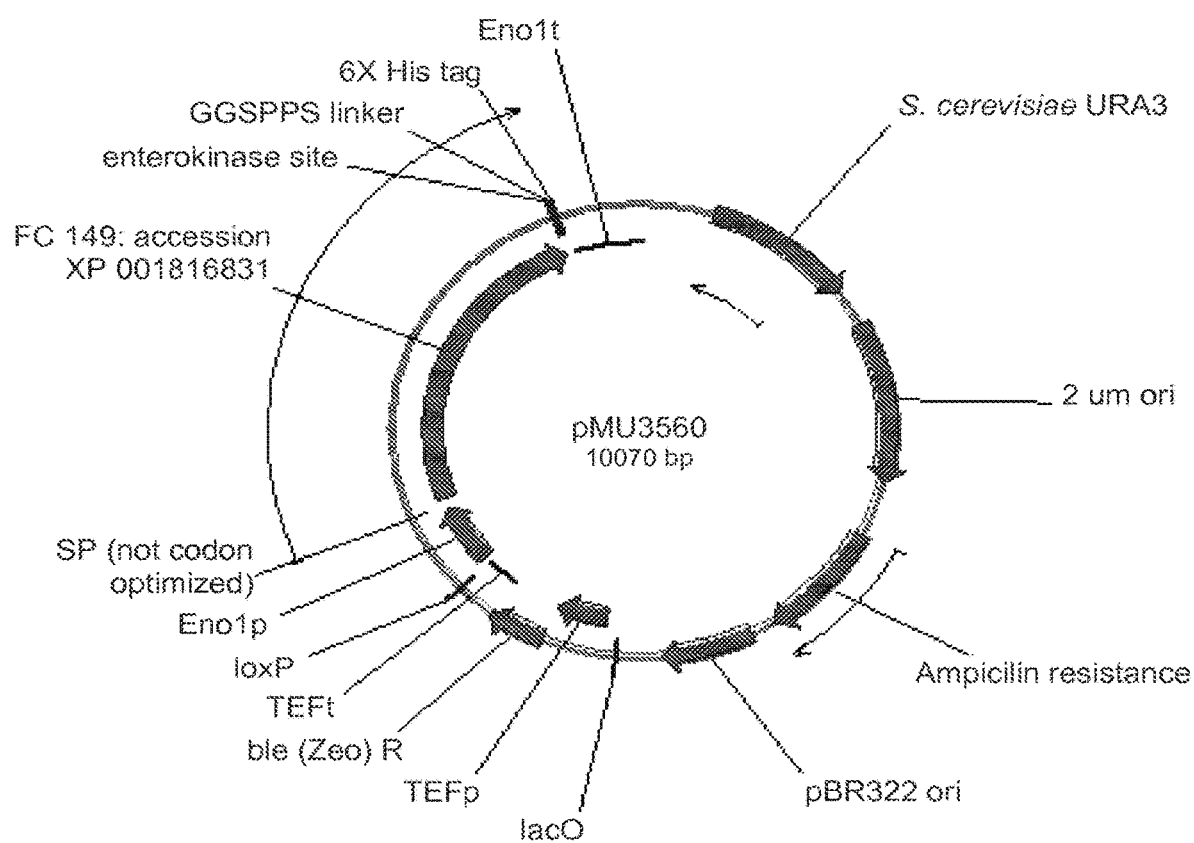
Figure 5:
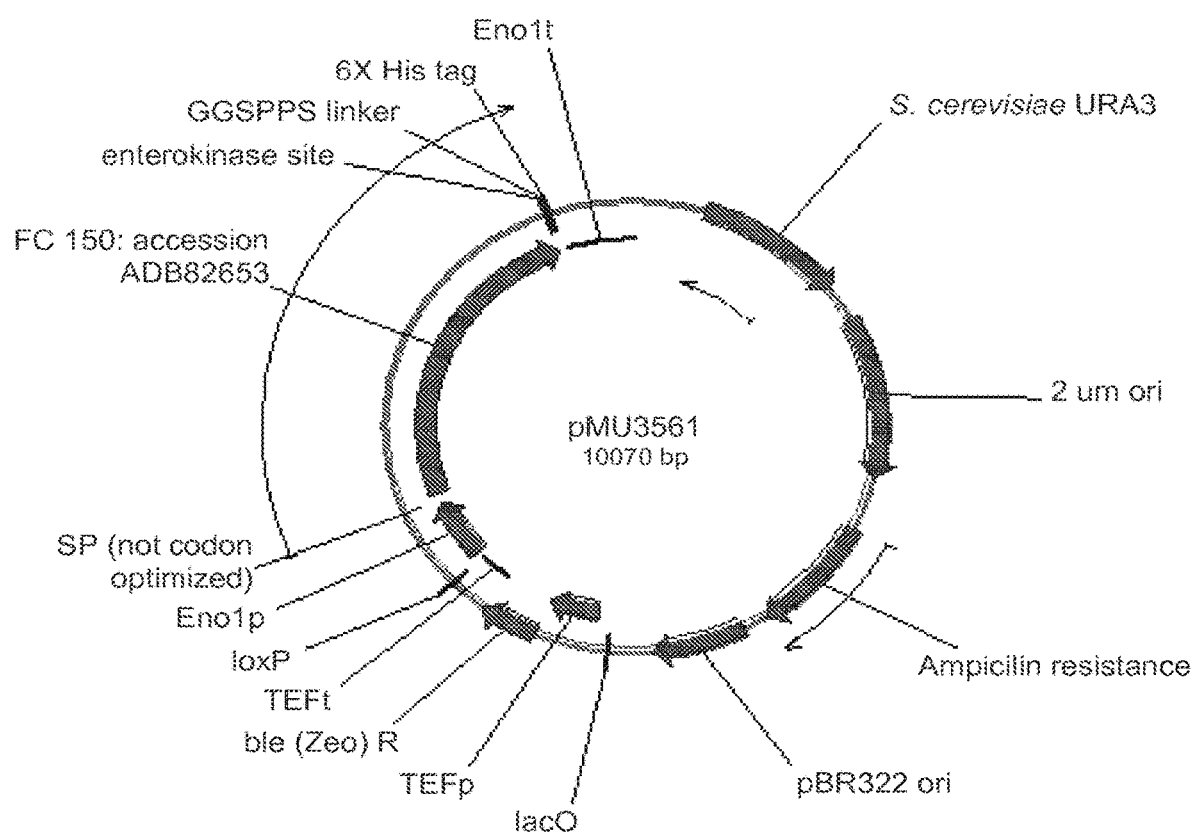
Figure 6:
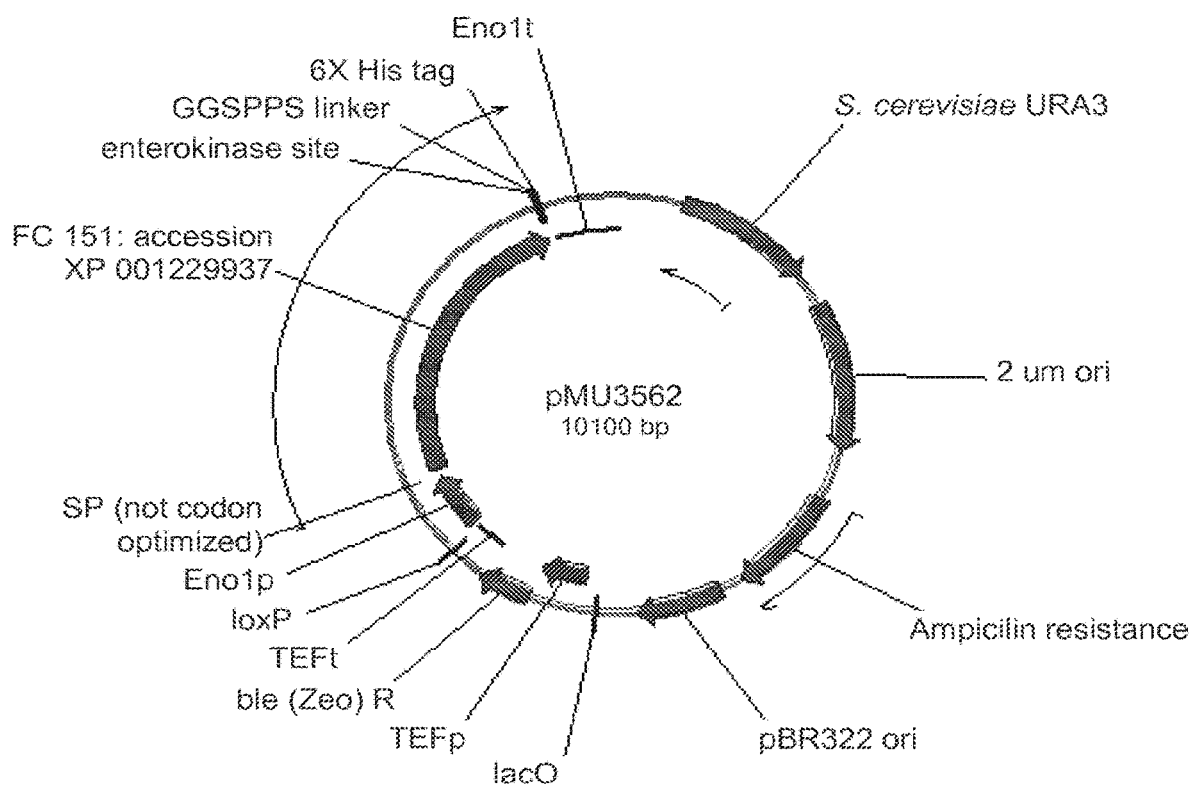
Figure 7:
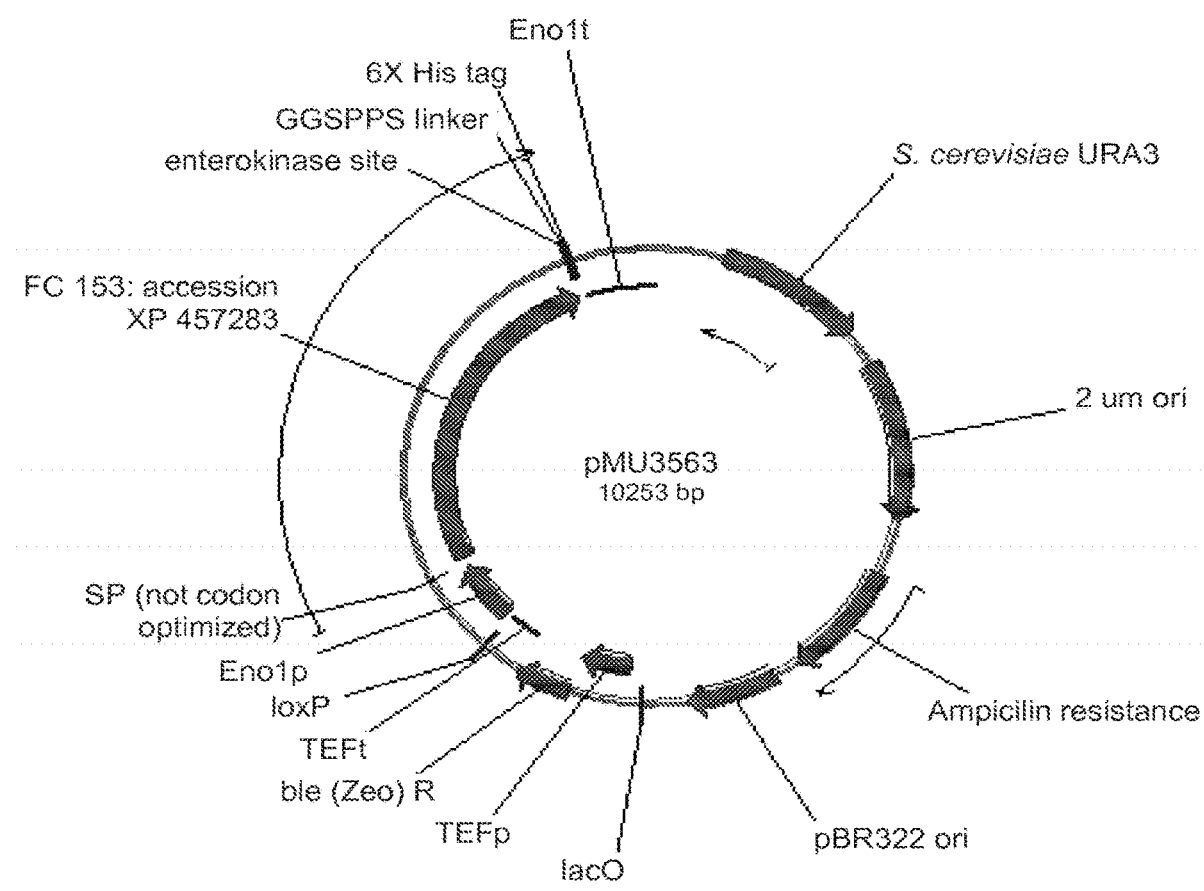
Figure 8:
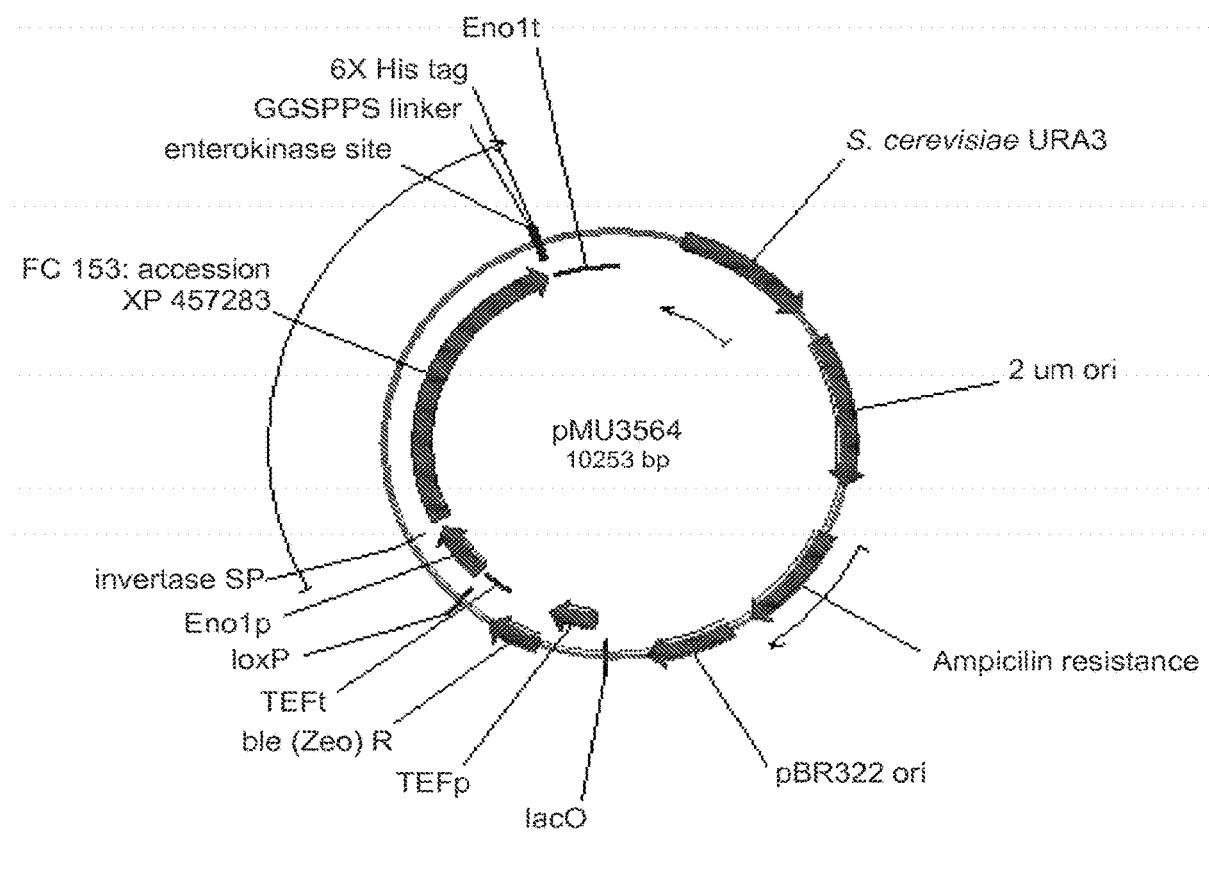
Figure 9:
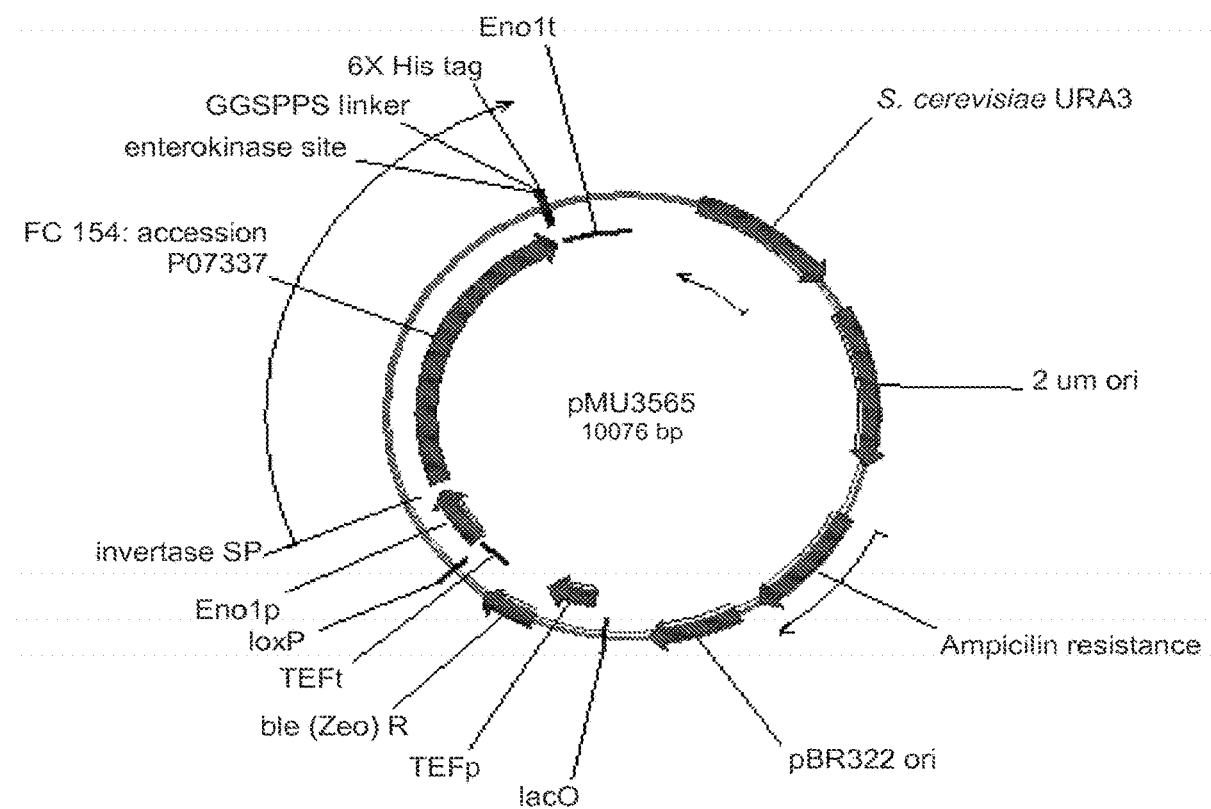
Figure 10:
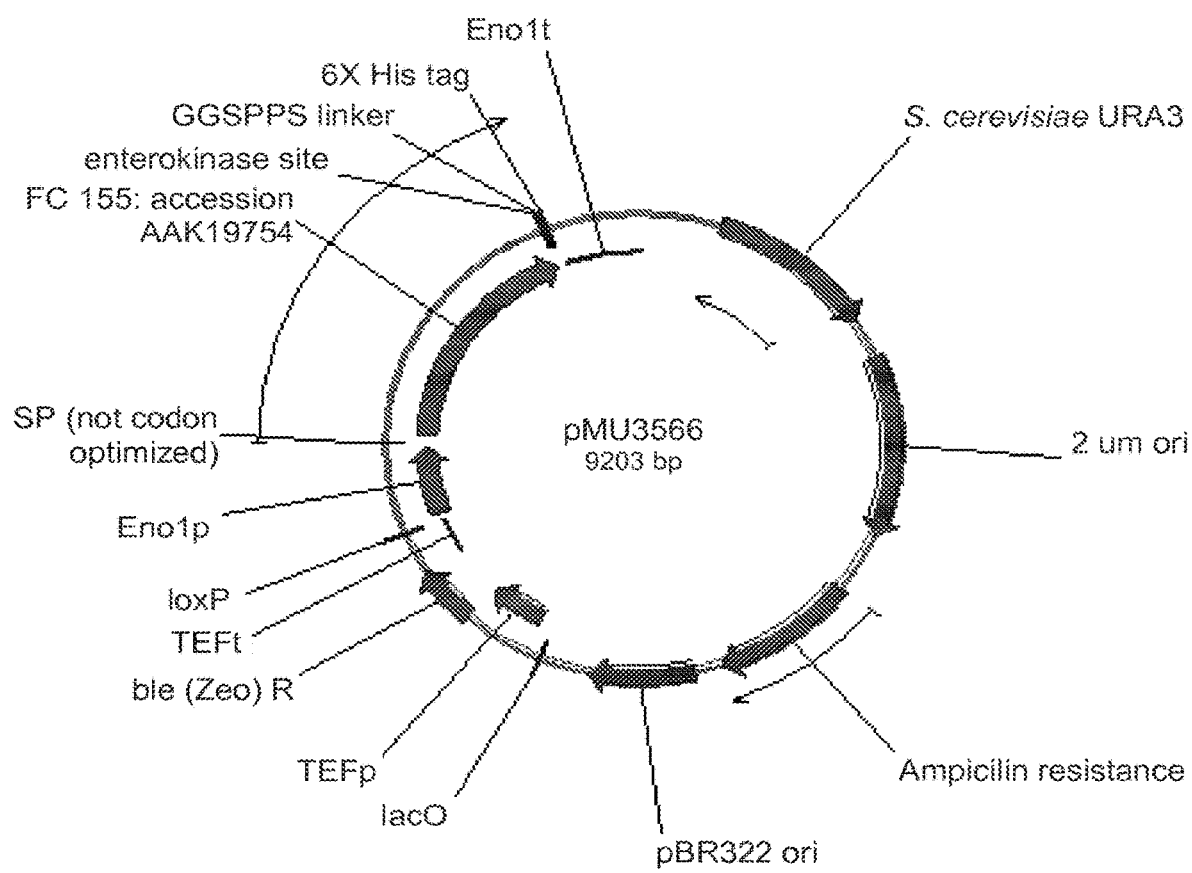
Figure 11:
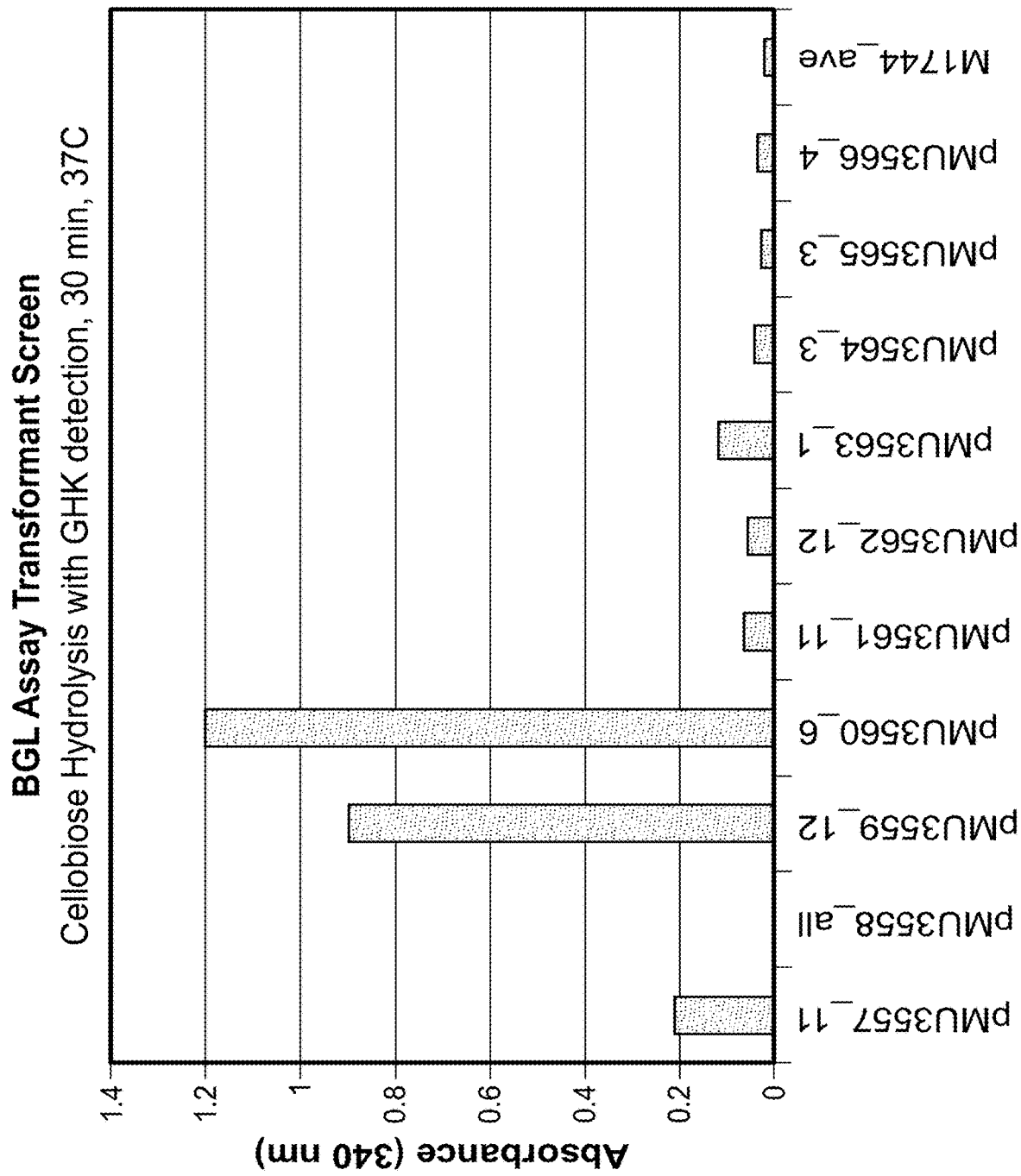
Figure 12B:
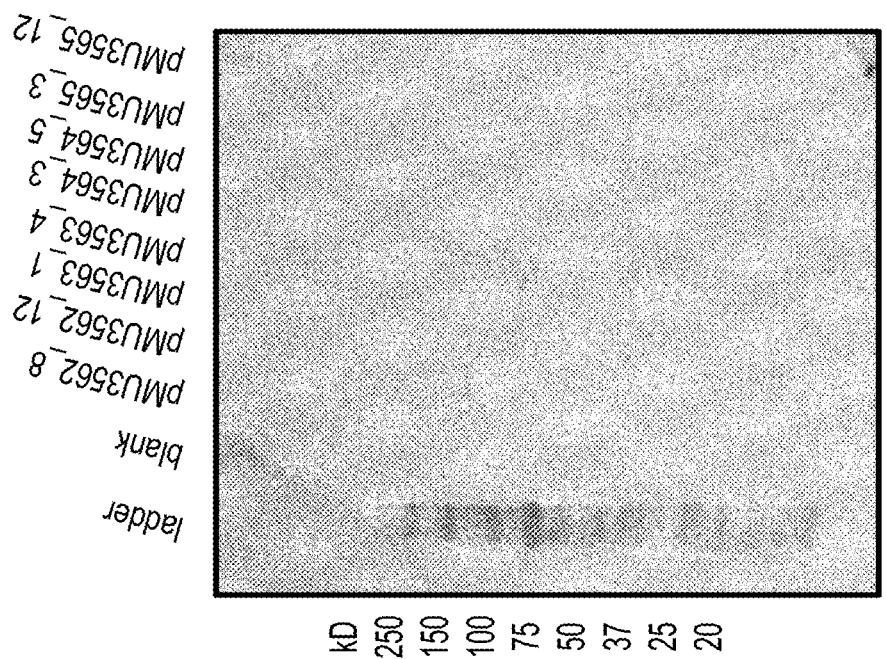
Figure 12B:
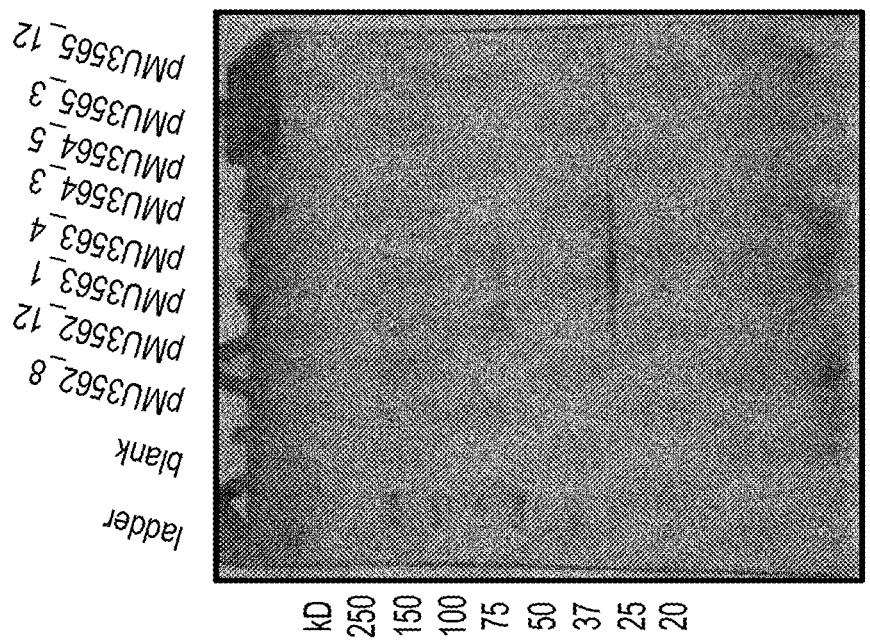
Figure 12C:
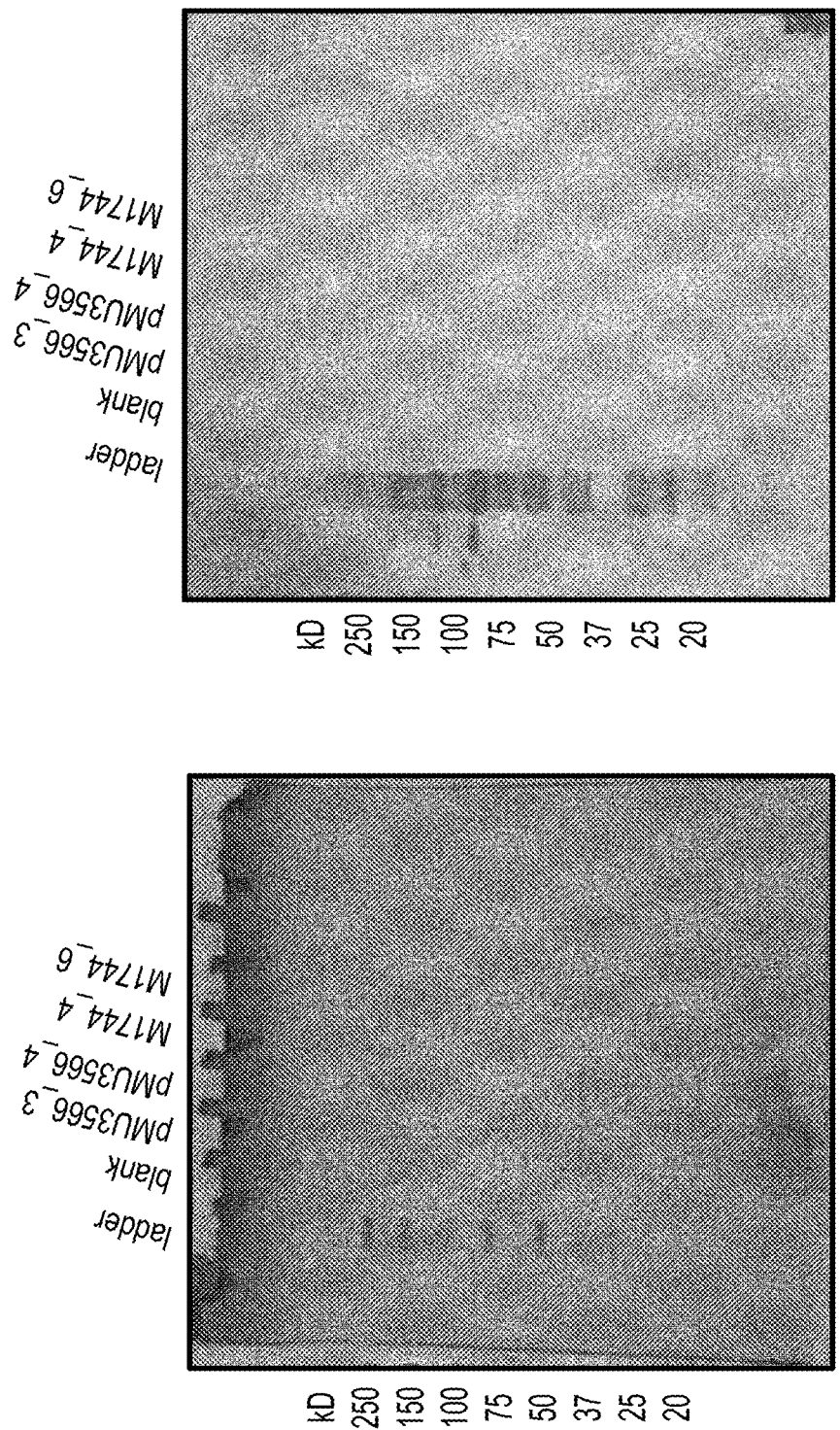
Figure 13:
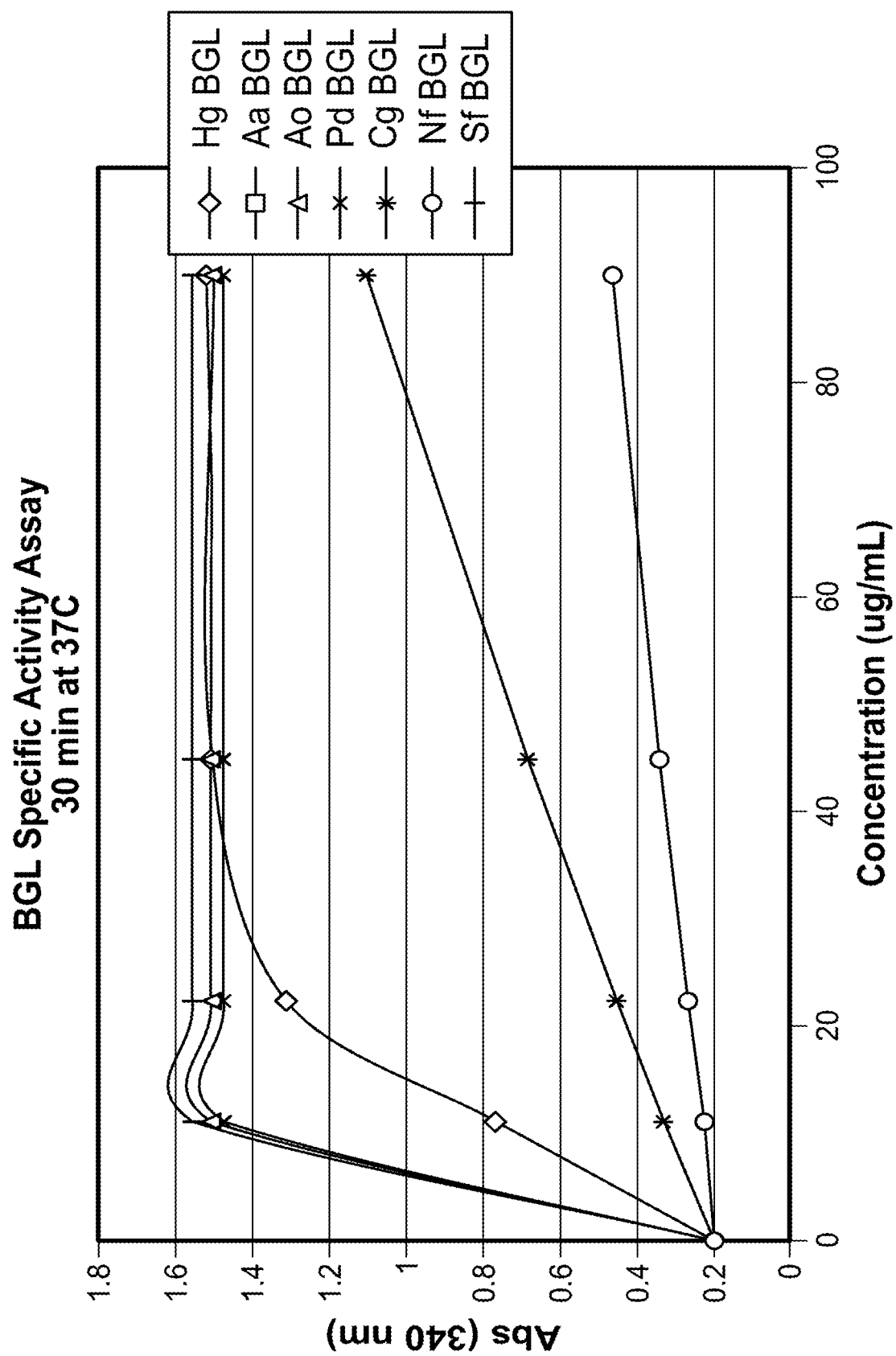
Figure 14:
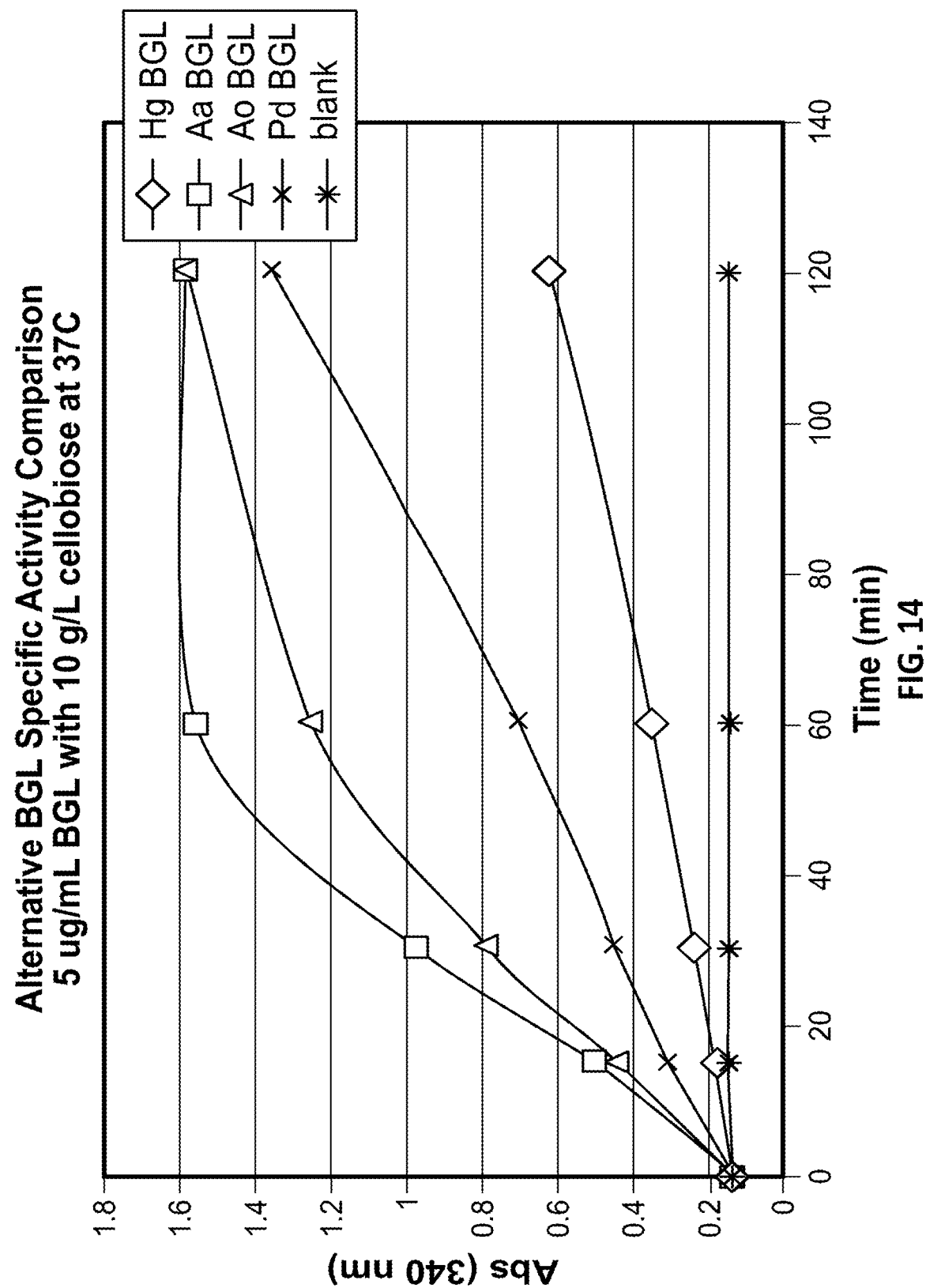
Figure 15:
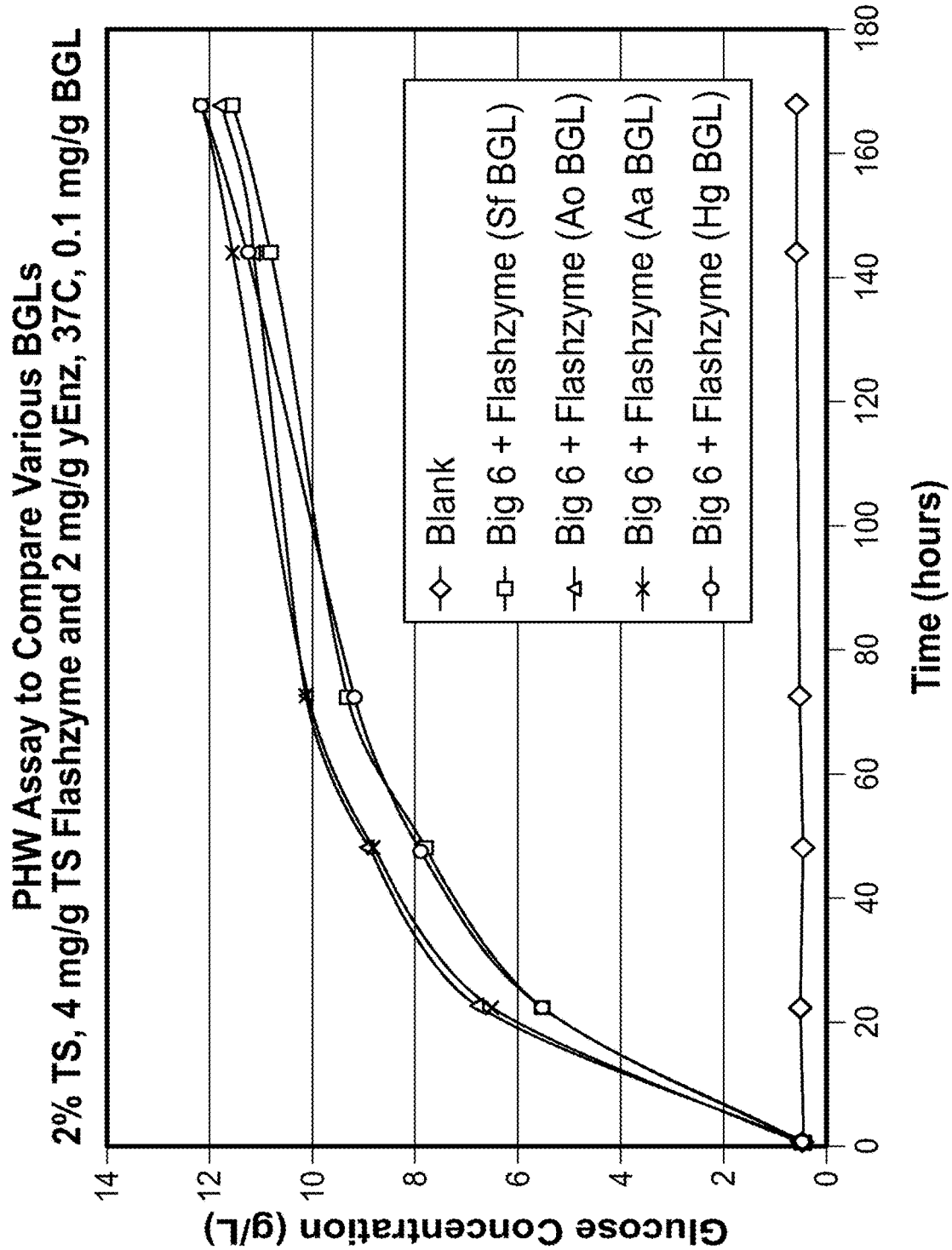

FIG. 1 depicts a plasmid map of pMU3557.
FIG. 2 depicts a plasmid map of pMU3558.
FIG. 3 depicts a plasmid map of pMU3559.
FIG. 4 depicts a plasmid map of pMU3560.
FIG. 5 depicts a plasmid map of pMU3561.
FIG. 6 depicts a plasmid map of pMU3562.
FIG. 7 depicts a plasmid map of pMU3563.
FIG. 8 depicts a plasmid map of pMU3564.
FIG. 9 depicts a plasmid map of pMU3565.
FIG. 10 depicts a plasmid map of pMU3566.
FIG. 11 depicts a beta-glucosidase activity assay with cellobiose of the transformants described in Example 1.
FIGS. 12A-12C depict SDS-PAGE and western blot analysis of the supernatants from beta-glucosidase (BGL) producing strains. The left-hand panels are SDS-PAGE gel results. The right-hand panels are western blot results.
FIG. 13 depicts a comparison of several BGL enzymes for activity against cellobiose at several protein loadings. The enzymes are identified by the two letter abbreviation of the source organism in the figure legend.
FIG. 14 depicts a comparison of several BGL enzymes for activity against cellobiose at a 5 ug/mL protein loading. The enzymes are identified by the two letter abbreviation of the source organism in the figure legend.
FIG. 15 depicts a comparison of several BGL enzymes for their impact on pretreated hardwood hydrolysis in a low concentration (2% total solids). "Big 6" refers to yeast made and purified cellulases, T. emersonii CBH1 with the *T. reesei* CBD, *C. lucknowense* CBH2, *A. fumigatus* EG1, *N. fischeri* EG3, *S. fibuligera* BGL, and *A. nige r*xylanase. 2 mg/g of total solids of this mixture along with 4 mg/g of a commercial enzyme preparation termed "flashzyme" was loaded in the assay, and additional purified BGL was added in small amounts (0.1 mg enzyme protein per gram of total solids) in addition to a commercial enzyme preparation which was loaded at a typical loading of 4 mg enzyme protein per gram of total solids. Released sugars were measured by HPLC.

Figure 16:
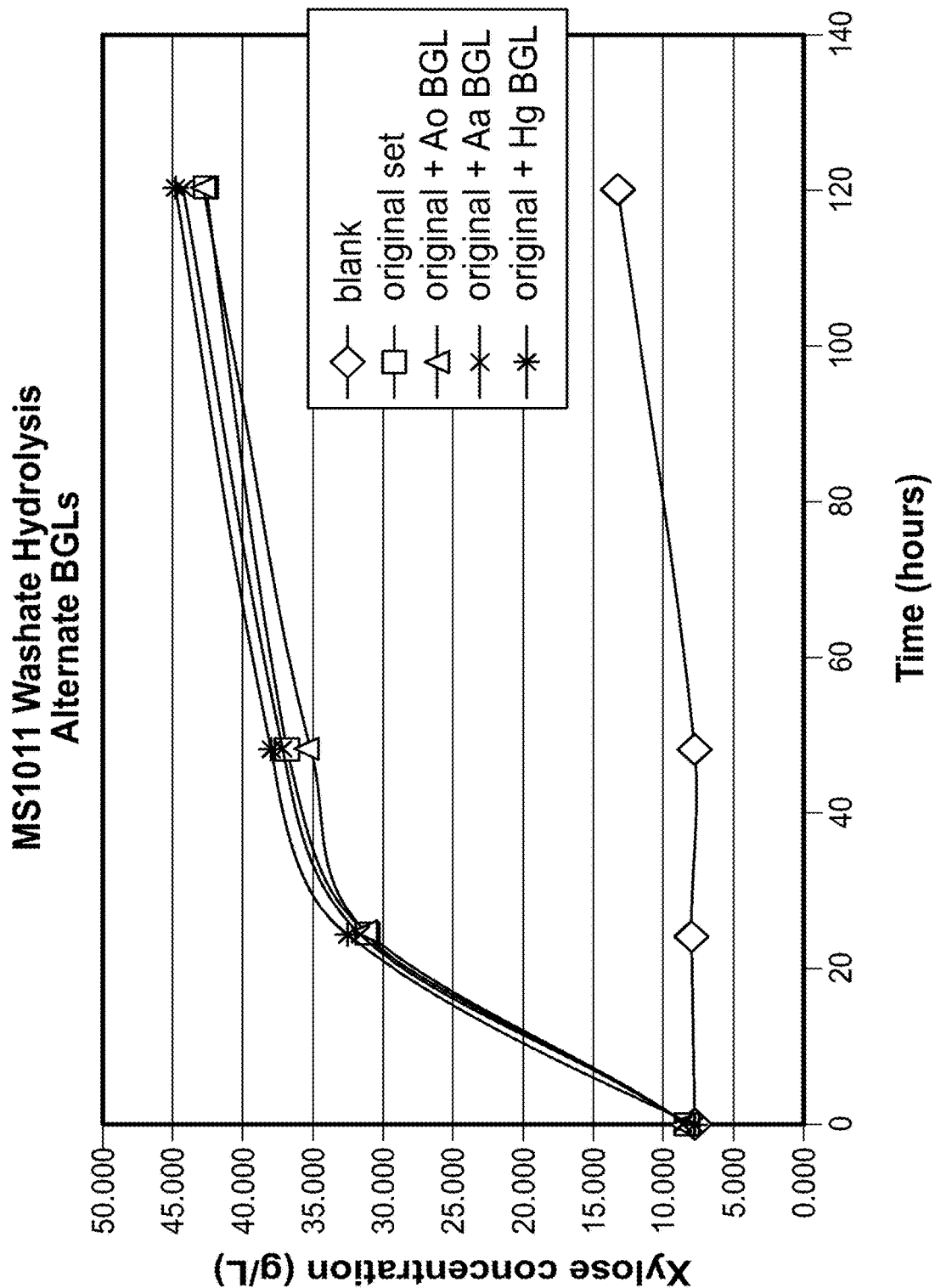

FIG. 16 depicts xylose (combination of xylose, galactose and mannose) release from pretreated hardwood derived C5 liquor during enzymatic assay using purified BGL enzymes. BGL was added in small amounts (0.2 mg enzyme protein per gram xylose) in addition to other yeast-made purified enzymes (all added at 0.2 mg/g xylose except xld=0.6 mg/g xylose). "Original set" represents the following set of genes: *A. niger* xylanase, P.t.r. xylosidase, *N. fischeri* AXE, *A. fumigatus* EG1, *T. reesei* AGL1, *T. reesei* beta-mannanase, *A. fumigatus* alpha-glucuronidase (FC110), *A. fumigatus* acetyl esterase (FC136), *N. fischeri* beta-mannosidase (FC124), and *S. fibuligera* BGL. "Original set +Ao BGL" represents the original set, except that the *S. fibuligera* BGL was not included, and the *A. oryzae* BGL was used in its place. Released sugars were measured by HPLC.

Figure 17:
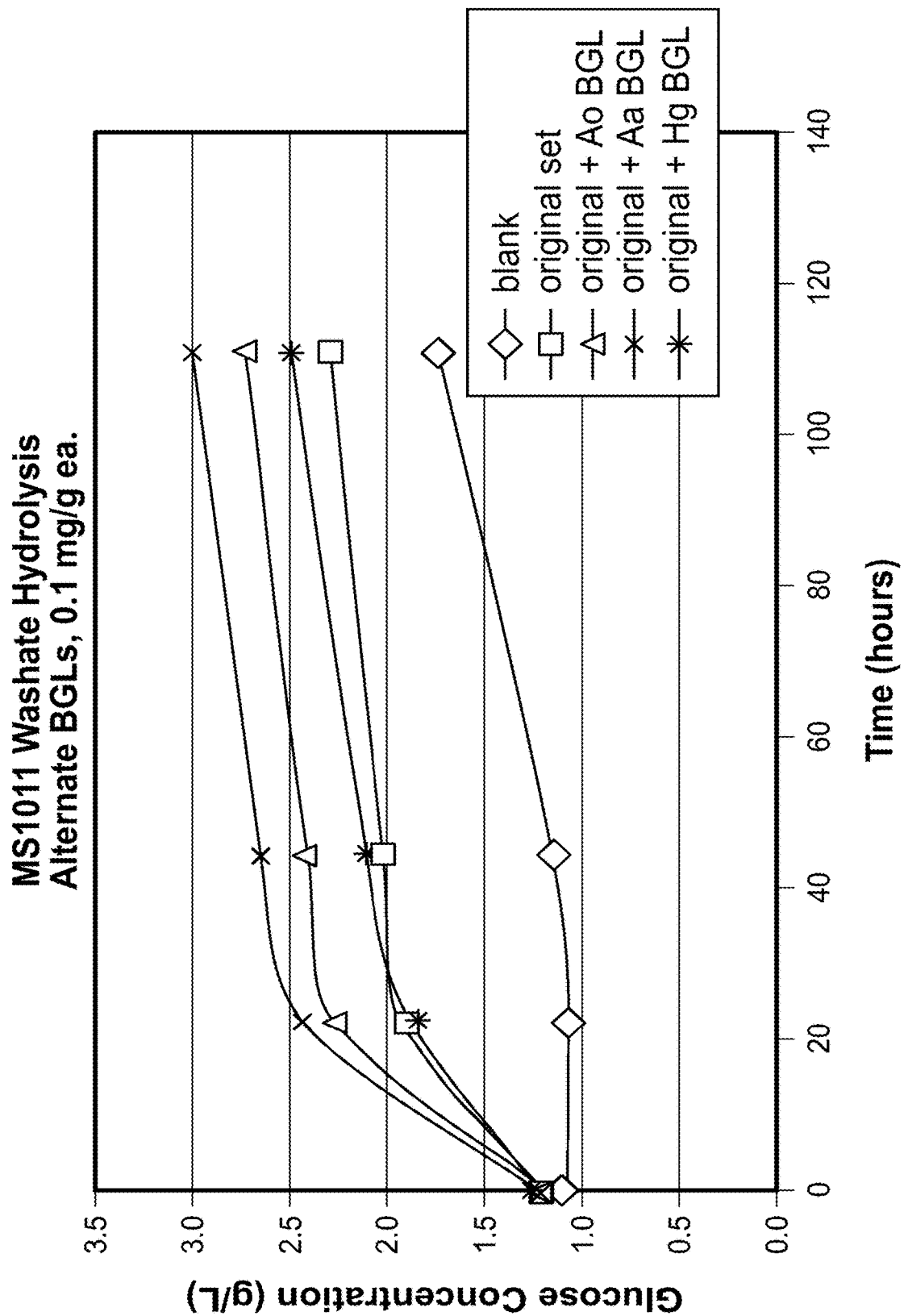

FIG. 17 depicts glucose release from pretreated hardwood derived C5 liquor during enzymatic assay using purified BGL enzymes. BGL was added in small amounts (0.2 mg enzyme protein per gram xylose) in addition to other yeast-made purified enzymes (all added at 0.2 mg/g xylose except xld=0.6 mg/g xylose). BGL was added in small amounts (0.1 mg enzyme protein per gram of total solids) in addition to a commercial enzyme preparation which was loaded at a typical loading of 4 mg enzyme protein per gram of total solids. Released sugars were measured by HPLC.

Figure 18:
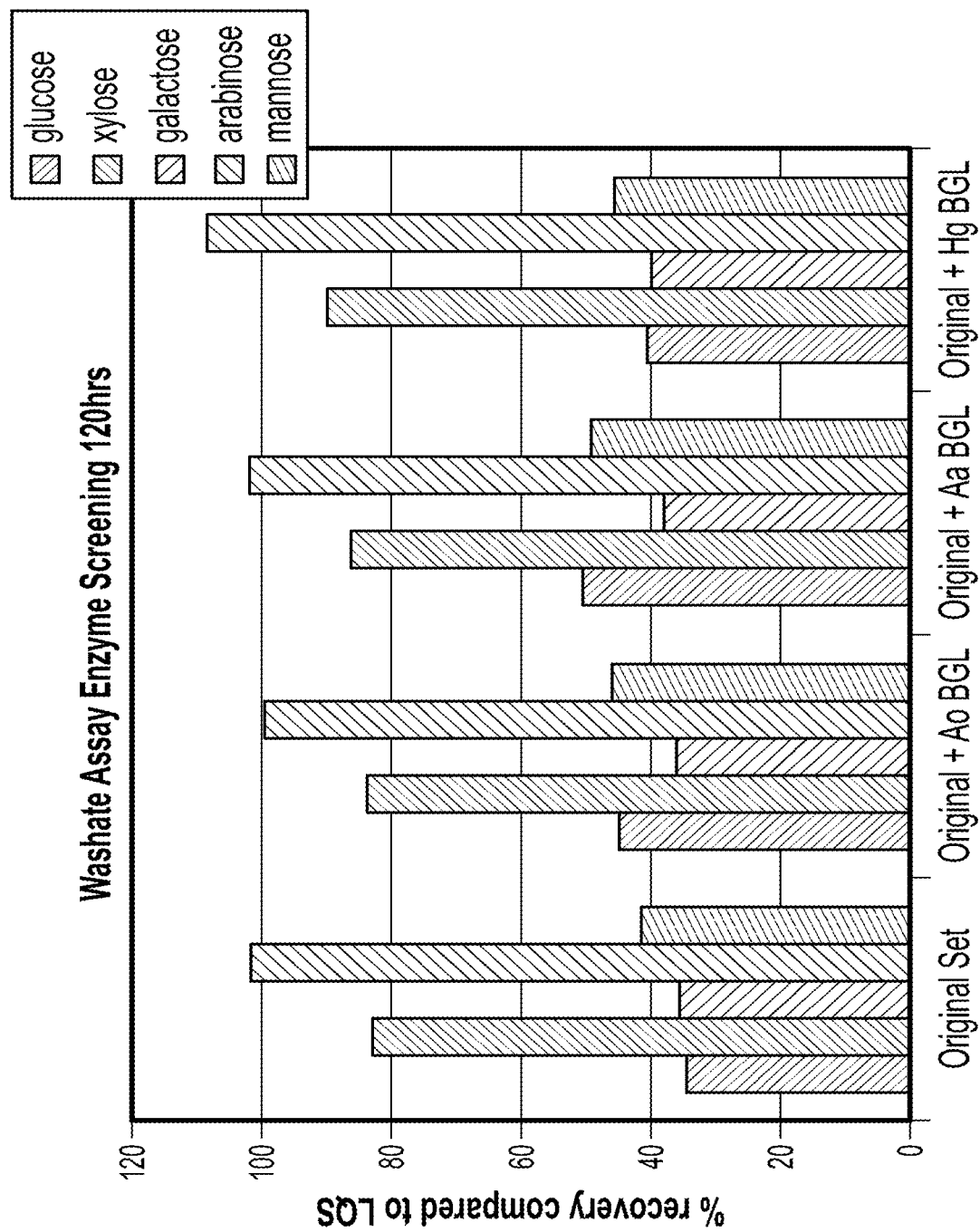

FIG. 18 depicts sugar release from pretreated hardwood derived C5 liquor during enzymatic assay using purified BGL enzymes. BGL was added in small amounts (0.2 mg enzyme protein per gram xylose) in addition to other yeast-made purified enzymes (all added at 0.2 mg/g xylose except xld=0.6 g/g xylose). BGL was added in small amounts (0.1 mg enzyme protein per gram of total solids) in addition to a commercial enzyme preparation which was loaded at a typical loading of 4 mg enzyme protein per gram of total solids. Released sugars were measured using HPLC using the BioRad Aminex 87P column to separate xylose, galactose, and mannose.

Figure 19:
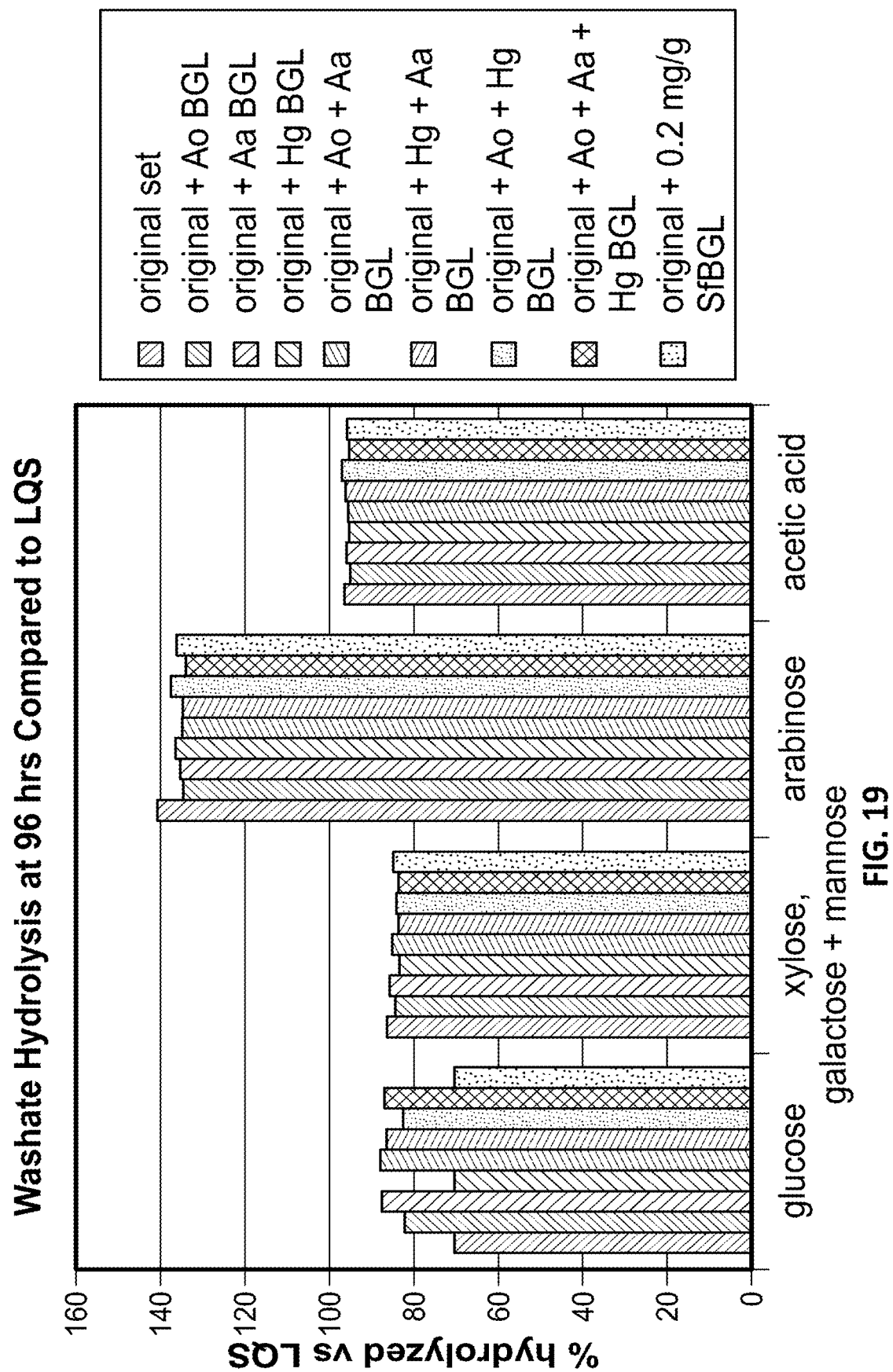

FIG. 19 depicts sugar release from pretreated hardwood derived C5 liquor during enzymatic assay using purified BGL enzymes. BGL was added in small amounts (0.2 mg enzyme protein per gram xylose) in addition to other yeast-made purified enzymes (all added at 0.2 mg/g xylose except xld=0.6 mg/g xylose). Also, BGL was added in small amounts (0.1 mg enzyme protein per gram of total solids) in addition to a commercial enzyme preparation which was loaded at a typical loading of 4 mg enzyme protein per gram of total solids. Sets with more than one BGL as indicated in the figure legend were created by adding an additional 0.2 mg/g xylose protein loading for the particular BGLs noted to the reaction. Released sugars were measured using HPLC using the BioRad Aminex 87H column to separate xylose, galactose, and mannose.

DETAILED DESCRIPTION OF THE INVENTION

The present invention relates to, inter alia, the heterologous expression of BGL genes from *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, and *Phytophthora infestans* in host cells, including yeast, e.g., *Saccharomyces cerevisiae*. The present invention provides important tools to enable growth of yeast on cellulosic substrates for production of products such as ethanol.

Definitions

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular.

A used herein, the terms "comprises," "comprising," "includes," "including," "has," "having," "contains," or "containing," or any other variation thereof, will be understood to imply the inclusion of a stated integer or group of integers but not the exclusion of any other integer or group of integers. For example, a composition, a mixture, a process, a method, an article, or an apparatus that comprises a list of elements not expressly listed or inherent to only those elements but can include other elements not expressly listed or inherent to such composition, mixture, process, method, article, or apparatus. Further, unless expressly stated to the contrary, "or" refers to an inclusive or and not to exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore, "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the application.

As used herein, the term "about" modifying a quantity or amount related to the invention refers to variation in the numerical quantity that can occur, for example, through typical measuring and liquid handling procedures used for making concentrates or solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, alternatively within 5% of the reported numerical value.

A "vector," e.g., a "plasmid" or "YAC" (yeast artificial chromosome) refers to an extrachromosomal element often carrying one or more genes that are not part of the central metabolism of the cell. They can be in the form of a circular double-stranded DNA molecule. Such elements can be autonomously replicating sequences, genome integrating sequences, or phage sequences. Such elements can be linear, circular, or supercoiled and can be single- or double-stranded. They can also be DNA or RNA, derived from any source. They can include a number of nucleotide sequences which have been joined or recombined into a unique construction which is capable of introducing a promoter fragment and DNA sequence for a selected gene product along with appropriate 3' untranslated sequence into a cell. The plasmids or vectors of the present invention can be stable and self-replicating. The plasmids or vectors of the present invention can also be suicide vectors, or vectors that cannot replicate in the host cell. Such vectors are useful for forcing insertion of the nucleotide sequence into the host chromosome.

An "expression vector" is a vector that is capable of directing the expression of at least one polypeptide encoded by a polynucleotide sequence of the vector.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of domains of BGL have been described and include, for example, a glycosyl hydrolase family 3 n-terminal domain, a glycosyl hydrolase family 3 c-terminal domain, and a fibronectin type III like domain.

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which can be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences are generally described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook et al., MOLECULAR CLONING: A LABORATORY MANUAL, Second Edition, Cold Spring Harbor Laboratory Press, Cold Spring Harbor, 1989, particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis at 11.7-11.8). In one embodiment the length for a hybridizable nucleic acid is at least about 10 nucleotides. A minimum length for a hybridizable nucleic acid can also be at least about 15 nucleotides, at least about 20 nucleotides, or at least 30 nucleotides. Furthermore, the skilled artisan will recognize that the temperature and wash solution salt concentration can be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence can include up to five point mutations per each 100 nucleotides of the reference nucleotide sequence encoding the particular polypeptide. In other words, to obtain a nucleic acid having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence.

As a practical matter, whether any particular nucleic acid molecule or polypeptide is at least about 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al., *Comp. App. Biosci.*, 6:237-245, 1990. In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

As known in the art, "similarity" between two polypeptides is determined by comparing the amino acid sequence and conserved amino acid substitutes thereto of the polypeptide to the sequence of a second polypeptide.

Suitable nucleic acid sequences or fragments thereof (isolated polynucleotides of the present invention) encode polypeptides that are at least about 70% to 75% identical to the amino acid sequences reported herein, at least about 80%, 85%, or 90% identical to the amino acid sequences reported herein, or at least about 95%, 96%, 97%, 98%, 99%, or 100% identical to the amino acid sequences reported herein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, at least 250 amino acids, at least 300 amino acids, or at least 350 amino acids.

The term "probe" refers to a single-stranded nucleic acid molecule that can base pair with a complementary single stranded target nucleic acid to form a double-stranded molecule.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

As used herein, the term "oligonucleotide" refers to a nucleic acid, generally of about 18 nucleotides, that is hybridizable to a genomic DNA molecule, a cDNA molecule, or an mRNA molecule. Oligonucleotides can be labeled, e.g., with 32P-nucleotides or nucleotides to which a label, such as biotin, has been covalently conjugated. An oligonucleotide can be used as a probe to detect the presence of a nucleic acid according to the invention. Similarly, oligonucleotides (one or both of which can be labeled) can be used as PCR primers, either for cloning full length or a fragment of a nucleic acid of the invention, or to detect the presence of nucleic acids according to the invention. Generally, oligonucleotides are prepared synthetically, for example, on a nucleic acid synthesizer. Accordingly, oligonucleotides can be prepared with non-naturally occurring phosphoester analog bonds, such as thioester bonds, etc.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions can include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths can have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression can also refer to translation of mRNA into a polypeptide.

Polynucleotides of the Invention

The present invention provides for the use of BGL polynucleotide sequences from *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans*. Nucleic acid sequences for BGL from *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* are available in GenBank and examples of such sequences are shown in Example 1.

The present invention also provides for the use of an isolated polynucleotide comprising a nucleic acid at least about 70%, at least about 75%, at least about 80%, at least about 85%, at least about 90%, at least about 95%, at least about 96%, at least about 97%, at least about 98%, at least about 99%, or 100% identical, or any range of values thereof, to any of SEQ ID NOs:3, 6, 9, 12, 15, 18, 21, 24, 27, or 30, or a fragment, variant, derivative, or codon-optimized version thereof. The present invention also provides for the use of an isolated polynucleotide comprising a nucleic acid having from about 70% to 100%, from about 75% to 100%, from about 80% to 100%, from about 85% to 100%, from about 90% to 100%, from about 95% to 100% identity to any of SEQ ID NOs:3, 6, 9, 12, 15, 18, 21, 24, 27, or 30, or a fragment, variant, derivative, or codon-optimized version thereof.

In certain aspects, the present invention relates to a polynucleotide comprising a nucleic acid encoding a functional and/or structural domain of a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL. The present invention also encompasses an isolated polynucleotide comprising a nucleic acid that is at least about 70%, at least about 75%, at least about 80%, at least about 85%, at least about 90%, at least about 95%, at least about 96%, at least about 97%, at least about 98%, at least about 99%, or 100% identical, or any range of values thereof, to a nucleic acid encoding a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL domain. The present invention also encompasses an isolated polynucleotide comprising a nucleic acid having from about 70% to 100%, from about 75% to 100%, from about 80% to 100%, from about 85% to 100%, from about 90% to 100%, from about 95% to 100% identity to a nucleic acid encoding a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL domain. Examples of BGL domains have been described and include, for example, a glycosyl hydrolase family 3 n-terminal domain, a glycosyl hydrolase family 3 c-terminal domain , and a fibronectin type III like domain.

The present invention also encompasses variants of BGL genes. Variants can contain alterations in the coding regions, non-coding regions, or both. Examples are polynucleotide variants containing alterations which produce silent substitutions, additions, or deletions, but do not alter the properties or activities of the encoded polypeptide. In certain embodiments, nucleotide variants are produced by silent substitutions due to the degeneracy of the genetic code. In further embodiments, *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polynucleotide variants can be produced for a variety of reasons, e.g., to optimize codon expression for a particular host (e.g., change codons in the BGL mRNA to those preferred by a host such as the yeast *Saccharomyces cerevisiae*). Codon-optimized polynucleotides of the present invention are discussed further herein.

The present invention also encompasses an isolated polynucleotide comprising a nucleic acid that is at least about 70%, at least about 75%, at least about 80%, at least about 85%, at least about 90%, at least about 95%, at least about 96%, at least about 97%, at least about 98%, at least about 99%, or 100% identical, or any range of values thereof, to a nucleic acid encoding a fusion protein, wherein the nucleic acid comprises (1) a first polynucleotide, where the first polynucleotide encodes for a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL, or domain, fragment, variant, or derivative thereof; and (2) a second polynucleotide.

The present invention also encompasses an isolated polynucleotide comprising a nucleic acid that is from about 70% to 100%, from about 75% to 100%, from about 80% to 100%, from about 85% to 100%, from about 90% to 100%, from about 95% to 100% identity to a nucleic acid encoding a fusion protein, wherein the nucleic acid comprises (1) a first polynucleotide, where the first polynucleotide encodes a *Humicola grisea, Candida wickerhamii, Aspergillus acu-*

*leatus, Aspergillus oryzae, Penicillium decumbens, Chaetomium globosum, Neocallimastix frontalis, Debaryomyces hansenii, Kluyveromyces marxianus,* or *Phytophthora infestans* BGL, or domain, fragment, variant, or derivative thereof; and (2) a second polynucleotide.

In further embodiments of the fusion polynucleotide, the first and second polynucleotides are in the same orientation, or the second polynucleotide is in the reverse orientation of the first polynucleotide. In additional embodiments, the first polynucleotide is either 5' or 3' to the second polynucleotide. In certain other embodiments, the first polynucleotide and/or the second polynucleotide are encoded by codon-optimized polynucleotides, for example, polynucleotides codon-optimized for expression in *S. cerevisiae*.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs:3, 6, 9, 12, 15, 18, 21, 24, 27 or 30, using information from the sequences disclosed herein or the clones deposited with the ATCC. For example, allelic variants and/or species homologs can be isolated and identified by making suitable probes or primers from the sequences provided herein and screening a suitable nucleic acid source for allelic variants and/or the desired homologue.

Polynucleotides comprising sequences that are at least about 70%, at least about 75%, at least about 80%, at least about 85%, at least about 90%, at least about 95%, at least about 96%, at least about 97%, at least about 98%, at least about 99%, or 100% identical, or any range of values thereof, to the entire sequence of any of SEQ ID NOs:3, 6, 9, 12, 15, 18, 21, 24, 27 or 30 or any fragment or domain therein can be used according to the methods described herein. In addition, polynucleotides comprising sequences that are from about 70% to 100%, from about 75% to 100%, from about 80% to 100%, from about 85% to 100%, from about 90% to 100%, from about 95% to 100% identity to the entire sequence of any of SEQ ID NOs:3, 6, 9, 12, 15, 18, 21, 24, 27 or 30 or any fragment or domain therein can be used according to the methods described herein. Some embodiments of the invention encompass a nucleic acid molecule comprising at least about 10, at least about 20, at least about 30, at least about 35, at least about 40, at least about 50, at least about 60, at least about 70, at least about 80, at least about 90, at least about 100, at least about 200, at least about 300, at least about 400, at least about 500, at least about 600, at least about 700, or at least about 800 consecutive nucleotides, or more, or any range of values thereof, of any of SEQ ID NOs:3, 6, 9, 12, 15, 18, 21, 24, 27 or 30, or domains, fragments, variants, or derivatives thereof.

In further aspects of the invention, nucleic acid molecules disclosed herein, encode a polypeptide having BGL functional activity. The phrase "a polypeptide having BGL functional activity" is intended to refer to a polypeptide exhibiting activity similar, but not necessarily identical, to a functional activity of the BGL polypeptides of the present invention, as measured, for example, in a particular biological assay. For example, a BGL functional activity can routinely be measured by determining the ability of a BGL polypeptide to hydrolyze oligomers of glucose which are linked via beta 1-4 type bonds, including dimers (cellobiose), where they usually have higher activity, as well as longer chain oligomers where they usually have less activity.

Of course, due to the degeneracy of the genetic code, one of ordinary skill in the art will immediately recognize that a large portion of the nucleic acid molecules having a sequence of a described identity to a nucleic acid sequence, or fragments thereof, will encode polypeptides "having BGL functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having BGL functional activity.

Fragments of the full length gene of the present invention can be used as a hybridization probe for a cDNA library to isolate the full length cDNA and to isolate other cDNAs which have a high sequence similarity to the BGL genes of the present invention, or a gene encoding for a protein with similar biological activity. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

In certain embodiments, a hybridization probe can have at least 30 bases and can contain, for example, 50 or more bases. The probe can also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of bacterial or fungal cDNA, genomic DNA or mRNA to determine to which members of the library the probe hybridizes.

The present invention further relates to polynucleotides which hybridize to the hereinabove-described sequences if there is at least about 70%, at least about 90%, or at least about 95% identity between the sequences. The present invention particularly relates to polynucleotides which hybridize under stringent conditions to the hereinabove-described polynucleotides. As herein used, the term "stringent conditions" means hybridization will occur only if there is at least about 95% or at least about 97% identity between the sequences. In certain aspects of the invention, the polynucleotides which hybridize to the hereinabove described polynucleotides encode polypeptides which either retain substantially the same biological function or activity as the mature polypeptide encoded by the DNAs of any of SEQ ID NOs:3, 6, 9, 12, 15, 18, 21, 24 or 30.

Alternatively, polynucleotides which hybridize to the hereinabove-described sequences can have at least 20 bases, at least 30 bases, or at least 50 bases which hybridize to a polynucleotide of the present invention and which has an identity thereto, as hereinabove described, and which may or may not retain activity. For example, such polynucleotides can be employed as probes for the polynucleotide of any of SEQ ID NOs:3, 6, 9, 12, 15, 18, 21, 24 or 30, for example, for recovery of the polynucleotide or as a diagnostic probe or as a PCR primer.

Hybridization methods are well defined and have been described above. Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

For example, genes encoding similar proteins or polypeptides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (see, e.g., Maniatis, 1989). Moreover, the entire sequences can be used directly to synthesize DNA probes by methods known to the skilled artisan such as random primers DNA labeling, nick translation, or end-labeling techniques, or RNA probes using available in vitro transcription systems.

In certain aspects of the invention, polynucleotides which hybridize to the hereinabove-described sequences having at least 20 bases, at least 30 bases, or at least 50 bases which hybridize to a polynucleotide of the present invention can be employed as PCR primers. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. Generally two short segments of the instant sequences can be used in polymerase chain reaction (PCR) protocols to amplify longer nucleic acid fragments encoding homologous genes from DNA or RNA. The polymerase chain reaction can also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence can be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA*, 86:5673, 1989; Loh et al., *Science*, 243 :217, 1989).

In addition, specific primers can be designed and used to amplify a part of or the full-length of the instant sequences. The resulting amplification products can be labeled directly during amplification reactions or labeled after amplification reactions, and used as probes to isolate full length DNA fragments under conditions of appropriate stringency.

Therefore, the nucleic acid sequences and fragments thereof of the present invention can be used to isolate genes encoding homologous proteins from the same or other fungal species or bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, Mullis et al., U.S. Pat. No. 4,683,202; ligase chain reaction (LCR) (Tabor et al., *Proc. Acad. Sci. USA,* 82:1074, 1985); or strand displacement amplification (SDA), (Walker et al., *Proc. Natl. Acad. Sci. USA,* 89:392, 1992).

The polynucleotides of the present invention also comprise nucleic acids encoding a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus,* or *Phytophthora infestans* BGL, or domain, fragment, variant, or derivative thereof, fused to a polynucleotide encoding a marker sequence which allows for selection and/or detection of the presence of the polynucleotide in an organism. Expression of the marker can be independent from expression of the BGL polypeptide. The marker sequence can be a yeast selectable marker such as one or more of URA3, HIS3, LEU2, TRP1, LYS2, ADE2 or SMR1. See, e.g., Casey et al., *J. Inst. Brew.,* 94:93-97, 1988.

In other embodiments of the present invention, the BGL is derived from *Saccharomycopsis fibuligera*. In other embodiments, the BGL is a beta-glucosidase I or a beta-glucosidase II isoform, paralogue or orthologue. In other embodiments, the BGL expressed by the cells of the present invention is recombinant beta-glucanase I from a *Saccharomycopsis fibuligera* source.

Codon Optimization

As used herein the term "codon-optimized" means a nucleic acid (e.g., a nucleic acid coding region) that has been adapted for expression in the cells of a given organism by replacing one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The Codon Adaptation Index is described in more detail in Sharp et al. (*Nucleic Acids Research,* 15:1281-1295, 1987), which is incorporated by reference herein in its entirety.

The CAI of codon-optimized sequences of the present invention correspond to from about 0.6 to about 1.0, from about 0.7 to about 1.0, from about 0.8 to about 1.0, from about 0.9 to about 1.0, from about 9.5 to about 1.0, or about 1.0. A codon-optimized sequence can be further modified for expression in a particular organism, depending on that organism's biological constraints. For example, large runs of "As" or "Ts" (e.g., runs greater than 4, 5, 6, 7, 8, 9, or 10 consecutive bases) can be removed from the sequences if these are known to effect transcription negatively. Furthermore, specific restriction enzyme sites can be removed for molecular cloning purposes. Examples of such restriction enzyme sites include PacI, AscI, BamHI, BglII, EcoRI and XhoI. Additionally, the DNA sequence can be checked for direct repeats, inverted repeats and mirror repeats with lengths of ten bases or longer, which can be modified manually by replacing codons with "second best" codons, i.e., codons that occur at the second highest frequency within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code.

|   | T | C | A | G |
|---|---|---|---|---|
| T | TTT Phe (F)<br>TTC Phe (F)<br>TTA Leu (L)<br>TTG Leu (L) | TCT Ser (S)<br>TCC Ser (S)<br>TCA Ser (S)<br>TCG Ser (S) | TAT Tyr (Y)<br>TAC Tyr (Y)<br>TAA Ter<br>TAG Ter | TGT Cys (C)<br>TGC Cys (C)<br>TGA Ter<br>TGG Trp (W) |
| C | CTT Leu (L)<br>CTC Leu (L)<br>CTA Leu (L)<br>CTG Leu (L) | CCT Pro (P)<br>CCC Pro (P)<br>CCA Pro (P)<br>CCG Pro (P) | CAT His (H)<br>CAC His (H)<br>CAA Gln (Q)<br>CAG Gln (Q) | CGT Arg (R)<br>CGC Arg (R)<br>CGA Arg (R)<br>CGG Arg (R) |
| A | ATT Ile (I)<br>ATC Ile (I)<br>ATA Ile (I)<br>ATG Met (M) | ACT Thr (T)<br>ACC Thr (T)<br>ACA Thr (T)<br>ACG Thr (T) | AAT Asn (N)<br>AAC Asn (N)<br>AAA Lys (K)<br>AAG Lys (K) | AGT Ser (S)<br>AGC Ser (S)<br>AGA Arg (R)<br>AGG Arg (R) |
| G | GTT Val (V)<br>GTC Val (V)<br>GTA Val (V)<br>GTG Val (V) | GCT Ala (A)<br>GCC Ala (A)<br>GCA AlA (A)<br>GCG Ala (A) | GAT Asp (D)<br>GAC Asp (D)<br>GAA Glu (E)<br>GAG Glu (E) | GGT Gly (G)<br>GGC Gly (G)<br>GGA Gly (G)<br>GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables and codon-optimizing programs are readily available, for example, at http://phenotype.biosci.umbc.edu/codon/sgd/index.php (visited Sep. 4, 2009) or at http://www.kazusa.or.jp/codon/ (visited Sep. 4, 2009), and these tables can be adapted in a number of ways. See Nakamura et al., *Nucl. Acids Res.* 28:292, 2000. Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |

TABLE 2-continued

Codon Usage Table for *Saccharomyces cerevisiae* Genes

| Amino Acid | Codon | Number | Frequency per hundred |
|---|---|---|---|
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus all the leucine residues in a given amino acid sequence would be assigned the codon UUG.

In another method, the actual frequencies of the codons are distributed randomly throughout the coding sequence. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG.

These frequencies would be distributed randomly throughout the leucine codons in the coding region encoding the hypothetical polypeptide. As will be understood by those of ordinary skill in the art, the distribution of codons in the sequence will can vary significantly using this method; however, the sequence always encodes the same polypeptide.

When using the methods above, the term "about" is used precisely to account for fractional percentages of codon frequencies for a given amino acid. For such methods, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at http://www.entelechon.com/bioinformatics/backtranslation.php?lang=eng (visited Mar. 14, 2013). Constructing a rudimentary algorithm to assign codons based on a given frequency can also easily be accomplished with basic mathematical functions by one of ordinary skill in the art.

A number of options are available for synthesizing codon-optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO° vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, an entire polypeptide sequence, or fragment, variant, or derivative thereof is codon-optimized by any of the methods described herein. Various desired fragments, variants or derivatives are designed, and each is then codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a yeast species such as *Saccharomyces cerevisiae*, in place of a codon that is normally used in the native nucleic acid sequence.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon-optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

Codon-optimized sequences (e.g., coding regions) can be versions encoding a BGL from *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus,* or *Phytophthora infestans*, or a domain, fragment, variant, or derivative thereof.

Codon optimization is carried out for a particular species by methods described herein. For example, in certain embodiments, codon-optimized sequences (e.g., coding regions) encoding polypeptides of a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus,* or *Phytophthora infestans* BGL, or a domain, fragment, variant, or derivative thereof are optimized according to yeast codon usage, e.g., *Saccharomyces cerevisiae*. In particular, the present invention relates to codon-optimized coding regions encoding polypeptides of a *Humicola grisea, Aspergillus aculeatus,* or *Aspergillus oryzae* BGL, or a domain, variant, or derivative thereof which have been optimized according to yeast codon usage, for example, *Saccharomyces cerevisiae* codon usage. Also provided are polynucleotides, vectors, and other expression constructs comprising codon-optimized coding regions encoding BGL polypeptides of *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus,* or *Phytophthora infestans* or a domain, fragment, variant, or derivative thereof, and various methods of using such polynucleotides, vectors and other expression constructs.

In certain embodiments described herein, a codon-optimized sequence encoding the polypeptide sequence of any of SEQ ID NOs:1, 4, 7, 10, 13, 16, 19, 22, 25 or 28, or a domain, fragment, variant, or derivative thereof, is optimized according to codon usage in yeast (*Saccharomyces cerevisiae*). Alternatively, a codon-optimized coding region encoding the polypeptide sequence of any of SEQ ID NOs:1, 4, 7, 10, 13, 16, 19, 22, 25 or 28, can be optimized according to codon usage in any plant, animal, or microbial species.

BGL Polypeptides

The present invention further relates to the expression of *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus,* and *Phytophthora infestans* BGL polypeptides. The sequences of these peptides are available in GenBank and examples are set forth in Example 1.

The present invention further encompasses polypeptides which comprise, or alternatively consist of, an amino acid sequence which is at least about 70%, at least about 75%, at least about 80%, at least about 85%, at least about 90%, at least about 95%, at least about 96%, at least about 97%, at least about 98%, at least about 99%, or 100% identical, or any range of values thereof, for example, to the polypeptide sequences shown in any of SEQ ID NOs:1, 4, 7, 10, 13, 16, 19, 22, 25, or 28, and/or domains, fragments, variants, or derivative thereof, of any of these polypeptides (e.g., those fragments described herein, or domains of any of SEQ ID NOs:1, 2, 4, 5, 7, 8, 10, 11, 13, 14, 16, 17, 19, 20, 22, 23, 25, 26, 28 or 29).

The present invention further encompasses polypeptides which comprise, or alternatively consist of, an amino acid sequence which is from about 70% to 100%, from about 75% to 100%, from about 80% to 100%, from about 85% to 100%, from about 90% to 100%, from about 95% to 100% identity, for example, to the polypeptide sequences shown in any of SEQ ID NOs:1, 4, 7, 10, 13, 16, 19, 22, 25, or 28, and/or domains, fragments, variants, or derivative thereof, of any of these polypeptides (e.g., those fragments described herein, or domains of any of SEQ ID NOs:1, 2, 4, 5, 7, 8, 10, 11, 13, 14, 16, 17, 19, 20, 22, 23, 25, 26, 28 or 29). Examples of BGL domains have been described and include, for example, a glycosyl hydrolase family 3 n-terminal domain, a glycosyl hydrolase family 3 c-terminal domain, and a fibronectin type III like domain.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence can include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence can be inserted, deleted or substituted with another amino acid. These alterations of the reference sequence can occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, any of the amino acid sequences of SEQ ID NOs:1, 2, 4, 5, 7, 8, 10, 11, 13, 14, 16, 17, 19, 20, 22, 23, 25, 26, 28 or 29 can be determined conventionally using known computer programs. As discussed above, a method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245(1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Also as discussed above, manual corrections can be made to the results in certain instances.

In certain aspects of the invention, the polypeptides and polynucleotides of the present invention are provided in an isolated form, e.g., purified to homogeneity.

The present invention also encompasses polypeptides which comprise, or alternatively consist of, an amino acid sequence which is at least about 70%, at least about 75%, at least about 80%, at least about 85%, at least about 90%, at least about 95%, at least about 96%, at least about 97%, at least about 98%, at least about 99%, or 100% identical, or any range of values thereof, to the polypeptide of any of SEQ ID NOs:1, 2, 4, 5, 7, 8, 10, 11, 13, 14, 16, 17, 19, 20, 22, 23, 25, 26, 28 or 29, or to portions of such polypeptide, wherein the portion can contain at least 30 amino acids, at least 50 amino acids, at least 100 amino acids, at least 150 amino acids, at least 200 amino acids, at least 250 amino acids, at least 300 amino acids, or at least 350 amino acids.

The present invention also encompasses polypeptides which comprise, or alternatively consist of, an amino acid sequence is from about 70% to 100%, from about 75% to 100%, from about 80% to 100%, from about 85% to 100%, from about 90% to 100%, from about 95% to 100% identical to the polypeptide of any of SEQ ID NOs:1, 2, 4, 5, 7, 8, 10, 11, 13, 14, 16, 17, 19, 20, 22, 23, 25, 26, 28 or 29, or to portions of such polypeptide, wherein the portion can contain at least 30 amino acids, at least 50 amino acids, at least 100 amino acids, at least 150 amino acids, at least 200 amino acids, at least 250 amino acids, at least 300 amino acids, or at least 350 amino acids.

The present invention further relates to a domain, fragment, variant, derivative, or analog of the polypeptide of any of SEQ ID NOs:1, 2, 4, 5, 7, 8, 10, 11, 13, 14, 16, 17, 19, 20, 22, 23, 25, 26, 28 or 29.

Fragments or portions of the polypeptides of the present invention can be employed for producing the corresponding full-length polypeptide by peptide synthesis, therefore, the fragments can be employed as intermediates for producing the full-length polypeptides.

Fragments of BGL polypeptides of the present invention can encompass domains, proteolytic fragments, and deletion fragments of *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus,* or *Phytophthora infestans* BGL polypeptides. The fragments can optionally retain a specific biological activity of the BGL protein. Exemplary fragments include those described in Example 1. Polypeptide fragments further include any portion of the polypeptide which comprises a catalytic activity of the BGL protein.

The variant, derivative or analog of the polypeptide of any of SEQ ID NOs:1, 2, 4, 5, 7, 8, 10, 11, 13, 14, 16, 17, 19, 20, 22, 23, 25, 26, 28 or 29 can be (i) one in which one or more of the amino acid residues are substituted with a conserved or non-conserved amino acid residue and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor. Such variants, derivatives and analogs are deemed to be within the scope of those skilled in the art from the teachings herein.

The polypeptides of the present invention further include variants of the polypeptides. A "variant" of the polypeptide can be a conservative variant, or an allelic variant. As used herein, a conservative variant refers to alterations in the amino acid sequence that does not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

By an "allelic variant" is intended alternate forms of a gene occupying a given locus on a chromosome of an organism. Genes II, Lewin, B., ed., John Wiley & Sons, New York (1985). Non-naturally occurring variants can be produced using art-known mutagenesis techniques. Allelic variants, though possessing a slightly different amino acid sequence than those recited above, will still have the same or similar biological functions associated with the *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL protein.

The allelic variants, the conservative substitution variants, and members of the BGL protein family, will have an amino acid sequence having at least 75%, at least 80%, at least 90%, at least 95%, at least 96%, at least 97%, at least 98%, at least 99% amino acid sequence identity, or any range of values thereof, with a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL amino acid sequence set forth in any one of SEQ ID NOs: 1, 2, 4, 5, 7, 8, 10, 11, 13, 14, 16, 17, 19, 20, 22, 23, 25, 26, 28 or 29. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N terminal, C terminal, or internal extensions, deletions, or insertions into the peptide sequence shall not be construed as affecting homology.

Thus, the proteins and peptides of the present invention include molecules comprising the amino acid sequence of any one of SEQ ID NOs:1, 2, 4, 5, 7, 8, 10, 11, 13, 14, 16, 17, 19, 20, 22, 23, 25, 26, 28 or 29 or fragments thereof having a consecutive sequence of at least about 3, 4, 5, 6, 10, 15, 20, 25, 30, 35, 50, 100, 150, 200, 250, 300, 350, or more amino acid residues, or any range of values thereof, of *the Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polypeptide sequence; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other organisms, the alleles or other naturally occurring variants of the family of proteins; and derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants can be generated to improve or alter the characteristics of the BGL polypeptides. For instance, one or more amino acids can be deleted from the N-terminus or C-terminus of the secreted protein without substantial loss of biological function.

Thus, the invention further includes *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly affect protein function (e.g., replacing one aliphatic amino acid with a second aliphatic amino acid), as further described below.

For example, guidance concerning how to make phenotypically silent amino acid substitutions is provided in Bowie et al., *Science*, 247:1306-1310, 1990, wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. See, e.g., Cunningham et al., *Science*, 244:1081-1085, 1989. The resulting mutant molecules can then be tested for biological activity.

As the authors state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polypeptide differing from the *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polypeptide, but retaining essential properties thereof. Generally, derivatives and analogs are overall closely similar, and, in many regions, identical to the *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polypeptide. The term "derivative" and "analog" when referring to *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, and *Phytophthora infestans* BGL polypeptides of the present invention include polypeptides which retain at least some of the activity of the corresponding native polypeptide.

Derivatives of *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, and *Phytophthora infestans* BGL polypeptides of the present invention are polypeptides which have been altered so as to exhibit additional features not found on the native polypeptide. Derivatives can be covalently modified by substitution, chemical, enzymatic, or other appropriate means with a moiety other than a naturally occurring amino acid (for example, a detectable moiety such as an enzyme or radioisotope). Examples of derivatives include fusion proteins.

An analog is another form of a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polypeptide of the present invention. An "analog" also retains substantially the same biological function or activity as the polypeptide of interest, i.e., functions as a beta-glucosidase. An analog includes a proprotein which can be activated by cleavage of the proprotein portion to produce an active mature polypeptide.

The polypeptide of the present invention can be a recombinant polypeptide, a natural polypeptide, or a synthetic polypeptide.

BGL Fusion Polypeptides

The present invention also encompasses fusion proteins comprising two or more polypeptides. For example, the fusion proteins can be a fusion of a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL and a second peptide. The BGL and the second peptide can be fused directly or indirectly, for example, through a linker sequence. The fusion protein can comprise for example, a second peptide that is N-terminal to the BGL and/or a second peptide that is C-terminal to the heterologous cellulase. Thus, in certain embodiments, the polypeptide of the present invention comprises a first polypeptide and a second polypeptide, wherein the first polypeptide comprises a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polypeptide.

According to the present invention, the fusion protein can comprise a first and second polypeptide wherein the first polypeptide comprises a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polypeptide and the second polypeptide comprises a signal sequence. The signal sequence can be from any organism. For example, in some embodiments, the second polypeptide is a *Saccharomyces cerevisiae* (*S. cerevisiae*) polypeptide. In one particular embodiment, the *S. cerevisiae* polypeptide is *S. cerevisiae* alpha mating factor signal sequence. In some embodiments, the signal sequence comprises the amino acid sequence of any one of SEQ ID NOs:2, 5, 8, 11, 17, 20, 23, 26 or 29, or any fragment or variant thereof described herein.

According to another embodiment, the fusion protein can comprise a first and second polypeptide, wherein the first polypeptide comprises a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polypeptide and the second polypeptide comprises a polypeptide used to facilitate purification or identification or a reporter peptide. The polypeptide used to facilitate purification or identification or the reporter peptide can be, for example, a HIS-tag, a GST-tag, an HA-tag, a FLAG-tag, a MYC-tag, or a fluorescent protein.

In certain other embodiments, the first polypeptide and the second polypeptide are fused via a linker sequence. The linker sequence can, in some embodiments, comprise the sequence: GGSPPS (SEQ ID NO:41). The linker sequence can, in other embodiments, be encoded by a codon-optimized polynucleotide of the invention described further herein.

In further embodiments of the fusion protein, the first and second polypeptide are in the same orientation, or the second polypeptide is in the reverse orientation of the first polypeptide. In additional embodiments, the first polypeptide is either N-terminal or C-terminal to the second polypeptide. In certain other embodiments, the first polypeptide and/or the second polypeptide are encoded by codon-optimized polynucleotides, for example, polynucleotides codon-optimized for *S. cerevisiae*.

Vectors and Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention can be employed for producing polypeptides by recombinant techniques. Thus, for example, the polynucleotide can be included in any one of a variety of expression vectors for expressing a polypeptide. Such vectors include chromosomal, nonchromosomal and synthetic DNA sequences, e.g., derivatives of SV40; bacterial plasmids; and yeast plasmids. Such vectors also include "suicide vectors" which are not self-replicating but can be replicated after insertion into the host chromosome. Other vectors can also be used.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Representative examples of such promoters are as follows:

TABLE 3

Promoters

| Gene | Organism | Systematic name | Reason for use/benefits |
|---|---|---|---|
| PGK1 | S. cerevisiae | YCR012W | Strong constitutive promoter |
| ENO1 | S. cerevisiae | YGR254W | Strong constitutive promoter |
| TDH3 | S. cerevisiae | YGR192C | Strong constitutive promoter |
| TDH2 | S. cerevisiae | YJR009C | Strong constitutive promoter |
| TDH1 | S. cerevisiae | YJL052W | Strong constitutive promoter |
| ENO2 | S. cerevisiae | YHR174W | Strong constitutive promoter |
| GPM1 | S. cerevisiae | YKL152C | Strong constitutive promoter |
| TPI1 | S. cerevisiae | YDR050C | Strong constitutive promoter |

In addition, *Escherichia coli* (*E. coli*) promoters, such as lac or trp, are known to control expression of genes in prokaryotic or lower eukaryotic cells. The expression vector can also contain a ribosome binding site for translation initiation and a transcription terminator. The vector can also include appropriate sequences for amplifying expression, or can include additional regulatory regions. The vector can also include an enterokinase site for linking to a C-terminal tag to allow for cleavage of the target protein following protein purification.

In addition, the expression vectors can contain one or more selectable marker genes to provide a phenotypic trait for selection of transformed host cells such as URA3, HIS3, LEU2, TRPJ, LYS2 or ADE2, dihydrofolate reductase or neomycin (G418) resistance or zeocin resistance for eukaryotic cell culture, or chloramphenicol, thiamphenicol, streptomycin, tetracycline, kanamycin, hygromycin, phleomycin or ampicillin resistance in *E. coli*.

The vector containing the appropriate DNA sequence as herein, as well as an appropriate promoter or control sequence, can be employed to transform an appropriate host to permit the host to express the protein.

Thus, in certain aspects, the present invention relates to host cells containing the above-described constructs. The host cell can be a higher eukaryotic cell, such as a mammalian cell, or a lower eukaryotic cell, such as a yeast cell, e.g., *Saccharomyces cerevisiae*, or the host cell can be a prokaryotic cell, such as a bacterial cell.

Representative examples of appropriate hosts include, for example, bacterial cells, such as *E. coli, Streptomyces, Salmonella typhimurium*; thermophilic or mesophlic bacteria; fungal cells, such as yeast; and plant cells, etc. The selection of an appropriate host is deemed to be within the scope of those skilled in the art from the teachings herein.

Appropriate fungal hosts include yeast. In certain aspects of the invention the yeast is *Saccharomyces cerevisiae, Saccharomyces pastorianus* (also known as *Saccharomyces carlsbergensis*), *Saccharomyces bayanus, Kluyveromyces lactis, Kluyveromyces marxianus, Schizosaccharomyces pombe, Candida albicans, Pichia pastoris, Pichia stipitis, Yarrowia hpolytica, Hansenula polymorpha, Phaffia rhodozyma, Candida utilis, Arxula adeninivorans, Debaryomyces hansenii, Debaryomyces polymorphus or Schwanniomyces occidentalis*. In some embodiments, the host cell can be an oleaginous yeast cell. In some particular embodiments, the oleaginous yeast cell is a *Blakeslea, Candida, Cryptococcus, Cunninghamella, Lipomyces, Mortierella, Mucor, Phycomces, Pythium, Rhodosporidium, Rhodotorula, Trichosporon* or *Yarrowia* cell.

According to the methods described herein, the yeast strains can be modified, e.g. to improve growth, selection, and/or stability. Thus, for example, the *Saccharomyces cerevisiae, Saccharomyces pastorianus* (also known as *Saccharomyces carlsbergensis*), *Saccharomyces bayanus, Kluyveromyces lactis, Kluyveromyces marxianus, Schizosaccharomyces pombe, Candida albicans, Pichia pastoris, Pichia stipitis, Yarrowia hpolytica, Hansenula polymorpha, Phaffia rhodozyma, Candida utilis, Arxula adeninivorans, Debaryomyces hansenii, Debaryomyces polymorphus or Schwanniomyces occidentalis* can include deletions, insertions, and/or rearrangements and still be considered *Saccharomyces cerevisiae, Saccharomyces pastorianus* (also known as *Saccharomyces carlsbergensis*), *Saccharomyces bayanus, Kluyveromyces lactis, Kluyveromyces marxianus, Schizosaccharomyces pombe, Candida albicans, Pichia pastoris, Pichia stipitis, Yarrowia hpolytica, Hansenula polymorpha, Phaffia rhodozyma, Candida utilis, Arxula adeninivorans, Debaryomyces hansenii, Debaryomyces polymorphus or Schwanniomyces occidentalis*. Derivatives of the aforementioned yeast cells, i.e., yeast that have been adapted sufficiently to diverge the genome to the extent that it is a different species can also be used according to the present methods. Thus, the host cells described herein include derivatives of *Saccharomyces cerevisiae, Saccharomyces pastorianus* (also known as *Saccharomyces carlsbergensis*), *Saccharomyces bayanus, Kluyveromyces lactis, Kluyveromyces marxianus, Schizosaccharomyces pombe, Candida albicans, Pichia pastoris, Pichia stipitis, Yarrowia hpolytica, Hansenula polymorpha, Phaffia rhodozyma, Candida utilis, Arxula adeninivorans, Debaryomyces hansenii, Debaryomyces polymorphus* and *Schwanniomyces occidentalis*.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In one aspect of this embodiment, the construct further comprises regulatory sequences, including, for example, a promoter, operably associated to the sequence. Large numbers of suitable vectors and promoters are known to those of skill in the art, and are commercially available. The following vectors are provided by way of example.

Yeast: Yeast vectors include those of five general classes, based on their mode of replication in yeast, YIp (yeast integrating plasmids), YRp (yeast replicating plasmids), YCp (yeast replicating plasmids with centromere (CEN) elements incorporated), YEp (yeast episomal plasmids), and YLp (yeast linear plasmids). With the exception of the YLp plasmids, all of these plasmids can be maintained in *E. coli* as well as in *Saccharomyces cerevisiae* and thus are also referred to as yeast shuttle vectors. In certain aspects, these plasmids contain two types of selectable genes: plasmid-encoded drug-resistance genes and cloned yeast genes, where the drug resistant gene is typically used for selection in bacterial cells and the cloned yeast gene is used for selection in yeast. Drug-resistance genes include ampicillin, kanamycin, tetracycline, neomycin and sulfometuron methyl. Cloned yeast genes include HIS3, LEU2, LYS2, TRP1, URA3, TRP1 and SMR1. pYAC vectors can also be utilized to clone large fragments of exogenous DNA on to artificial linear chromosomes.

In certain aspects of the invention, YCp plasmids, which have high frequencies of transformation and increased stability due to the incorporated centromere elements, are utilized. In certain other aspects of the invention, YEp plasmids, which provide for high levels of gene expression in yeast, are utilized. In additional aspects of the invention, YRp plasmids are utilized.

In certain embodiments, the vector comprises (1) a first polynucleotide, where the first polynucleotide encodes for a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus,* or *Phytophthora infestans* BGL, or domain, fragment, variant, or derivative thereof; and (2) a second polynucleotide, where the second polynucleotide encodes for a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus,* or *Phytophthora infestans* BGL, or domain, fragment, variant, or derivative thereof.

In further embodiments, the first and second polynucleotides are in the same orientation, or the second polynucleotide is in the reverse orientation of the first polynucleotide. In additional embodiments, the first polynucleotide is either N-terminal or C-terminal to the second polynucleotide. In certain other embodiments, the first polynucleotide and/or the second polynucleotide are encoded by codon-optimized polynucleotides, for example, polynucleotides codon-optimized for *S. cerevisiae*.

In particular embodiments, the vector of the present invention is a plasmid selected from pMU3557, pMU3558, pMU3559, pMU3560, pMU3561, pMU3562, pMU3563, pMU3564, pMU3565, or pMU3566 (SEQ ID NOs:31-40). Descriptions of these plasmids are found in Example 1 and FIGS. 1-10. However, any other plasmid or vector can be used as long as they are replicable and viable in the host.

Promoter regions can be selected from any desired gene. Particular named yeast promoters include the ENO1 promoter, the PGK1 promoter, the TEF1 promoter, and the HXT7 promoter. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

Introduction of the construct into a host yeast cell, e.g., *Saccharomyces cerevisiae*, can be effected by lithium acetate transformation, spheroplast transformation, or transformation by electroporation, as described, for example, in Current Protocols in Molecular Biology, 13.7.1-13.7.10.

Introduction of the construct in other host cells can be effected by calcium phosphate transfection, DEAE-Dextran mediated transfection, or electroporation. See e.g., Davis et al., Basic Methods in Molecular Biology, 1986.

The constructs in host cells can be used in a conventional manner to produce the gene product encoded by the recombinant sequence. Alternatively, the polypeptides of the invention can be synthetically produced by conventional peptide synthesizers.

Following creation of a suitable host cell and growth of the host cell to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Yeast cells, e.g., *Saccharomyces cerevisiae*, employed in expression of proteins can be manipulated as follows. The BGL polypeptides can be secreted by cells and therefore can be easily recovered from supernatant using methods known to those of skill in the art. Proteins can also be recovered and purified from recombinant cell cultures by methods including spheroplast preparation and lysis, cell disruption using glass beads, and cell disruption using liquid nitrogen, for example.

Various mammalian cell culture systems can also be employed to express recombinant protein. Expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences.

Additional methods include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The BGL polypeptides can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

BGL polypeptides are provided in an isolated form, and, in certain aspects, are substantially purified. A recombinantly produced version of a BGL polypeptide can be substantially purified using techniques described herein or otherwise known in the art, such as, for example, by the one-step method described in Smith et al., *Gene*, 67:31-40, 1988. BGL polypeptides also can be purified from natural, synthetic or recombinant sources using techniques described herein or otherwise known in the art.

The BGL polypeptides of the present invention can be in the mature form, or can be a part of a larger protein, such as a fusion protein. It can be advantageous to include an additional amino acid sequence which contains secretory or leader sequences, pro-sequences, sequences which aid in purification, such as multiple histidine residues, or an additional sequence for stability during recombinant production.

Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion can be accomplished by the incorporation of a DNA sequence that codes for a secretion signal which is functional in the host production host. Methods for choosing appropriate signal sequences are well known in the art (see, e.g., European Pub. No. 546049; Int'l. Pub. No. WO 93/24631). The secretion signal DNA or facilitator can be located between the expression-controlling DNA and the instant gene or gene fragment, and in the same reading frame with the latter.

Heterologous Expression of BGL Polypeptides in Host Cells

In order to address the limitations of the previous systems, the present invention provides *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces*

*marxianus*, or *Phytophthora infestans* BGL polypeptides, and domains, variants, and derivatives thereof that can be effectively and efficiently utilized in a consolidated bioprocessing system.

In particular, the invention relates to the production of a heterologous beta-glucosidase (BGL) in a host organism. In certain embodiments, this host organism is yeast, such as *Saccharomyces cerevisiae*.

In certain embodiments of the present invention, a host cell comprising a vector which encodes and expresses a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL that is utilized for consolidated bioprocessing is co-cultured with additional host cells expressing one or more additional heterologous cellulases. Additional heterologous cellulases can be derived from for example, a fungal or bacterial source.

In some embodiments, the cellulase is a xylanase, xylosidase, acetylxylanesterase (AXE), endoglucanase, alpha-galactosidase, glucosidase, mannanase, alpha-glucuronidase, acetyl esterase, beta-mannosidase, glucuronyl esterase, cellobiohydrolase (CBH), or combinations thereof. In other embodiments, the endogluconase is *Aspergillus fumigatus* (*A. fumigatus*) endoglucanase I, *Neosartorya fischeri* (*N. fischeri*) endoglucanase III, *Trichoderma reesei* (*T. reesei*) endogluconase I, *Coptotermes formosanus* (*C. formosanus*) endoglucanase I, or combinations thereof. In some embodiments, the CBH is CBH1 or CBH2, or combinations thereof. In some embodiments, the CBH is *Talaromyces emersonii* (*T. emersonii*) cellobiohydrolase I, *Chrysosporium lucknowense* (*C. lucknowense*) cellobiohydrolase IIb, *T. reesei* cellobiohydrolase II, or combinations thereof. In other embodiments of the invention, the CBH is a CBH1 or CBH2 isoform, paralogue or orthologue.

In certain embodiments of the invention, the endoglucanase can be an endoglucanase I or an endoglucanase II isoform, paralogue or orthologue. In another embodiment, the endoglucanase expressed by the host cells of the present invention can be recombinant endo-1,4-β-glucanase. In certain embodiments of the present invention, the endoglucanase is an endoglucanase I from *T. reesei, A. fumigatus* EG1, *N. fischeri* EG3, *C. formosanus* endoglucanase I, or combinations thereof.

In some embodiments, a host cell of the invention can further comprise a polynucleotide encoding *Saccharomycopsis fibuligera* (*S. fibuligera*) BGL.

In some embodiments, a host cell of the invention can further comprise one or more polynucleotides encoding *T. emersonii* CBH1, *T. reesei* CBD, *C. lucknowense* CBH2, *A. fumigatus* EG1, *N. fischeri* EG3, *S. fibuligera* BGL, or *Aspergillus niger* xylanase. In other embodiments, a host cell of the invention can further comprise one or more polynucleotides encoding *A. niger* xylanase, P.t.r. xylosidase, *N. fischeri* AXE, *A. fumigatus* EG1, *T. reesei* AGL1, *T. reesei* beta-mannanase, *A. fumigatus* alpha-glucuronidase (FC110), *A. fumigatus* acetyl esterase (FC136), *N. fischeri* beta-mannosidase (FC124), or *S. fibuligera* BGL.

DNA and polypeptide sequences encoding these cellulases, and other exemplary cellulases, are available in GenBank and described, for example, in Int'l Pub. No. WO 2011/051806, Intl Pub. No. WO 2011/153516, Int'l Pub. No. WO 2010/005553, Int'l Pub. No. WO 2009/139839, Int'l Pub. No. WO 2009/138877, Int'l Pub. No. WO 2010/060056, Intl Appl. No. PCT/US2012/057952, filed Sep. 28, 2012 and U.S. Appl. No. 61/694,690, filed Aug. 28, 2012, which are incorporated by reference herein in their entireties.

The transformed host cells or cell cultures described herein are measured for recombinant protein content. For the use of secreted cellulases, protein content can be determined by analyzing the host (e.g., yeast) cell supernatants. Proteins, including tethered heterologous biomass degrading enzymes, can also be recovered and purified from recombinant cell cultures by methods including spheroplast preparation and lysis, cell disruption using glass beads, and cell disruption using liquid nitrogen for example. Additional protein purification methods include trichloroacetic acid, ammonium sulfate or ethanol precipitation, acid extraction, anion or cation exchange chromatography, phosphocellulose chromatography, hydrophobic interaction chromatography, affinity chromatography, hydroxylapatite chromatography, gel filtration, and lectin chromatography. Protein refolding steps can be used, as necessary, in completing configuration of the mature protein. Finally, high performance liquid chromatography (HPLC) can be employed for final purification steps.

Protein analysis methods include methods such as the traditional Lowry method, the bicinchoninic acid protein assay reagent (Pierce) or the protein assay method according to BioRad's manufacturer's protocol. Using such methods, the protein content of saccharolytic enzymes can be estimated. Additionally, to accurately measure protein concentration a BGL can be expressed with a tag, for example a His-tag or HA-tag and purified by standard methods using, for example, antibodies against the tag, a standard nickel resin purification technique or similar approach.

The transformed host cells or cell cultures described herein can be further analyzed for hydrolysis of cellulase (e.g., by a sugar detection assay), for a particular type of cellulase activity (e.g., by measuring the individual enzyme activity) or for total cellulase activity. Endoglucanase activity can be determined, for example, by measuring an increase of reducing ends in an endogluconase specific carboxymethylcellulose (CMC) substrate. Cellobiohydrolase activity can be measured, for example, by using insoluble cellulosic substrates such as the amorphous substrate phosphoric acid swollen cellulose (PASC) or microcrystalline cellulose (Avicel) and determining the extent of the substrate's hydrolysis. BGL activity, such as the "specific activity" described herein, can be measured by a variety of assays, for example, using cellobiose. Unit measurements of BGL activity and hydrolysis include, for example, umol glucose/mol or mg BGL/time (for example, seconds). Alternatively, one unit of BGL activity can be defined as the amount of enzyme required to liberate 1 umol of para-nitrophenol (pNP) from a pNP beta-glucoside or cellobiose per minute under assay conditions.

A total cellulase activity, which can include, for example, the activity of endoglucanase, CBHI, CBHII and BGL, can hydrolyze crystalline cellulose synergistically. Total cellulase activity can thus be measured using insoluble substrates including pure cellulosic substrates such as Whatman No. 1 filter paper, cotton linter, microcrystalline cellulose, bacterial cellulose, algal cellulose, and cellulose-containing substrates such as dyed cellulose, alpha-cellulose or pretreated lignocellulose.

It will be appreciated that suitable lignocellulosic material can be any feedstock that contains soluble and/or insoluble cellulose, where the insoluble cellulose can be in a crystalline or non-crystalline form. In various embodiments, the lignocellulosic biomass comprises, for example, wood, corn, corn cobs, corn stover, corn fiber, sawdust, bark, leaves, agricultural and forestry residues, grasses such as switchgrass, cord grass, rye grass or reed canary grass, miscanthus, ruminant digestion products, municipal wastes, paper mill effluent, newspaper, cardboard, miscanthus, sugar-processing residues, sugarcane bagasse, agricultural wastes, rice straw, rice hulls, barley straw, cereal straw, wheat straw, canola straw, oat straw, oat hulls, stover, soybean stover, forestry wastes, recycled wood pulp fiber, paper sludge, sawdust, hardwood, softwood or combinations thereof.

In certain embodiments of the present invention, a host cell comprising a vector which encodes and expresses a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL that is utilized for consolidated bioprocessing is co-cultured with additional host cells expressing one or more additional heterologous cellulases. In other embodiments of the invention, a host cell transformed with a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL is transformed with and/or expresses one or more other heterologous xylanase, xylosidase, AXE, endoglucanase, alpha-galactosidase, glucosidase, mannanase, alpha-glucuronidase, acetyl esterase, beta-mannosidase, glucuronyl esterase, or CBH, as described further herein.

Specific activity of cellulases can also be detected by methods known to one of ordinary skill in the art. To accurately measure protein concentration a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL can be expressed with a tag, for example a His-tag or hemagglutinin (HA)-tag and purified by standard methods using, for example, antibodies against the tag, a standard nickel resin purification technique or similar approach.

In other embodiments, the host cell produces the BGL in a culture. In some embodiments, BGL is produced in an amount of at least about 0.6 mg, at least about 0.7 mg, at least about 0.8 mg, at least about 0.9 mg, at least about 1 mg, at least about 1.5 mg, at least about 2 mg, at least about 2.5 mg, at least about 3 mg, at least about 3.5 mg, at least about 4 mg, at least about 4.5 mg, at least about 5 mg, at least about 6 mg, at least about 7 mg, at least about 8 mg, at least about 9 mg or at least about 10 mg, of any ranges thereof. In other embodiments, BGL is produced in an amount of from about 0.6 mg to about 10 mg, from about 1 mg to about 10 mg, or from about 1 mg to about 5 mg.

In other embodiments, the host cell produces the BGL in a concentration of at least about 0.2 mg/ml in culture. In some embodiments, the concentration is at least about 0.2 mg/ml, at least about 0.5 mg/ml, at least about 1 mg/ml, at least about 1.5 mg/ml, at least about 2 mg/ml, at least about 2.5 mg/ml, at least about 3 mg/ml, at least about 3.5 mg/ml, at least about 4 mg/ml, at least about 4.5 mg/ml, at least about 5 mg/ml, at least about 5.5 mg/ml, or at least about 6 mg/ml, or any range of values thereof. In some embodiments, the concentration is from about 0.2 mg/ml to about 6 mg/ml, from about 0.2 mg/ml to about 5 mg/ml, from about 0.2 mg/ml to about 0.2 mg/ml to about 3 mg/ml.

In other embodiments, the present invention also provides a method for hydrolyzing a cellulosic substrate. In embodiments, the method comprises contacting the cellulosic substrate with a host cell, co-culture, composition, peptide or purified peptide of the invention. In some embodiments, the cellulosic substrate comprises a lignocellulosic biomass. In other embodiments, the lignocellulosic biomass is grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, or combinations thereof. In other embodiments, the cellulosic substrate can be hydrolyzed to xylose, glucose, mannose, galactose, arabinose, or combinations thereof. In some embodiments, the cellulose substrate is hydrolyzed to cellulosic substrate is hydrolyzed to xylose, glucose, mannose, galactose or arabinose at a rate at least about 10% greater than the rate of a host cell comprising a polynucleotide encoding a BGL from *S. fibuligera*. In other embodiments, the rate is at least about 10% greater, at least about 20% greater, at least about 30% greater, at least about 40% greater, at least about 50% greater, at least about 60% greater, at least about 70% greater, at least about 80% greater, at least about 90% greater, or at least about 100% greater, or any range of values thereof. In other embodiments, the rate is from about 10% greater to about 100% greater, from about 10% greater to about 70% greater, from about 10% greater to about 60% greater, from about 10% greater to about 50% greater, from about 20% greater to about 70% greater, from about 30% greater to about 70% greater, or from about 30% greater to about 60% greater.

In some embodiments of the methods of the invention, the BGL is present in an amount of about 0.2 mg or less per gram of xylose.

The present invention also provides a method of fermenting cellulose, comprising culturing a host cell, co-culture, composition, peptide or purified peptide of the invention in medium. In some embodiments, the medium contains crystalline cellulose. In some embodiments, the culturing is under suitable conditions for a period sufficient to allow saccharification and fermentation of the cellulose. In other embodiments, the host cell produces ethanol.

In additional embodiments, the transformed host cells or cell cultures are assayed for ethanol production. Ethanol production can be measured by techniques known to one or ordinary skill in the art. For example, the quantity of ethanol in fermentation samples can be assessed using HPLC analysis. Many ethanol assay kits are commercially available that use, for example, alcohol oxidase enzyme based assays. Methods of determining ethanol production are within the scope of those skilled in the art from the teachings herein.

Co-Cultures

The present invention is also directed to co-cultures comprising at least two yeast host cells wherein the at least one yeast host cell comprises a polynucleotide encoding a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polypeptide and at least one other yeast host cell comprises a polynucleotide encoding a heterologous cellulase. As used herein, "co-culture" refers to growing two different strains or species of host cells together in the same vessel. In some embodiments of the invention, at least one host cell of the co-culture comprises a heterologous polynucleotide comprising a nucleic acid which encodes an endoglucanase, at least one host cell of the co-culture comprises a heterologous polynucleotide comprising a nucleic acid which encodes a β-glucosidase and at least one host cell comprises a heterologous polynucleotide comprising a nucleic acid which encodes a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL polypeptide. In a further embodiment, the co-culture further comprises a host cell comprising a heterologous polynucleotide comprising a nucleic acid which encodes a second BGL.

The co-culture can comprise two or more strains of yeast host cells and the heterologous cellulases can be expressed in any combination in the two or more strains of host cells. For example, according to the present invention, the co-culture can comprise two strains: one strain of host cells that expresses one or more cellulases described herein and a second strain of host cells that expresses a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL. Alternatively, the co-culture can comprise three, four, five, six, seven, eight, or more strains of host cells that each express one or more cellulases described herein and/or a *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL.

The various host cell strains in the co-culture can be present in equal numbers, or one strain or species of host cell can significantly outnumber another second strain or species of host cells. For example, in a co-culture comprising two strains or species of host cells the ratio of one host cell to another can be about 1:1, 1:2, 1:3, 1:4, 1:5, 1:10, 1:100, 1:500 or 1:1000. Similarly, in a co-culture comprising three or more strains or species of host cells, the strains or species of host cells can be present in equal or unequal numbers.

The co-cultures of the present invention can include tethered cellulases, secreted cellulases or both tethered and secreted cellulases. In addition, other cellulases, such as externally added cellulases can be present in the co-culture.

According to the methods described herein, a host cell or group of host cells can comprise a vector or vectors which encode and express a combination of heterologous cellulases including one or more cellulases selected from *Humicola grisea, Candida wickerhamii, Aspergillus aculeatus, Aspergillus oryzae, Penicillium decumbens, Chaetomium globosum, Neocallimastix frontalis, Debaryomyces hansenii, Kluyveromyces marxianus*, or *Phytophthora infestans* BGL. For example, a single host cell may express endoglucanase, BGL, CBH1 and CBH2. Alternatively, a group of cells could express a combination of cellulases, for example such that a first host cell expresses endoglucanase, a second host cell expresses BGL, a third host cell expresses CBH1, and a fourth host cell expresses a CBH2. Similarly, a first host cell can express both endoglucanase and BGL and a second host cell can express both CBH1 and CBH2.

EXAMPLES

Materials and Methods

Media and Strain Cultivation

Unless otherwise specified, yeast strains were routinely grown in YPD (10 g/L yeast extract, 20 g/L peptone, 20 g/L glucose), YPC (10 g/L yeast extract, 20 g/L peptone, 20 g/L cellobiose), or YNB+glucose (6.7 g/L Yeast Nitrogen Base without amino acids, and supplemented with appropriate amino acids for strain, 20 g/L glucose) media and, if needed, antibiotics for selection. 15 g/L agar was added for solid media.

Molecular Methods

Unless otherwise specified, standard protocols were followed for DNA manipulations (Sambrook et al. 1989). Polymerase chain reaction (PCR) was performed using Phusion polymerase (New England Biolabs) for cloning, and Taq polymerase (New England Biolabs) for screening transformants, and in some cases Advantage Polymerase (Clontech) for PCR of genes for correcting auxotrophies. Manufacturers guidelines were followed as supplied. Restriction enzymes were purchased from New England Biolabs and digests were set up according to the supplied guidelines. Ligations were performed using the Quick ligation kit (New England Biolabs) as specified by the manufacturer. Gel purification was performed using either Qiagen or Zymo research kits, PCR product and digest purifications were performed using Zymo research kits, and Qiagen midi and miniprep kits were used for purification of plasmid DNA.

Yeast Transformation

A protocol for electrotransformation of yeast was developed based on Cho et al. (*Enzyme And Microbial Technology*, 25:23-30, 1999) and Ausubel et al. (Current Protocols in Molecular Biology. USA: John Wiley and Sons, Inc., 1994). Linear fragments of DNA are created by restriction enzyme digestion utilizing unique restriction sites within the plasmid. The fragments are purified by precipitation with 3M sodium acetate and ice cold ethanol, subsequent washing with 70% ethanol, and resuspension in USB dH2O (DNAse and RNAse free, sterile water) after drying in a 70° C. vacuum oven.

Unless otherwise specified, yeast cells, e.g., *Saccharomyces cerevisiae*, for transformation were prepared by growing to saturation in 5 mL YPD cultures. 4 mL of the culture was sampled, washed 2× with cold distilled water, and resuspended in 640 µL cold distilled water. 80 µL of 100 mM Tris-HCl, 10 mM EDTA, pH 7.5 (10× TE buffer—filter sterilized) and 80 µL of 1M lithium acetate, pH 7.5 (10× liAc—filter sterilized) was added and the cell suspension incubated at 30° C. for 45 minutes with gentle shaking. 20 µL of 1M DTT was added and incubation continued for 15 minutes. The cells were then centrifuged, washed once with cold distilled water, and once with electroporation buffer (1M sorbitol, 20 mM HEPES), and finally resuspended in 267 µL electroporation buffer.

For electroporation, 10 µg of linearized DNA (measured by estimation on gel) was combined with 50 µL of the cell suspension in a sterile 1.5 mL microcentrifuge tube. The mixture was then transferred to a 0.2 cm electroporation cuvette, and a pulse of 1.4 kV (200Ω, 25 µF) applied to the sample using, e.g., the BioRad Gene Pulser device. 1 mL of YPD with 1M sorbitol adjusted to pH 7.0 (YPDS) was placed in the cuvette and the cells allowed to recover for ~3 hrs. 100-200 µL of cell suspension was spread out on YPDS agar plates with appropriate selection, which were incubated at 30° C. for 3-4 days until colonies appeared.

SDS-PAGE and Gel Staining

Unless otherwise specified, SDS-PAGE (sodium dodecyl sulfate polyacrylamide gel electrophoresis) was carried out as described by Laemmli (*Nature*, 227:680-685, 1970) on a 10% gel at 100 V. A 20 µl sample of culture supernatant was mixed with SDS-PAGE loading buffer and incubated at 95° C. for 5 minutes before loading onto the gel. After protein separation, the gels were silver stained. Silver staining was performed by incubating the gels with shaking at room temperature in 1) 30% ethanol and 0.5% acetic acid (3×30 min); 2) 20% ethanol (10 min); 3) water (10 min); 4) sodium thiosulfate (0.2 g/L) (1 min); 5) water (2×20 seconds); 6) silver nitrate (2 g/L) (30 min); 7) water (5-10 seconds); 8) 37% formaldehyde (0.7 ml/L) and potassium carbonate (anhydr.) (30 g/L) and sodium thiosulfate (10 mg/L) (2×3 min or to desired intensity); 9) Tris base (50 g/L) and 2.5% acetic acid (1 min); and 10) water.

Determination of Protein Concentration

To estimate specific activity of the BGLs the Bradford method (BioRad protein assay) was used as it is prescribed for use in microtiter plates, using the Gamma globulin standard. Before determination of protein concentration, supernatant samples were first subjected to the buffer exchange procedure as directed for the 2 mL Zeba desalt spin columns (Thermo Scientific).

Western Blot Protocol for Supernatants of Strains:

1. Test top performing strains for activity, along with randomly selected alpha-glucuronidase strains (no activity assay available) and run on a 4-20% Tris glycine SDS-PAGE gel (Invitrogen, EC6025BOX), transfer to PVDF membrane (Amersham Hybond P, GE Healthcare, RPN303F) and block overnight in TBS (10 mM Tris, 150 mM NaCl, pH 7.5)+2% BSA (bovine serum albumin)
2. Dilute primary Qiagen muα Penta-His 1:5000 in TBST (TBS with 0.1% Tween 20). Pour off blocker and add primary antibody. Incubate at room temperature for 1 h.
3. Pour off primary antibody and wash 3×5min in THST (10 mM Tris, 500 mM NaCl, pH 7.5 with 0.1% Tween 20).
4. Dilute Thermo gtαmu-HRP (cat. No. 31439) 1:7500 in TBST and add to blots. Incubate at room temperature for 1 h, pour off and wash again with THST
5. Add ECL (Thermo, 32166) substrate and visualize using a Syngene G:BOX with a CCD camera.

BGL Activity Assay on Cellobiose

Standard curve and samples in duplicate:
100 μg/mL Bgl-His diluted in 50 mM Na citrate, pH 5.5; then 1:2
Samples diluted 1:10 in 50 mM Na citrate, pH 5.5
To a PCR plate, add
50 μL sample or standard
50 μL 50 mM Na citrate, pH 5.5
50 μL 50 mM Na citrate, 20 mM cellobiose, pH 5.5
For the blank, use 50 μL sample+100 μL 50 mM Na citrate, pH 5.5 (no cellobiose)
Incubate×45-60 min at 35° C.
Heat 100° C.×5 min in the thermocycler
To flat bottom clear plate, add
10 μL sample
100 μL HK reagent
  Add 0.15 M Tris base to the vial to improve buffer capacity
  Sigma kit—GAHK20 glucose HK kit
  Unused reagent can be stored at −20° C.
Incubate×2 hours to overnight at RT
Read at 340 nm
Subtract the results from the blank (residual glucose from the media) from the sample results Purification of His Tagged BGL
  Grow cells in YPD
  Centrifuge cells, filter thru 0.2 um membrane then concentrate in a 10 kDa MWCO filter
  pH adjust the sample to ~7 with 1M Tris, pH 9
  Purify on the FPLC with the following conditions:
  Column: GE HisTrap 5 mL column
  Mobile phase A: 25 mM Tris, pH 6.8
  Mobile phase B: 25 mM Tris, 150 mM imidazole, pH 6.8
  Flow rate: 5 mL/min
  Step elution to 100% B
  Collect 1 mL fractions
  Buffer exchange into 50 mM NaAc, pH 5
  Determine concentration by absorbance at 280 nm using the theoretical molar extinction coefficient of the protein based on its amino acid sequence (Edelhoch, (1967), Biochemistry, 6, 1948-1954).

Example 1

Screening of Yeast Produced Beta-Glucosidases for Efficient Cellobiose and Oligomer Hydrolysis In order to find beta-glucosidase (BGL) enzymes that are well expressed in *Saccharomyces cerevisiae*, and highly active on hardwood derived substrates, several BGLs were designed and synthesized by DNA 2.0. The enzymes and sequences tested are below in Table 4.

TABLE 4

| Beta-glucosidase enzymes tested for expression in yeast | | | | | | | |
|---|---|---|---|---|---|---|---|
| (FC)# | Cazy family | E.C. # | Activity | Source Organism | Accession # | Strain # | Plasmid # |
| 141 | GH3 | 3.2.1.21 | Beta-glucosidase | *Saccharomycopsis fibuligera* | P22506 | M1429 | pMU1172* |
| 146 | GH1 | 3.2.1.21 | Beta-glucosidase | *Humicola grisea* | BAA74958 | M4860 | pMU3557 |
| 147 | GH1 | 3.2.1.21 | Beta-glucosidase | *Candida Wickerhamii* | AAC49036 | | pMU3558 |
| 148 | GH3 | 3.2.1.21 | Beta-glucosidase | *Aspergillus Aculeatus* | P48825 | M4861 | pMU3559 |
| 149 | GH3 | 3.2.1.21 | Beta-glucosidase | *Aspergillus oryzae* | XP_001816831 | M4862 | pMU3560 |
| 150 | GH3 | 3.2.1.21 | Beta-glucosidase | *Penicillium decumbens* | ADB82653 | M4863 | pMU3561 |
| 151 | GH3 | 3.2.1.21 | Beta-glucosidase | *Chaetomium globosum* | XP_001229937 | M4864 | pMU3562 |
| 152 | GH3 | 3.2.1.21 | Beta-glucosidase | *Neocallimastix frontalis* | AEX92706 | M4865 | pMU3563 |
| 153 | GH3 | 3.2.1.21 | Beta-glucosidase | *Debaryomyces hansenii* | XP_457283 | | pMU3564 |

TABLE 4-continued

Beta-glucosidase enzymes tested for expression in yeast

| Cazy (FC)# family | E.C. # | Activity | Source Organism | Accession # | Strain # | Plasmid # |
|---|---|---|---|---|---|---|
| 154 GH3 | 3.2.1.21 | Beta-glucosidase | Kluyveromyces marxianus | P07337 | | pMU3565 |
| 155 GH30 | 3.2.1.21 | Beta-glucosidase/ Beta-xylosidase | Phytophthora infestans | AAK19754 | | pMU3566 |

*As described, for example, in Int'l Pub. No. WO 2011/153516, which is incorporated by reference herein.

A six-repeat histidine (6× HIS) tag was added to the C-terminus of these synthetic genes and they were cloned into an expression vector for testing in yeast.

The full amino acid sequence, with signal peptide, for Humicola grisea beta-glucosidase (Accession No. BAA74958) is in SEQ ID NO:1.

The native signal peptide for Humicola grisea beta-glucosidase (Accession No. BAA74958) is in SEQ ID NO:2.

The corresponding Humicola grisea beta-glucosidase DNA sequence is in SEQ ID NO:3.

The full amino acid sequence, with signal peptide, for Candida wickerhamii beta-glucosidase (Accession No. AAC49036) is in SEQ ID NO:4.

The native signal peptide for Candida wickerhamii beta-glucosidase (Accession No. AAC49036) is in SEQ ID NO:5.

The corresponding Candida wickerhamii beta-glucosidase DNA sequence is in SEQ ID NO:6.

The full amino acid sequence, with signal peptide, for Aspergillus aculeatus beta-glucosidase (Accession No. P48825) is in SEQ ID NO:7.

The native signal peptide for Aspergillus aculeatus beta-glucosidase (Accession No. P48825) is in SEQ ID NO:8.

The corresponding Aspergillus aculeatus beta-glucosidase DNA sequence is in SEQ ID NO:9.

The full amino acid sequence, with signal peptide, for Aspergillus oryzae beta-glucosidase (Accession No. XP_001816831) is in SEQ ID NO:10.

The native signal peptide for Aspergillus oryzae beta-glucosidase (Accession No. XP_001816831) is in SEQ ID NO:11.

The corresponding Aspergillus oryzae beta-glucosidase DNA sequence is in SEQ ID NO:12.

The full amino acid sequence, with signal peptide, for Penicillium decumbens beta-glucosidase (Accession No. ADB82653) is in SEQ ID NO:13.

The native signal peptide for Penicillium decumbens beta-glucosidase (Accession No. ADB82653) is in SEQ ID NO:14.

The corresponding Penicillium decumbens beta-glucosidase DNA sequence is in SEQ ID NO:15.

The full amino acid sequence, with signal peptide, for Chaetomium globosum beta-glucosidase (Accession No. XP_001229937) is in SEQ ID NO:16.

The native signal peptide for Chaetomium globosum beta-glucosidase (Accession No. XP_001229937) is in SEQ ID NO:17.

The corresponding Chaetomium globosum beta-glucosidase DNA sequence is SEQ ID NO:18.

The full amino acid sequence, with signal peptide, for Neocallimastix frontalis beta-glucosidase (Accession No. AEX92706) is in SEQ ID NO:19.

The native signal peptide for Neocallimastix frontalis beta-glucosidase (Accession No. AEX92706) is in SEQ ID NO:20.

The corresponding Neocallimastix frontalis beta-glucosidase DNA sequence is in SEQ ID NO:21.

The full amino acid sequence, with signal peptide, for Debaryomyces hansenii beta-glucosidase (Accession No. XP_457283) is in SEQ ID NO:22.

The added signal peptide for Debaryomyces hansenii beta-glucosidase is in SEQ ID NO:23.

The corresponding Debaryomyces hansenii beta-glucosidase DNA sequence is in SEQ ID NO:24.

The full amino acid sequence, with signal peptide, for Kluyveromyces marxianus beta-glucosidase (Accession No. P07337) is in SEQ ID NO:25.

The added signal peptide for Kluyveromyces marxianus beta-glucosidase is in SEQ ID NO:26.

The corresponding Kluyveromyces marxianus beta-glucosidase DNA sequence is in SEQ ID NO:27.

The full amino acid sequence, with signal peptide, for Phytophthora infestans beta-glucosidase (Accession No. AAK19754) is in SEQ ID NO:28.

The native signal peptide for Phytophthora infestans beta-glucosidase (Accession No. AAK19754) is in SEQ ID NO:29.

The corresponding Phytophthora infestans beta-glucosidase DNA sequence is in SEQ ID NO:30.

The sequence of pMU3557 is in SEQ ID NO:31 (see also FIG. 1).

The sequence of pMU3558 is in SEQ ID NO:32 (see also FIG. 2).

The sequence of pMU3559 is in SEQ ID NO:33 (see also FIG. 3).

The sequence of pMU3560 is in SEQ ID NO:34 (see also FIG. 4).

The sequence of pMU3561 is in SEQ ID NO:35 (see also FIG. 5).

The sequence of pMU3562 is in SEQ ID NO:36 (see also FIG. 6).

The sequence of pMU3563 is in SEQ ID NO:37 (see also FIG. 7).

The sequence of pMU3564 is in SEQ ID NO:38 (see also FIG. 8).

The sequence of pMU3565 is in SEQ ID NO:39 (see also FIG. 9).

The sequence of pMU3566 is in SEQ ID NO:40 (see also FIG. 10).

The plasmids described in Table 4 above were transformed into the yeast strain M1744 (described in, for example, Int'l Pub. No. WO 2011/153516), and selected on synthetic complete media without uracil (SD-ura) in order to isolate transformants. These transformants were then screened for activity using a beta-glucosidase activity assay with cellobiose as the substrate to assess if functional protein was being produced (FIG. 11). FIG. 11 shows the results of screening 12 colonies for each plasmid transformed. In each case, the colony showing the best activity is shown. These results show BGL enzyme activity was present in transformants. BGL from *Aspergillus aculeatus, Aspergillus oryzae*, and *Humicola grisea* showed the highest functional activity.

SDS-PAGE was also used to assess if BGL protein was being produced in the transformants (FIGS. 12A-12C, left panel). These results show recombinant BGL protein was present in the transformants. BGL from *Aspergillus aculeatus* and *Aspergillus oryzae* showed the highest levels of production. In addition, western blots were conducted to further assess the presence of recombinant BGL protein. FIGS. 12A-12C (right panel) shows the results of these blots. These results show recombinant BGL protein was present in the transformants. BGL protein produced by strains harboring the pMU3557, pMU3559 and pMU3560 plasmids showed the highest levels of production.

BGLs that showed activity and/or protein production were subsequently purified and used in hydrolysis assays with both pretreated hardwood solids and concentrated C5 liquor. Several strains were grown in shake flask culture in order to purify the beta-glucosidase enzyme via the associated 6× HIS tag. These strains included: M4860, M4861, M4862, M4863, M4864 and M4865. The associated BGL protein concentration recovered after purification is listed below in Table 5.

TABLE 5

Amount of protein purified from cultures of BGL producing strains of *S. cerevisiae*

| Strain | Source Organism | Concentration (mg/mL) | Volume (mL) | Total Protein (mg) |
| --- | --- | --- | --- | --- |
| M4860 | *Humicola grisea* | 0.2 | 3 | 0.6 |
| M4861 | *Aspergillus Aculeatus* | 0.6 | 2 | 1.2 |
| M4862 | *Aspergillus oryzae* | 3.2 | 1.5 | 4.8 |
| M4863 | *Penicillium decumbens* | 0.11 | 1.5 | 0.165 |
| M4864 | *Chaetomium globosum* | 0.26 | 4 | 1.04 |
| M4865 | *Neocallimastix frontalis* | 0.09 | 1 | 0.09 |

The data in Table 5 indicate BGL protein was present in the strains. BGL from *Aspergillus aculeatus, Aspergillus oryzae* and *Chaetomium globosum* showed the highest concentrations.

After the BGL enzymes were purified, their specific activities were compared by hydrolysis assays on cellobiose at pH 5 and 37° C. (FIGS. 13 and 14). The hydrolysis assays contained pretreated hardwood solids (2% solids loading) or diluted C5 liquor, along with sodium citrate buffered to pH 5.2, purified enzyme and sodium azide to prevent contamination. The resultant sugars were analyzed by BioRad Aminex 87H and 87P high performance liquid chromatography (HPLC) to determine the usefulness of each enzyme. The 87H column can measure acetic acid, but also results in xylose, galactose, and mannose co-eluting, while the 87P column can resolve xylose, galactose, and mannose, but cannot measure acetic acid release. For this reason, both columns were employed to analyze the release of sugars.

Over the range of enzyme loadings tested in FIG. 13, it is clear that the purified BGLs had specific activity against cellobiose. BGL from *Aspergillus oryzae, Aspergillus aculeatus, Penicillium decumbens*, and *Saccharomycopsis fibuligera* enzymes showed the highest specific activity. In FIG. 14, a lower enzyme loading was tested. BGL from *Aspergillus aculeatus* and *Aspergillus oryzae* showed the highest specific activity at the lower enzyme loading.

The purified BGL enzymes were also tested for their activity on both pretreated hardwood solids and C5 liquor derived from pretreated hardwoods. FIG. 15 demonstrates that the addition of small quantities of the BGLs increase hydrolysis rates. BGL from *Aspergillus oryzae* and *Aspergillus aculeatus* showed the highest hydrolysis rates relative to a control BGL from *Saccharomycopsis fibuligera*. In addition, BGL from *Aspergillus aculeatus* and *Humicola grisea* lead to the highest total yields at the end of hydrolysis. For FIG. 15, the purified BGLs were added along with *Saccharomycopsis fibuligera* BGL and were compared to a reaction where additional *Saccharomycopsis fibuligera* BGL was added. FIG. 15 indicates that the test BGL enzymes had hydrolysis rates greater than a reaction where additional *Saccharomycopsis fibuligera* BGL was added.

The BGL enzymes also improved hydrolysis of C5 oligomers from hardwoods. FIGS. 16 and 17 show the time course release of xylose and glucose, respectively, from C5 oligomers in an assay where the BGLs were added with other enzymes targeting hydrolysis of the oligomers, and where BGLs were used in place of *Saccharomycopsis* BGL. In contrast to the assays on hardwood solids, the enzyme mixtures in these assays utilized either the *Saccharomycopsis* BGL or the test BGLs at equal loadings. FIG. 16 shows that xylose release in the assay stayed constant, whereas glucose release increased by >35% for reactions where the new BGLs were included. In particular, inclusion of the *Aspergillus aculeatus* enzyme resulted in the highest yield of glucose.

FIG. 18 shows data collected from the same assay using the Biorad Aminex 87P column. This data also shows increases in glucose and mannose relative to control by the addition of the test BGL enzymes. The hydrolysis of glucose relative to acid hydrolysis increased from ~35% to ~50% (~40% increase), and the hydrolysis of mannose increased from ~42% to ~50% (a 16% increase) by adding the *Aspergillus aculeatus* BGL enzyme. Finally, several mixtures of BGLs were added to hydrolyze the C5 oligomers, and there was an increase in glucose release in all mixtures containing *Aspergillus aculeatus* and *Aspergillus oryzae* BGLs (FIG. 19).

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A recombinant yeast host cell comprising a polynucleotide encoding a functional heterologous beta-glucosidase (BGL) having
   (i) an amino acid sequence at least 95% identical to SEQ ID NO: 10; or
   (ii) an amino acid sequence at least 95% identical to a fragment of SEQ ID NO: 10 without a signal peptide, wherein said polynucleotide is codon-optimized for expression in the yeast host cell;
   wherein the codon adaptation index (CAI) of the codon-optimized polynucleotide is about 0.8 to about 1.0.

2. The host cell of claim 1, wherein the polynucleotide is at least 90%, 95% or 100% identical to SEQ ID NO. 12.

3. The host cell of claim 1, wherein the signal peptide comprises an amino acid sequence at least 90%, 95% or 100% identical to any one of SEQ ID NOs: 2,5, 11, 14, 17, 20, 23, 26 or 29.

4. The host cell of claim 1, further comprising one or more additional polynucleotides encoding a heterologous cellulase; preferably the heterologous cellulase is a xylanase, xylosidase, acetylxylanesterase (AXE), endoglucanase, alpha-galactosidase, glucosidase, mannanase, alpha-glucuronidase, acetyl esterase, beta-mannosidase, glucuronyl esterase, cellobiohydrolase (CBH), or combinations thereof; more preferably, the CBH is CBH1 or CBH2.

5. The host cell of claim 4, wherein the endoglucanase is A. fumigatus endoglucanase I, N. fischeri endoglucanase III, T. reesei endoglucanase I, or C. formosanus endoglucanase I.

6. The host cell of claim 4, wherein the CBH is T. emersonii cellobiohydrolase I, C. lucknowense cellobiohydrolase IIb or T. reesei cellobiohydrolase II.

7. The host cell of claim 4, further comprising a polynucleotide encoding S. fibuligera BGL and/or one or more polynucleotides encoding T. emersonii CBH1, T. reesei CBD, C. lucknowense CBH2, A. fumigatus EG1, N. fischeri EG3, S. fibuligera BGL or A. niger xylanase and/or one or more polynucleotides encoding A. niger xylanase, P. t. r. xylosidase, N. fischeri AXE, A. fumigatus EG1, T. reesei AGL1 , T. reesei beta-mannanase, A. fumigatus alpha-glucuronidase (FC110), A. fumigatus acetyl esterase (FC136), N. fischeri beta-mannosidase (FC124), or S. fibuligera BGL.

8. The host cell of claim 1, wherein the host cell can saccharify crystalline cellulose, preferably the host cell can ferment the crystalline cellulose, or the host cell can hydrolyze hardwood solids or C5 liquor derived from hardwoods.

9. The host cell of claim 1, wherein the host cell produces the BGL in an amount of at least 0.6 mg in culture, preferably the host cell produces the BGL in a concentration of at least 0.2 mg/ml in culture.

10. The host cell of claim 1, wherein the yeast is Saccharomyces cerevisiae, Saccharomyces pastorianus, Saccharomyces bayanus, Kluyveromyces lactis, Kluyveromyces marxianus, Schizosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe, Schwanniomyces occidentalis, or derivatives thereof; preferably the yeast is Saccharomyces cerevisiae.

11. A co-culture comprising (i) a host cell of claim 1 and (ii) a second host cell comprising one or more polynucleotides encoding a xylanase, xylosidase, AXE, endoglucanase, alpha-galactosidase, glucosidase, mannanase, alpha-glucuronidase, acetyl esterase, beta-mannosidase, glucuronyl esterase or CBH.

12. The host cell of claim 1, wherein the yeast host cell is Saccharomyces strain.

13. The host cell of claim 1, wherein the yeast host cell is Saccharomyces cerevisiae strain.

14. The host cell of claim 1, wherein said functional BGL polypeptide is able to hydrolyze a glucose oligomer having glucose units linked via a beta 1-4 type bond.

* * * * *

SEQUENCE LISTING

<160> NUMBER OF SEQ ID NOS: 41

<210> SEQ ID NO 1
<211> LENGTH: 494
<212> TYPE: PRT
<213> ORGANISM: Humicola grisea
<220> FEATURE:
<221> NAME/KEY: misc_feature
<222> LOCATION: (1)..(494)
<223> OTHER INFORMATION: beta-glucosidase

<400> SEQUENCE: 1

Met Leu Leu Gln Ala Phe Leu Phe Leu Leu Ala Gly Phe Ala Ala Lys
1               5                   10                  15

Ile Ser Ala Ser Leu Pro Pro Asp Phe Lys Trp Gly Phe Ala Thr Ala
            20                  25                  30

Ala Tyr Gln Ile Glu Gly Ser Val Asn Glu Asp Gly Arg Gly Pro Ser
        35                  40                  45

Ile Trp Asp Thr Phe Cys Ala Ile Pro Gly Lys Ile Ala Asp Gly Ser
    50                  55                  60

Ser Gly Ala Val Ala Cys Asp Ser Tyr Lys Arg Thr Lys Glu Asp Ile
65                  70                  75                  80

Ala Leu Leu Lys Glu Leu Gly Ala Asn Ser Tyr Arg Phe Ser Ile Ser
                85                  90                  95

Trp Ser Arg Ile Ile Pro Leu Gly Gly Arg Asn Asp Pro Ile Asn Gln
            100                 105                 110

Lys Gly Ile Asp His Tyr Val Lys Phe Val Asp Leu Ile Glu Ala
        115                 120                 125

Gly Ile Thr Pro Phe Ile Thr Leu Phe His Trp Asp Leu Pro Asp Ala
    130                 135                 140

Leu Asp Lys Arg Tyr Gly Gly Phe Leu Asn Lys Glu Glu Phe Ala Ala
145                 150                 155                 160

Asp Phe Glu Asn Tyr Ala Arg Ile Met Phe Lys Ala Ile Pro Lys Cys
                165                 170                 175

Lys His Trp Ile Thr Phe Asn Glu Pro Trp Cys Ser Ala Ile Leu Gly
            180                 185                 190

Tyr Asn Thr Gly Tyr Phe Ala Pro Gly His Thr Ser Asp Arg Ser Lys
        195                 200                 205

Ser Pro Val Gly Asp Ser Ala Arg Glu Pro Trp Ile Val Gly His Asn
    210                 215                 220

Ile Leu Ile Ala His Ala Arg Ala Val Lys Ala Tyr Arg Glu Asp Phe
225                 230                 235                 240

Lys Pro Thr Gln Gly Gly Glu Ile Gly Ile Thr Leu Asn Gly Asp Ala
                245                 250                 255

Thr Leu Pro Trp Asp Pro Glu Asp Pro Ala Asp Ile Glu Ala Cys Asp
            260                 265                 270

Arg Lys Ile Glu Phe Ala Ile Ser Trp Phe Ala Asp Pro Ile Tyr Phe
        275                 280                 285

Gly Lys Tyr Pro Asp Ser Met Arg Lys Gln Leu Gly Asp Arg Leu Pro
    290                 295                 300

Glu Phe Thr Pro Glu Glu Val Ala Leu Val Lys Gly Ser Asn Asp Phe
305                 310                 315                 320

Tyr Gly Met Asn His Tyr Thr Ala Asn Tyr Ile Lys His Lys Thr Gly
                325                 330                 335

Val Pro Pro Glu Asp Asp Phe Leu Gly Asn Leu Glu Thr Leu Phe Tyr
            340                 345                 350

```
Asn Lys Tyr Gly Asp Cys Ile Gly Pro Glu Thr Gln Ser Phe Trp Leu
        355                 360                 365

Arg Pro His Ala Gln Gly Phe Arg Asp Leu Leu Asn Trp Leu Ser Lys
    370                 375                 380

Arg Tyr Gly Tyr Pro Lys Ile Tyr Val Thr Glu Asn Gly Thr Ser Leu
385                 390                 395                 400

Lys Gly Glu Asn Asp Met Pro Leu Glu Gln Val Leu Glu Asp Asp Phe
                405                 410                 415

Arg Val Lys Tyr Phe Asn Asp Tyr Val Arg Ala Met Ala Ala Ala Val
            420                 425                 430

Ala Glu Asp Gly Cys Asn Val Arg Gly Tyr Leu Ala Trp Ser Leu Leu
                435                 440                 445

Asp Asn Phe Glu Trp Ala Glu Gly Tyr Glu Thr Arg Phe Gly Val Thr
    450                 455                 460

Tyr Val Asp Tyr Ala Asn Asp Gln Lys Arg Tyr Pro Lys Lys Ser Ala
465                 470                 475                 480

Lys Ser Leu Lys Pro Leu Phe Asp Ser Leu Ile Arg Lys Glu
                485                 490

<210> SEQ ID NO 2
<211> LENGTH: 19
<212> TYPE: PRT
<213> ORGANISM: Humicola grisea
<220> FEATURE:
<221> NAME/KEY: misc_feature
<222> LOCATION: (1)..(19)
<223> OTHER INFORMATION: native signal peptide - beta-glucosidase

<400> SEQUENCE: 2

Met Leu Leu Gln Ala Phe Leu Phe Leu Leu Ala Gly Phe Ala Ala Lys
1               5                   10                  15

Ile Ser Ala

<210> SEQ ID NO 3
<211> LENGTH: 1770
<212> TYPE: DNA
<213> ORGANISM: Humicola grisea
<220> FEATURE:
<221> NAME/KEY: misc_feature
<222> LOCATION: (1)..(1770)
<223> OTHER INFORMATION: beta-glucosidase

<400> SEQUENCE: 3
atgcaggtga tcaagcccct tgaactacgtg ctggcattgc tggcgatgca ggttgtgagc      60
gctgctacaa acagttgcac atcttggtct gaaagatttc agaaaaatct ggaaggcgtg     120
tgcgtttgtt cagaagctac ttgtgataca atcgataatg gttcaagtca tttgtcaggc     180
tccgaagcag gcgttttac cacttctaaa gctggagata gactaacatt tcaacagta      240 gacatggagg caacagcaaa tgaagctgcc gactttgtca ttgacacaac aaagacttat     300
caatcaatta tagggtttgg tggcgccttc actgattcta gtgctatcaa cttgcacatg     360
ctcaattcta gttgcaaga gcattccaga actacttact ttggagatga tggattacaa     420
tacacgattg gtagaatacc aattggctct acgatttct ctttaaccat ctacagctat     480
aatgatgtgg aaggggattt ggctatggaa aacttctcta ttgatatgga taggataaa     540 aagattccat tcattcatag agcaatgggc aaatcttcaa gaggtttgaa attgtacgcg     600
tcatcttggg cacctcctgc ctggatgaca actgaaaata cgactataaa ctgtgcagtt     660
```

```
caaggttacc caggtggaga atactggaag gctttagctt tgtactattc caaatttgtt    720
tccgcctatg aggctgaggg aatcccaatc tgggcgatga ctactcaaaa cgagcctaca    780
caacaattcg ccttcaaata ctggcaaagt ctgagattca atgttaccac agaacgagat    840
ttcataaaga gagatttggg tccacaaatg aaaactgacc atccagactt gaagatcata    900
atgatggacg atcaaaaaga ccttttgcta gattgggacg caaccctact ggatgccgaa    960
tcagcacagt acgtttctgg tgctggtgtt cattggtaca aaaacttgga tttccttgtg   1020
gatactgccg gtaattttgc ggacctcgaa acttttcacg aaaaataccc agacttattc   1080
attctggcca ccgaggcttg tgaaggctac ctacttgacg gtatcgtaac tggagcaggc   1140
cctacgcttc aaaatcctac atttgcctgg caaagagcac aaatctacgc tagggatatc   1200
attggtgatc ttgcacatta cgccgcaggt tggaccgatt ggaacttagt acttaataca   1260
acaggcggtc aacatggat cgacaacttg attgattcac ctatacttat cgatgaagct   1320
gggggagctg aatttacaa gcaaccaatg tattatgcta tgggtcattt ttctaagttt   1380
ttgccagctg acagtgtcag agtttctcta tctactagct cctcagcttc ctcaaccctc   1440
gcaaaagttg attctgtcgc attttttgaca ccagataatc aagtagtcct aattctctcc   1500
aatcgtgata cttctgccca tgacatcact ttatcattaa gctcacaaca gctttcaaca   1560
tcagttacat ggaagccttt aagtatcaaa actctagtca ttggagagct agaggaaaca   1620
gcggttccag ctagagtgag aaggcaagca ctccaaccag ttccaccatc ccgtagacca   1680
gtcagacctg acccaccact tgcggtatta gcattggatg atgatgacaa aggtggttct   1740
cctccttctc atcatcacca ccaccactaa                                    1770
```

<210> SEQ ID NO 4
<211> LENGTH: 609
<212> TYPE: PRT
<213> ORGANISM: Candida wickerhamii
<220> FEATURE:
<221> NAME/KEY: misc_feature
<222> LOCATION: (1)..(609)
<223> OTHER INFORMATION: beta-glucosidase

<400> SEQUENCE: 4

Met Phe Ser Gln Lys Tyr Leu Leu Ser Leu Ala Ala Ile Ile Ala Ile
1               5                   10                  15

Ala Lys Ala Ala Pro Ala Asp Asp Ala Ser Lys Pro Gly Ile Gly Lys
            20                  25                  30

Phe Ala Pro Gly Gln Leu Gly Phe Arg Tyr Tyr Ile Asp Thr Thr Thr
        35                  40                  45

Glu Tyr Ala Thr Pro Ala Thr Ala Thr Ala Pro Ala Ser Ser Thr Thr
    50                  55                  60

Tyr Ala Ala Pro Tyr Ala Glu Leu Ser Ser Leu Val Gly Asn Leu Ser
65                  70                  75                  80

Thr Thr Thr Trp Gly Asn Trp Tyr Pro Asp Ala Thr Glu Ala Ala Thr
                85                  90                  95

Asp Thr Asp Asp Pro Tyr Gly Gln Tyr Ala Trp Ser Gln Leu Trp Glu
            100                 105                 110

Ala Thr Thr Phe Pro Asn Phe Thr Arg Gly Ile Tyr Ser Thr Thr Val
        115                 120                 125

Asp Pro Thr Pro Ile Pro Thr Glu Ser Leu Val Val Pro Pro Asp Asp
    130                 135                 140

Pro Val Lys Arg Ala Phe Gln Asp Leu Gly Ile Lys Phe Pro Leu Gly
145                 150                 155                 160

```
Phe Ile Gln Gly Val Ala Gly Ser Ala Ala Gln Ile Glu Gly Ala Val
                165                 170                 175

Ala Asp Glu Gly Arg Ser Pro Thr Asn Leu Glu Val Ser Ser Ala Ser
            180                 185                 190

Arg His Leu Pro Glu Asp Phe Val Thr Asn Glu Asn Tyr Tyr Leu Tyr
        195                 200                 205

Lys Gln Asp Ile Thr Arg Leu Ala Ala Ile Gly Val Glu Tyr Tyr Ser
    210                 215                 220

Phe Thr Ile Pro Trp Thr Arg Ile Leu Pro Phe Ala Tyr Pro Gly Ser
225                 230                 235                 240

Pro Val Asn Gln Gln Gly Leu Asp His Tyr Asp Leu Ile Asn Thr
                245                 250                 255

Val Leu Ala Tyr Gly Met Lys Pro Ile Val Thr Leu Ile His Phe Asp
            260                 265                 270

Ser Pro Leu Gln Leu Val Asp Phe Asn Ala Thr Leu Glu Leu Gly Leu
        275                 280                 285

Pro Gly Gly Tyr Glu Gly Glu Asp Phe Val Glu Ala Phe Val Asn Tyr
    290                 295                 300

Gly Lys Ile Val Met Thr His Phe Ala Asp Arg Val Pro Leu Trp Ile
305                 310                 315                 320

Ile Phe Asn Glu Pro Val Gln Phe Ala Thr Asn Gly Leu Gly Val Lys
                325                 330                 335

His Val Val Gln Ala Thr Ala Gln Leu Tyr Asp Phe Tyr His Asn Glu
            340                 345                 350

Ile Asn Gly Ser Gly Lys Ile Gly Met Lys Phe Ser His Ile Phe Gly
        355                 360                 365

Phe Pro Glu Asp Pro Thr Asn Pro Glu His Val Ala Ala Ala Asp Arg
    370                 375                 380

Ser Asn Glu Leu Gln Leu Gly Leu Phe Ala Asp Pro Leu Phe Leu Gly
385                 390                 395                 400

Glu Asp Tyr Pro Asp Ser Phe Lys Thr Thr Leu Leu Lys Thr Gln Pro
                405                 410                 415

Ala Leu Ala Trp Thr Leu Asp Glu Leu Ala Ala Val Lys Gly Lys Cys
            420                 425                 430

Asp Phe Phe Gly Val Asp Pro Tyr Thr Tyr Asn Thr Ile Lys Pro Leu
        435                 440                 445

Asp Asn Gly Thr Ala Ser Cys Glu Ala Asn Val Thr Asp Thr Tyr Trp
450                 455                 460

Pro Thr Cys Val Asn Val Thr Val Thr Glu Ala Asp Asn Trp Ser Ile
465                 470                 475                 480

Gly Tyr Arg Ser Gln Ser Tyr Val Tyr Ile Thr Pro Arg Gln Leu Arg
                485                 490                 495

Val Ser Leu Asn Tyr Ile Trp Gln His Trp His Val Pro Ile Phe Ile
            500                 505                 510

Thr Glu Phe Gly Phe Pro Glu Trp Arg Glu Gly Glu Lys Leu Leu Val
        515                 520                 525

Asp Gln Val Gln Asp Leu Asp Arg Ser Ile Tyr Tyr Arg Ser Phe Leu
    530                 535                 540

Thr Ala Ala Leu Glu Ala Ser Gln Tyr Asp Gly Val Glu Ile Met Gly
545                 550                 555                 560

Ala Leu Ala Trp Ser Phe Ala Asp Asn Trp Glu Phe Gly Asp Tyr Asn
                565                 570                 575
```

Gln Gln Phe Gly Leu Gln Val Val Asn Arg Thr Thr Gln Glu Arg Phe
            580                 585                 590

Tyr Lys Lys Ser Phe Phe Asp Phe Val Gly Phe Ile Asn Asp Asn Arg
        595                 600                 605

Ala

<210> SEQ ID NO 5
<211> LENGTH: 20
<212> TYPE: PRT
<213> ORGANISM: Candida wickerhamii
<220> FEATURE:
<221> NAME/KEY: misc_feature
<222> LOCATION: (1)..(20)
<223> OTHER INFORMATION: native signal peptide - beta-glucosidase

<400> SEQUENCE: 5

Met Phe Ser Gln Lys Tyr Leu Leu Ser Leu Ala Ala Ile Ile Ala Ile
1               5                   10                  15

Ala Lys Ala Ala
            20

<210> SEQ ID NO 6
<211> LENGTH: 1881
<212> TYPE: DNA
<213> ORGANISM: Candida wickerhamii
<220> FEATURE:
<221> NAME/KEY: misc_feature
<222> LOCATION: (1)..(1881)
<223> OTHER INFORMATION: beta-glucosidase

<400> SEQUENCE: 6
atgttctcac aaaagtatct tttatcatta gctgcaataa ttgcaatcgc taaagcagct       60
ccagctgacg atgcctctaa gcctggtata ggcaagtttg cccctggtca actgggttc      120 agatactata ttgatactac cactgaatac gcaaccccag caacagctac agctcctgct      180
agttctacta cttacgcagc cccatacgct gaactatcta gtttggtggg caatctgtca      240
acaactactt ggggcaactg gtatccagat gctactgaag ctgctactga tacagatgat      300
ccttacggtc aatacgcgtg gtcacagctc tgggaagcga ctaccttcc taactttacg       360 agaggaatct actcaaccac agtagatcca accccaatcc ctacagaaag ccttgtagtt      420
ccaccagacg acccagtcaa aagagccttt caagacttag gataaagtt tccattaggc       480 tttatccaag gggtggctgg atctgctgcg cagatagaag gcgctgtcgc tgatgagggc      540
agaagtccta caaatctcga agtgtcatct gcatccagac atttgccaga ggatttcgtg      600
acaaatgaaa actactacct ttacaaacaa gatattactc gattggcagc cataggtgtc      660
gaatattact cctttacaat tccttggact cgtatattgc catttgcata ccctggttca      720
ccagttaatc aacaaggtct ggaccattat gacgatttga ttaatacagt tctagcctac      780
ggaatgaaac ctatcgtcac tcttattcat ttcgactctc cattacaatt ggttgatttt      840
aacgcaacac ttgaattagg attgccagga ggttatgaag cgaagatttt tgtggaagcc      900
tttgtcaatt atggtaagat tgtgatgaca cattttgcag atagagtacc actatggatc      960
atcttcaacg aaccagtaca attcgcaact aacggcctag gagtaaagca tgtagttcaa     1020
gcgaccgcac agttgtatga tttctaccat aatgagatta acggttcagg taaaatcggt     1080
atgaaattca gtcacatctt cgggttccct gaagatccaa caaacccaga acatgtcgcc     1140
gcagctgata ggtctaacga actgcaattg ggattatttg ctgacccatt gttttagga     1200 gaggattacc cagattcctt taagacaaca ttactgaaaa cacaacctgc tttggcctgg     1260

-continued

```
acactagacg aattggccgc tgttaaaggt aagtgcgact ttttcggggt tgatccatac    1320
acttacaata caattaaacc actggataat ggtacagcat cctgtgaggc caatgttacg    1380
gatacttact ggcctacctg tgttaatgta accgttacag aagctgacaa ttggagtatc    1440
ggatataggt cacaaagcta cgtctacatt actccaagac aattaagagt ttctctaaac    1500
tacatttggc agcactggca tgttccaatc tttatcacag aatttggttt cccagaatgg    1560
agagaaggtg agaaacttct cgtagaccaa gttcaagatt tggacagatc catctactac    1620
agatcatttc tgaccgctgc cctagaggct tctcagtatg atggtgtcga ataatgggt    1680 gccttagctt ggtctttcgc agacaactgg gagtttgggg actataatca acagttcggc    1740
ttgcaagtgg ttaatagaac tacacaagag cgttttttaca aaaagtcttt ctttgatttc    1800
gttggcttta tcaatgataa tagagctgat gatgatgaca aggtggttc tcctccttct    1860 catcatcacc accaccacta a                                              1881
```

<210> SEQ ID NO 7
<211> LENGTH: 860
<212> TYPE: PRT
<213> ORGANISM: Aspergillus aculeatus
<220> FEATURE:
<221> NAME/KEY: misc_feature
<222> LOCATION: (1)..(860)
<223> OTHER INFORMATION: beta-glucosidase

<400> SEQUENCE: 7

```
Met Lys Leu Ser Trp Leu Glu Ala Ala Leu Thr Ala Ala Ser Val
1               5                   10                  15

Val Ser Ala Asp Glu Leu Ala Phe Ser Pro Pro Phe Tyr Pro Ser Pro
                20                  25                  30

Trp Ala Asn Gly Gln Gly Glu Trp Ala Glu Ala Tyr Gln Arg Ala Val
            35                  40                  45

Ala Ile Val Ser Gln Met Thr Leu Asp Glu Lys Val Asn Leu Thr Thr
        50                  55                  60

Gly Thr Gly Trp Glu Leu Glu Lys Cys Val Gly Gln Thr Gly Gly Val
65                  70                  75                  80

Pro Arg Leu Asn Ile Gly Gly Met Cys Leu Gln Asp Ser Pro Leu Gly
                85                  90                  95

Ile Arg Asp Ser Asp Tyr Asn Ser Ala Phe Pro Ala Gly Val Asn Val
                100                 105                 110

Ala Ala Thr Trp Asp Lys Asn Leu Ala Tyr Leu Arg Gly Gln Ala Met
            115                 120                 125

Gly Gln Glu Phe Ser Asp Lys Gly Ile Asp Val Gln Leu Gly Pro Ala
        130                 135                 140

Ala Gly Pro Leu Gly Arg Ser Pro Asp Gly Gly Arg Asn Trp Glu Gly
145                 150                 155                 160

Phe Ser Pro Asp Pro Ala Leu Thr Gly Val Leu Phe Ala Glu Thr Ile
                165                 170                 175

Lys Gly Ile Gln Asp Ala Gly Val Val Ala Thr Ala Lys His Tyr Ile
                180                 185                 190

Leu Asn Glu Gln Glu His Phe Arg Gln Val Ala Glu Ala Ala Gly Tyr
            195                 200                 205

Gly Phe Asn Ile Ser Asp Thr Ile Ser Ser Asn Val Asp Asp Lys Thr
        210                 215                 220

Ile His Glu Met Tyr Leu Trp Pro Phe Ala Asp Ala Val Arg Ala Gly
225                 230                 235                 240
```

```
Val Gly Ala Ile Met Cys Ser Tyr Asn Gln Ile Asn Ser Tyr Gly
            245                 250                 255

Cys Gln Asn Ser Tyr Thr Leu Asn Lys Leu Leu Lys Ala Glu Leu Gly
        260                 265                 270

Phe Gln Gly Phe Val Met Ser Asp Trp Gly Ala His His Ser Gly Val
        275                 280                 285

Gly Ser Ala Leu Ala Gly Leu Asp Met Ser Met Pro Gly Asp Ile Thr
        290                 295                 300

Phe Asp Ser Ala Thr Ser Phe Trp Gly Thr Asn Leu Thr Ile Ala Val
305                 310                 315                 320

Leu Asn Gly Thr Val Pro Gln Trp Arg Val Asp Asp Met Ala Val Arg
                325                 330                 335

Ile Met Ala Ala Tyr Tyr Lys Val Gly Arg Asp Arg Leu Tyr Gln Pro
                340                 345                 350

Pro Asn Phe Ser Ser Trp Thr Arg Asp Glu Tyr Gly Phe Lys Tyr Phe
                355                 360                 365

Tyr Pro Gln Glu Gly Pro Tyr Glu Lys Val Asn His Phe Val Asn Val
            370                 375                 380

Gln Arg Asn His Ser Glu Val Ile Arg Lys Leu Gly Ala Asp Ser Thr
385                 390                 395                 400

Val Leu Leu Lys Asn Asn Asn Ala Leu Pro Leu Thr Gly Lys Glu Arg
                405                 410                 415

Lys Val Ala Ile Leu Gly Glu Asp Ala Gly Ser Asn Ser Tyr Gly Ala
                420                 425                 430

Asn Gly Cys Ser Asp Arg Gly Cys Asp Asn Gly Thr Leu Ala Met Ala
            435                 440                 445

Trp Gly Ser Gly Thr Ala Glu Phe Pro Tyr Leu Val Thr Pro Glu Gln
        450                 455                 460

Ala Ile Gln Ala Glu Val Leu Lys His Lys Gly Ser Val Tyr Ala Ile
465                 470                 475                 480

Thr Asp Asn Trp Ala Leu Ser Gln Val Glu Thr Leu Ala Lys Gln Ala
                485                 490                 495

Ser Val Ser Leu Val Phe Val Asn Ser Asp Ala Gly Glu Gly Tyr Ile
                500                 505                 510

Ser Val Asp Gly Asn Glu Gly Asp Arg Asn Asn Leu Thr Leu Trp Lys
            515                 520                 525

Asn Gly Asp Asn Leu Ile Lys Ala Ala Ala Asn Asn Cys Asn Asn Thr
        530                 535                 540

Ile Val Val Ile His Ser Val Gly Pro Val Leu Val Asp Glu Trp Tyr
545                 550                 555                 560

Asp His Pro Asn Val Thr Ala Ile Leu Trp Ala Gly Leu Pro Gly Gln
                565                 570                 575

Glu Ser Gly Asn Ser Leu Ala Asp Val Leu Tyr Gly Arg Val Asn Pro
            580                 585                 590

Gly Ala Lys Ser Pro Phe Thr Trp Gly Lys Thr Arg Glu Ala Tyr Gly
        595                 600                 605

Asp Tyr Leu Val Arg Glu Leu Asn Asn Gly Asn Gly Ala Pro Gln Asp
        610                 615                 620

Asp Phe Ser Glu Gly Val Phe Ile Asp Tyr Arg Gly Phe Asp Lys Arg
625                 630                 635                 640

Asn Glu Thr Pro Ile Tyr Glu Phe Gly His Gly Leu Ser Tyr Thr Thr
                645                 650                 655
```

```
Phe Asn Tyr Ser Gly Leu His Ile Gln Val Leu Asn Ala Ser Ser Asn
            660                 665                 670

Ala Gln Val Ala Thr Glu Thr Gly Ala Ala Pro Thr Phe Gly Gln Val
        675                 680                 685

Gly Asn Ala Ser Asp Tyr Val Tyr Pro Glu Gly Leu Thr Arg Ile Ser
    690                 695                 700

Lys Phe Ile Tyr Pro Trp Leu Asn Ser Thr Asp Leu Lys Ala Ser Ser
705                 710                 715                 720

Gly Asp Pro Tyr Tyr Gly Val Asp Thr Ala Glu His Val Pro Glu Gly
                725                 730                 735

Ala Thr Asp Gly Ser Pro Gln Pro Val Leu Pro Ala Gly Gly Gly Ser
            740                 745                 750

Gly Gly Asn Pro Arg Leu Tyr Asp Glu Leu Ile Arg Val Ser Val Thr
        755                 760                 765

Val Lys Asn Thr Gly Arg Val Ala Gly Asp Ala Val Pro Gln Leu Tyr
    770                 775                 780

Val Ser Leu Gly Gly Pro Asn Glu Pro Lys Val Val Leu Arg Lys Phe
785                 790                 795                 800

Asp Arg Leu Thr Leu Lys Pro Ser Glu Glu Thr Val Trp Thr Thr Thr
                805                 810                 815

Leu Thr Arg Arg Asp Leu Ser Asn Trp Asp Val Ala Ala Gln Asp Trp
            820                 825                 830

Val Ile Thr Ser Tyr Pro Lys Lys Val His Val Gly Ser Ser Ser Arg
        835                 840                 845

Gln Leu Pro Leu His Ala Leu Pro Lys Val Gln
    850                 855                 860

<210> SEQ ID NO 8
<211> LENGTH: 19
<212> TYPE: PRT
<213> ORGANISM: Aspergillus aculeatus
<220> FEATURE:
<221> NAME/KEY: misc_feature
<222> LOCATION: (1)..(19)
<223> OTHER INFORMATION: native signal peptide - beta-glucosidase

<400> SEQUENCE: 8

Met Lys Leu Ser Trp Leu Glu Ala Ala Ala Leu Thr Ala Ala Ser Val
1               5                   10                  15

Val Ser Ala

<210> SEQ ID NO 9
<211> LENGTH: 2637
<212> TYPE: DNA
<213> ORGANISM: Aspergillus aculeatus
<220> FEATURE:
<221> NAME/KEY: misc_feature
<222> LOCATION: (1)..(2637)
<223> OTHER INFORMATION: beta-glucosidase

<400> SEQUENCE: 9
atgatgaagc tcagttggct tgaggcggct gccttgacgg ctgcttcagt cgtcagcgct      60
gatgaattag cctttccccc accatttac ccatctcctt gggctaatgg acaaggcgaa      120
tgggccgaag cataccagag agccgttgct attgttagtc agatgacact tgatgaaaaa     180
gtgaatttga ctacaggtac ggggtgggaa ttagaaaagt gtgtaggtca aactggtgga     240
gttccaagat aaacatcgg agggatgtgc ttacaagata gtccactagg tatcagagat      300
tctgattaca attctgcttt tcctgcaggc gttaatgttg ccgcaacgtg ggacaaaaac     360
```

```
ttagcctacc taagaggtca agctatgggt caggaatttt cagataaggg catcgatgtc    420
caattaggcc cagccgcagg accattggga cgatctccag atggtgggag aaactgggag    480
ggattctcac ctgaccctgc acttactggt gttctgtttg cagaaactat caaaggtata    540
caagacgccg gtgttgttgc gacagctaaa cactacattt tgaatgaaca agagcatttt    600
agacaagtgg ctgaggccgc tgggtacggt tcaacatat ccgatacaat ctcatcaaat     660
gtggacgaca agacgattca tgagatgtat ttgtggccat tgctgatgc agtgagagca     720 ggcgttgggg ctataatgtg cagctacaat caaatcaata atagttatgg ctgtcaaaac    780
tcatacactc tcaataagtt attgaaggct gaactgggtt tccaaggttt cgtaatgtca    840
gattggggtg cccatcactc cggtgtcggt tctgctttag ctggtcttga catgtctatg    900
cctggtgaca ttacatttga ctccgcaaca tctttctggg gaacaaatct gacaattgcc    960
gtccttaacg gcaccgtgcc acagtggaga gttgacgaca tggcagtccg tattatggct   1020
gcatattaca aagtcggccg tgaccgactg taccaaccac aaacttcag ctcctggact    1080 agagatgaat acggctttaa gtacttttat ccacaggagg gaccatacga aaaagttaat   1140
cactttgtca atgtccagag gaatcattcc gaagtcatca gaaagctagg tgcagattct   1200
acagttttgt tgaaaaacaa taacgcattg cctttaacag gtaaagagcg aaaggttgcc   1260
atcttgggtg aagatgcggg ttctaatagt tacggagcca atgggtgttc agatagaggc   1320
tgcgataacg gtactttagc aatggcctgg ggatcaggca cagctgaatt ccatacctt    1380 gtgacacctg aacaagcaat ccaagctgaa gtattgaaac ataaagggtc agtttatgct   1440
ataaccgaca attgggcatt gtctcaagtc gaaaccctcg caaaacaagc ctctgttagt   1500
ttggtttttg tgaatagtga tgctggtgaa gggtacattt cagttgatgg aaacgaaggc   1560
gatagaaata acctcacatt gtggaaaaat ggcgataatc ttattaaggc tgctgcgaac   1620
aattgtaaca atactattgt ggttatccat tctgtagggc ctgtccttgt tgacgaatgg   1680
tacgaccatc caaatgtgac agctatacta tgggcaggct taccaggtca agagtctgga   1740
aattccttag cagatgtact ctacggacgt gtcaatcctg gagctaagtc tccattcaca   1800
tggggtaaga ctagagaggc ttacggagat tacttagtaa gagaattgaa caatggcaac   1860
ggtgcgccac aagatgattt ctctgaaggt gttttatcg attatagagg gttcgacaag    1920
agaaacgaga ctccaatcta cgagtttggt catggtttga gttatacaac ttttaactac   1980
tcagggcttc atattcaagt actaaacgca tcttctaacg cccaagtagc aacggaaact   2040
ggcgcagctc caactttcgg tcaggtgggt aatgcctcag attatgttta ccagaaggc   2100 ctcacaagga tttcaaagtt catataccct tggctaaact ctacagattt gaaagcatca   2160
tccggtgatc catactatgg tgttgatact gcagaacatg tgcctgaagg cgctactgac   2220
ggatcaccac aacctgttct gcctgctgga ggtggttcag gagggaaccc tagactctat   2280
gatgagttaa ttagggtatc tgttactgtg aaaaacacag ggagagtggc gggtgatgcc   2340
gtgcctcaac tatacgtgtc tcttggagga ccaaatgaac caaaagtagt tttgagaaaa   2400
ttcgacagat taacattgaa accatccgag gaaactgttt ggactactac cctgacccgt   2460
agagatttgt ctaattggga cgtagctgcc caagattggg tcatcacaag ttaccctaag   2520
aaagtacatg ttggctctag ttccagacaa cttccattac acgctgccct gccaaaagtg   2580
caagatgatg atgacaaagg tggttctcct ccttctcatc atcaccacca ccactaa      2637
```

<210> SEQ ID NO 10

```
<211> LENGTH: 861
<212> TYPE: PRT
<213> ORGANISM: Aspergillus oryzae
<220> FEATURE:
<221> NAME/KEY: misc_feature
<222> LOCATION: (1)..(861)
<223> OTHER INFORMATION: beta-glucosidase

<400> SEQUENCE: 10
```

Met Lys Leu Gly Trp Ile Glu Val Ala Ala Leu Ala Ala Ala Ser Val
1               5                   10                  15

Val Ser Ala Lys Asp Asp Leu Ala Tyr Ser Pro Pro Phe Tyr Pro Ser
            20                  25                  30

Pro Trp Ala Asp Gly Gln Gly Glu Trp Ala Glu Val Tyr Lys Arg Ala
        35                  40                  45

Val Asp Ile Val Ser Gln Met Thr Leu Thr Glu Lys Val Asn Leu Thr
    50                  55                  60

Thr Gly Thr Gly Trp Gln Leu Glu Arg Cys Val Gly Gln Thr Gly Ser
65                  70                  75                  80

Val Pro Arg Leu Asn Ile Pro Ser Leu Cys Leu Gln Asp Ser Pro Leu
                85                  90                  95

Gly Ile Arg Phe Ser Asp Tyr Asn Ser Ala Phe Pro Ala Gly Val Asn
            100                 105                 110

Val Ala Ala Thr Trp Asp Lys Thr Leu Ala Tyr Leu Arg Gly Gln Ala
        115                 120                 125

Met Gly Glu Glu Phe Ser Asp Lys Gly Ile Asp Val Gln Leu Gly Pro
    130                 135                 140

Ala Ala Gly Pro Leu Gly Ala His Pro Asp Gly Gly Arg Asn Trp Glu
145                 150                 155                 160

Gly Phe Ser Pro Asp Pro Ala Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Met Asn Glu Gln Glu His Phe Arg Gln Gln Pro Glu Ala Ala Gly
        195                 200                 205

Tyr Gly Phe Asn Val Ser Asp Ser Leu Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Glu Asn Ser Glu Thr Leu Asn Lys Leu Leu Lys Ala Glu Leu
            260                 265                 270

Gly Phe Gln Gly Phe Val Met Ser Asp Trp Thr Ala His His Ser Gly
        275                 280                 285

Val Gly Ala Ala Leu Ala Gly Leu Asp Met Ser Met Pro Gly Asp Val
    290                 295                 300

Thr Phe Asp Ser Gly Thr Ser Phe Trp Gly Ala Asn Leu Thr Val Gly
305                 310                 315                 320

Val Leu Asn Gly Thr Ile Pro Gln Trp Arg Val Asp Asp Met Ala Val
                325                 330                 335

Arg Ile Met Ala Ala Tyr Tyr Lys Val Gly Arg Asp Thr Lys Tyr Thr
            340                 345                 350

Pro Pro Asn Phe Ser Ser Trp Thr Arg Asp Glu Tyr Gly Phe Ala His
        355                 360                 365

-continued

| | | | | | | | | | | | |
|---|---|---|---|---|---|---|---|---|---|---|---|
|Asn|His|Val|Ser|Glu|Gly|Ala|Tyr|Glu|Arg|Val|Asn|
|370| | | | |375| | | |380| | |
|Glu|Phe|Val|Asp| | | | | | | | |

Val Gln Arg Asp His Ala Asp Leu Ile Arg Arg Ile Gly Ala Gln Ser
385                 390                 395                 400

Thr Val Leu Leu Lys Asn Lys Gly Ala Leu Pro Leu Ser Arg Lys Glu
            405                 410                 415

Lys Leu Val Ala Leu Leu Gly Glu Asp Ala Gly Ser Asn Ser Trp Gly
            420                 425                 430

Ala Asn Gly Cys Asp Asp Arg Gly Cys Asp Asn Gly Thr Leu Ala Met
            435                 440                 445

Ala Trp Gly Ser Gly Thr Ala Asn Phe Pro Tyr Leu Val Thr Pro Glu
        450                 455                 460

Gln Ala Ile Gln Asn Glu Val Leu Gln Gly Arg Gly Asn Val Phe Ala
465                 470                 475                 480

Val Thr Asp Ser Trp Ala Leu Asp Lys Ile Ala Ala Ala Arg Gln
            485                 490                 495

Ala Ser Val Ser Leu Val Phe Val Asn Ser Asp Ser Gly Glu Gly Tyr
            500                 505                 510

Leu Ser Val Asp Gly Asn Glu Gly Asp Arg Asn Asn Ile Thr Leu Trp
            515                 520                 525

Lys Asn Gly Asp Asn Val Val Lys Thr Ala Ala Asn Asn Cys Asn Asn
530                 535                 540

Thr Val Val Ile Ile His Ser Val Gly Pro Val Leu Ile Asp Glu Trp
545                 550                 555                 560

Tyr Asp His Pro Asn Val Thr Gly Ile Leu Trp Ala Gly Leu Pro Gly
            565                 570                 575

Gln Glu Ser Gly Asn Ser Ile Ala Asp Val Leu Tyr Gly Arg Val Asn
            580                 585                 590

Pro Gly Ala Lys Ser Pro Phe Thr Trp Gly Lys Thr Arg Glu Ser Tyr
            595                 600                 605

Gly Ser Pro Leu Val Lys Asp Ala Asn Gly Asn Gly Ala Pro Gln
            610                 615                 620

Ser Asp Phe Thr Gln Gly Val Phe Ile Asp Tyr Arg His Phe Asp Lys
625                 630                 635                 640

Phe Asn Glu Thr Pro Ile Tyr Glu Phe Gly Tyr Gly Leu Ser Tyr Thr
            645                 650                 655

Thr Phe Glu Leu Ser Asp Leu His Val Gln Pro Leu Asn Ala Ser Arg
            660                 665                 670

Tyr Thr Pro Thr Ser Gly Met Thr Glu Ala Ala Lys Asn Phe Gly Glu
            675                 680                 685

Ile Gly Asp Ala Ser Glu Tyr Val Tyr Pro Glu Gly Leu Glu Arg Ile
            690                 695                 700

His Glu Phe Ile Tyr Pro Trp Ile Asn Ser Thr Asp Leu Lys Ala Ser
705                 710                 715                 720

Ser Asp Asp Ser Asn Tyr Gly Trp Glu Asp Ser Lys Tyr Ile Pro Glu
            725                 730                 735

Gly Ala Thr Asp Gly Ser Ala Gln Pro Arg Leu Pro Ala Ser Gly Gly
            740                 745                 750

Ala Gly Gly Asn Pro Gly Leu Tyr Glu Asp Leu Phe Arg Val Ser Val
            755                 760                 765

Lys Val Lys Asn Thr Gly Asn Val Ala Gly Asp Glu Val Pro Gln Leu
770                 775                 780

Tyr Val Ser Leu Gly Gly Pro Asn Glu Pro Lys Val Val Leu Arg Lys

```
                        785                 790                 795                 800
               Phe Glu Arg Ile His Leu Ala Pro Ser Gln Glu Ala Val Trp Thr Thr
                                805                 810                 815

Thr Leu Thr Arg Arg Asp Leu Ala Asn Trp Asp Val Ser Ala Gln Asp
                                820                 825                 830

Trp Thr Val Thr Pro Tyr Pro Lys Thr Ile Tyr Val Gly Asn Ser Ser
                                835                 840                 845

Arg Lys Leu Pro Leu Gln Ala Ser Leu Pro Lys Ala Gln
                                850                 855                 860

<210> SEQ ID NO 11
<211> LENGTH: 19
<212> TYPE: PRT
<213> ORGANISM: Aspergillus oryzae
<220> FEATURE:
<221> NAME/KEY: misc_feature
<222> LOCATION: (1)..(19)
<223> OTHER INFORMATION: native signal peptide - beta-glucosidase

<400> SEQUENCE: 11

Met Lys Leu Gly Trp Ile Glu Val Ala Ala Leu Ala Ala Ala Ser Val
1               5                   10                  15

Val Ser Ala

<210> SEQ ID NO 12
<211> LENGTH: 2637
<212> TYPE: DNA
<213> ORGANISM: Aspergillus oryzae
<220> FEATURE:
<221> NAME/KEY: misc_feature
<222> LOCATION: (1)..(2637)
<223> OTHER INFORMATION: beta-glucosidase

<400> SEQUENCE: 12
atgaagcttg gttggatcga ggtggccgca ttggcggctg cctcagtagt cagtgccaag      60
gatgacctcg catattcacc tccattttac cctagccctt gggcagatgg ccagggcgaa     120
tgggccgaag tctacaaaag agctgtggat attgtctctc aaatgacttt gacagaaaaa     180
gtgaacttaa cgactggtac tgggtggcaa ttggaaagat gtgtaggaca aacaggttct     240
gtcccaaggc tcaatattcc atcactatgc ttgcaagact cccctcttgg tattagattc     300
tctgattaca attcagcatt tccagccggt gttaatgttg ctgcgacctg gacaaaacc     360 cttgcctatt tgagaggaca agcaatgggc gaagagttct ctgataaggg tattgatgtt     420
caattaggtc ctgctgcagg cccactgggt gcccatccag acggtggacg taactgggaa     480
ggtttcagtc cagatcctgc attgactggt gtgcttttcg ccgaaacaat taaggtata     540 caggacgctg tgtaattgc tactgccaaa cattacatca tgaacgaaca agagcatttc     600
agacaacaac cagaagctgc cggatatggt tttaatgttt ccgattcatt atcttcaaat     660
gttgatgata aacaatgca tgaactatac ctttggccat tgcagacgc cgttagagct     720 ggggttggag ctgtgatgtg ctcatacaat caaatcaaca atagttacgg ctgcgaaaat     780
tctgaaacat gaacaaact tttgaaagct gagttgggat ttcagggttt cgttatgtcc     840
gactggacag cacaccattc aggagtgggc gctgcactgg ctggtttaga tatgagtatg     900
ccaggggatg tgacttttga ttctggtaca tctttttggg gagctaattt gaccgtgggg     960
gtactaaacg gtacgatccc tcaatggaga gtagatgata tggccgttag aataatggcc    1020
gcttattaca aggtggggag agatacaaag tatactcctc aaacttctc ctcatggact    1080
```

| | | |
|---|---|---|
| agagatgaat acggattcgc acataatcac gtatctgaag gtgcctatga aagagttaat | 1140 |
| gaatttgtag atgtacaaag ggaccacgca gacttaataa gacgtatagg ggcacagtca | 1200 |
| actgttttac tgaaaaacaa gggtgctcta ccattatctc gtaaggaaaa attggttgcg | 1260 |
| ctattaggtg aggatgctgg ctctaattcc tggggtgcta atggatgtga cgatagagga | 1320 |
| tgtgataatg gcactttagc aatggcatgg ggttctggca ctgctaattt tccatatctt | 1380 |
| gttactccag agcaagctat tcaaaacgaa gttttgcagg gtagaggcaa tgttttcgca | 1440 |
| gttactgatt catgggcttt agacaagatc gcagcagcgg cacgacaggc gtcagtgagc | 1500 |
| ttggtttttg tcaacagtga cagcggtgaa ggatacctat ctgtcgatgg aaacgagggt | 1560 |
| gatagaaata acattactct gtggaaaaat ggtgacaatg ttgttaagac agcggccaac | 1620 |
| aattgtaaca acaccgtggt cattatccac tccgtcggac cagtgctaat tgatgaatgg | 1680 |
| tatgatcatc caaatgttac gggcatctta tgggctggct tgcctggaca agagtcagga | 1740 |
| aattctatcg ctgatgtttt atacggcaga gtcaacccag gagcgaaatc ccctttttaca | 1800 |
| tgggggaaaa caagagaaag ttatggttca ccactcgtaa aggatgcaaa caatggaaat | 1860 |
| ggcgcaccac aaagtgattt tacccaaggt gtgttcatcg attacagaca ttttgataag | 1920 |
| ttcaacgaaa ctcctatcta cgaatttggc tacggcctgt cttataccac atttgaatta | 1980 |
| tctgatttgc atgtccaacc actcaatgct tcaagatata ctcctacatc tggtatgacg | 2040 |
| gaagccgcta aaactttggg ggaaataggt gacgcgtctg aatacgtcta cccagaaggt | 2100 |
| ttggaaagga ttcatgagtt catctaccct tggatcaatt ctacagacct aaaggcatca | 2160 |
| tcagatgatt caaattacgg ctgggaggac agtaagtaca ttccagaggg agctacagac | 2220 |
| ggttctgccc agcctaggtt accagcatct ggaggggctg ggggtaaccc aggtctttac | 2280 |
| gaggatctgt ttagagtatc cgttaaagtc aaaaatacag gaaatgttgc cggagatgaa | 2340 |
| gtcccacaat tgtacgtgtc cttgggcgga ccaaatgaac ctaaagtagt cctcagaaaa | 2400 |
| ttcgagagaa tccatttggc cccttcccaa gaggcagtgt ggactaccac attaacaaga | 2460 |
| cgtgaccttg ctaattggga cgtaagcgcg caagattgga cagttacacc ttacccaaaa | 2520 |
| acaatatacg tcggtaatag ttccagaaag ctcccactgc aagctagtct accaaaaagct | 2580 |
| caagatgatg atgacaaagg tggttctcct ccttctcatc atcaccacca ccactaa | 2637 |

<210> SEQ ID NO 13
<211> LENGTH: 861
<212> TYPE: PRT
<213> ORGANISM: Penicillium decumbens
<220> FEATURE:
<221> NAME/KEY: misc_feature
<222> LOCATION: (1)..(861)
<223> OTHER INFORMATION: beta-glucosidase

<400> SEQUENCE: 13

Met Lys Leu Glu Trp Leu Glu Ala Thr Val Leu Ala Ala Ala Thr Val
1               5                   10                  15

Ala Ser Ala Lys Asp Leu Ala Tyr Ser Pro Pro Phe Tyr Pro Ser Pro
                20                  25                  30

Trp Ala Thr Gly Glu Gly Glu Trp Ala Glu Ala Tyr Lys Lys Ala Val
            35                  40                  45

Asp Phe Val Ser Gly Leu Thr Leu Ala Glu Lys Val Asn Ile Thr Thr
        50                  55                  60

Gly Ala Gly Trp Glu Gln Glu Arg Cys Val Gly Glu Thr Gly Gly Val
65                  70                  75                  80

```
Pro Arg Leu Gly Met Trp Gly Met Cys Met Gln Asp Ser Pro Leu Gly
                85                  90                  95

Val Arg Asn Ala Asp Tyr Ser Ser Ala Phe Pro Ala Gly Val Asn Val
            100                 105                 110

Ala Ala Thr Trp Asp Arg Arg Leu Ala Tyr Gln Arg Gly Thr Ala Met
        115                 120                 125

Gly Glu Glu His Arg Asp Lys Gly Val Asp Val Gln Leu Gly Pro Val
    130                 135                 140

Ala Gly Pro Leu Gly Lys Asn Pro Asp Gly Arg Gly Trp Glu Gly
145                 150                 155                 160

Phe Ser Pro Asp Pro Val Leu Thr Gly Val Met Met Ala Glu Thr Ile
                165                 170                 175

Lys Gly Ile Gln Asp Ala Gly Val Ile Ala Cys Ala Lys His Phe Ile
            180                 185                 190

Met Asn Glu Gln Glu His Phe Arg Gln Ala Gly Glu Ala Gln Gly Tyr
        195                 200                 205

Gly Phe Asn Ile Ser Gln Ser Leu Ser Ser Asn Val Asp Asp Lys Thr
    210                 215                 220

Met His Glu Leu Tyr Leu Trp Pro Phe Val Asp Ser Val Arg Ala Gly
225                 230                 235                 240

Val Gly Ser Val Met Cys Ser Tyr Asn Gln Ile Asn Asn Ser Tyr Gly
                245                 250                 255

Cys Ser Asn Ser Tyr Thr Leu Asn Lys Leu Leu Lys Gly Glu Leu Gly
            260                 265                 270

Phe Gln Gly Phe Val Met Ser Asp Trp Gly Ala His His Ser Gly Val
        275                 280                 285

Gly Asp Ala Leu Ala Gly Leu Asp Met Ser Met Pro Gly Asp Val Ile
    290                 295                 300

Leu Gly Ser Pro Tyr Ser Phe Trp Gly Thr Asn Leu Thr Val Ser Val
305                 310                 315                 320

Leu Asn Ser Thr Ile Pro Glu Trp Arg Leu Asp Asp Met Ala Val Arg
                325                 330                 335

Ile Met Ala Ala Tyr Tyr Lys Val Gly Arg Asp Arg His Arg Thr Pro
            340                 345                 350

Pro Asn Phe Ser Ser Trp Thr Arg Asp Glu Tyr Gly Tyr Glu His Phe
        355                 360                 365

Ile Val Gln Glu Asn Tyr Val Lys Leu Asn Glu Arg Val Asn Val Gln
    370                 375                 380

Arg Asp His Ala Asn Val Ile Arg Lys Ile Gly Ser Asp Ser Ile Val
385                 390                 395                 400

Met Leu Lys Asn Asn Gly Gly Leu Pro Leu Thr His Gln Glu Arg Leu
                405                 410                 415

Val Ala Ile Leu Gly Glu Asp Ala Gly Ser Asn Ala Tyr Gly Ala Asn
            420                 425                 430

Gly Cys Ser Asp Arg Gly Cys Asp Asn Gly Thr Leu Ala Met Gly Trp
        435                 440                 445

Gly Ser Gly Thr Ala Asn Phe Pro Tyr Leu Ile Thr Pro Glu Gln Ala
    450                 455                 460

Ile Gln Asn Glu Val Leu Asn Tyr Gly Asn Gly Asp Thr Asn Val Phe
465                 470                 475                 480

Ala Val Thr Asp Asn Gly Ala Leu Ser Gln Met Ala Ala Leu Ala Ser
                485                 490                 495

Thr Ala Ser Val Ala Leu Val Phe Val Asn Ala Asp Ser Gly Glu Gly
```

```
                500             505             510
Tyr Ile Ser Val Asp Gly Asn Glu Gly Asp Arg Lys Asn Met Thr Leu
            515                 520                 525
Trp Lys Asn Gly Glu Glu Leu Ile Lys Thr Ala Thr Ala Asn Cys Asn
        530                 535                 540
Asn Thr Ile Val Ile Met His Thr Pro Asn Ala Val Leu Val Asp Ser
545                 550                 555                 560
Trp Tyr Asp Asn Glu Asn Ile Thr Ala Ile Leu Trp Ala Gly Met Pro
                565                 570                 575
Gly Gln Glu Ser Gly Arg Ser Leu Val Asp Val Leu Tyr Gly Arg Thr
            580                 585                 590
Asn Pro Gly Gly Lys Thr Pro Phe Thr Trp Gly Lys Glu Arg Lys Asp
        595                 600                 605
Trp Gly Ser Pro Leu Leu Thr Lys Pro Asn Asn Gly His Gly Ala Pro
        610                 615                 620
Gln Asp Asp Phe Thr Asp Val Leu Ile Asp Tyr Arg Arg Phe Asp Lys
625                 630                 635                 640
Asp Asn Val Glu Pro Ile Phe Glu Phe Gly Phe Gly Leu Ser Tyr Thr
                645                 650                 655
Lys Phe Glu Phe Ser Asp Ile Gln Val Lys Ala Leu Asn His Gly Glu
            660                 665                 670
Tyr Asn Ala Thr Val Gly Lys Thr Lys Pro Ala Pro Ser Leu Gly Lys
        675                 680                 685
Pro Gly Asn Ala Ser Asp His Leu Phe Pro Ser Asn Ile Asn Arg Val
        690                 695                 700
Arg Gln Tyr Leu Tyr Pro Tyr Leu Asn Ser Thr Asp Leu Lys Ala Ser
705                 710                 715                 720
Ala Asn Asp Pro Asp Tyr Gly Met Asn Ala Ser Ala Tyr Ile Pro Pro
                725                 730                 735
His Ala Thr Asp Ser Asp Pro Gln Asp Leu Leu Pro Ala Ser Gly Pro
            740                 745                 750
Ser Gly Gly Asn Pro Gly Leu Phe Glu Asp Leu Ile Glu Val Thr Ala
        755                 760                 765
Thr Val Thr Asn Thr Gly Ser Val Thr Gly Asp Glu Val Pro Gln Leu
770                 775                 780
Tyr Val Ser Leu Gly Gly Ala Asp Asp Pro Val Lys Val Leu Arg Ala
785                 790                 795                 800
Phe Asp Arg Val Thr Ile Ala Pro Gly Gln Lys Leu Arg Trp Thr Ala
                805                 810                 815
Thr Leu Asn Arg Arg Asp Leu Ser Asn Trp Asp Val Pro Ser Gln Asn
            820                 825                 830
Trp Ile Ile Ser Asp Ala Pro Lys Lys Val Trp Val Gly Asn Ser Ser
        835                 840                 845
Arg Lys Leu Pro Leu Ser Ala Asp Leu Pro Lys Val Gln
    850                 855                 860

<210> SEQ ID NO 14
<211> LENGTH: 19
<212> TYPE: PRT
<213> ORGANISM: Penicillium decumbens
<220> FEATURE:
<221> NAME/KEY: misc_feature
<222> LOCATION: (1)..(19)
<223> OTHER INFORMATION: native signal peptide - beta-glucosidase

<400> SEQUENCE: 14
```

Met Lys Leu Glu Trp Leu Glu Ala Thr Val Leu Ala Ala Ala Thr Val
1               5                   10                  15

Ala Ser Ala

<210> SEQ ID NO 15
<211> LENGTH: 2637
<212> TYPE: DNA
<213> ORGANISM: Penicillium decumbens
<220> FEATURE:
<221> NAME/KEY: misc_feature
<222> LOCATION: (1)..(2637)
<223> OTHER INFORMATION: beta-glucosidase

<400> SEQUENCE: 15

| | | | | | |
|---|---|---|---|---|---|
| atgaagctcg | agtggctgga | agccacggtg | cttgcggccg | ccacggttgc | tagtgcaaag | 60 |
| gacttggcct | actctccacc | attttaccca | tctccttggg | ctaccggtga | aggcgaatgg | 120 |
| gccgaagcct | acaaaaaggc | cgtagatttc | gtttccggat | tgaccctagc | tgaaaaagtt | 180 |
| aatatcacca | ctggtgccgg | ttgggaacag | gaaagatgtg | tcggagaaac | aggtggtgtc | 240 |
| cctagactag | gcatgtgggg | gatgtgtatg | caagactcac | cactaggtgt | gagaaatgca | 300 |
| gactactctt | cagcttttccc | agctggagtc | aatgttgctg | ccacatggga | tagaagattg | 360 |
| gcgtatcaaa | ggggaactgc | aatgggtgag | gaacatagag | acaaaggagt | tgatgtccaa | 420 |
| cttggtccag | tcgcgggtcc | tttgggaaag | aaccctgatg | gcggcagagg | gtgggaggga | 480 |
| ttttctccag | atccagttct | aactggtgta | atgatggcag | aaacaattaa | aggtatacaa | 540 |
| gacgccggag | tgatcgcatg | tgctaagcac | ttcattatga | cgaacagga | acactttaga | 600 |
| caagcagggg | aggcacaggg | ttacggcttt | aacatctctc | aatctttgtc | ctcaaatgtc | 660 |
| gatgacaaaa | ctatgcatga | attatacttg | tggccttttg | ttgattctgt | aagagcaggg | 720 |
| gtgggttcag | tgatgtgctc | atataatcaa | atcaataact | catacggttg | ctctaatagt | 780 |
| tacactttga | acaaattgct | taaaggtgaa | ttgggctttc | aaggatttgt | aatgtcagat | 840 |
| tggggtgccc | accatagcgg | tgttggtgac | gcattagctg | gactcgatat | gtctatgcct | 900 |
| ggtgatgtca | ttttgggctc | cccatattca | ttctggggca | caaacctaac | tgtctccgtg | 960 |
| ctaaactcca | ctattccaga | gtggcgtctg | gatgacatgg | ctgtcagaat | aatggctgcc | 1020 |
| tactacaaag | tgggccgaga | tagacataga | actccaccaa | atttctcttc | atggacaaga | 1080 |
| gatgaatacg | gctatgaaca | tttcattgtt | caagagaatt | atgttaaact | taacgaacgt | 1140 |
| gttaatgtcc | aaagggacca | cgcaaatgta | atcagaaaga | tcggatctga | ttcaattgtg | 1200 |
| atgttgaaaa | caacggtgg | actaccacta | acacatcagg | aaagactcgt | tgcaatctta | 1260 |
| ggggaagatg | caggatcaaa | tgcttacggt | gccaatggtt | gttctgatag | gggatgtgat | 1320 |
| aacggcactt | tagctatggg | ctgggggtca | ggtacagcga | atttcccata | cttaataaca | 1380 |
| ccagaacaag | ctatacaaaa | cgaggttttg | aattatggaa | acggtgatac | aaatgtcttt | 1440 |
| gctgttactg | ataatggagc | attgtcacaa | atggcggctt | tagccagtac | agcttccgtt | 1500 |
| gctctggttt | tcgtgaatgc | tgattctgga | gaaggataca | tttctgtaga | tggtaatgaa | 1560 |
| ggcgacagaa | agaacatgac | attgtggaaa | atggtgagg | aattaatcaa | gacagcaact | 1620 |
| gcaaattgca | ataatactat | cgttattatg | catacaccta | atgctgtcct | ggttgactct | 1680 |
| tggtacgata | acgagaatat | tacagctata | ttgtgggctg | gtatgccagg | caagagtcc | 1740 |
| ggaagatcat | tggtagatgt | cctctacggg | agaaccaatc | ctggtggcaa | aacacctttc | 1800 |
| acatggggga | aagagagaaa | ggattggggt | tctccattac | ttaccaaacc | aaataacggt | 1860 |

-continued

```
catggtgctc ctcaggacga tttcacagac gtactgatag actacagacg atttgataag    1920
gacaatgtgg aaccaatctt tgaatttggc tttggtttgt catatactaa gtttgagttt    1980
tctgatattc aagtaaaagc gcttaatcat ggagaatata acgcaacggt tggaaagacc    2040
aagccagctc ctagccttgg taaacctggt aacgcttctg atcatctgtt cccatccaat    2100
atcaacagag ttcgacaata cttatatcct tatctgaact ctactgacct aaaagctagt    2160
gctaatgacc ctgactacgg gatgaacgca tctgcgtaca tcccacctca tgcaaccgat    2220
tccgatccac aggatctcct gccagcttct ggaccatcag gtggtaatcc aggcttgttc    2280
gaagatttga ttgaagttac cgcaacagtc actaacactg cagtgttac aggcgatgaa    2340 gtgccacaat tatacgtgtc acttggcgga gcagatgacc cagttaaagt attgcgtgct    2400
tttgatagag tgacaatcgc acctggccaa aaactgcgtt ggacggcgac tcttaacaga    2460
agagacttat ccaactggga tgttccatcc caaaattgga ttatcagcga cgctcctaaa    2520
aaggtatggg taggtaattc atccagaaaa cttccattaa gtgctgattt gccaaaggta    2580
caagatgatg atgacaaagg tggttctcct ccttctcatc atcaccacca ccactaa       2637
```

<210> SEQ ID NO 16
<211> LENGTH: 871
<212> TYPE: PRT
<213> ORGANISM: Chaetomium globosum
<220> FEATURE:
<221> NAME/KEY: misc_feature
<222> LOCATION: (1)..(871)
<223> OTHER INFORMATION: beta-glucosidase

<400> SEQUENCE: 16

```
Met Lys Ala Ala Thr Ala Leu Ser Cys Leu Ala Gly Gly Ser Leu Ala
1               5                   10                  15

Ala Ala Gly Thr Ile Asn Pro Ala Asn Lys Ile Gln Lys Arg Ala Leu
            20                  25                  30

Gln Thr Ser Asp Pro His Tyr Pro Ser Pro Trp Met Asn Pro Asp Ala
        35                  40                  45

Asp Gly Trp Ala Glu Ala Tyr Ala Gln Ala Arg Asp Phe Val Ser Gln
    50                  55                  60

Leu Thr Leu Pro Glu Lys Val Asn Leu Thr Thr Gly Val Gly Trp Gln
65                  70                  75                  80

Gly Glu Gln Cys Val Gly Gln Thr Gly Ala Ile Pro Arg Phe Gly Leu
                85                  90                  95

Arg Ser Leu Cys Met His Asp Ala Pro Leu Gly Ile Arg Gly Ser Asp
            100                 105                 110

Tyr Asn Ser Ala Phe Pro Ser Gly Gln Thr Ala Ala Thr Trp Asp
        115                 120                 125

Arg Gly Leu Met Tyr Arg Gly Tyr Ala Met Gly Lys Glu Ala Lys
    130                 135                 140

Gly Lys Gly Ile Asn Val Leu Leu Gly Pro Val Ala Gly Pro Leu Gly
145                 150                 155                 160

Arg Met Pro Ala Ala Gly Arg Asn Trp Glu Gly Phe Ala Pro Asp Pro
                165                 170                 175

Val Leu Thr Gly Val Gly Met Ser Glu Thr Val Lys Gly Thr Gln Asp
            180                 185                 190

Ala Gly Val Val Ala Cys Ala Lys His Phe Ile Gly Asn Glu Gln Glu
        195                 200                 205

Asn Phe Arg Gln Val Gly Glu Ala Gln Gly Tyr Gly His Asn Ile Ser
```

```
                   210                 215                 220
Glu Thr Leu Ser Ser Asn Ile Asp Asp Lys Thr Met His Glu Leu Tyr
225                 230                 235                 240

Leu Trp Pro Phe Ala Asp Ala Val Arg Ala Gly Val Gly Ser Val Met
                245                 250                 255

Cys Ser Tyr Gln Gln Val Asn Asn Ser Tyr Gly Cys Gln Asn Ser Lys
            260                 265                 270

Leu Leu Asn Asp Leu Leu Lys Asn Glu Leu Gly Phe Gln Gly Phe Val
        275                 280                 285

Met Ser Asp Trp Gln Ala Gln His Thr Gly Ala Ala Ser Ala Val Ala
290                 295                 300

Gly Leu Asp Met Thr Met Pro Gly Asp Thr Ser Phe Asn Thr Gly Leu
305                 310                 315                 320

Ser Phe Trp Gly Thr Asn Leu Thr Leu Ala Val Leu Asn Gly Thr Val
                325                 330                 335

Pro Ala Tyr Arg Val Asp Asp Met Ala Met Arg Ile Met Ala Ser Ile
            340                 345                 350

Phe Lys Val Ser Lys Thr Thr Asp Phe Asp Pro Ile Asn Phe Ser Phe
        355                 360                 365

Trp Thr Leu Asp Thr Tyr Gly Pro Val His Trp Val Ala Lys Glu Gly
    370                 375                 380

Tyr Gln Glu Ile Asn Ser His Val Asp Val Arg Glu Asp His Gly Lys
385                 390                 395                 400

Leu Ile Arg Glu Ile Ala Ala Lys Gly Thr Val Leu Leu Lys Asn Ser
                405                 410                 415

Gly Ala Leu Pro Leu Gln Lys Pro Lys Phe Val Ala Val Ile Gly Glu
            420                 425                 430

Asp Ala Gly Gly Asn Pro Asn Gly Pro Asn Gly Cys Ser Asp Arg Gly
        435                 440                 445

Cys Asp Asp Gly Thr Leu Ala Met Gly Trp Gly Ser Gly Thr Ala Asn
450                 455                 460

Phe Pro Tyr Leu Val Thr Pro Asp Ala Ala Leu Gln Ala Arg Ala Ile
465                 470                 475                 480

Glu Asp Gly Ser Arg Tyr Glu Ser Ile Leu Ser Asn Tyr Ala His Asp
                485                 490                 495

Lys Thr Asp Ala Leu Val Ser Gln Ala Asn Val Thr Ala Ile Val Phe
            500                 505                 510

Val Asn Ala Asp Ser Gly Glu Gly Tyr Ile Asn Val Asp Gly Asn Met
        515                 520                 525

Gly Asp Arg Lys Asn Leu Thr Leu Trp Lys Asn Gly Asp Asp Leu Val
530                 535                 540

Lys Arg Val Ser Gly Ala Cys Ser Asn Thr Ile Val Val Ile His Ser
545                 550                 555                 560

Thr Gly Pro Val Leu Leu Thr Glu Trp Tyr Glu Ser Pro Asn Ile Thr
                565                 570                 575

Ala Ile Leu Trp Ala Gly Leu Pro Gly Gln Glu Ser Gly Asn Ser Ile
            580                 585                 590

Ala Asp Val Leu Tyr Gly Asp Val Asn Pro Ala Ala Arg Ser Pro Phe
        595                 600                 605

Thr Trp Gly Lys Thr Arg Glu Ser Tyr Gly Ala Asp Val Leu Tyr Glu
610                 615                 620

Pro Asn Asn Gly Asn Gly Ala Pro Gln Gln Asp Phe Ser Glu Gly Val
625                 630                 635                 640
```

```
Phe Ile Asp Tyr Arg Tyr Phe Asp Lys Gln Asn Ser Ser Val Ile Tyr
                645                 650                 655
Glu Phe Gly His Gly Leu Ser Tyr Thr Thr Phe Glu Tyr Ser Asn Ile
            660                 665                 670
Arg Val Glu Lys Ser Asn Ala Gly Glu Tyr Lys Pro Thr Thr Gly Ser
        675                 680                 685
Thr Ala Ala Pro Thr Phe Gly Asn Phe Ser Thr Asp Leu Lys Asp
    690                 695                 700
Tyr Leu Phe Pro Lys Glu Asp Phe Ser Tyr Ile Tyr Gln Tyr Ile Tyr
705                 710                 715                 720
Pro Tyr Val Asn Thr Thr Asp Ala Lys Lys Ala Ser Ala Asp Pro His
                725                 730                 735
Tyr Gly Gln Thr Ala Glu Glu Phe Leu Pro Pro His Val Leu Asp Ala
            740                 745                 750
Asp Ala Gln Pro Leu Leu Arg Ser Ser Gly Gly Asn Ser Pro Gly Gly
        755                 760                 765
Asn Arg Gln Leu Tyr Asp Ile Met Tyr Thr Ile Thr Ala Asp Ile Thr
    770                 775                 780
Asn Thr Gly Ala Ile Val Gly Glu Glu Val Pro Gln Leu Tyr Val Ser
785                 790                 795                 800
Leu Gly Gly Pro Glu Asp Pro Lys Val Gln Leu Arg Asp Phe Asp Arg
                805                 810                 815
Met Arg Ile Asp Pro Gly Glu Thr Lys Gln Phe Thr Gly Arg Leu Thr
            820                 825                 830
Arg Arg Asp Leu Ser Asn Trp Asp Ile Glu Val Gln Asp Trp Val Val
        835                 840                 845
Ser Glu His Lys Lys Thr Ala Phe Val Gly Lys Ser Ser Arg Lys Leu
    850                 855                 860
Asp Leu Lys Ile Glu Leu Pro
865                 870

<210> SEQ ID NO 17
<211> LENGTH: 16
<212> TYPE: PRT
<213> ORGANISM: Chaetomium globosum
<220> FEATURE:
<221> NAME/KEY: misc_feature
<222> LOCATION: (1)..(16)
<223> OTHER INFORMATION: native signal peptide - beta-glucosidase

<400> SEQUENCE: 17

Met Lys Ala Ala Thr Ala Leu Ser Cys Leu Ala Gly Gly Ser Leu Ala
1               5                   10                  15

<210> SEQ ID NO 18
<211> LENGTH: 2667
<212> TYPE: DNA
<213> ORGANISM: Chaetomium globosum
<220> FEATURE:
<221> NAME/KEY: misc_feature
<222> LOCATION: (1)..(2667)
<223> OTHER INFORMATION: beta-glucosidase

<400> SEQUENCE: 18
atgaaagctg ctactgcgct ttcctgcctc gctggcggca gtcttgctgc tgctgggacc      60
attaatccag ctaacaagat acagaaaagg gctttgcaaa cctcagatcc acactaccca     120
tctccttgga tgaaccctga cgcagacgga tgggctgagg cttatgccca agcaagagac     180
```

```
tttgtgtcac aattaacatt accagagaaa gtgaacttga ctactggtgt tggctggcaa      240
ggtgaacaat gtgtcggcca aacaggtgca atcccaagat ttggccttcg ttctctgtgt      300
atgcatgatg ctccattggg cattaggggt tctgactaca actcagcttt cccttctgga      360
caaacagctg cagccacttg ggatagaggc taatgtata dacgagggta cgctatgggc       420
aaggaggcta aggtaaggg tattaatgtc ttattgggac cagtagcagg tccactggga       480
cgaatgccag ctgcaggtag aaattgggaa ggatttgcac ctgatccagt gcttacaggc      540
gttggcatgt ctgagactgt taagggtaca caagatgccg gagtagtcgc ctgtgccaaa      600
cactttatcg gtaacgagca agagaatttc agacaagtgg gcgaagctca aggatacggg      660
cataacattt cagaaaccct aagctctaat atcgatgata agaccatgca tgaactatac      720
ttgtggccat tgctgacgc agtacgagcg ggtgttggat ctgttatgtg cagttatcaa       780
caggttaata actcctatgg atgtcaaaat tcaaaacttt tgaatgattt gctcaaaaat      840
gaactgggct ttcaaggttt cgtgatgagc gattggcaag ctcaacacac aggtgctgca      900
tctgcggtcg ctggtttgga tatgacgatg cctggtgaca catctttcaa cacaggtctt      960
tccttttggg gtacaaatct gactttggca gtcttaaacg gaacagttcc agcataccgt     1020
gttgacgata tggccatgag aattatggcc tctattttca agtaagtaa gactacggat     1080 ttcgacccta tcaacttctc tttttggacc ctagatactt atggtccagt ccattgggtg     1140
gccaaggagg gttaccagga aattaactct catgttgacg ttagagaaga tcacggcaaa     1200
ctcataagag aaatcgctgc aaagggtaca gtgttactta aaactcagg tgccctgcca      1260 ttgcagaaac caaaatttgt ggccgtcatt ggtgaggacg ctggtggtaa tccaaatggt     1320
cctaacggtt gttctgacag aggttgcgat gatggaacat tagcaatggg gtggggctct     1380
ggaactgcaa actttcctta cctagtgact cctgatgcag cattgcaagc tagagcaata     1440
gaagatggat ctaggtacga aagtatctta tcaaattacg ctcatgataa acagacgct      1500 ctagtttcac aagccaatgt tacggctatt gtatttgtta atgccgacag cggtgaaggt     1560
tacatcaatg tagatggaaa tatgggcgac agaaagaatc ttaccctatg gaaaaatggc     1620
gacgatctag ttaaaagagt gtctggggcg tgttctaata ccattgttgt tattcattca     1680
acaggacctg tgctgctaac cgaatggtat gaatcaccaa acataactgc catcttgtgg     1740
gcaggactcc ctggtcagga atcaggtaac tcaatagctg atgtacttta cggcgatgtg     1800
aaccctgcag ctaggagtcc ttttacttgg ggaaaaacta gagaatccta cggtgccgat     1860
gtgctttatg agcctaataa tggtaacggt gcccctcaac aagatttctc tgaaggtgtt     1920
ttcatcgatt acagatactt tgataaacaa aatagtagcg taatctacga atttgggcat     1980
ggcctgagtt acacaacatt tgaatatagc aatatcagag tagaaaaatc taatgcgggt     2040
gaatacaaac caactactgg ttcaactgct gctgccccta cattcggaaa cttctcaact     2100
gatttgaaag actacttatt cccaaaggaa gattttttcct atatctacca gtacattttat    2160 ccatacgtca acacaactga cgccaaaaag gcatccgccg atccacatta cggtcaaact     2220
gcggaagagt ttctccctcc acatgtcttg gatgcggatg cacaaccact tttaagatca     2280
tccggtggga actctccagg gggtaacaga caattgtacg atataatgta cacgatcaca     2340
gctgatatca ctaatacagg agccatagtc ggcgaagagg ttccacagct atatgtttcc     2400
ttgggcggtc cagaagatcc aaaggttcaa cttagagatt ttgatagaat gagaatcgac     2460
ccaggggaaa ctaaacaatt cacaggaaga ttaacacgta gagatttgtc taattgggat     2520
attgaagtac aggattgggt agtttcagag cataagaaaa cagcttttgt cggcaagtcc     2580
```

```
agcagaaagt tggacttaaa gatcgaattg ccagatgatg atgacaaagg tggttctcct    2640
ccttctcatc atcaccacca ccactaa                                       2667
```

<210> SEQ ID NO 19
<211> LENGTH: 786
<212> TYPE: PRT
<213> ORGANISM: Neocallimastix frontalis
<220> FEATURE:
<221> NAME/KEY: misc_feature
<222> LOCATION: (1)..(786)
<223> OTHER INFORMATION: beta-glucosidase

<400> SEQUENCE: 19

```
Met Asn Arg Ser Ser Gln Val Ser Tyr Gln Leu Leu Leu Phe Phe Leu
1               5                   10                  15

Ser Ala Asn Thr Leu Ala Met Thr Trp Glu Glu Ala Asp Ala Lys Ala
            20                  25                  30

Arg Glu Trp Cys Ala Asp Leu Thr Asn Glu Lys Ile Ser Leu Val
        35                  40                  45

Thr Gly Arg Glu Asn Met Thr Gly Val Cys Val Gly Ser Ile Asp Pro
    50                  55                  60

Ile Glu Arg Lys Gly Phe Lys Gly Leu Cys Leu Gln Asp Gly Pro Ala
65                  70                  75                  80

Gly Val Arg Phe Ala Lys Gly Thr Ala Thr Ser Trp Gln Ala Gly Ile
                85                  90                  95

Asn Asn Ala Ala Thr Phe Asp Arg Gln Leu Met Arg Lys Val Gly Glu
            100                 105                 110

Ala Gln Gly Asn Glu Phe Tyr Gln Arg Gly Ile Asn Phe Ala Leu Gly
        115                 120                 125

Pro Ala Met Asn Ile Gln Arg Ala Pro Ala Ala Gly Arg Ile Trp Glu
    130                 135                 140

Ser Phe Gly Glu Asp Pro Phe Leu Ala Gly Gln Cys Gly Ile Glu Val
145                 150                 155                 160

Val Lys Gly Met Gln Ser Ser Gly Val Ile Ala Thr Ser Lys His Phe
                165                 170                 175

Val Gly Asn Asp Gln Glu Asn Asn Arg Gly Ala Ser Ser Asn Ile
            180                 185                 190

Pro Glu Gln Ala Leu Trp Glu Val Tyr Ile Glu Pro Phe Tyr Arg Val
        195                 200                 205

Val Lys Glu Ala Glu Thr Asn Ala Ile Met Ser Ser Tyr Asn Ala Val
    210                 215                 220

Asn Gly Thr Tyr Leu Val Gln Asn Lys Arg Leu Leu Thr Asp Val Leu
225                 230                 235                 240

Lys Gly Lys Leu Gly Phe Gln Gly Met Val Met Ser Asp Trp Trp Ser
                245                 250                 255

Ile Tyr Asp Val Glu Lys Ser Phe Gly Ala Gly Met Asp Met Asn Met
            260                 265                 270

Pro Gly Gly Lys Tyr Trp Gly Pro Asp Tyr Val Gly Asp Ser Phe Trp
        275                 280                 285

Gly Glu His Ile Gln Glu Cys Ile Asp Asn Gly Val Phe Pro Gln Glu
    290                 295                 300

Arg Leu Asp Asp Ala Ala Leu Arg Ile Ile Arg Thr Leu Tyr Lys Ala
305                 310                 315                 320

Gly Gln Met Glu Asp Tyr Pro Asp Val Asn Leu Tyr Val Asp Thr Asn
                325                 330                 335
```

-continued

```
Asn Glu Glu Asn Thr Ala Leu Asn Arg Lys Val Ala Ala Asp Ser Thr
            340                 345                 350
Val Leu Leu Lys Asn Glu Ala Val Leu Pro Ile Lys Gly Val Lys Lys
            355                 360                 365
Ile Ala Ile Ile Gly Lys Asp Ala Met Pro Ala Asn Phe Cys Glu Asp
370                 375                 380
Met Lys Cys Ala Asp Gly Thr Val Ala Leu Gly Trp Gly Ser Gly Thr
385                 390                 395                 400
Thr Asp Phe Lys Tyr Val Ala Asp Pro Leu Ser Ser Ile Thr Glu Arg
                405                 410                 415
Ala Lys Lys Asp Asn Ile Glu Ile Val Ser Ser Gly Glu Asp Asp Ala
            420                 425                 430
Glu Ala Gly Ala Glu Val Ala Lys Asp Ala Asp Leu Ala Ile Val Phe
            435                 440                 445
Val Gln Ala Asp Ser Gly Glu Glu Tyr Ile Val Val Glu Gly Asn Lys
            450                 455                 460
Gly Asp Arg Leu Asn Leu Asp Leu Trp His Asn Gly Asn Glu Leu Val
465                 470                 475                 480
Asp Ala Val Ala Ser Val Asn Glu Asn Thr Ile Val Val Ile His Ala
                485                 490                 495
Pro Gly Pro Val Asn Val Pro Phe Leu Asp Lys Val Lys Gly Ile Val
            500                 505                 510
Phe Ala Gly Met Pro Gly Gln Glu Ser Gly Asn Ala Ile Ala Asp Val
            515                 520                 525
Leu Phe Gly Asp Val Asn Pro Ser Gly His Leu Pro Tyr Thr Trp Ala
530                 535                 540
Pro Arg Glu Asp Phe Pro Thr Asp Val Asn Tyr Asp Pro Ser Leu Pro
545                 550                 555                 560
Gly Gly Gly Glu Glu Lys Thr Gln Tyr Asp Tyr Asn Glu Gly Leu Phe
                565                 570                 575
Val Gly Tyr Arg Trp Phe Asp Lys Gln Gly Ile Asp Pro Thr Phe Ala
            580                 585                 590
Phe Gly Tyr Gly Leu Ser Tyr Thr Thr Phe Glu Tyr Ser Asn Leu Lys
            595                 600                 605
Ala Gln Met Glu Glu Asp Gly Leu His Val Thr Leu Thr Val Ser Asn
            610                 615                 620
Thr Gly Asp Val Ala Gly Ala Ala Val Pro Met Ile Phe Leu Ser Phe
625                 630                 635                 640
Pro Asp Val Val Lys Asp Tyr Pro Ser Arg Leu Phe Lys Gly Phe Asp
                645                 650                 655
Lys Val Leu Leu Glu Ala Gly Glu Ser Lys Glu Val Lys Ile Leu Val
            660                 665                 670
Asp Asn His Asp Leu Ser Tyr Tyr Asp Val Asp Ala Ala Asp Phe Val
            675                 680                 685
Lys Pro Ala Glu Gly Glu Tyr Thr Val Leu Ala Gly Ser Asn Ala Arg
            690                 695                 700
Asp Leu Pro Leu Lys Val Thr Val Ser Ala Asp Gly Thr Asn Ala Gly
705                 710                 715                 720
Asn Ala Glu Glu Val Thr Glu Glu Cys Ser Ser Glu Glu Glu Glu Val
                725                 730                 735
Thr Gly Val Asn Gly Asp Asp Val Thr Ala Glu Asp Ser Ala Glu Asp
            740                 745                 750
```

```
Asp Val Gln Glu Ile Asp Ala Asp Ala Glu Val Glu Glu Ala Glu Asp
            755                 760                 765
Ser Ala Asn Glu Ala Asp Glu Ala Glu Leu Arg Lys Arg Ala Tyr Lys
        770                 775                 780
Leu Tyr
785

<210> SEQ ID NO 20
<211> LENGTH: 22
<212> TYPE: PRT
<213> ORGANISM: Neocallimastix frontalis
<220> FEATURE:
<221> NAME/KEY: misc_feature
<222> LOCATION: (1)..(22)
<223> OTHER INFORMATION: native signal peptide - beta-glucosidase

<400> SEQUENCE: 20

Met Asn Arg Ser Ser Gln Val Ser Tyr Gln Leu Leu Leu Phe Phe Leu
1               5                   10                  15
Ser Ala Asn Thr Leu Ala
            20

<210> SEQ ID NO 21
<211> LENGTH: 2820
<212> TYPE: DNA
<213> ORGANISM: Neocallimastix frontalis
<220> FEATURE:
<221> NAME/KEY: misc_feature
<222> LOCATION: (1)..(2820)
<223> OTHER INFORMATION: beta-glucosidase

<400> SEQUENCE: 21
```

| | | | | | |
|---|---|---|---|---|---|
| atgcttttgc | aagctttcct | tttcctttg | gctggttttg | cagccaaaat | atctgcaatc | 60 |
| actaaaaggt | gcttgcatat | cttgaacaga | aaatgtacac | gtatccattt | ttcctctgtg | 120 |
| tctttcctca | atatggaatt | tgatccagat | cataattact | tagtatttgt | cgatatcaaa | 180 |
| ggtggcccat | cttgcaagtc | aaccaataac | tgtaagaaaa | ctacgggtta | ttatcacatt | 240 |
| gttcaattgc | ttattatgtc | tgagttcaat | atagagagca | cactggctca | acttacatta | 300 |
| caggaaaaga | ttggcttact | tgctgggatc | gattttggc | ataccttcgc | tgttgaaaga | 360 |
| ttgaatattc | catccctgag | attttccgat | ggccctaatg | gcttgagagg | gacaaagttt | 420 |
| ttcgactccg | tgccttcagc | ctgtttccca | tgtggtacgg | ctttggctgc | cacttttgat | 480 |
| aaagagttgt | tatttgaggc | aggtcgattg | atgggcgacg | aagctaaaca | taagggcgca | 540 |
| caagttgtct | tgggaccaac | aatgaatatc | caaagagggc | ctttgggtgg | aagaggcttc | 600 |
| gagtctttct | ctgaagatgc | gcacttaaca | ggtcaatcag | ctgcctcaat | tatcaatggc | 660 |
| atacaagaca | agggaattgc | tgctacaatt | aaacattttg | tctgcaatga | cttagaggat | 720 |
| caacgtaact | cttcagatag | cattttaacg | gaaagagcgc | tcagagaaat | ctacctagag | 780 |
| ccattcagat | tagcaatcaa | acattcaaac | ccagttgcac | ttatgacagg | ttacaacaag | 840 |
| gttaatggag | agcacgtgag | ccaatctgaa | agacttatcc | aagatatcct | gagaaaagag | 900 |
| tgggactggg | atggtacaac | aatgtccgac | tggtacggaa | cttacacttc | taaagaggct | 960 |
| atagaaaatg | gacttgacat | agaaatgcca | ggtccatcc | tctttagaaa | tcagtccgaa | 1020 |
| gtagccgcta | tggtaaccac | caaagagttg | cacatcaaaa | agattgatga | agagttact | 1080 |
| aatgtcttaa | agttgatcaa | atacgctctg | aagtctggag | tgccagaaaa | tgctccagaa | 1140 |
| actagcaacg | gcaatacacc | agagactgca | gccctactga | gaaagctggc | tcatgattct | 1200 |

```
gtcgttctat tgaaaaacga caataatgtt ctgcctttat ctaaagacga caaaattgcc    1260
gtaatcggtc caaatgcaaa attcgccgca tattgtggtg gaggctctgc atctctgaga    1320
gcgtactaca cgacaacccc atttgattca atctctaaaa agctcaataa ggacccagaa    1380
tacactattg gtgcatacgg tcacagattg ctacctgcct tgggcccaca actggttaat    1440
cctaaaacgg gcaacgccgg ttataacttg aaatactact tggaaccaaa atccacaagc    1500
gagagaacct taattgatga acgtgatctt gacctgtcta acatctttct cgttgactac    1560
tacaataaga aaatcaagga tgatttgttt ttcatcgatt ttgatgggca attcactcca    1620
gaagagacag ctgattacga gtttggcctg cagtcttgg gaaccgctca attgtttgtt     1680
gatggtaagt tggttgtaga taacaaaaca gtccagcaga gaggtaatag tttctttaac    1740
tcaggtagta acgaggttag gaactctatt agtcttgaga agggaaaaac atattctata    1800
aagatagaat ttggctcagc tccaacattc acagttccat ctcatgactc agtgtcattt    1860
ggaggaggtg gaggtattaa tcttggatta gctaaagtga tcaatcctaa ggacgaaatt    1920
gctaaagccg cagaacttgc gaagaaagtt gacaaagtag tcctgaacat aggtttgaac    1980
caggaatggg aaagtgaagg tttcgataga ccagatatga aattgatagg ccatatcaat    2040
gaacttgttg atgctgtctt ggacgcaaat ccaaatacgg tagtcgttaa tcaatctgga    2100
actccagttg agttcccttg gatcaaaaag gctaatgcgc tcgttcaagc atggtacggt    2160
ggtaatgaat taggtaatgg aatagcagac gtgttgttcg gcgatgtgaa cccttcaggc    2220
aaactatctc tctcatttcc tgtcaaaaat gtggataacc ctgcatacct aactttaaa    2280 actgagaagg gcagagtttt gtacggtgag gacatcttcg ttggctataa gtattatgaa    2340
aagctagaac gtgaagttgc cttctccttc ggattcggct tgagttatac aaagtttgat    2400
atatccggta gtaaagtctc cgtggatgaa aaggatgata acttgactgt gtcagtgaac    2460
gtgaaaaaca caggtaaaat cgacggatca gaggtagttc agttttacat ctccaaagat    2520
gaatctgatg taattagacc agtgaaggaa ctaaaaggat tgaaaaggt acatctcaag    2580 gctggagctg attctactgt ttcactgaaa ttaagcctca aggattctat ttcattttc    2640 gatgaatacc aagacgaatg gtcagttgag aaaggtgatt acaaagtgca tgtaggtaat    2700
tcaagcgata atatcacttc aactttgcct tttaagatcg aaaaggactt cctctggtct    2760
ggtatggatg atgatgacaa aggtggttct cctccttctc atcatcacca ccaccactaa    2820
```

<210> SEQ ID NO 22
<211> LENGTH: 922
<212> TYPE: PRT
<213> ORGANISM: Debaryomyces hansenii
<220> FEATURE:
<221> NAME/KEY: misc_feature
<222> LOCATION: (1)..(922)
<223> OTHER INFORMATION: beta-glucosidase

<400> SEQUENCE: 22

Met Leu Leu Gln Ala Phe Leu Phe Leu Leu Ala Gly Phe Ala Ala Lys
1               5                   10                  15

Ile Ser Ala Ile Thr Lys Arg Cys Leu His Ile Leu Asn Arg Lys Cys
            20                  25                  30

Thr Arg Ile His Phe Ser Ser Val Ser Phe Leu Asn Met Glu Phe Asp
        35                  40                  45

Pro Asp His Asn Tyr Leu Val Phe Val Asp Ile Lys Gly Gly Pro Ser
    50                  55                  60

Cys Lys Ser Thr Asn Asn Cys Lys Lys Thr Thr Gly Tyr Tyr His Ile

```
                65                  70                  75                  80
Val Gln Leu Leu Ile Met Ser Glu Phe Asn Ile Glu Ser Thr Leu Ala
                        85                  90                  95

Gln Leu Thr Leu Gln Glu Lys Ile Gly Leu Ala Gly Ile Asp Phe
            100                 105                 110

Trp His Thr Phe Ala Val Glu Arg Leu Asn Ile Pro Ser Leu Arg Phe
            115                 120                 125

Ser Asp Gly Pro Asn Gly Leu Arg Gly Thr Lys Phe Phe Asp Ser Val
    130                 135                 140

Pro Ser Ala Cys Phe Pro Cys Gly Thr Ala Leu Ala Ala Thr Phe Asp
145                 150                 155                 160

Lys Glu Leu Leu Phe Glu Ala Gly Arg Leu Met Gly Asp Glu Ala Lys
                165                 170                 175

His Lys Gly Ala Gln Val Val Leu Gly Pro Thr Met Asn Ile Gln Arg
            180                 185                 190

Gly Pro Leu Gly Gly Arg Gly Phe Glu Ser Phe Ser Glu Asp Ala His
            195                 200                 205

Leu Thr Gly Gln Ser Ala Ala Ser Ile Ile Asn Gly Ile Gln Asp Lys
    210                 215                 220

Gly Ile Ala Ala Thr Ile Lys His Phe Val Cys Asn Asp Leu Glu Asp
225                 230                 235                 240

Gln Arg Asn Ser Ser Asp Ser Ile Leu Thr Glu Arg Ala Leu Arg Glu
                245                 250                 255

Ile Tyr Leu Glu Pro Phe Arg Leu Ala Ile Lys His Ser Asn Pro Val
            260                 265                 270

Ala Leu Met Thr Gly Tyr Asn Lys Val Asn Gly Glu His Val Ser Gln
            275                 280                 285

Ser Glu Arg Leu Ile Gln Asp Ile Leu Arg Lys Glu Trp Asp Trp Asp
    290                 295                 300

Gly Thr Thr Met Ser Asp Trp Tyr Gly Thr Tyr Thr Ser Lys Glu Ala
305                 310                 315                 320

Ile Glu Asn Gly Leu Asp Ile Glu Met Pro Gly Pro Ser Ile Phe Arg
                325                 330                 335

Asn Gln Ser Glu Val Ala Ala Met Val Thr Thr Lys Glu Leu His Ile
            340                 345                 350

Lys Lys Ile Asp Glu Arg Val Thr Asn Val Leu Lys Leu Ile Lys Tyr
            355                 360                 365

Ala Leu Lys Ser Gly Val Pro Glu Asn Ala Pro Glu Thr Ser Asn Gly
    370                 375                 380

Asn Thr Pro Glu Thr Ala Ala Leu Leu Arg Lys Leu Ala His Asp Ser
385                 390                 395                 400

Val Val Leu Leu Lys Asn Asp Asn Val Leu Pro Leu Ser Lys Asp
                405                 410                 415

Asp Lys Ile Ala Val Ile Gly Pro Asn Ala Lys Phe Ala Tyr Cys
            420                 425                 430

Gly Gly Gly Ser Ala Ser Leu Arg Ala Tyr Tyr Thr Thr Pro Phe
            435                 440                 445

Asp Ser Ile Ser Lys Lys Leu Asn Lys Asp Pro Glu Tyr Thr Ile Gly
    450                 455                 460

Ala Tyr Gly His Arg Leu Leu Pro Ala Leu Gly Pro Gln Leu Val Asn
465                 470                 475                 480

Pro Lys Thr Gly Asn Ala Gly Tyr Asn Leu Lys Tyr Tyr Leu Glu Pro
                485                 490                 495
```

```
Lys Ser Thr Ser Glu Arg Thr Leu Ile Asp Glu Arg Asp Leu Asp Leu
            500                 505                 510

Ser Asn Ile Phe Leu Val Asp Tyr Asn Lys Lys Ile Lys Asp Asp
        515                 520                 525

Leu Phe Phe Ile Asp Phe Asp Gly Gln Phe Thr Pro Glu Glu Thr Ala
    530                 535                 540

Asp Tyr Glu Phe Gly Leu Ala Val Leu Gly Thr Ala Gln Leu Phe Val
545                 550                 555                 560

Asp Gly Lys Leu Val Val Asp Asn Lys Thr Val Gln Gln Arg Gly Asn
            565                 570                 575

Ser Phe Phe Asn Ser Gly Ser Asn Glu Val Arg Asn Ser Ile Ser Leu
        580                 585                 590

Glu Lys Gly Lys Thr Tyr Ser Ile Lys Ile Glu Phe Gly Ser Ala Pro
    595                 600                 605

Thr Phe Thr Val Pro Ser His Asp Ser Val Ser Phe Gly Gly Gly Gly
    610                 615                 620

Gly Ile Asn Leu Gly Leu Ala Lys Val Ile Asn Pro Lys Asp Glu Ile
625                 630                 635                 640

Ala Lys Ala Ala Glu Leu Ala Lys Lys Val Asp Lys Val Val Leu Asn
            645                 650                 655

Ile Gly Leu Asn Gln Glu Trp Glu Ser Glu Gly Phe Asp Arg Pro Asp
        660                 665                 670

Met Lys Leu Ile Gly His Ile Asn Glu Leu Val Asp Ala Val Leu Asp
    675                 680                 685

Ala Asn Pro Asn Thr Val Val Asn Gln Ser Gly Thr Pro Val Glu
    690                 695                 700

Phe Pro Trp Ile Lys Lys Ala Asn Ala Leu Val Gln Ala Trp Tyr Gly
705                 710                 715                 720

Gly Asn Glu Leu Gly Asn Gly Ile Ala Asp Val Leu Phe Gly Asp Val
            725                 730                 735

Asn Pro Ser Gly Lys Leu Ser Leu Ser Phe Pro Val Lys Asn Val Asp
        740                 745                 750

Asn Pro Ala Tyr Leu Asn Phe Lys Thr Glu Lys Gly Arg Val Leu Tyr
    755                 760                 765

Gly Glu Asp Ile Phe Val Gly Tyr Lys Tyr Tyr Glu Lys Leu Glu Arg
    770                 775                 780

Glu Val Ala Phe Pro Phe Gly Phe Gly Leu Ser Tyr Thr Lys Phe Asp
785                 790                 795                 800

Ile Ser Gly Ser Lys Val Ser Val Asp Glu Lys Asp Asp Asn Leu Thr
            805                 810                 815

Val Ser Val Asn Val Lys Asn Thr Gly Lys Ile Asp Gly Ser Glu Val
        820                 825                 830

Val Gln Phe Tyr Ile Ser Lys Asp Glu Ser Asp Val Ile Arg Pro Val
    835                 840                 845

Lys Glu Leu Lys Gly Phe Glu Lys Val His Leu Lys Ala Gly Ala Asp
    850                 855                 860

Ser Thr Val Ser Leu Lys Leu Ser Leu Lys Asp Ser Ile Ser Phe Phe
865                 870                 875                 880

Asp Glu Tyr Gln Asp Glu Trp Ser Val Glu Lys Gly Asp Tyr Lys Val
            885                 890                 895

His Val Gly Asn Ser Ser Asp Asn Ile Thr Ser Thr Leu Pro Phe Lys
        900                 905                 910
```

```
Ile Glu Lys Asp Phe Leu Trp Ser Gly Met
        915                 920
```

```
<210> SEQ ID NO 23
<211> LENGTH: 19
<212> TYPE: PRT
<213> ORGANISM: Debaryomyces hansenii
<220> FEATURE:
<221> NAME/KEY: misc_feature
<222> LOCATION: (1)..(19)
<223> OTHER INFORMATION: native signal peptide - beta-glucosidase

<400> SEQUENCE: 23
```

```
Met Leu Leu Gln Ala Phe Leu Phe Leu Leu Ala Gly Phe Ala Ala Lys
1               5                   10                  15

Ile Ser Ala
```

```
<210> SEQ ID NO 24
<211> LENGTH: 2820
<212> TYPE: DNA
<213> ORGANISM: Debaryomyces hansenii
<220> FEATURE:
<221> NAME/KEY: misc_feature
<222> LOCATION: (1)..(2820)
<223> OTHER INFORMATION: beta-glucosidase

<400> SEQUENCE: 24
```

| | | | | | |
|---|---|---|---|---|---|
| atgcttttgc | aagctttcct | tttccttttg | gctggttttg | cagccaaaat | atctgcaatc | 60 |
| actaaaaggt | gcttgcatat | cttgaacaga | aaatgtacac | gtatccattt | ttcctctgtg | 120 |
| tctttcctca | atatggaatt | tgatccagat | cataattact | tagtatttgt | cgatatcaaa | 180 |
| ggtggcccat | cttgcaagtc | aaccaataac | tgtaagaaaa | ctacgggtta | ttatcacatt | 240 |
| gttcaattgc | ttattatgtc | tgagttcaat | atagagagca | cactggctca | acttacatta | 300 |
| caggaaaaga | ttggcttact | tgctgggatc | gattttggc | ataccttcgc | tgttgaaaga | 360 |
| ttgaatattc | catccctgag | attttccgat | ggccctaatg | gcttgagagg | gacaaagttt | 420 |
| ttcgactccg | tgccttcagc | ctgtttccca | tgtggtacgg | cttttggctgc | cacttttgat | 480 |
| aaagagttgt | tatttgaggc | aggtcgattg | atgggcgacg | aagctaaaca | taagggcgca | 540 |
| caagttgtct | tgggaccaac | aatgaatatc | aaagagggc | ctttgggtgg | aagaggcttc | 600 |
| gagtctttct | ctgaagatgc | gcacttaaca | ggtcaatcag | ctgcctcaat | tatcaatggc | 660 |
| atacaagaca | agggaattgc | tgctacaatt | aaacattttg | tctgcaatga | cttagaggat | 720 |
| caacgtaact | cttcagatag | cattttaacg | gaaagagcgc | tcagagaaat | ctacctagag | 780 |
| ccattcagat | tagcaatcaa | acattcaaac | ccagttgcac | ttatgacagg | ttacaacaag | 840 |
| gttaatggag | agcacgtgag | ccaatctgaa | agacttatcc | aagatatcct | gagaaaagag | 900 |
| tgggactggg | atggtacaac | aatgtccgac | tggtacggaa | cttcacttc | taaagaggct | 960 |
| atagaaaatg | gacttgacat | agaaatgcca | ggtccatcca | tctttagaaa | tcagtccgaa | 1020 |
| gtagccgcta | tggtaaccac | caaagagttg | cacatcaaaa | agattgatga | agagttact | 1080 |
| aatgtcttaa | agttgatcaa | atacgctctg | aagtctggag | tgccagaaaa | tgctccagaa | 1140 |
| actagcaacg | gcaatacacc | agagactgca | gccctactga | aaagctggc | tcatgattct | 1200 |
| gtcgttctat | tgaaaaacga | caataatgtt | ctgcctttat | ctaaagacga | caaaattgcc | 1260 |
| gtaatcggtc | caaatgcaaa | attgccgca | tattgtggtg | gaggctctgc | atctctgaga | 1320 |
| gcgtactaca | cgacaacccc | atttgattca | atctctaaaa | agctcaataa | ggacccagaa | 1380 |
| tacactattg | gtgcatacgg | tcacagattg | ctacctgcct | tgggcccaca | actggttaat | 1440 |

```
cctaaaacgg gcaacgccgg ttataacttg aaatactact tggaaccaaa atccacaagc   1500
gagagaacct taattgatga acgtgatctt gacctgtcta acatctttct cgttgactac   1560
tacaataaga aaatcaagga tgatttgttt tcatcgatt ttgatgggca attcactcca    1620
gaagagacag ctgattacga gtttggcctg gcagtcttgg gaaccgctca attgtttgtt   1680
gatggtaagt tggttgtaga taacaaaaca gtccagcaga gaggtaatag tttctttaac   1740
tcaggtagta acgaggttag gaactctatt agtcttgaga agggaaaaac atattctata   1800
aagatagaat ttggctcagc tccaacattc acagttccat ctcatgactc agtgtcattt   1860
ggaggaggtg gaggtattaa tcttggatta gctaaagtga tcaatcctaa ggacgaaatt   1920
gctaaagccg cagaacttgc gaagaaagtt gacaaagtag tcctgaacat aggtttgaac   1980
caggaatggg aaagtgaagg tttcgataga ccagatatga aattgatagg ccatatcaat   2040
gaacttgttg atgctgtctt ggacgcaaat ccaaatacgg tagtcgttaa tcaatctgga   2100
actccagttg agttcccttg gatcaaaaag gctaatgcgc tcgttcaagc atggtacggt   2160
ggtaatgaat taggtaatgg aatagcagac gtgttgttcg gcgatgtgaa cccttcaggc   2220
aaactatctc tctcatttcc tgtcaaaaat gtggataacc ctgcatacct taactttaaa   2280
actgagaagg gcagagtttt gtacggtgag gacatcttcg ttggctataa gtattatgaa   2340
aagctagaac gtgaagttgc ctttcctttc ggattcggct tgagttatac aaagtttgat   2400
atatccggta gtaaagtctc cgtggatgaa aaggatgata acttgactgt gtcagtgaac   2460
gtgaaaaaca caggtaaaat cgacggatca gaggtagttc agttttacat ctccaaagat   2520
gaatctgatg taattagacc agtgaaggaa ctaaaaggat ttgaaaaggt acatctcaag   2580
gctggagctg attctactgt ttcactgaaa ttaagcctca aggattctat ttcatttttc   2640
gatgaatacc aagacgaatg gtcagttgag aaaggtgatt acaaagtgca tgtaggtaat   2700
tcaagcgata atatcacttc aactttgcct tttaagatcg aaaaggactt cctctggtct   2760
ggtatggatg atgatgacaa aggtggttct cctccttctc atcatcacca ccaccactaa   2820
```

<210> SEQ ID NO 25
<211> LENGTH: 863
<212> TYPE: PRT
<213> ORGANISM: Kluyveromyces marxianus
<220> FEATURE:
<221> NAME/KEY: misc_feature
<222> LOCATION: (1)..(863)
<223> OTHER INFORMATION: beta-glucosidase

<400> SEQUENCE: 25

```
Met Leu Leu Gln Ala Phe Leu Phe Leu Ala Gly Phe Ala Ala Lys
1               5                   10                  15

Ile Ser Ala Ser Lys Phe Asp Val Glu Gln Leu Leu Ser Glu Leu Asn
            20                  25                  30

Gln Asp Glu Lys Ile Ser Leu Leu Ser Ala Val Asp Phe Trp His Thr
        35                  40                  45

Lys Lys Ile Glu Arg Leu Gly Ile Pro Ala Val Arg Val Ser Asp Gly
    50                  55                  60

Pro Asn Gly Ile Arg Gly Thr Lys Phe Phe Asp Gly Val Pro Ser Gly
65                  70                  75                  80

Cys Phe Pro Asn Gly Thr Gly Leu Ala Ser Thr Phe Asp Arg Asp Leu
                85                  90                  95

Leu Glu Thr Ala Gly Lys Leu Met Ala Lys Glu Ser Ile Ala Lys Asn
            100                 105                 110
```

-continued

```
Ala Ala Val Ile Leu Gly Pro Thr Thr Asn Met Gln Arg Gly Pro Leu
        115                 120                 125
Gly Gly Arg Gly Phe Glu Ser Phe Ser Glu Asp Pro Tyr Leu Ala Gly
    130                 135                 140
Met Ala Thr Ser Ser Val Val Lys Gly Met Gln Gly Glu Gly Ile Ala
145                 150                 155                 160
Ala Thr Val Lys His Phe Val Cys Asn Asp Leu Glu Asp Gln Arg Phe
                165                 170                 175
Ser Ser Asn Ser Ile Val Ser Glu Arg Ala Leu Arg Glu Ile Tyr Leu
            180                 185                 190
Glu Pro Phe Arg Leu Ala Val Lys His Ala Asn Pro Val Cys Ile Met
        195                 200                 205
Thr Ala Tyr Asn Lys Val Asn Gly Asp His Cys Ser Gln Ser Lys Lys
    210                 215                 220
Leu Leu Ile Asp Ile Leu Arg Asp Glu Trp Lys Trp Asp Gly Met Leu
225                 230                 235                 240
Met Ser Asp Trp Phe Gly Thr Tyr Thr Thr Ala Ala Ile Lys Asn
                245                 250                 255
Gly Leu Asp Ile Glu Phe Pro Gly Pro Thr Arg Trp Arg Thr Arg Ala
            260                 265                 270
Leu Val Ser His Ser Leu Asn Ser Arg Glu Gln Ile Thr Thr Glu Asp
        275                 280                 285
Val Asp Asp Arg Val Arg Gln Val Leu Lys Met Ile Lys Phe Val Val
    290                 295                 300
Asp Asn Leu Glu Lys Thr Gly Ile Val Glu Asn Gly Pro Glu Ser Thr
305                 310                 315                 320
Ser Asn Asn Thr Lys Glu Thr Ser Asp Leu Leu Arg Glu Ile Ala Ala
                325                 330                 335
Asp Ser Ile Val Leu Leu Lys Asn Lys Asn Asn Tyr Leu Thr Ser Lys
            340                 345                 350
Glu Arg Arg Gln Tyr His Val Ile Gly Pro Asn Ala Lys Ala Lys Thr
        355                 360                 365
Ser Ser Gly Gly Gly Ser Ala Ser Met Asn Ser Tyr Tyr Val Val Ser
    370                 375                 380
Pro Tyr Glu Gly Ile Val Asn Lys Leu Gly Lys Glu Val Asp Tyr Thr
385                 390                 395                 400
Val Gly Ala Tyr Ser His Lys Ser Ile Gly Gly Leu Ala Glu Ser Ser
                405                 410                 415
Leu Ile Asp Ala Ala Lys Pro Ala Asp Ala Glu Asn Ala Gly Leu Ile
            420                 425                 430
Ala Lys Phe Tyr Ser Asn Pro Val Glu Glu Arg Ser Glu Asp Glu Glu
        435                 440                 445
Pro Phe His Val Thr Lys Val Asn Arg Ser Asn Val His Leu Phe Asp
    450                 455                 460
Phe Lys His Glu Lys Val Asp Pro Lys Asn Pro Tyr Phe Phe Val Thr
465                 470                 475                 480
Leu Thr Gly Gln Tyr Val Pro Gln Glu Asp Gly Asp Tyr Ile Phe Ser
                485                 490                 495
Leu Gln Val Tyr Gly Ser Gly Leu Phe Tyr Leu Asn Asp Glu Leu Ile
            500                 505                 510
Ile Asp Gln Lys His Asn Gln Glu Arg Gly Ser Phe Cys Phe Gly Ala
        515                 520                 525
```

```
Gly Thr Lys Glu Arg Thr Lys Lys Leu Thr Leu Lys Lys Gly Gln Val
    530                 535                 540
Tyr Asn Val Arg Val Glu Tyr Gly Ser Gly Pro Thr Ser Gly Leu Val
545                 550                 555                 560
Gly Glu Phe Gly Ala Gly Gly Phe Gln Ala Gly Val Ile Lys Ala Ile
                565                 570                 575
Asp Asp Asp Glu Glu Ile Arg Asn Ala Ala Glu Leu Ala Ala Lys His
            580                 585                 590
Asp Lys Ala Val Leu Ile Ile Gly Leu Asn Gly Glu Trp Glu Thr Glu
        595                 600                 605
Gly Tyr Asp Arg Glu Asn Met Asp Leu Pro Lys Arg Thr Asn Glu Leu
    610                 615                 620
Val Arg Ala Val Leu Lys Ala Asn Pro Asn Thr Val Ile Val Asn Gln
625                 630                 635                 640
Ser Gly Thr Pro Val Glu Phe Pro Trp Leu Glu Ala Asn Ala Leu
                645                 650                 655
Val Gln Ala Trp Tyr Gly Gly Asn Glu Leu Gly Asn Ala Ile Ala Asp
            660                 665                 670
Val Leu Tyr Gly Asp Val Val Pro Asn Gly Lys Leu Ser Leu Ser Trp
        675                 680                 685
Pro Phe Lys Leu Gln Asp Asn Pro Ala Phe Leu Asn Phe Lys Thr Glu
    690                 695                 700
Phe Gly Arg Val Val Tyr Gly Glu Asp Ile Phe Val Gly Tyr Arg Tyr
705                 710                 715                 720
Tyr Glu Lys Leu Gln Arg Lys Val Ala Phe Pro Phe Gly Tyr Gly Leu
                725                 730                 735
Ser Tyr Thr Thr Phe Glu Leu Asp Ile Ser Asp Phe Lys Val Thr Asp
            740                 745                 750
Asp Lys Ile Asp Ile Ser Val Asp Val Lys Asn Thr Gly Asp Lys Phe
        755                 760                 765
Ala Gly Ser Glu Val Val Gln Val Tyr Phe Ser Ala Leu Asn Ser Lys
    770                 775                 780
Val Ser Arg Pro Val Lys Glu Leu Lys Gly Phe Glu Lys Val His Leu
785                 790                 795                 800
Glu Pro Gly Glu Lys Lys Thr Val Asn Ile Glu Leu Glu Leu Lys Asp
                805                 810                 815
Ala Ile Ser Tyr Phe Asn Glu Leu Gly Lys Trp His Val Glu Ala
            820                 825                 830
Gly Glu Tyr Leu Val Ser Val Gly Thr Ser Ser Asp Asp Ile Leu Ser
        835                 840                 845
Val Lys Glu Phe Lys Val Glu Lys Asp Leu Tyr Trp Lys Gly Leu
    850                 855                 860

<210> SEQ ID NO 26
<211> LENGTH: 17
<212> TYPE: PRT
<213> ORGANISM: Kluyveromyces marxianus
<220> FEATURE:
<221> NAME/KEY: misc_feature
<222> LOCATION: (1)..(17)
<223> OTHER INFORMATION: native signal peptide - beta-glucosidase

<400> SEQUENCE: 26

Met Leu Leu Gln Ala Phe Leu Phe Leu Leu Ala Gly Phe Ala Ala Lys
1               5                   10                  15

Ile
```

<210> SEQ ID NO 27
<211> LENGTH: 2643
<212> TYPE: DNA
<213> ORGANISM: Kluyveromyces marxianus
<220> FEATURE:
<221> NAME/KEY: misc_feature
<222> LOCATION: (1)..(2643)
<223> OTHER INFORMATION: beta-glucosidase

<400> SEQUENCE: 27

| | | | | | |
|---|---|---|---|---|---|
| atgcttttgc | aagctttcct | tttccttttg | gctggttttg | cagccaaaat | atctgcatca | 60 |
| aaatttgatg | tcgaacaact | cttatctgaa | cttaatcagg | atgaaaagat | ttctcttctg | 120 |
| tctgccgttg | attttggca | tactaaaaag | atagaacgat | taggtatccc | tgctgttaga | 180 |
| gtctctgatg | ggcctaatgg | gatcaggggt | acaaaattct | tgacggtgt | accaagtggt | 240 |
| tgtttcccta | acggtacagg | tttggccagc | acttttgaca | gagacttact | agaaactgca | 300 |
| gggaagttga | tggctaaaga | gtctatcgct | aaaaatgccg | ctgttatatt | gggacctaca | 360 |
| acaaatatgc | aaagaggtcc | actaggtggc | agaggatttg | agagcttttc | agaagatcca | 420 |
| tacttggctg | gcatggcgac | ttcctcagta | gttaaaggta | tgcaaggcga | gggtattgca | 480 |
| gctacagtaa | agcactttgt | ttgcaatgac | ttagaagatc | aaagattcag | ctcaaatagt | 540 |
| attgtctctg | aaagagcgct | aagagaaata | taccttgaac | cttttagact | agctgttaaa | 600 |
| catgctaatc | cagtttgcat | catgacagct | tacaacaaag | ttaatggcga | tcactgttca | 660 |
| caatccaaaa | agctccttat | cgatatcttg | agagatgagt | ggaaatggga | tggcatgttg | 720 |
| atgtcagatt | ggttcggcac | ttatacaacc | gcagctgcca | tcaaaaatgg | gttagatatt | 780 |
| gaatttcctg | acctactcg | ttggagaaca | agggcattgg | tttctcactc | tttgaatagt | 840 |
| agagaacaaa | tcactacgga | agatgttgat | gatagggtgc | gacaagtttt | gaaaatgatc | 900 |
| aaatttgtgg | tagataattt | ggagaaaacc | ggtattgtag | aaaacggtcc | tgaatctact | 960 |
| tctaataaca | ctaaggagac | atctgacttg | ttgagagaaa | tagccgctga | ttcaatcgtc | 1020 |
| cttttgaaaa | acaaaaacaa | ttacctaacg | agtaaagaga | ggaggcaata | ccatgtaatt | 1080 |
| ggtccaaatg | cgaaagcaaa | gacctcttca | ggaggaggat | ctgcttcaat | gaactcatac | 1140 |
| tacgtggttt | ctccatacga | aggtatcgta | aacaaacttg | gtaaggaggt | tgattacacc | 1200 |
| gtaggtgcat | attcccacaa | atcaattggc | ggtcttgccg | aatcatctct | gattgacgcg | 1260 |
| gcaaagccag | cagacgctga | gaacgctggt | ttaattgcca | agttttactc | caatccagtc | 1320 |
| gaagagagat | ccgaagatga | ggagccattc | catgttacaa | aagttaatag | aagtaatgtt | 1380 |
| cacctattcg | actttaagca | tgaaaaggta | gatccaaaga | atccttactt | tttcgttact | 1440 |
| ttgaccggac | aatacgtccc | acaggaagat | ggggactata | tcttctcct | ccaagtttac | 1500 |
| ggtagtgggt | tgttttactt | gaatgacgag | ttaatcattg | atcaaaagca | taatcaagag | 1560 |
| agaggctcct | tctgtttcgg | tgcaggaaca | aaggagagaa | ctaaaaagct | aacgctcaaa | 1620 |
| aagggtcaag | tttacaacgt | tagagttgag | tatggcagtg | ggccaacatc | aggactggtc | 1680 |
| ggtgaatttg | tgctggtgg | ttttcaggca | ggcgtgatta | aggccatcga | tgatgacgaa | 1740 |
| gagattagaa | atgcagcaga | actggctgcc | aagcatgata | aagcagtatt | gataataggt | 1800 |
| ctgaacggag | aatgggaaac | cgaagggtat | gaccgtgaga | catggatct | gccaagagaa | 1860 |
| actaacgaat | tagtcagagc | cgttttgaag | gccaatccaa | acacagtcat | cgtaaaccag | 1920 |
| agcgggactc | cagtagagtt | cccttggttg | gaggaagcta | atgcactcgt | acaagcctgg | 1980 |

```
tatggaggga atgaattagg caatgctatt gcagatgtgc tatacggcga cgttgttcct   2040
aacggaaagt tatcactatc ttggccattc aaattgcaag acaatccagc atttttgaac   2100
tttaaaacag agtttggcag agtagtgtat ggtgaagata ttttcgtcgg ctacagatat   2160
tacgaaaagc tgcagagaaa agtcgcattt ccatttggat atggtttgtc ctacacgact   2220
ttcgaactgg atatttctga ctttaaggtc accgatgaca aaatcgatat cagtgtggac   2280
gttaaaaaca ctggtgataa gtttgccgga tctgaagttg tacaagttta cttctctgcg   2340
ctgaactcca aagtatctcg tcctgtgaag gaattaaagg gattcgaaaa agtccatctt   2400
gaaccaggcg agaagaaaac agtgaatatc gagctagagt taaaagacgc aatcagttat   2460
ttcaacgaag agttaggaaa atggcatgtg gaagcgggtg aatacttagt ttcagttgga   2520
acaagttctg atgatattct atctgtaaaa gagtttaaag ttgaaaaaga tttgtactgg   2580
aaggggttag atgatgatga caaaggtggt tctcctcctt ctcatcatca ccaccaccac   2640
taa                                                                 2643
```

```

<210> SEQ ID NO 28
<211> LENGTH: 572
<212> TYPE: PRT
<213> ORGANISM: Phytophthora infestans
<220> FEATURE:
<221> NAME/KEY: misc_feature
<222> LOCATION: (1)..(572)
<223> OTHER INFORMATION: beta-glucosidase

<400> SEQUENCE: 28

Met Gln Val Ile Lys Pro Leu Asn Tyr Val Leu Ala Leu Leu Ala Met
1               5                   10                  15

Gln Val Val Ser Ala Ala Thr Asn Ser Cys Thr Ser Trp Ser Glu Arg
            20                  25                  30

Phe Gln Lys Asn Leu Glu Gly Val Cys Val Cys Ser Glu Ala Thr Cys
        35                  40                  45

Asp Thr Ile Asp Asn Gly Ser Ser His Leu Ser Gly Ser Glu Ala Gly
    50                  55                  60

Val Phe Thr Thr Ser Lys Ala Gly Asp Arg Leu Thr Phe Ser Thr Val
65                  70                  75                  80

Asp Met Glu Ala Thr Ala Asn Glu Ala Ala Asp Phe Val Ile Asp Thr
                85                  90                  95

Thr Lys Thr Tyr Gln Ser Ile Ile Gly Phe Gly Gly Ala Phe Thr Asp
            100                 105                 110

Ser Ser Ala Ile Asn Leu His Met Leu Asn Ser Lys Leu Gln Glu His
        115                 120                 125

Ser Arg Thr Thr Tyr Phe Gly Asp Asp Gly Leu Gln Tyr Thr Ile Gly
    130                 135                 140

Arg Ile Pro Ile Gly Ser Thr Asp Phe Ser Leu Thr Ile Tyr Ser Tyr
145                 150                 155                 160

Asn Asp Val Glu Gly Asp Leu Ala Met Glu Asn Phe Ser Ile Asp Met
                165                 170                 175

Asp Lys Asp Lys Lys Ile Pro Phe Ile His Arg Ala Met Gly Lys Ser
            180                 185                 190

Ser Arg Gly Leu Lys Leu Tyr Ala Ser Ser Trp Ala Pro Pro Ala Trp
        195                 200                 205

Met Thr Thr Glu Asn Thr Thr Ile Asn Cys Ala Val Gln Gly Tyr Pro
    210                 215                 220

Gly Gly Glu Tyr Trp Lys Ala Leu Ala Leu Tyr Tyr Ser Lys Phe Val
```

225 230 235 240

Ser Ala Tyr Glu Ala Glu Gly Ile Pro Ile Trp Ala Met Thr Thr Gln
245 250 255

Asn Glu Pro Thr Gln Gln Phe Ala Phe Lys Tyr Trp Gln Ser Leu Arg
260 265 270

Phe Asn Val Thr Thr Glu Arg Asp Phe Ile Lys Arg Asp Leu Gly Pro
275 280 285

Gln Met Lys Thr Asp His Pro Asp Leu Lys Ile Ile Met Met Asp Asp
290 295 300

Gln Lys Asp Leu Leu Leu Asp Trp Asp Ala Thr Leu Leu Asp Ala Glu
305 310 315 320

Ser Ala Gln Tyr Val Ser Gly Ala Gly Val His Trp Tyr Lys Asn Leu
325 330 335

Asp Phe Leu Val Asp Thr Ala Gly Asn Phe Ala Asp Leu Glu Thr Phe
340 345 350

His Glu Lys Tyr Pro Asp Leu Phe Ile Leu Ala Thr Glu Ala Cys Glu
355 360 365

Gly Tyr Leu Leu Asp Gly Ile Val Thr Gly Ala Gly Pro Thr Leu Gln
370 375 380

Asn Pro Thr Phe Ala Trp Gln Arg Ala Gln Ile Tyr Ala Arg Asp Ile
385 390 395 400

Ile Gly Asp Leu Ala His Tyr Ala Ala Gly Trp Thr Asp Trp Asn Leu
405 410 415

Val Leu Asn Thr Thr Gly Gly Pro Thr Trp Ile Asp Asn Leu Ile Asp
420 425 430

Ser Pro Ile Leu Ile Asp Glu Ala Gly Gly Ala Glu Phe Tyr Lys Gln
435 440 445

Pro Met Tyr Tyr Ala Met Gly His Phe Ser Lys Phe Leu Pro Ala Asp
450 455 460

Ser Val Arg Val Ser Leu Ser Thr Ser Ser Ser Ala Ser Ser Thr Leu
465 470 475 480

Ala Lys Val Asp Ser Val Ala Phe Leu Thr Pro Asp Asn Gln Val Val
485 490 495

Leu Ile Leu Ser Asn Arg Asp Thr Ser Ala His Asp Ile Thr Leu Ser
500 505 510

Leu Ser Ser Gln Gln Leu Ser Thr Ser Val Thr Leu Glu Ala Leu Ser
515 520 525

Ile Lys Thr Leu Val Ile Gly Glu Leu Glu Glu Thr Ala Val Pro Ala
530 535 540

Arg Val Arg Arg Gln Ala Leu Gln Pro Val Pro Pro Ser Arg Arg Pro
545 550 555 560

Val Arg Pro Asp Pro Pro Leu Ala Val Leu Ala Leu
565 570

<210> SEQ ID NO 29
<211> LENGTH: 21
<212> TYPE: PRT
<213> ORGANISM: Phytophthora infestans
<220> FEATURE:
<221> NAME/KEY: misc_feature
<222> LOCATION: (1)..(21)
<223> OTHER INFORMATION: native signal peptide - beta-glucosidase

<400> SEQUENCE: 29

Met Gln Val Ile Lys Pro Leu Asn Tyr Val Leu Ala Leu Leu Ala Met
1 5 10 15

Gln Val Val Ser Ala
        20

<210> SEQ ID NO 30
<211> LENGTH: 1770
<212> TYPE: DNA
<213> ORGANISM: Phytophthora infestans
<220> FEATURE:
<221> NAME/KEY: misc_feature
<222> LOCATION: (1)..(1770)
<223> OTHER INFORMATION: beta-glucosidase

<400> SEQUENCE: 30

| | | | | | |
|---|---|---|---|---|---|
| atgcaggtga | tcaagccctt | gaactacgtg | ctggcattgc | tggcgatgca | ggttgtgagc | 60 |
| gctgctacaa | acagttgcac | atcttggtct | gaaagatttc | agaaaaatct | ggaaggcgtg | 120 |
| tgcgtttgtt | cagaagctac | ttgtgataca | atcgataatg | gttcaagtca | tttgtcaggc | 180 |
| tccgaagcag | gcgttttta c| cacttctaaa | gctggagata | gactaacatt | ttcaacagta | 240 |
| gacatggagg | caacagcaaa | tgaagctgcc | gactttgtca | ttgacacaac | aaagacttat | 300 |
| caatcaatta | tagggtttgg | tggcgccttc | actgattcta | gtgctatcaa | cttgcacatg | 360 |
| ctcaattcta | agttgcaaga | gcattccaga | actacttact | ttggagatga | tggattacaa | 420 |
| tacacgattg | gtagaatacc | aattggctct | acggatttct | ctttaaccat | ctacagctat | 480 |
| aatgatgtgg | aagggggattt | ggctatggaa | aacttctcta | ttgatatgga | taaggataaa | 540 |
| aagattccat | tcattcatag | agcaatgggc | aaatcttcaa | gaggtttgaa | attgtacgcg | 600 |
| tcatcttggg | cacctcctgc | ctggatgaca | actgaaaata | cgactataaa | ctgtgcagtt | 660 |
| caaggttacc | caggtggaga | atactggaag | gctttagctt | tgtactattc | caaatttgtt | 720 |
| tccgcctatg | aggctgaggg | aatcccaatc | tgggcgatga | ctactcaaaa | cgagcctaca | 780 |
| caacaattcg | ccttcaaata | ctggcaaagt | ctgagattca | atgttaccac | agaacgagat | 840 |
| ttcataaaga | gagatttggg | tccacaaatg | aaaactgacc | atccagactt | gaagatcata | 900 |
| atgatggacg | atcaaaaaga | ccttttgcta | gattgggacg | caaccctact | ggatgccgaa | 960 |
| tcagcacagt | acgtttctgg | tgctggtgtt | cattggtaca | aaaacttgga | tttccttgtg | 1020 |
| gatactgccg | gtaattttgc | ggacctcgaa | acttttcacg | aaaaataccc | agacttattc | 1080 |
| attctggcca | ccgaggcttg | tgaaggctac | ctacttgacg | gtatcgtaac | tggagcaggc | 1140 |
| cctacgcttc | aaaatcctac | atttgcctgg | caaagagcac | aaatctacgc | tagggatatc | 1200 |
| attggtgatc | ttgcacatta | cgccgcaggt | tggaccgatt | ggaacttagt | acttaataca | 1260 |
| acaggcggtc | caacatggat | cgacaacttg | attgattcac | ctatacttat | cgatgaagct | 1320 |
| gggggagctg | aattttacaa | gcaaccaatg | tattatgcta | tgggtcattt | ttctaagttt | 1380 |
| ttgccagctg | acagtgtcag | agtttctcta | tctactagct | cctcagcttc | ctcaacccte | 1440 |
| gcaaaagttg | attctgtcgc | atttttgaca | ccagataatc | aagtagtcct | aattctctcc | 1500 |
| aatcgtgata | cttctgccca | tgacatcact | ttatcattaa | gctcacaaca | gctttcaaca | 1560 |
| tcagttacat | tggaagcctt | aagtatcaaa | actctagtca | ttggagagct | agaggaaaca | 1620 |
| gcggttccag | ctagagtgag | aaggcaagca | ctccaaccag | ttccaccatc | ccgtagacca | 1680 |
| gtcagacctg | acccaccact | tgcggtatta | gcattggatg | atgatgacaa | aggtggttct | 1740 |
| cctccttctc | atcatcacca | ccaccactaa | | | | 1770 |

<210> SEQ ID NO 31
<211> LENGTH: 8969

```
<212> TYPE: DNA
<213> ORGANISM: Humicola grisea
<220> FEATURE:
<221> NAME/KEY: misc_feature
<222> LOCATION: (1)..(8969)
<223> OTHER INFORMATION: plasmid pMU3557

<400> SEQUENCE: 31
```

| | | | | | |
|---|---|---|---|---|---|
| ggccgcaagc | taattcgcgc | gaagctagct | tggcactggc | cgtcgtttta | caacgtcgtg | 60 |
| actgggaaaa | ccctggcgtt | acccaactta | atcgccttgc | agcacatccc | cccttcgcca | 120 |
| gctggcgtaa | tagcgaagag | gcccgcaccg | atcgccctc | ccaacagttg | cgcagcctga | 180 |
| atggcgaatg | gcgcctgatg | cggtattttc | tccttacgca | tctgtgcggt | atttcacacc | 240 |
| gcataggaga | tctaagctct | ggcgtaatag | cgaagaggcc | cgcaccgatc | gcccttccca | 300 |
| acagttgcgc | agcctgaatg | gcgaatggcg | cctgatgcgg | tattttctcc | ttacgcatct | 360 |
| gtgcggtatt | tcacaccgca | tagggtaata | actgatataa | ttaaattgaa | gctctaattt | 420 |
| gtgagtttag | tatacatgca | tttacttata | atacagtttt | ttagttttgc | tggccgcatc | 480 |
| ttctcaaata | tgcttcccag | cctgcttttc | tgtaacgttc | accctctacc | ttagcatccc | 540 |
| ttccctttgc | aaatagtcct | cttccaacaa | taataatgtc | agatcctgta | gagaccacat | 600 |
| catccacggt | tctatactgt | tgacccaatg | cgtctccctt | gtcatctaaa | cccacaccgg | 660 |
| gtgtcataat | caaccaatcg | taaccttcat | ctcttccacc | catgtctctt | tgagcaataa | 720 |
| agccgataac | aaaatctttg | tcgctcttcg | caatgtcaac | agtacccta | gtatattctc | 780 |
| cagtagatag | ggagcccttg | catgacaatt | ctgctaacat | caaaaggcct | ctaggttcct | 840 |
| ttgttacttc | ttctgccgcc | tgcttcaaac | cgctaacaat | acctgggccc | accacaccgt | 900 |
| gtgcattcgt | aatgtctgcc | cattctgcta | ttctgtatac | acccgcagag | tactgcaatt | 960 |
| tgactgtatt | accaatgtca | gcaaattttc | tgtcttcgaa | gagtaaaaaa | ttgtacttgg | 1020 |
| cggataatgc | ctttagcggc | ttaactgtgc | cctccatgga | aaaatcagtc | aagatatcca | 1080 |
| catgtgtttt | tagtaaacaa | attttgggac | ctaatgcttc | aactaactcc | agtaattcct | 1140 |
| tggtggtacg | aacatccaat | gaagcacaca | agtttgtttg | cttttcgtgc | atgatattaa | 1200 |
| atagcttggc | agcaacagga | ctaggatgag | tagcagcacg | ttccttatat | gtagctttcg | 1260 |
| acatgattta | tcttcgtttc | ggttttgtt | ctgtgcagtt | gggttaagaa | tactgggcaa | 1320 |
| tttcatgttt | cttcaacact | acatatgcgt | atatatacca | atctaagtct | gtgctccttc | 1380 |
| cttcgttctt | ccttctgttc | ggagattacc | gaatcaaaaa | aatttcaaag | aaaccgaaat | 1440 |
| caaaaaaag | aataaaaaaa | aaatgatgaa | ttgaaaagct | cttgttaccc | atcattgaat | 1500 |
| tttgaacatc | cgaacctggg | agttttccct | gaaacagata | gtatatttga | acctgtataa | 1560 |
| taatatatag | tctagcgctt | tacgaagac | aatgtatgta | tttcggttcc | tggagaaact | 1620 |
| attgcatcta | ttgcataggt | aatcttgcac | gtcgcatccc | cggttcattt | tctgcgtttc | 1680 |
| catcttgcac | ttcaatagca | tatctttgtt | aacgaagcat | ctgtgcttca | ttttgtagaa | 1740 |
| caaaaatgca | acgcgagagc | gctaattttt | caaacaaaga | atctgagctg | catttttaca | 1800 |
| gaacagaaat | gcaacgcgaa | agcgctattt | taccaacgaa | gaatctgtgc | ttcatttttg | 1860 |
| taaaacaaaa | atgcaacgcg | agagcgctaa | ttttcaaac | aaagaatctg | agctgcattt | 1920 |
| ttacagaaca | gaaatgcaac | gcgagagcgc | tattttacca | acaaagaatc | tatacttctt | 1980 |
| ttttgttcta | caaaaatgca | tcccgagagc | gctatttttc | taacaaagca | tcttagatta | 2040 |
| cttttttct | cctttgtgcg | ctctataatg | cagtctcttg | ataactttt | gcactgtagg | 2100 |

```
tccgttaagg ttagaagaag gctactttgg tgtctatttt ctcttccata aaaaaagcct   2160
gactccactt cccgcgttta ctgattacta gcgaagctgc gggtgcalttt tttcaagata   2220 aaggcatccc cgattatatt ctataccgat gtggattgcg catactttgt gaacagaaag   2280
tgatagcgtt gatgattctt cattggtcag aaaattatga acggtttctt ctattttgtc   2340
tctatatact acgtatagga aatgtttaca ttttcgtatt gttttcgatt cactctatga   2400
atagttctta ctacaatttt tttgtctaaa gagtaatact agagataaac ataaaaaatg   2460
tagaggtcga gtttagatgc aagttcaagg agcgaaaggt ggatgggtag gttatatagg   2520
gatatagcac agagatatat agcaaagaga ctttttgag caatgtttgt ggaagcggta   2580
ttcgcaatat tttagtagct cgttacagtc cggtgcgttt ttggtttttt gaaagtgcgt   2640
cttcagagcg cttttggttt tcaaaagcgc tctgaagttc ctatactttc tagctagaga   2700
ataggaactt cggaatagga acttcaaagc gtttccgaaa acgagcgctt ccgaaaatgc   2760
aacgcgagct gcgcacatac agctcactgt tcacgtcgca cctatatctg cgtgttgcct   2820
gtatatatat atacatgaga agaacggcat agtgcgtgtt tatgcttaaa tgcgttatgg   2880
tgcactctca gtacaatctg ctctgatgcc gcatagttaa gccagcccg acacccgcca    2940 acaccegctg acgcgccctg acgggcttgt ctgctcccgg catccgctta cagacaagct   3000
gtgaccgtct ccgggagctg catgtgtcag aggttttcac cgtcatcacc gaaacgcgcg   3060
agacgaaagg gcctcgtgat acgcctattt ttataggtta atgtcatgat aataatggtt   3120
tcttagacgt caggtggcac ttttcgggga atgtgcgcg gaacccctat ttgtttattt     3180
ttctaaatac attcaaatat gtatccgctc atgagacaat aaccctgata aatgcttcaa   3240
taatattgaa aaggaagag tatgagtatt caacatttcc gtgtcgccct tattcccttt     3300
tttgcggcat tttgccttcc tgttttgct cacccagaaa cgctggtgaa agtaaaagat     3360
gctgaagatc agttgggtgc acgagtgggt tacatcgaac tggatctcaa cagcggtaag   3420
atccttgaga gttttcgccc cgaagaacgt tttccaatga tgagcacttt taaagttctg   3480
ctatgtggcg cggtattatc ccgtattgac gccgggcaag agcaactcgg tcgccgcata   3540
cactattctc agaatgactt ggttgagtac tcaccagtca cagaaaagca tcttacggat   3600
ggcatgacag taagagaatt atgcagtgct gccataacca tgagtgataa cactgcggcc   3660
aacttacttc tgacaacgat cggaggaccg aaggagctaa ccgcttttt gcacaacatg   3720 ggggatcatg taactcgcct tgatcgttgg gaaccggagc tgaatgaagc cataccaaac   3780
gacgagcgtg acaccacgat gcctgtagca atggcaacaa cgttgcgcaa actattaact   3840
ggcgaactac ttactctagc ttcccggcaa caattaatag actggatgga ggcggataaa   3900
gttgcaggac cacttctgcg ctcggccctt ccggctggct ggtttattgc tgataaatct   3960
ggagccggtg agcgtgggtc tcgcggtatc attgcagcac tggggccaga tggtaagccc   4020
tcccgtatcg tagttatcta cacgacgggg agtcaggcaa ctatggatga acgaaataga   4080
cagatcgctg agataggtgc ctcactgatt aagcattggt aactgtcaga ccaagtttac   4140
tcatatatac tttagattga tttaaaactt cattttaat ttaaaaggat ctaggtgaag    4200
atcctttttg ataatctcat gaccaaaatc ccttaacgtg agttttcgtt ccactgagcg   4260
tcagaccccg tagaaaagat caaaggatct tcttgagatc ctttttttct gcgcgtaatc   4320
tgctgcttgc aaacaaaaaa accaccgcta ccagcggtgg tttgtttgcc ggatcaagag   4380
ctaccaactc tttttccgaa ggtaactggc ttcagcagag cgcagatacc aaatactgtc   4440
cttctagtgt agccgtagtt aggccaccac ttcaagaact ctgtagcacc gcctacatac   4500
```

```
ctcgctctgc taatcctgtt accagtggct gctgccagtg gcgataagtc gtgtcttacc   4560
gggttggact caagacgata gttaccggat aaggcgcagc ggtcgggctg aacgggggt    4620 tcgtgcacac agcccagctt ggagcgaacg acctacaccg aactgagata cctacagcgt   4680
gagcattgag aaagcgccac gcttcccgaa gggagaaagg cggacaggta tccggtaagc   4740
ggcagggtcg gaacaggaga gcgcacgagg gagcttccag ggggaaacgc ctggtatctt   4800
tatagtcctg tcgggtttcg ccacctctga cttgagcgtc gattttgtg atgctcgtca    4860 gggggcgga gcctatggaa aaacgccagc aacgcggcct ttttacggtt cctggccttt    4920
tgctggcctt tgctcacat gttctttcct gcgttatccc ctgattctgt ggataaccgt    4980
attaccgcct ttgagtgagc tgataccgct cgccgcagcc gaacgaccga gcgcagcgag   5040
tcagtgagcg aggaagcgga agagcgccca atacgcaaac cgcctctccc cgcgcgttgg   5100
ccgattcatt aatccaggat cccaattaat gtgagttacc tcactcatta ggcaccccag   5160
gctttacact ttatgcttcc ggctcgtatg ttgtgtggaa ttgtgagcgg ataacaattt   5220
cacacaggaa acagctatga ccatgattac gaattaattc gagctcggta cccggggatc   5280
gatccactag agatctgttt agcttgcctc gtccccgccg ggtcacccgg ccagcgacat   5340
ggaggcccag aataccctcc ttgacagtct tgacgtgcgc agctcagggg catgatgtga   5400
ctgtcgcccg tacatttagc ccatacatcc ccatgtataa tcatttgcat ccatacattt   5460
tgatggccgc acggcgcgaa gcaaaaatta cggctcctcg ctgcagacct gcgagcaggg   5520
aaacgctccc ctcacagacg cgttgaattg tccccacgcc gcgcccctgt agagaaatat   5580
aaaaggttag gatttgccac tgaggttctt cttttcatata cttcctttta aaatcttgct   5640
aggatacagt tctcacatca catccgaaca taaacaacca tggccgacca agcgacgccc   5700
aacctgccat cacgagattt cgattccacg gccgccttct atgaaaggtt gggcttcgga   5760
atcgttttcc gggacgccgg ctggatgatc ctccagcgcg gggatctcaa gctggagttc   5820
ttcgcccacc ccgggctcga tcccctcgcg agttggttca gctgctgcct gaggctggac   5880
gacctcgcgg agttctaccg gcagtgcaaa tccgtcggca tccaggaaac cagcagcggc   5940
tatccgcgca tccatgcccc cgaactgcag gagtggggag gcacgatggc cgctttggtc   6000
gacccggacg ggacgctcct gcgcctgata cagaacgaat tgcttgcagg catctcatga   6060
tcagtactga caataaaaag attcttgttt tcaagaactt gtcatttgta tagtttttt    6120 atattgtagt tgttctattt taatcaaatg ttagcgtgat ttatatttt tttcgcctcg    6180 acatcatctg cccagatgcg aagttaagtg cgcagaaagt aatatcatgc gtcaatcgta   6240
tgtgaatgct ggtcgctata ctgctgtcga ttcgatacta acgccgccat ccagtgtcga   6300
aaacgagctc tcgagaaccc ttaatataac ttcgtataat gtatgctata cgaagttatt   6360
aggtgatatc agatccacta gtcttctagg cgggttatct actgatccga gcttccacta   6420
ggatagcacc caaacacctg catatttgga cgacctttac ttacaccacc aaaaaccact   6480
ttcgcctctc ccgcccctga taacgtccac taattgagcg attacctgag cggtcctctt   6540
ttgtttgcag catgagactt gcatactgca atcgtaagt agcaacgtct caaggtcaaa    6600
actgtatgga aaccttgtca cctcacttaa ttctagctag cctaccctgc aagtcaagag   6660
gtctccgtga ttcctagcca cctcaaggta tgcctctccc cggaaactgt ggccttttct   6720
ggcacacatg atctccacga tttcaacata taaatagctt ttgataatgg caatattaat   6780
caaatttatt ttacttcttt cttgtaacat ctctcttgta atcccttatt ccttctagct   6840
```

```
atttttcata aaaaaccaag caactgctta tcaacacaca aacactaaat caaagaattc    6900
ttaattaaac aatgcttttg caagctttcc ttttcctttt ggctggtttt gcagccaaaa    6960
tatctgcatc tttgccacca gatttcaaat ggggcttcgc tactgccgct tatcaaatcg    7020
agggttctgt caatgaagat ggtagaggtc catccatttg gacacattt tgcgcaatcc     7080
caggcaaaat cgctgacgga agctcaggtg cggtagcttg cgattcatac aagagaacca    7140
aggaagatat cgcattgtta aaggaattgg gagccaacag ttacagattt tctatctcct    7200
ggtccagaat tattcctctg ggtggcagaa acgatccaat taatcagaaa ggtatcgacc    7260
attacgtcaa attcgtggat gacttaattg aagctggaat cactccattc atcactcttt    7320
tccattggga tttgcctgac gcattggata agcgatacgg aggatttctg aacaaagagg    7380
aatttgccgc tgattttgaa aactacgcta gaattatgtt taaagcaatc ccaaagtgta    7440
aacattggat tacgtttaat gaaccttggt gttctgcaat actaggctat aatactggct    7500
actttgctcc aggacacaca tccgacagat caaaatctcc tgttggggat tctgcgagag    7560
aaccttggat tgtaggtcac aatatcttga tagctcatgc aagagctgta aaggcctata    7620
gagaagattt taagccaacc caaggcggag aaatcggtat cacactcaat ggggatgcga    7680
cacttccttg ggaccctgaa gatccagctg acatagaggc ctgtgatcgt aagattgaat    7740
ttgcaatatc atggttcgct gacccaatat actttggtaa gtacccagat tcaatgagaa    7800
aacaactggg cgataggtta ccagagttta caccagaaga ggttgccctc gtcaaaggat    7860
caaacgactt ttatggtatg aatcattata cagcgaatta cattaagcat aaaacaggtg    7920
ttcctccaga agatgatttt ctgggaaacc tagaaaccct gttttacaac aaatatggtg    7980
attgtattgg gccagagact caaagtttct ggttaagacc tcatgcccaa ggctttcgtg    8040
atttgttaaa ctggctttct aagagatatg gttaccctaa aatctacgtt actgaaaatg    8100
ggacaagttt aaaaggcgaa aatgacatgc cattagagca ggttttagag gatgacttta    8160
gagtgaaata cttcaacgac tatgtgagag caatggccgc tgcagtagct gaagatgggt    8220
gcaatgttag aggttaccta gcgtggtcat tgctagataa tttcgaatgg gcagaaggtt    8280
acgaaacaag gttcggcgtt acttacgtgg attacgctaa tgatcaaaag agatacccaa    8340
agaaatccgc caagtcttta aaaccattgt tcgactcact aattcgaaaa gaggatgatg    8400
atgacaaagg tggttctcct ccttctcatc atcaccacca ccactaaggc gcgcccctcga   8460
gagcttttga ttaagccttc tagtccaaaa aacacgtttt tttgtcattt atttcatttt    8520
cttagaatag tttagtttat tcattttata gtcacgaatg ttttatgatt ctatataggg    8580
ttgcaaacaa gcatttttca ttttatgtta aaacaatttc aggtttacct tttattctgc    8640
ttgtggtgac gcgtgtatcc gcccgctctt ttggtcaccc atgtatttaa ttgcataaat    8700
aattcttaaa agtggagcta gtctatttct atttacatac ctctcatttc tcatttcctc    8760
ctaatgtgtc aatgatcata ttcttaactg gaccgatctt attcgtcaga ttcaaaccaa    8820
aagttcttag ggctaccaca ggaggaaaat tagtgtgata taatttaaat aatttatccg    8880
ccattcctaa tagaacgttg ttcgacggat atctttctgc ccaaaagggt tctaagctca    8940
atgaagagcc aatgtctaaa cctctttgc                                      8969
```

<210> SEQ ID NO 32
<211> LENGTH: 9314
<212> TYPE: DNA
<213> ORGANISM: Candida Wickerhamii
<220> FEATURE:
<221> NAME/KEY: misc_feature
<222> LOCATION: (1)..(9314)
<223> OTHER INFORMATION: plasmid pMU3558

<400> SEQUENCE: 32

| | | | | | |
|---|---|---|---|---|---|
| ggccgcaagc | taattcgcgc | gaagctagct | tggcactggc | cgtcgtttta | caacgtcgtg | 60 |
| actgggaaaa | ccctggcgtt | acccaactta | atcgccttgc | agcacatccc | ccttcgccagctggcgtaa | 120 |
| gctggcgtaa | tagcgaagag | gcccgcaccg | atcgcccttc | ccaacagttg | cgcagcctga | 180 |
| atggcgaatg | gcgcctgatg | cggtattttc | tccttacgca | tctgtgcggt | atttcacacc | 240 |
| gcataggaga | tctaagctct | ggcgtaatag | cgaagaggcc | cgcaccgatc | gcccttccca | 300 |
| acagttgcgc | agcctgaatg | gcgaatggcg | cctgatgcgg | tattttctcc | ttacgcatct | 360 |
| gtgcggtatt | tcacaccgca | tagggtaata | actgatataa | ttaaattgaa | gctctaattt | 420 |
| gtgagtttag | tatacatgca | tttacttata | atacagtttt | ttagttttgc | tggccgcatc | 480 |
| ttctcaaata | tgcttcccag | cctgcttttc | tgtaacgttc | accctctacc | ttagcatccc | 540 |
| ttccctttgc | aaatagtcct | cttccaacaa | taataatgtc | agatcctgta | gagaccacat | 600 |
| catccacggt | tctatactgt | tgacccaatg | cgtctccctt | gtcatctaaa | cccacaccgg | 660 |
| gtgtcataat | caaccaatcg | taaccttcat | ctcttccacc | catgtctctt | tgagcaataa | 720 |
| agccgataac | aaaatctttg | tcgctcttcg | caatgtcaac | agtacccttt a | gtatattctc | 780 |
| cagtagatag | ggagcccttg | catgacaatt | ctgctaacat | caaaaggcct | ctaggttcct | 840 |
| ttgttacttc | ttctgccgcc | tgcttcaaac | cgctaacaat | acctgggccc | accacaccgt | 900 |
| gtgcattcgt | aatgtctgcc | cattctgcta | ttctgtatac | acccgcagag | tactgcaatt | 960 |
| tgactgtatt | accaatgtca | gcaaattttc | tgtcttcgaa | gagtaaaaaa | ttgtacttgg | 1020 |
| cggataatgc | ctttagcggc | ttaactgtgc | cctccatgga | aaaatcagtc | aagatatcca | 1080 |
| catgtgtttt | tagtaaacaa | attttgggac | ctaatgcttc | aactaactcc | agtaattcct | 1140 |
| tggtggtacg | aacatccaat | gaagcacaca | agtttgtttg | cttttcgtgc | atgatattaa | 1200 |
| atagcttggc | agcaacagga | ctaggatgag | tagcagcacg | ttccttatat | gtagctttcg | 1260 |
| acatgattta | tcttcgtttc | ggttttttgtt | ctgtgcagtt | gggttaagaa | tactgggcaa | 1320 |
| tttcatgttt | cttcaacact | acatatgcgt | atatatacca | atctaagtct | gtgctccttc | 1380 |
| cttcgttctt | ccttctgttc | ggagattacc | gaatcaaaaa | aatttcaaag | aaaccgaaat | 1440 |
| caaaaaaaag | aataaaaaaa | aaatgatgaa | ttgaaaagct | cttgttaccc | atcattgaat | 1500 |
| tttgaacatc | cgaacctggg | agttttccct | gaaacagata | gtatatttga | acctgtataa | 1560 |
| taatatatag | tctagcgctt | tacgaagac | aatgtatgta | tttcggttcc | tggagaaact | 1620 |
| attgcatcta | ttgcataggt | aatcttgcac | gtcgcatccc | cggttcattt | tctgcgtttc | 1680 |
| catcttgcac | ttcaatagca | tatctttgtt | aacgaagcat | ctgtgcttca | ttttgtagaa | 1740 |
| caaaaatgca | acgcgagagc | gctaattttt | caaacaaaga | atctgagctg | cattttaca | 1800 |
| gaacagaaat | gcaacgcgaa | agcgctattt | accaacgaa | gaatctgtgc | ttcatttttg | 1860 |
| taaaacaaaa | atgcaacgcg | agagcgctaa | ttttcaaac | aaagaatctg | agctgcattt | 1920 |
| ttacagaaca | gaaatgcaac | gcgagagcgc | tattttacca | acaaagaatc | tatacttctt | 1980 |
| ttttgttcta | caaaaatgca | tcccgagagc | gctatttttc | taacaaagca | tcttagatta | 2040 |
| ctttttttct | cctttgtgcg | ctctataatg | cagtctcttg | ataactttt | gcactgtagg | 2100 |
| tccgttaagg | ttagaagaag | ctacttggg | tgtctatttt | ctcttccata | aaaaaagcct | 2160 |
| gactccactt | cccgcgttta | ctgattacta | gcgaagctgc | gggtgcattt | tttcaagata | 2220 |

```
aaggcatccc cgattatatt ctataccgat gtggattgcg catactttgt gaacagaaag    2280
tgatagcgtt gatgattctt cattggtcag aaaattatga acggtttctt ctattttgtc    2340
tctatatact acgtatagga aatgtttaca ttttcgtatt gttttcgatt cactctatga    2400
atagttctta ctacaatttt tttgtctaaa gagtaatact agagataaac ataaaaaatg    2460
tagaggtcga gtttagatgc aagttcaagg agcgaaaggt ggatgggtag gttatatagg    2520
gatatagcac agagatatat agcaaagaga tacttttgag caatgtttgt ggaagcggta    2580
ttcgcaatat tttagtagct cgttacagtc cggtgcgttt ttggtttttt gaaagtgcgt    2640
cttcagagcg cttttggttt tcaaaagcgc tctgaagttc ctatactttc tagctagaga    2700
ataggaactt cggaatagga acttcaaagc gtttccgaaa acgagcgctt ccgaaaatgc    2760
aacgcgagct gcgcacatac agctcactgt tcacgtcgca cctatatctg cgtgttgcct    2820
gtatatatat atacatgaga agaacggcat agtgcgtgtt tatgcttaaa tgcgttatgg    2880
tgcactctca gtacaatctg ctctgatgcc gcatagttaa gccagccccg acacccgcca    2940
acacccgctg acgcgccctg acgggcttgt ctgctcccgg catccgctta cagacaagct    3000
gtgaccgtct ccgggagctg catgtgtcag aggttttcac cgtcatcacc gaaacgcgcg    3060
agacgaaagg gcctcgtgat acgcctattt ttataggtta atgtcatgat aataatggtt    3120
tcttagacgt caggtggcac ttttcgggga atgtgcgcg gaaccccat ttgtttattt    3180
ttctaaatac attcaaatat gtatccgctc atgagacaat aaccctgata aatgcttcaa    3240
taatattgaa aaaggaagag tatgagtatt caacatttcc gtgtcgccct tattccctt    3300
tttgcggcat tttgccttcc tgtttttgct cacccagaaa cgctggtgaa agtaaaagat    3360
gctgaagatc agttgggtgc acgagtgggt tacatcgaac tggatctcaa cagcggtaag    3420
atccttgaga gttttcgccc cgaagaacgt tttccaatga tgagcacttt taaagttctg    3480
ctatgtggcg cggtattatc ccgtattgac gccgggcaag agcaactcgg tcgccgcata    3540
cactattctc agaatgactt ggttgagtac tcaccagtca cagaaaagca tcttacggat    3600
ggcatgacag taagagaatt atgcagtgct gccataacca tgagtgataa cactgcggcc    3660
aacttacttc tgacaacgat cggaggaccg aaggagctaa ccgcttttt gcacaacatg    3720
ggggatcatg taactcgcct tgatcgttgg gaaccggagc tgaatgaagc cataccaaac    3780
gacgagcgtg acaccacgat gcctgtagca atggcaacaa cgttgcgcaa actattaact    3840
ggcgaactac ttactctagc ttcccggcaa caattaatag actggatgga ggcggataaa    3900
gttgcaggac cacttctgcg ctcggccctt ccggctggct ggtttattgc tgataaatct    3960
ggagccggtg agcgtgggtc tcgcggtatc attgcagcac tggggccaga tggtaagccc    4020
tcccgtatcg tagttatcta cacgacgggg agtcaggcaa ctatggatga acgaaataga    4080
cagatcgctg agataggtgc ctcactgatt aagcattggt aactgtcaga ccaagtttac    4140
tcatatatac tttagattga tttaaaactt cattttaat ttaaaaggat ctaggtgaag    4200
atcctttttg ataatctcat gaccaaaatc ccttaacgtg agttttcgtt ccactgagcg    4260
tcagaccccg tagaaaagat caaaggatct tcttgagatc cttttttct gcgcgtaatc    4320
tgctgcttgc aaacaaaaaa accaccgcta ccagcggtgg tttgtttgcc ggatcaagag    4380
ctaccaactc tttttccgaa ggtaactggc ttcagcagag cgcagatacc aaatactgtc    4440
cttctagtgt agccgtagtt aggccaccac ttcaagaact ctgtagcacc gcctacatac    4500
ctcgctctgc taatcctgtt accagtggct gctgccagtg gcgataagtc gtgtcttacc    4560
gggttggact caagacgata gttaccggat aaggcgcagc ggtcgggctg aacggggggt    4620
```

```
tcgtgcacac agcccagctt ggagcgaacg acctacaccg aactgagata cctacagcgt    4680
gagcattgag aaagcgccac gcttcccgaa gggagaaagg cggacaggta tccggtaagc    4740
ggcagggtcg gaacaggaga gcgcacgagg gagcttccag ggggaaacgc ctggtatctt    4800
tatagtcctg tcgggtttcg ccacctctga cttgagcgtc gattttttgtg atgctcgtca    4860 ggggggcgga gcctatggaa aaacgccagc aacgcggcct ttttacggtt cctggccttt    4920
tgctggcctt ttgctcacat gttctttcct gcgttatccc ctgattctgt ggataaccgt    4980
attaccgcct ttgagtgagc tgataccgct cgccgcagcc gaacgaccga gcgcagcgag    5040
tcagtgagcg aggaagcgga agagcgccca atacgcaaac cgcctctccc cgcgcgttgg    5100
ccgattcatt aatccaggat cccaattaat gtgagttacc tcactcatta gcaccccag    5160 gctttacact ttatgcttcc ggctcgtatg ttgtgtggaa ttgtgagcgg ataacaattt    5220
cacacaggaa acagctatga ccatgattac gaattaattc gagctcggta cccggggatc    5280
gatccactag agatctgttt agcttgcctc gtccccgccg gtcacccgg ccagcgacat    5340 ggaggcccag aatacccctcc ttgacagtct tgacgtgcgc agctcagggg catgatgtga    5400
ctgtcgcccg tacatttagc ccatacatcc ccatgtataa tcatttgcat ccatacattt    5460
tgatggccgc acggcgcgaa gcaaaaatta cggctcctcg ctgcagacct gcgagcaggg    5520
aaacgctccc ctcacagacg cgttgaattg tccccacgcc gcgcccctgt agagaaatat    5580
aaaaggttag gatttgccac tgaggttctt cttttcatata cttccttta aaatcttgct    5640 aggatacagt tctcacatca catccgaaca taaacaacca tggccgacca agcgacgccc    5700
aacctgccat cacgagattt cgattccacg gccgccttct atgaaaggtt gggcttcgga    5760
atcgttttcc gggacgccgg ctggatgatc ctccagcgcg gggatctcaa gctggagttc    5820
ttcgcccacc ccgggctcga tccctcgcg agttggttca gctgctgcct gaggctggac    5880
gacctcgcgg agttctaccg gcagtgcaaa tccgtcggca tccaggaaac cagcagcggc    5940
tatccgcgca tccatgcccc cgaactgcag gagtggggag gcacgatggc cgctttggtc    6000
gacccggacg ggacgctcct gcgcctgata cagaacgaat tgcttgcagg catctcatga    6060
tcagtactga caataaaaag attcttgttt tcaagaactt gtcatttgta tagttttttt    6120
atattgtagt tgttctattt taatcaaatg ttagcgtgat ttatattttt tttcgcctcg    6180
acatcatctg cccagatgcg aagttaagtg cgcagaaagt aatatcatgc gtcaatcgta    6240
tgtgaatgct ggtcgctata ctgctgtcga ttcgatacta acgccgccat ccagtgtcga    6300
aaacgagctc tcgagaaccc ttaatataac ttcgtataat gtatgctata cgaagttatt    6360
aggtgatatc agatccacta gtcttctagg cgggttatct actgatccga gcttccacta    6420
ggatagcacc caaacacctg catatttgga cgacctttac ttacaccacc aaaaaccact    6480
ttcgcctctc ccgcccctga taacgtccac taattgagcg attacctgag cggtcctctt    6540
ttgtttgcag catgagactt gcatactgca atcgtaagt agcaacgtct caaggtcaaa    6600
actgtatgga aaccttgtca cctcacttaa ttctagctag cctaccctgc aagtcaagag    6660
gtctccgtga ttcctagcca cctcaaggta tgcctctccc cggaaactgt ggccttttct    6720
ggcacacatg atctccacga tttcaacata taaatagctt ttgataatgg caatattaat    6780
caaatttatt ttacttcttt cttgtaacat ctctcttgta atcccttatt ccttctagct    6840 attttttcata aaaaaccaag caactgctta tcaacacaca aacactaaat caaagaattc    6900
ttaattaaac aatgttctca caaaagtatc ttttatcatt agctgcaata attgcaatcg    6960
```

```
ctaaagcagc tccagctgac gatgcctcta agcctggtat aggcaagttt gccccctggtc    7020
aactgggggtt cagatactat attgatacta ccactgaata cgcaaccccca gcaacagcta   7080
cagctcctgc tagttctact acttacgcag ccccatacgc tgaactatct agtttggtgg    7140
gcaatctgtc aacaactact tggggcaact ggtatccaga tgctactgaa gctgctactg    7200
atacagatga tccttacggt caatacgcgt ggtcacagct ctgggaagcg actacctttc    7260
ctaactttac gagaggaatc tactcaacca cagtagatcc aaccccaatc cctacagaaa    7320
gccttgtagt tccaccagac gacccagtca aaagagcctt tcaagactta gggataaagt    7380
ttccattagg ctttatccaa ggggtggctg gatctgctgc gcagatagaa ggcgctgtcg    7440
ctgatgaggg cagaagtcct acaaatctcg aagtgtcatc tgcatccaga catttgccag    7500
aggatttcgt gacaaatgaa aactactacc tttacaaaca agatattact cgattggcag    7560
ccataggtgt cgaatattac tcctttacaa ttccttggac tcgtatattg ccatttgcat    7620
accctggttc accagttaat caacaaggtc tggaccatta tgacgatttg attaatacag    7680
ttctagccta cggaatgaaa cctatcgtca ctcttattca tttcgactct ccattacaat    7740
tggttgattt taacgcaaca cttgaattag gattgccagg aggttatgaa ggcgaagatt    7800
ttgtggaagc ctttgtcaat tatggtaaga ttgtgatgac acattttgca gatagagtac    7860
cactatggat catcttcaac gaaccagtac aattcgcaac taacggccta ggagtaaagc    7920
atgtagttca agcgaccgca cagttgtatg atttctacca taatgagatt aacggttcag    7980
gtaaaatcgg tatgaaattc agtcacatct tcgggttccc tgaagatcca acaaacccag    8040
aacatgtcgc cgcagctgat aggtctaacg aactgcaatt gggattattt gctgacccat    8100
tgttttttagg agaggattac ccagattcct ttaagacaac attactgaaa acacaacctg    8160
ctttggcctg gacactagac gaattggccg ctgttaaagg taagtgcgac ttttttcgggg    8220
ttgatccata cacttacaat acaattaaac cactggataa tggtacagca tcctgtgagg    8280
ccaatgttac ggatacttac tggcctacct gtgttaatgt aaccgttaca gaagctgaca    8340
attggagtat cggatatagg tcacaaagct acgtctacat tactccaaga caattaagag    8400
tttctctaaa ctacatttgg cagcactggc atgttccaat ctttatcaca gaatttggtt    8460
tcccagaatg gagagaaggt gagaaacttc tcgtagacca agttcaagat ttggacagat    8520
ccatctacta cagatcattt ctgaccgctg ccctagaggc ttctcagtat gatggtgtcg    8580
aaataatggg tgccttagct tggtctttcg cagacaactg ggagtttggg gactataatc    8640
aacagttcgg cttgcaagtg gttaatagaa ctacacaaga gcgttttttac aaaaagtctt    8700
tctttgattt cgttggcttt atcaatgata atagagctga tgatgatgac aaaggtggtt    8760
ctcctccttc tcatcatcac caccaccact aaggcgcgcc ctcgagagct tttgattaag    8820
ccttctagtc caaaaaacac gttttttttgt catttatttc attttcttag aatagtttag    8880
tttattcatt ttatagtcac gaatgttttta tgattctata tagggttgca aacaagcatt    8940
tttcatttta tgttaaaaca atttcaggtt tacctttttat tctgcttgtg gtgacgcgtg    9000
tatccgcccg ctcttttggt cacccatgta tttaattgca taaataattc ttaaaagtgg    9060
agctagtcta tttctatttta catcctctc atttctcatt tcctcctaat gtgtcaatga    9120
tcatattctt aactggaccg atcttattcg tcagattcaa accaaaagtt cttagggcta    9180
ccacaggagg aaaattagtg tgatataatt taaataattt atccgccatt cctaatagaa    9240
cgttgttcga cggatatctt tctgcccaaa agggttctaa gctcaatgaa gagccaatgt    9300
ctaaacctct ttgc                                                      9314
```

<210> SEQ ID NO 33
<211> LENGTH: 10070
<212> TYPE: DNA
<213> ORGANISM: Aspergillus Aculeatus
<220> FEATURE:
<221> NAME/KEY: misc_feature
<222> LOCATION: (1)..(10070)
<223> OTHER INFORMATION: plasmid pMU3559

<400> SEQUENCE: 33

```
ggccgcaagc taattcgcgc gaagctagct tggcactggc cgtcgtttta caacgtcgtg      60
actgggaaaa ccctggcgtt acccaactta atcgccttgc agcacatccc cccttcgcca     120
gctggcgtaa tagcgaagag gcccgcaccg atcgcccttc ccaacagttg cgcagcctga     180
atggcgaatg gcgcctgatg cggtattttc tccttacgca tctgtgcggt atttcacacc     240
gcataggaga tctaagctct ggcgtaatag cgaagaggcc cgcaccgatc gcccttccca     300
acagttgcgc agcctgaatg gcgaatggcg cctgatgcgg tattttctcc ttacgcatct     360
gtgcggtatt tcacaccgca tagggtaata actgatataa ttaaattgaa gctctaattt     420
gtgagtttag tatacatgca tttacttata atacagtttt ttagttttgc tggccgcatc     480
ttctcaaata tgcttcccag cctgcttttc tgtaacgttc accctctacc ttagcatccc     540
ttccctttgc aaatagtcct cttccaacaa taataatgtc agatcctgta gagaccacat     600
catccacggt tctatactgt tgacccaatg cgtctccctt gtcatctaaa cccacaccgg     660
gtgtcataat caaccaatcg taaccttcat ctcttccacc catgtctctt tgagcaataa     720
agccgataac aaaatctttg tcgctcttcg caatgtcaac agtacccctta gtatattctc     780
cagtagatag ggagcccttg catgacaatt ctgctaacat caaaaggcct ctaggttcct     840
tgttacttc ttctgccgcc tgcttcaaac cgctaacaat acctgggccc accacaccgt     900
gtgcattcgt aatgtctgcc cattctgcta ttctgtatac acccgcagag tactgcaatt     960
tgactgtatt accaatgtca gcaaattttc tgtcttcgaa gagtaaaaaa ttgtacttgg    1020
cggataatgc ctttagcggc ttaactgtgc cctccatgga aaaatcagtc aagatatcca    1080
catgtgtttt tagtaaacaa attttgggac ctaatgcttc aactaactcc agtaattcct    1140
tggtggtacg aacatccaat gaagcacaca agtttgtttg cttttcgtgc atgatattaa    1200
atagcttggc agcaacagga ctaggatgag tagcagcacg ttccttatat gtagctttcg    1260
acatgattta tcttcgtttc ggttttttgtt ctgtgcagtt gggttaagaa tactgggcaa    1320
tttcatgttt cttcaacact acatatgcgt atatatacca atctaagtct gtgctccttc    1380
cttcgttctt ccttctgttc ggagattacc gaatcaaaaa aatttcaaag aaaccgaaat    1440
caaaaaaag aataaaaaaa aaatgatgaa ttgaaaagct cttgttaccc atcattgaat    1500
tttgaacatc cgaacctggg agttttccct gaaacagata gtatatttga acctgtataa    1560
taatatatag tctagcgctt tacggaagac aatgtatgta tttcggttcc tggagaaact    1620
attgcatcta ttgcataggt aatcttgcac gtcgcatccc cggttcattt tctgcgtttc    1680
catcttgcac ttcaatagca tatctttgtt aacgaagcat ctgtgcttca ttttgtagaa    1740
caaaaatgca acgcgagagc gctaattttt caaacaaaga atctgagctg cattttaca    1800
gaacagaaat gcaacgcgaa agcgctattt taccaacgaa gaatctgtgc ttcatttttg    1860
taaaacaaaa atgcaacgcg agagcgctaa ttttttcaaac aaagaatctg agctgcatttt    1920
ttacagaaca gaaatgcaac gcgagagcgc tattttacca acaaagaatc tatacttctt    1980
```

```
ttttgttcta caaaaatgca tcccgagagc gctattttt taacaaagca tcttagatta    2040
cttttttct cctttgtgcg ctctataatg cagtctcttg ataacttttt gcactgtagg    2100
tccgttaagg ttagaagaag gctactttgg tgtctatttt ctcttccata aaaaaagcct   2160
gactccactt cccgcgttta ctgattacta gcgaagctgc gggtgcattt tttcaagata   2220
aaggcatccc cgattatatt ctataccgat gtggattgcg catactttgt gaacagaaag   2280
tgatagcgtt gatgattctt cattggtcag aaaattatga acggtttctt ctattttgtc   2340
tctatatact acgtatagga aatgtttaca ttttcgtatt gttttcgatt cactctatga   2400
atagttctta ctacaatttt tttgtctaaa gagtaatact agagataaac ataaaaaatg   2460
tagaggtcga gtttagatgc aagttcaagg agcgaaaggt ggatgggtag gttatatagg   2520
gatatagcac agagatatat agcaaagaga tacttttgag caatgtttgt ggaagcggta   2580
ttcgcaatat tttagtagct cgttacagtc cggtgcgttt ttggtttttt gaaagtgcgt   2640
cttcagagcg cttttggttt tcaaaagcgc tctgaagttc ctatactttc tagctagaga   2700
ataggaactt cggaatagga acttcaaagc gtttccgaaa acgagcgctt ccgaaaatgc   2760
aacgcgagct gcgcacatac agctcactgt tcacgtcgca cctatatctg cgtgttgcct   2820
gtatatatat atacatgaga agaacggcat agtgcgtgtt tatgcttaaa tgcgttatgg   2880
tgcactctca gtacaatctg ctctgatgcc gcatagttaa gccagccccg acacccgcca   2940
acacccgctg acgcgccctg acgggcttgt ctgctcccgg catccgctta cagacaagct   3000
gtgaccgtct ccgggagctg catgtgtcag aggttttcac cgtcatcacc gaaacgcgcg   3060
agacgaaagg gcctcgtgat acgcctattt ttataggtta atgtcatgat aataatggtt   3120
tcttagacgt caggtggcac ttttcgggga atgtgcgcg gaaccctat ttgtttattt    3180
ttctaaatac attcaaatat gtatccgctc atgagacaat aaccctgata aatgcttcaa   3240
taatattgaa aaaggaagag tatgagtatt caacatttcc gtgtcgccct tattcccttt   3300
tttgcggcat tttgccttcc tgtttttgct cacccagaaa cgctggtgaa agtaaaagat   3360
gctgaagatc agttgggtgc acgagtgggt tacatcgaac tggatctcaa cagcggtaag   3420
atccttgaga gttttcgccc cgaagaacgt tttccaatga tgagcacttt taaagttctg   3480
ctatgtggcg cggtattatc ccgtattgac gccgggcaag agcaactcgg tcgccgcata   3540
cactattctc agaatgactt ggttgagtac tcaccagtca cagaaaagca tcttacggat   3600
ggcatgacag taagagaatt atgcagtgct gccataacca tgagtgataa cactgcggcc   3660
aacttacttc tgacaacgat cggaggaccg aaggagctaa ccgcttttt gcacaacatg   3720
ggggatcatg taactcgcct tgatcgttgg gaaccggagc tgaatgaagc cataccaaac   3780
gacgagcgtg acaccacgat gcctgtagca atggcaacaa cgttgcgcaa actattaact   3840
ggcgaactac ttactctagc ttcccggcaa caattaatag actggatgga ggcggataaa   3900
gttgcaggac cacttctgcg ctcggccctt ccggctggct ggtttattgc tgataaatct   3960
ggagccggtg agcgtgggtc tcgcggtatc attgcagcac tggggccaga tggtaagccc   4020
tcccgtatcg tagttatcta cacgacgggg agtcaggcaa ctatggatga acgaaataga   4080
cagatcgctg agataggtgc ctcactgatt aagcattggt aactgtcaga ccaagtttac   4140
tcatatatac tttagattga tttaaaactt cattttttaat ttaaaggat ctaggtgaag   4200
atccttttg ataatctcat gaccaaaatc ccttaacgtg agttttcgtt ccactgagcg   4260
tcagaccccg tagaaaagat caaaggatct tcttgagatc ctttttttct gcgcgtaatc   4320
tgctgcttgc aaacaaaaaa accaccgcta ccagcggtgg tttgtttgcc ggatcaagag   4380
```

```
ctaccaactc tttttccgaa ggtaactggc ttcagcagag cgcagatacc aaatactgtc   4440
cttctagtgt agccgtagtt aggccaccac ttcaagaact ctgtagcacc gcctacatac   4500
ctcgctctgc taatcctgtt accagtggct gctgccagtg gcgataagtc gtgtcttacc   4560
gggttggact caagacgata gttaccggat aaggcgcagc ggtcgggctg aacgggggt    4620 tcgtgcacac agcccagctt ggagcgaacg acctacaccg aactgagata cctacagcgt   4680
gagcattgag aaagcgccac gcttcccgaa gggagaaagg cggacaggta tccggtaagc   4740
ggcagggtcg gaacaggaga gcgcacgagg gagcttccag ggggaaacgc ctggtatctt   4800
tatagtcctg tcgggtttcg ccacctctga cttgagcgtc gattttttgtg atgctcgtca   4860 ggggggcgga gcctatggaa aaacgccagc aacgcggcct ttttacggtt cctggccttt   4920
tgctggcctt ttgctcacat gttctttcct gcgttatccc ctgattctgt ggataaccgt   4980
attaccgcct ttgagtgagc tgataccgct cgccgcagcc gaacgaccga gcgcagcgag   5040
tcagtgagcg aggaagcgga agagcgccca atacgcaaac cgcctctccc cgcgcgttgg   5100
ccgattcatt aatccaggat cccaattaat gtgagttacc tcactcatta ggcacccag    5160 gctttacact ttatgcttcc ggctcgtatg ttgtgtggaa ttgtgagcgg ataacaattt   5220
cacacaggaa acagctatga ccatgattac gaattaattc gagctcggta cccggggatc   5280
gatccactag agatctgttt agcttgcctc gtccccgccg ggtcacccgg ccagcgacat   5340
ggaggcccag aatacccctcc ttgacagtct tgacgtgcgc agctcagggg catgatgtga   5400
ctgtcgcccg tacatttagc ccatacatcc ccatgtataa tcatttgcat ccatacattt   5460
tgatggccgc acggcgcgaa gcaaaaatta cggctcctcg ctgcagacct gcgagcaggg   5520
aaacgctccc ctcacagacg cgttgaattg tccccacgcc gcgcccctgt agagaaatat   5580
aaaaggttag gatttgccac tgaggttctt ctttcatata cttccttttta aaatcttgct   5640 aggatacagt tctcacatca catccgaaca taaacaacca tggccgacca agcgacgccc   5700
aacctgccat cacgagattt cgattccacg gccgccttct atgaaaggtt gggcttcgga   5760
atcgttttcc gggacgccgg ctggatgatc ctccagcgcg gggatctcaa gctggagttc   5820
ttcgcccacc ccgggctcga tcccctcgcg agttggttca gctgctgcct gaggctggac   5880
gacctcgcgg agttctaccg gcagtgcaaa tccgtcggca tccaggaaac cagcagcggc   5940
tatccgcgca tccatgcccc cgaactgcag gagtggggag gcacgatggc cgcttttggtc   6000 gacccggacg ggacgctcct gcgcctgata cagaacgaat tgcttgcagg catctcatga   6060
tcagtactga caataaaaag attcttgttt tcaagaactt gtcatttgta tagttttttt   6120
atattgtagt tgttctattt taatcaaatg ttagcgtgat ttatattttt tttcgcctcg   6180
acatcatctg cccagatgcg aagttaagtg cgcagaaagt aatatcatgc gtcaatcgta   6240
tgtgaatgct ggtcgctata ctgctgtcga ttcgatacta acgccgccat ccagtgtcga   6300
aaacgagctc tcgagaaccc ttaatataac ttcgtataat gtatgctata cgaagttatt   6360
aggtgatatc agatccacta gtcttctagg cgggttatct actgatccga gcttccacta   6420
ggatagcacc caaacacctg catatttgga cgacctttac ttacaccacc aaaaaccact   6480
ttcgcctctc ccgcccctga taacgtccac taattgagcg attacctgag cggtcctctt   6540
ttgtttgcag catgagactt gcatactgca aatcgtaagt agcaacgtct caaggtcaaa   6600
actgtatgga aaccttgtca cctcacttaa ttctagctag cctaccctgc aagtcaagag   6660
gtctccgtga ttcctagcca cctcaaggta tgcctctccc cggaaactgt ggcctttttct   6720
```

```
ggcacacatg atctccacga tttcaacata taaatagctt ttgataatgg caatattaat    6780
caaatttatt ttacttcttt cttgtaacat ctctcttgta atcccttatt ccttctagct    6840 attttttcata aaaaaccaag caactgctta tcaacacaca aacactaaat caaagaattc    6900
ttaattaaac aatgatgaag ctcagttggc ttgaggcggc tgccttgacg gctgcttcag    6960
tcgtcagcgc tgatgaatta gccttttccc caccatttta cccatctcct tgggctaatg    7020
gacaaggcga atgggccgaa gcataccaga gagccgttgc tattgttagt cagatgacac    7080
ttgatgaaaa agtgaatttg actacaggta cggggtggga attagaaaag tgtgtaggtc    7140
aaactggtgg agttccaaga ttaaacatcg gagggatgtg cttacaagat agtccactag    7200
gtatcagaga ttctgattac aattctgctt ttcctgcagg cgttaatgtt gccgcaacgt    7260
gggacaaaaa cttagcctac ctaagaggtc aagctatggg tcaggaatttt tcagataagg    7320 gcatcgatgt ccaattaggc ccagccgcag gaccattggg acgatctcca gatggtggga    7380
gaaactggga gggattctca cctgaccctg cacttactgg tgttctgttt gcagaaacta    7440
tcaaaggtat acaagacgcc ggtgttgttg cgacagctaa acactacatt ttgaatgaac    7500
aagagcattt tagacaagtg gctgaggccg ctgggtacgg tttcaacata tccgatacaa    7560
tctcatcaaa tgtggacgac aagacgattc atgagatgta tttgtggcca tttgctgatg    7620
cagtgagagc aggcgttggg gctataatgt gcagctacaa tcaaatcaat aatagttatg    7680
gctgtcaaaa ctcatacact ctcaataagt tattgaaggc tgaactgggt ttccaaggtt    7740
tcgtaatgtc agattggggt gcccatcact ccggtgtcgg ttctgcttta gctggtcttg    7800
acatgtctat gcctggtgac attacatttg actccgcaac atctttctgg ggaacaaatc    7860
tgacaattgc cgtccttaac ggcaccgtgc cacagtggag agttgacgac atggcagtcc    7920
gtattatggc tgcatattac aaagtcggcc gtgaccgact gtaccaacca ccaaacttca    7980
gctcctggac tagagatgaa tacggcttta agtactttta tccacaggag ggaccatacg    8040
aaaaagttaa tcactttgtc aatgtccaga ggaatcattc cgaagtcatc agaaagctag    8100
gtgcagattc tacagttttg ttgaaaaaca ataacgcatt gcctttaaca ggtaaagagc    8160
gaaaggttgc catcttgggt gaagatgcgg gttctaatag ttacggagcc aatgggtgtt    8220
cagatagagg ctgcgataac ggtactttag caatggcctg gggatcaggc acagctgaat    8280 ttccataccct tgtgacacct gaacaagcaa tccaagctga agtattgaaa cataaagggt    8340
cagtttatgc tataaccgac aattgggcat tgtctcaagt cgaaaccctc gcaaaacaag    8400
cctctgttag tttggttttt gtgaatagtg atgctggtga agggtacatt tcagttgatg    8460
gaaacgaagg cgatagaaat aacctcacat tgtggaaaaa tggcgataat cttattaagg    8520
ctgctgcgaa caattgtaac aatactattg tggttatcca ttctgtaggg cctgtccttg    8580
ttgacgaatg gtacgaccat ccaaatgtga cagctatact atgggcaggc ttaccaggtc    8640
aagagtctgg aaattcctta gcagatgtac tctacggacg tgtcaatcct ggagctaagt    8700
ctccattcac atggggtaag actagagagg cttacgagaa ttacttagta agagaattga    8760
acaatggcaa cggtgcgcca caagatgatt tctctgaagg tgtttttatc gattatagag    8820
ggttcgacaa gagaaacgag actccaatct acgagtttgg tcatggtttg agttatacaa    8880
cttttaacta ctcagggctt catattcaag tactaaacgc atcttctaac gcccaagtag    8940
caacggaaac tggcgcagct ccaactttcg gtcaggtggg taatgcctca gattatgttt    9000
atccagaagg cctcacaagg atttcaaagt tcatataccc ttggctaaac tctacagatt    9060
tgaaagcatc atccggtgat ccatactatg gtgttgatac tgcagaacat gtgcctgaag    9120
```

```
gcgctactga cggatcacca caacctgttc tgcctgctgg aggtggttca ggagggaacc    9180
ctagactcta tgatgagtta attagggtat ctgttactgt gaaaaacaca gggagagtgg    9240
cgggtgatgc cgtgcctcaa ctatacgtgt ctcttggagg accaaatgaa ccaaaagtag    9300
ttttgagaaa attcgacaga ttaacattga aaccatccga ggaaactgtt tggactacta    9360
ccctgacccg tagagatttg tctaattggg acgtagctgc ccaagattgg gtcatcacaa    9420
gttaccctaa gaaagtacat gttggctcta gttccagaca acttccatta cacgctgccc    9480
tgccaaaagt gcaagatgat gatgacaaag gtggttctcc tccttctcat catcaccacc    9540
accactaagg cgcgccctcg agagcttttg attaagcctt ctagtccaaa aaacacgttt    9600
ttttgtcatt tatttcattt tcttagaata gtttagttta ttcattttat agtcacgaat    9660
gttttatgat tctatatagg gttgcaaaca agcatttttc attttatgtt aaaacaattt    9720
caggtttacc ttttattctg cttgtggtga cgcgtgtatc cgcccgctct tttggtcacc    9780
catgtattta attgcataaa taattcttaa aagtggagct agtctatttc tatttacata    9840
cctctcattt ctcatttcct cctaatgtgt caatgatcat attcttaact ggaccgatct    9900
tattcgtcag attcaaacca aaagttctta gggctaccac aggaggaaaa ttagtgtgat    9960
ataatttaaa taatttatcc gccattccta atagaacgtt gttcgacgga tatctttctg   10020
cccaaaaggg ttctaagctc aatgaagagc caatgtctaa acctctttgc              10070

<210> SEQ ID NO 34
<211> LENGTH: 10070
<212> TYPE: DNA
<213> ORGANISM: Aspergillus oryzae
<220> FEATURE:
<221> NAME/KEY: misc_feature
<222> LOCATION: (1)..(10070)
<223> OTHER INFORMATION: plasmid pMU3560

<400> SEQUENCE: 34
ggccgcaagc taattcgcgc gaagctagct tggcactggc cgtcgtttta caacgtcgtg      60
actgggaaaa ccctggcgtt acccaactta atcgccttgc agcacatccc cccttcgcca     120
gctggcgtaa tagcgaagag gcccgcaccg atcgcccttc ccaacagttg cgcagcctga     180
atggcgaatg cgcctgatg cggtattttc tccttacgca tctgtgcggt atttcacacc      240
gcataggaga tctaagctct ggcgtaatag cgaagaggcc cgcaccgatc gcccttccca     300
acagttgcgc agcctgaatg gcgaatggcg cctgatgcgg tattttctcc ttacgcatct     360
gtgcggtatt tcacaccgca tagggtaata actgatataa ttaaattgaa gctctaattt     420
gtgagtttag tatacatgca tttacttata atacagtttt ttagttttgc tggccgcatc     480
ttctcaaata tgcttcccag cctgcttttc tgtaacgttc accctctacc ttagcatccc     540 ttcccttttgc aaatagtcct cttccaacaa taataatgtc agatcctgta gagaccacat     600
catccacggt tctatactgt tgacccaatg cgtctccctt gtcatctaaa cccacaccgg     660
gtgtcataat caaccaatcg taaccttcat ctcttccacc catgtctctt tgagcaataa     720
agccgataac aaaatctttg tcgctcttcg caatgtcaac agtacccctta gtatattctc     780 cagtagatag ggagcccttg catgacaatt ctgctaacat caaaaggcct ctaggttcct     840
ttgttacttc ttctgccgcc tgcttcaaac cgctaacaat acctgggccc accacaccgt     900
gtgcattcgt aatgtctgcc cattctgcta ttctgtatac acccgcagag tactgcaatt     960
tgactgtatt accaatgtca gcaaattttc tgtcttcgaa gagtaaaaaa ttgtacttgg    1020
```

```
cggataatgc ctttagcggc ttaactgtgc cctccatgga aaaatcagtc aagatatcca    1080
catgtgtttt tagtaaacaa attttgggac ctaatgcttc aactaactcc agtaattcct    1140
tggtggtacg aacatccaat gaagcacaca agtttgtttg cttttcgtgc atgatattaa    1200
atagcttggc agcaacagga ctaggatgag tagcagcacg ttccttatat gtagctttcg    1260
acatgattta tcttcgtttc ggttttttgtt ctgtgcagtt gggttaagaa tactgggcaa    1320
tttcatgttt cttcaacact acatatgcgt atatatacca atctaagtct gtgctccttc    1380
cttcgttctt ccttctgttc ggagattacc gaatcaaaaa aatttcaaag aaaccgaaat    1440
caaaaaaaag aataaaaaaa aaatgatgaa ttgaaaagct cttgttaccc atcattgaat    1500
tttgaacatc cgaacctggg agttttccct gaaacagata gtatatttga acctgtataa    1560
taatatatag tctagcgctt tacggaagac aatgtatgta tttcggttcc tggagaaact    1620
attgcatcta ttgcataggt aatcttgcac gtcgcatccc cggttcattt tctgcgtttc    1680
catcttgcac ttcaatagca tatctttgtt aacgaagcat ctgtgcttca ttttgtagaa    1740
caaaaatgca acgcgagagc gctaatttt caaacaaaga atctgagctg cattttaca    1800 gaacagaaat gcaacgcgaa agcgctattt taccaacgaa gaatctgtgc ttcattttg    1860 taaaacaaaa atgcaacgcg agagcgctaa ttttcaaac aaagaatctg agctgcattt    1920
ttacagaaca gaaatgcaac gcgagagcgc tattttacca acaaagaatc tatacttctt    1980
ttttgttcta caaaaatgca tcccgagagc gctatttttc taacaaagca tcttagatta    2040 cttttttct cctttgtgcg ctctataatg cagtctcttg ataactttt gcactgtagg    2100 tccgttaagg ttagaagaag gctactttgg tgtctatttt ctcttccata aaaaaagcct    2160
gactccactt cccgcgttta ctgattacta gcgaagctgc gggtgcattt tttcaagata    2220
aaggcatccc cgattatatt ctataccgat gtggattgcg catactttgt gaacagaaag    2280
tgatagcgtt gatgattctt cattggtcag aaaattatga acggtttctt ctattttgtc    2340
tctatatact acgtatagga aatgtttaca ttttcgtatt gttttcgatt cactctatga    2400
atagttctta ctacaatttt tttgtctaaa gagtaatact agagataaac ataaaaaatg    2460
tagaggtcga gttagatgc aagttcaagg agcgaaaggt ggatgggtag gttatatagg    2520
gatatagcac agagatatat agcaaagaga tactttgag caatgtttgt ggaagcggta    2580
ttcgcaatat tttagtagct cgttacagtc cggtgcgttt ttggtttttt gaaagtgcgt    2640
cttcagagcg cttttggttt tcaaaagcgc tctgaagttc ctatactttc tagctagaga    2700
ataggaactt cggaatagga acttcaaagc gtttccgaaa acgagcgctt ccgaaaatgc    2760
aacgcgagct gcgcacatac agctcactgt tcacgtcgca cctatatctg cgtgttgcct    2820
gtatatatat atacatgaga agaacggcat agtgcgtgtt tatgcttaaa tgcgttatgg    2880
tgcactctca gtacaatctg ctctgatgcc gcatagttaa gccagccccg acacccgcca    2940
acacccgctg acgcgccctg acgggcttgt ctgctcccgg catccgctta cagacaagct    3000
gtgaccgtct ccgggagctg catgtgtcag aggttttcac cgtcatcacc gaaacgcgcg    3060
agacgaaagg gcctcgtgat acgcctattt ttataggtta atgtcatgat aataatggtt    3120
tcttagacgt caggtggcac ttttcgggga atgtgcgcg aaccccctat tgttttattt    3180
ttctaaatac attcaaatat gtatccgctc atgagacaat aaccctgata aatgcttcaa    3240
taatattgaa aaaggaagag tatgagtatt caacatttcc gtgtcgccct tattcccttt    3300
tttgcggcat tttgccttcc tgttttttgct cacccagaaa cgctggtgaa agtaaaagat    3360
gctgaagatc agttgggtgc acgagtgggt tacatcgaac tggatctcaa cagcggtaag    3420
```

| | |
|---|---|
| atccttgaga gttttcgccc cgaagaacgt tttccaatga tgagcacttt taaagttctg | 3480 |
| ctatgtggcg cggtattatc ccgtattgac gccgggcaag agcaactcgg tcgccgcata | 3540 |
| cactattctc agaatgactt ggttgagtac tcaccagtca cagaaaagca tcttacggat | 3600 |
| ggcatgacag taagagaatt atgcagtgct gccataacca tgagtgataa cactgcggcc | 3660 |
| aacttacttc tgacaacgat cggaggaccg aaggagctaa ccgcttttt gcacaacatg | 3720 |
| ggggatcatg taactcgcct tgatcgttgg aaccggagc tgaatgaagc cataccaaac | 3780 |
| gacgagcgtg acaccacgat gcctgtagca atggcaacaa cgttgcgcaa actattaact | 3840 |
| ggcgaactac ttactctagc ttcccggcaa caattaatag actggatgga ggcggataaa | 3900 |
| gttgcaggac cacttctgcg ctcggccctt ccggctggct ggtttattgc tgataaatct | 3960 |
| ggagccggtg agcgtgggtc tcgcggtatc attgcagcac tggggccaga tggtaagccc | 4020 |
| tcccgtatcg tagttatcta cacgacgggg agtcaggcaa ctatggatga acgaaataga | 4080 |
| cagatcgctg agataggtgc ctcactgatt aagcattggt aactgtcaga ccaagtttac | 4140 |
| tcatatatac tttagattga tttaaaactt cattttaat ttaaaaggat ctaggtgaag | 4200 |
| atccttttg ataatctcat gaccaaaatc ccttaacgtg agttttcgtt ccactgagcg | 4260 |
| tcagacccg tagaaaagat caaaggatct tcttgagatc ctttttttct gcgcgtaatc | 4320 |
| tgctgcttgc aaacaaaaaa accaccgcta ccagcggtgg tttgtttgcc ggatcaagag | 4380 |
| ctaccaactc tttttccgaa ggtaactggc ttcagcagag cgcagatacc aaatactgtc | 4440 |
| cttctagtgt agccgtagtt aggccaccac ttcaagaact ctgtagcacc gcctacatac | 4500 |
| ctcgctctgc taatcctgtt accagtggct gctgccagtg gcgataagtc gtgtcttacc | 4560 |
| gggttggact caagacgata gttaccggat aaggcgcagc ggtcgggctg aacgggggt | 4620 |
| tcgtgcacac agcccagctt ggagcgaacg acctacaccg aactgagata cctacagcgt | 4680 |
| gagcattgag aaagcgccac gcttcccgaa gggagaaagg cggacaggta tccggtaagc | 4740 |
| ggcagggtcg gaacaggaga gcgcacgagg gagcttccag ggggaaacgc ctggtatctt | 4800 |
| tatagtcctg tcgggtttcg ccacctctga cttgagcgtc gatttttgtg atgctcgtca | 4860 |
| ggggggcgga gcctatggaa aaacgccagc aacgcggcct ttttacggtt cctggccttt | 4920 |
| tgctggcctt tgctcacat gttctttcct gcgttatccc ctgattctgt ggataaccgt | 4980 |
| attaccgcct ttgagtgagc tgataccgct cgccgcagcc gaacgaccga gcgcagcgag | 5040 |
| tcagtgagcg aggaagcgga agagcgccca atacgcaaac cgcctctccc gcgcgttgg | 5100 |
| ccgattcatt aatccaggat cccaattaat gtgagttacc tcactcatta ggcaccccag | 5160 |
| gctttacact ttatgcttcc ggctcgtatg ttgtgtggaa ttgtgagcgg ataacaattt | 5220 |
| cacacaggaa acagctatga ccatgattac gaattaattc gagctcggta cccggggatc | 5280 |
| gatccactag agatctgttt agcttgcctc gtccccgccg ggtcacccgg ccagcgacat | 5340 |
| ggaggcccag ataccctcc ttgacagtct tgacgtgcgc agctcagggg catgatgtga | 5400 |
| ctgtcgcccg tacatttagc ccatacatcc ccatgtataa tcatttgcat ccatacattt | 5460 |
| tgatggccgc acggcgcgaa gcaaaaatta cggctcctcg ctgcagacct gcgagcaggg | 5520 |
| aaacgctccc ctcacagacg cgttgaattg tccccacgcc gcgcccctgt agagaaatat | 5580 |
| aaaaggttag gatttgccac tgaggttctt ctttcatata cttccttta aaatcttgct | 5640 |
| aggatacagt tctcacatca catccgaaca taaacaacca tggccgacca agcgacgccc | 5700 |
| aacctgccat cacgagattt cgattccacg gccgccttct atgaaaggtt gggcttcgga | 5760 |

```
atcgttttcc gggacgccgg ctggatgatc ctccagcgcg gggatctcaa gctggagttc    5820
ttcgcccacc ccgggctcga tcccctcgcg agttggttca gctgctgcct gaggctggac    5880
gacctcgcgg agttctaccg gcagtgcaaa tccgtcggca tccaggaaac cagcagcggc    5940
tatccgcgca tccatgcccc cgaactgcag gagtggggag gcacgatggc cgctttggtc    6000
gacccggacg ggacgctcct gcgcctgata cagaacgaat tgcttgcagg catctcatga    6060
tcagtactga caataaaaag attcttgttt caagaactt gtcatttgta tagtttttt     6120 atattgtagt tgttctattt taatcaaatg ttagcgtgat ttatattttt tttcgcctcg    6180
acatcatctg cccagatgcg aagttaagtg cgcagaaagt aatatcatgc gtcaatcgta    6240
tgtgaatgct ggtcgctata ctgctgtcga ttcgatacta acgccgccat ccagtgtcga    6300
aaacgagctc tcgagaaccc ttaatataac ttcgtataat gtatgctata cgaagttatt    6360
aggtgatatc agatccacta gtcttctagg cgggttatct actgatccga gcttccacta    6420
ggatagcacc caaacacctg catatttgga cgacctttac ttacaccacc aaaaaccact    6480
ttcgcctctc ccgcccctga taacgtccac taattgagcg attacctgag cggtcctctt    6540
ttgtttgcag catgagactt gcatactgca atcgtaagt agcaacgtct caaggtcaaa     6600
actgtatgga aaccttgtca cctcacttaa ttctagctag cctaccctgc aagtcaagag    6660
gtctccgtga ttcctagcca cctcaaggta tgcctctccc cggaaactgt ggcctttct     6720 ggcacacatg atctccacga tttcaacata taaatagctt ttgataatgg caatattaat    6780
caaatttatt ttacttcttt cttgtaacat ctctcttgta atcccttatt ccttctagct    6840 attttcata aaaaaccaag caactgctta tcaacacaca aacactaaat caagaattc      6900 ttaattaaac aatgaagctt ggttggatcg aggtggccgc attggcggct gcctcagtag    6960
tcagtgccaa ggatgacctc gcatattcac ctccatttta ccctagccct tgggcagatg    7020
gccagggcga atgggccgaa gtctacaaaa gagctgtgga tattgtctct caaatgactt    7080
tgacagaaaa agtgaactta acgactggta ctgggtggca attggaaaga tgtgtaggac    7140
aaacaggttc tgtcccaagg ctcaatattc catcactatg cttgcaagac tcccctcttg    7200
gtattagatt ctctgattac aattcagcat ttccagccgg tgttaatgtt gctgcgacct    7260
gggacaaaac ccttgcctat ttgagaggac aagcaatggg cgaagagttc tctgataagg    7320
gtattgatgt tcaattaggt cctgctgcag gcccactggg tgcccatcca gacggtggac    7380
gtaactggga aggtttcagt ccagatcctg cattgactgg tgtgcttttc gccgaaacaa    7440
ttaaaggtat acaggacgct ggtgtaattg ctactgccaa acattcatc atgaacgaac     7500 aagagcattt cagacaacaa ccagaagctg ccggatatgg ttttaatgtt tccgattcat    7560
tatcttcaaa tgttgatgat aaaacaatgc atgaactata cctttggcca tttgcagacg    7620
ccgttagagc tggggttgga gctgtgatgt gctcatacaa tcaaatcaac aatagttacg    7680
gctgcgaaaa ttctgaaaca ttgaacaaac ttttgaaagc tgagttggga tttcagggtt    7740
tcgttatgtc cgactggaca gcacaccatt caggagtggg cgctgcactg gctggtttag    7800
atatgagtat gccaggggat gtgacttttg attctggtac atcttttgg ggagctaatt     7860 tgaccgtggg ggtactaaac ggtacgatcc ctcaatggag agtagatgat atggccgtta    7920
gaataatggc cgcttattac aaggtgggga gagatacaaa gtatactcct ccaaacttct    7980
cctcatggac tagagatgaa tacgattcg cacataatca cgtatctgaa ggtgcctatg     8040
aaagagttaa tgaatttgta gatgtacaaa gggaccacgc agacttaata agacgtatag    8100
gggcacagtc aactgtttta ctgaaaaaca agggtgctct accattatct cgtaaggaaa    8160
```

```
aattggttgc gctattaggt gaggatgctg gctctaattc ctggggtgct aatggatgtg    8220
acgatagagg atgtgataat ggcactttag caatggcatg gggttctggc actgctaatt    8280
ttccatatct tgttactcca gagcaagcta ttcaaaacga agttttgcag ggtagaggca    8340
atgttttcgc agttactgat tcatgggctt tagacaagat cgcagcagcg gcacgacagg    8400
cgtcagtgag cttggttttt gtcaacagtg acagcggtga aggataccta tctgtcgatg    8460
gaaacgaggg tgatagaaat aacattactc tgtggaaaaa tggtgacaat gttgttaaga    8520
cagcggccaa caattgtaac aacaccgtgg tcattatcca ctccgtcgga ccagtgctaa    8580
ttgatgaatg gtatgatcat ccaaatgtta cgggcatctt atgggctggc ttgcctggac    8640
aagagtcagg aaattctatc gctgatgttt tatacggcag agtcaaccca ggagcgaaat    8700
cccctttac atgggggaaa acaagagaaa gttatggttc accactcgta aaggatgcaa    8760
acaatggaaa tggcgcacca caaagtgatt ttacccaagg tgtgttcatc gattacagac    8820
attttgataa gttcaacgaa actcctatct acgaatttgg ctacggcctg tcttatacca    8880
catttgaatt atctgatttg catgtccaac cactcaatgc ttcaagatat actcctacat    8940
ctggtatgac ggaagccgct aaaaactttg gggaaatagg tgacgcgtct gaatacgtct    9000
acccagaagg tttggaaagg attcatgagt tcatctaccc ttggatcaat tctacagacc    9060
taaaggcatc atcagatgat tcaaattacg gctgggagga cagtaagtac attccagagg    9120
gagctacaga cggttctgcc cagcctaggt taccagcatc tggaggggct gggggtaacc    9180
caggtcttta cgaggatctg tttagagtat ccgttaaagt caaaaataca ggaaatgttg    9240
ccggagatga agtcccacaa ttgtacgtgt ccttgggcgg accaaatgaa cctaaagtag    9300
tcctcagaaa attcgagaga atccatttgg ccccttccca agaggcagtg tggactacca    9360
cattaacaag acgtgacctt gctaattggg acgtaagcgc gcaagattgg acagttacac    9420
cttacccaaa aacaatatac gtcggtaata gttccagaaa gctcccactg caagctagtc    9480
taccaaaagc tcaagatgat gatgacaaag gtggttctcc tccttctcat catcaccacc    9540
accactaagg cgcgccctcg agagcttttg attaagcctt ctagtccaaa aaacacgttt    9600
ttttgtcatt tatttcattt tcttagaata gtttagttta ttcattttat agtcacgaat    9660
gtttatgat tctatatagg gttgcaaaca agcatttttc attttatgtt aaaacaattt    9720
caggtttacc ttttattctg cttgtggtga cgcgtgtatc cgcccgctct tttggtcacc    9780
catgtattta attgcataaa taattcttaa aagtggagct agtctatttc tatttacata    9840
cctctcattt ctcatttcct cctaatgtgt caatgatcat attcttaact ggaccgatct    9900
tattcgtcag attcaaacca aaagttctta gggctaccac aggaggaaaa ttagtgtgat    9960
ataatttaaa taatttatcc gccattccta atagaacgtt gttcgacgga tatctttctg   10020
cccaaaaggg ttctaagctc aatgaagagc caatgtctaa acctctttgc                10070
```

<210> SEQ ID NO 35
<211> LENGTH: 10070
<212> TYPE: DNA
<213> ORGANISM: Penicillium decumbens
<220> FEATURE:
<221> NAME/KEY: misc_feature
<222> LOCATION: (1)..(10070)
<223> OTHER INFORMATION: plasmid pMU3561

<400> SEQUENCE: 35

```
ggccgcaagc taattcgcgc gaagctagct tggcactggc cgtcgtttta caacgtcgtg      60
```

| | |
|---|---|
| actgggaaaa ccctggcgtt acccaactta atcgccttgc agcacatccc cccttcgcca | 120 |
| gctggcgtaa tagcgaagag gcccgcaccg atcgcccttc ccaacagttg cgcagcctga | 180 |
| atggcgaatg gcgcctgatg cggtattttc tccttacgca tctgtgcggt atttcacacc | 240 |
| gcataggaga tctaagctct ggcgtaatag cgaagaggcc cgcaccgatc gcccttccca | 300 |
| acagttgcgc agcctgaatg gcgaatggcg cctgatgcgg tattttctcc ttacgcatct | 360 |
| gtgcggtatt tcacaccgca tagggtaata actgatataa ttaaattgaa gctctaattt | 420 |
| gtgagtttag tatacatgca tttacttata atacagtttt ttagttttgc tggccgcatc | 480 |
| ttctcaaata tgcttcccag cctgcttttc tgtaacgttc accctctacc ttagcatccc | 540 |
| ttccctttgc aaatagtcct cttccaacaa taataatgtc agatcctgta gagaccacat | 600 |
| catccacggt tctatactgt tgacccaatg cgtctccctt gtcatctaaa cccacaccgg | 660 |
| gtgtcataat caaccaatcg taaccttcat ctcttccacc catgtctctt tgagcaataa | 720 |
| agccgataac aaaatcttg tcgctcttcg caatgtcaac agtacccta gtatattctc | 780 |
| cagtagatag ggagcccttg catgacaatt ctgctaacat caaaaggcct ctaggttcct | 840 |
| ttgttacttc ttctgccgcc tgcttcaaac cgctaacaat acctgggccc accacaccgt | 900 |
| gtgcattcgt aatgtctgcc cattctgcta ttctgtatac acccgcagag tactgcaatt | 960 |
| tgactgtatt accaatgtca gcaaattttc tgtcttcgaa gagtaaaaaa ttgtacttgg | 1020 |
| cggataatgc ctttagcggc ttaactgtgc cctccatgga aaaatcagtc aagatatcca | 1080 |
| catgtgtttt tagtaaacaa attttgggac ctaatgcttc aactaactcc agtaattcct | 1140 |
| tggtggtacg aacatccaat gaagcacaca agtttgtttg cttttcgtgc atgatattaa | 1200 |
| atagcttggc agcaacagga ctaggatgag tagcagcacg ttccttatat gtagctttcg | 1260 |
| acatgattta tcttcgtttc ggttttttgtt ctgtgcagtt gggttaagaa tactgggcaa | 1320 |
| tttcatgttt cttcaacact acatatgcgt atatatacca atctaagtct gtgctccttc | 1380 |
| cttcgttctt ccttctgttc ggagattacc gaatcaaaaa aatttcaaag aaaccgaaat | 1440 |
| caaaaaaag aataaaaaaa aaatgatgaa ttgaaaagct cttgttaccc atcattgaat | 1500 |
| tttgaacatc cgaacctggg agttttccct gaaacagata gtatatttga acctgtataa | 1560 |
| taatatatag tctagcgctt tacggaagac aatgtatgta tttcggttcc tggagaaact | 1620 |
| attgcatcta ttgcataggt aatcttgcac gtcgcatccc cggttcattt tctgcgtttc | 1680 |
| catcttgcac ttcaatagca tatctttgtt aacgaagcat ctgtgcttca ttttgtagaa | 1740 |
| caaaaatgca acgcgagagc gctaattttt caaacaaaga atctgagctg cattttaca | 1800 |
| gaacagaaat gcaacgcgaa agcgctattt taccaacgaa gaatctgtgc ttcattttg | 1860 |
| taaaacaaaa atgcaacgcg agagcgctaa ttttttcaaac aaagaatctg agctgcatt | 1920 |
| ttacagaaca gaaatgcaac gcgagagcgc tattttacca caaagaatc tatacttctt | 1980 |
| ttttgttcta caaaaatgca tcccgagagc gctattttc taacaaagca tcttagatta | 2040 |
| ctttttttct cctttgtgcg ctctataatg cagtctcttg ataacttttt gcactgtagg | 2100 |
| tccgttaagg ttagaagaag gctactttgg tgtctatttt ctcttccata aaaaagcct | 2160 |
| gactccactt cccgcgttta ctgattacta gcgaagctgc gggtgcattt tttcaagata | 2220 |
| aaggcatccc cgattatatt ctataccgat gtggattgcg catactttgt gaacagaaag | 2280 |
| tgatagcgtt gatgattctt cattggtcag aaaattatga acggtttctt ctattttgtc | 2340 |
| tctatatact acgtatagga aatgtttaca ttttcgtatt gttttcgatt cactctatga | 2400 |
| atagttctta ctacaatttt tttgtctaaa gagtaatact agagataaac ataaaaaatg | 2460 |

```
tagaggtcga gtttagatgc aagttcaagg agcgaaaggt ggatgggtag gttatatagg    2520
gatatagcac agagatatat agcaaagaga tactttgag caatgtttgt ggaagcggta     2580
ttcgcaatat tttagtagct cgttacagtc cggtgcgttt ttggttttt gaaagtgcgt     2640 cttcagagcg cttttggttt tcaaaagcgc tctgaagttc ctatactttc tagctagaga   2700
ataggaactt cggaatagga acttcaaagc gttccgaaa acgagcgctt ccgaaaatgc    2760
aacgcgagct gcgcacatac agctcactgt tcacgtcgca cctatatctg cgtgttgcct    2820
gtatatatat atacatgaga agaacggcat agtgcgtgtt tatgcttaaa tgcgttatgg    2880
tgcactctca gtacaatctg ctctgatgcc gcatagttaa gccagccccg cacccgcca    2940 acaccgctg acgcgccctg acgggcttgt ctgctcccgg catccgctta cagacaagct     3000
gtgaccgtct ccgggagctg catgtgtcag aggttttcac cgtcatcacc gaaacgcgcg   3060
agacgaaagg gcctcgtgat acgcctattt ttataggtta atgtcatgat aataatggtt    3120
tcttagacgt caggtggcac ttttcgggga aatgtgcgcg gaaccctat ttgttattt     3180 ttctaaatac attcaaatat gtatccgctc atgagacaat aaccctgata aatgcttcaa   3240
taatattgaa aaaggaagag tatgagtatt caacatttcc gtgtcgccct tattcccttt   3300
tttgcggcat tttgccttcc tgtttttgct cacccagaaa cgctggtgaa agtaaaagat   3360
gctgaagatc agttgggtgc acgagtggg tacatcgaac tggatctcaa cagcggtaag    3420
atccttgaga gttttcgccc cgaagaacgt tttccaatga tgagcacttt taaagttctg   3480
ctatgtggcg cggtattatc ccgtattgac gccgggcaag agcaactcgg tcgccgcata   3540
cactattctc agaatgactt ggttgagtac tcaccagtca cagaaaagca tcttacggat    3600
ggcatgacag taagagaatt atgcagtgct gccataacca tgagtgataa cactgcggcc   3660
aacttacttc tgacaacgat cggaggaccg aaggagctaa ccgcttttt gcacaacatg    3720 ggggatcatg taactcgcct tgatcgttgg gaaccggagc tgaatgaagc cataccaaac   3780
gacgagcgtg acaccacgat gcctgtagca atggcaacaa cgttgcgcaa actattaact    3840
ggcgaactac ttactctagc ttcccggcaa caattaatag actggatgga gcggataaa    3900 gttgcaggac cacttctgcg ctcggccctt ccggctggct ggtttattgc tgataaatct    3960
ggagccggtg agcgtgggtc tcgcggtatc attgcagcac tggggccaga tggtaagccc   4020
tcccgtatcg tagttatcta cacgacgggg agtcaggcaa ctatggatga acgaaataga   4080
cagatcgctg agataggtgc ctcactgatt aagcattggt aactgtcaga ccaagtttac    4140
tcatatatac tttagattga tttaaaactt cattttaat ttaaaaggat ctaggtgaag    4200
atcctttttg ataatctcat gaccaaaatc ccttaacgtg agtttcgtt ccactgagcg    4260 tcagaccccg tagaaaagat caaaggatct tcttgagatc cttttttct gcgcgtaatc    4320 tgctgcttgc aaacaaaaaa accaccgcta ccagcggtgg tttgttgcc ggatcaagag    4380 ctaccaactc tttttccgaa ggtaactggc ttcagcagag cgcagatacc aaatactgtc    4440
cttctagtgt agccgtagtt aggccaccac ttcaagaact ctgtagcacc gcctacatac   4500
ctcgctctgc taatcctgtt accagtggct gctgccagtg gcgataagtc gtgtcttacc    4560
gggttggact caagacgata gttaccggat aaggcgcagc ggtcgggctg aacgggggt    4620 tcgtgcacac agcccagctt ggagcgaacg acctacaccg aactgagata cctacagcgt   4680
gagcattgag aaagcgccac gcttcccgaa gggagaaagg cggacaggta tccggtaagc   4740
ggcagggtcg gaacaggaga gcgcacgagg gagcttccag ggggaaacgc ctggtatctt   4800
```

| | |
|---|---|
| tatagtcctg tcgggtttcg ccacctctga cttgagcgtc gattttttgtg atgctcgtca | 4860 |
| gggggggcgga gcctatggaa aaacgccagc aacgcggcct ttttacggtt cctggccttt | 4920 |
| tgctggcctt ttgctcacat gttctttcct gcgttatccc ctgattctgt ggataaccgt | 4980 |
| attaccgcct ttgagtgagc tgataccgct cgccgcagcc gaacgaccga gcgcagcgag | 5040 |
| tcagtgagcg aggaagcgga agagcgccca atacgcaaac cgcctctccc cgcgcgttgg | 5100 |
| ccgattcatt aatccaggat cccaattaat gtgagttacc tcactcatta ggaccccag | 5160 |
| gctttacact ttatgcttcc ggctcgtatg ttgtgtggaa ttgtgagcgg ataacaattt | 5220 |
| cacacaggaa acagctatga ccatgattac gaattaattc gagctcggta cccggggatc | 5280 |
| gatccactag agatctgttt agcttgcctc gtccccgccg ggtcacccgg ccagcgacat | 5340 |
| ggaggcccag aataccctcc ttgacagtct tgacgtgcgc agctcagggg catgatgtga | 5400 |
| ctgtcgcccg tacatttagc ccatacatcc ccatgtataa tcatttgcat ccatacattt | 5460 |
| tgatggccgc acggcgcgaa gcaaaaatta cggctcctcg ctgcagacct gcgagcaggg | 5520 |
| aaacgctccc ctcacagacg cgttgaattg tccccacgcc gcgccctgt agagaaatat | 5580 |
| aaaaggttag gatttgccac tgaggttctt ctttcatata cttccttta aaatcttgct | 5640 |
| aggatacagt tctcacatca catccgaaca taaacaacca tggccgacca agcgacgccc | 5700 |
| aacctgccat cacgagattt cgattccacg gccgccttct atgaaaggtt gggcttcgga | 5760 |
| atcgttttcc gggacgccgg ctggatgatc ctccagcgcg ggatctcaa gctggagttc | 5820 |
| ttcgcccacc ccgggctcga tcccctcgcg agttggttca gctgctgcct gaggctggac | 5880 |
| gacctcgcgg agttctaccg gcagtgcaaa tccgtcggca tccaggaaac cagcagcggc | 5940 |
| tatccgcgca tccatgcccc cgaactgcag gagtggggag gcacgatggc cgctttggtc | 6000 |
| gacccggacg ggacgctcct gcgcctgata cagaacgaat tgcttgcagg catctcatga | 6060 |
| tcagtactga caataaaaag attcttgttt tcaagaactt gtcatttgta tagttttttt | 6120 |
| atattgtagt tgttctattt taatcaaatg ttagcgtgat ttatatttt tttcgcctcg | 6180 |
| acatcatctg cccagatgcg aagttaagtg cgcagaaagt aatatcatgc gtcaatcgta | 6240 |
| tgtgaatgct ggtcgctata ctgctgtcga ttcgatacta acgccgccat ccagtgtcga | 6300 |
| aaacgagctc tcgagaaccc ttaatataac ttcgtataat gtatgctata cgaagttatt | 6360 |
| aggtgatatc agatccacta gtcttctagg cgggttatct actgatccga gcttccacta | 6420 |
| ggatagcacc caaacacctg catatttgga cgacctttac ttacaccacc aaaaaccact | 6480 |
| ttcgcctctc ccgcccctga taacgtccac taattgagcg attacctgag cggtcctctt | 6540 |
| ttgtttgcag catgagactt gcatactgca atcgtaagt agcaacgtct caaggtcaaa | 6600 |
| actgtatgga aaccttgtca cctcacttaa ttctagctag cctaccctgc aagtcaagag | 6660 |
| gtctccgtga ttcctagcca cctcaaggta tgcctctccc cggaaactgt ggcctttttct | 6720 |
| ggcacacatg atctccacga tttcaacata taaatagctt ttgataatgg caatattaat | 6780 |
| caaatttatt ttacttcttt cttgtaacat ctctcttgta atcccttatt ccttctagct | 6840 |
| attttttcata aaaaaccaag caactgctta tcaacacaca aacactaaat caagaattc | 6900 |
| ttaattaaac aatgaagctc gagtggctgg aagccacggt gcttgcggcc gcacggttg | 6960 |
| ctagtgcaaa ggacttggcc tactctccac cattttaccc atctccttgg gctaccggtg | 7020 |
| aaggcgaatg ggccgaagcc tacaaaaagg ccgtagattt cgtttccgga ttgacccctag | 7080 |
| ctgaaaaagt aatatcacc actggtgccg gttgggaaca ggaagatgt gtcggagaaa | 7140 |
| caggtggtgt ccctagacta ggcatgtggg ggatgtgtat gcaagactca ccactaggtg | 7200 |

```
tgagaaatgc agactactct tcagctttcc cagctggagt caatgttgct gccacatggg   7260
atagaagatt ggcgtatcaa aggggaactg caatgggtga ggaacataga gacaaaggag   7320
ttgatgtcca acttggtcca gtcgcgggtc ctttgggaaa gaaccctgat ggcggcagag   7380
ggtgggaggg attttctcca gatccagttc taactggtgt aatgatggca gaaacaatta   7440
aaggtataca agacgccgga gtgatcgcat gtgctaagca cttcattatg aacgaacagg   7500
aacactttag acaagcaggg gaggcacagg gttacggctt taacatctct caatctttgt   7560
cctcaaatgt cgatgacaaa actatgcatg aattatactt gtggccttttt gttgattctg   7620 taagagcagg ggtgggttca gtgatgtgct catataatca aatcaataac tcatacggtt   7680
gctctaatag ttacactttg aacaaattgc ttaaaggtga attgggcttt caaggatttg   7740
taatgtcaga ttggggtgcc caccatacgc gtgttggtga cgcattagct ggactcgata   7800
tgtctatgcc tggtgatgtc attttgggct ccccatattc attctggggc acaaacctaa   7860
ctgtctccgt gctaaactcc actattccag agtggcgtct ggatgacatg gctgtcagaa   7920
taatggctgc ctactacaaa gtgggccgag atagacatag aactccacca aatttctctt   7980
catggacaag agatgaatac ggctatgaac atttcattgt tcaagagaat tatgttaaac   8040
ttaacgaacg tgttaatgtc caaagggacc acgcaaatgt aatcagaaag atcggatctg   8100
attcaattgt gatgttgaaa acaacggtg gactaccact aacacatcag gaaagactcg   8160
ttgcaatctt aggggaagat gcaggatcaa atgcttacgg tgccaatggt tgttctgata   8220
ggggatgtga taacggcact ttagctatgg gctgggggtc aggtacagcg aatttcccat   8280
acttaataac accagaacaa gctatacaaa acgaggtttt gaattatgga aacggtgata   8340
caaatgtctt tgctgttact gataatggag cattgtcaca aatggcggct ttagccagta   8400
cagcttccgt tgctctggtt ttcgtgaatg ctgattctgg agaaggatac atttctgtag   8460
atggtaatga aggcgacaga aagaacatga cattgtggaa aaatggtgag gaattaatca   8520
agacagcaac tgcaaattgc aataatacta tcgttattat gcatacacct aatgctgtcc   8580
tggttgactc ttggtacgat aacgagaata ttacagctat attgtgggct ggtatgccag   8640
ggcaagagtc cggaagatca ttggtagatg tcctctacgg gagaaccaat cctggtggca   8700
aaacaccttt cacatggggg aaagagagaa aggattgggg ttctccatta cttaccaaac   8760
caaataacgg tcatggtgct cctcaggacg atttcacaga cgtactgata gactacagac   8820
gatttgataa ggacaatgtg gaaccaatct ttgaatttgg ctttggtttg tcatatacta   8880
agtttgagtt ttctgatatt caagtaaaag cgcttaatca tggagaatat aacgcaacgg   8940
ttggaaagac caagccagct cctagccttg gtaaacctgg taacgcttct gatcatctgt   9000
tcccatccaa tatcaacaga gttcgacaat acttatatcc ttatctgaac tctactgacc   9060
taaaagctag tgctaatgac cctgactacg ggatgaacgc atctgcgtac atcccacctc   9120
atgcaaccga ttccgatcca caggatctcc tgccagcttc tggaccatca ggtggtaatc   9180
caggcttgtt cgaagatttg attgaagtta ccgcaacagt cactaacact ggcagtgtta   9240
caggcgatga agtgccacaa ttatacgtgt cacttggcgg agcagatgac ccagttaaag   9300
tattgcgtgc ttttgataga gtgacaatcg cacctggcca aaaactgcgt tggacggcga   9360
ctcttaacag aagagactta tccaactggg atgttccatc ccaaaattgg attatcagcg   9420
acgctcctaa aaaggtatgg gtaggtaatt catccagaaa acttccatta agtgctgatt   9480
tgccaaaggt acaagatgat gatgacaaag gtggttctcc tccttctcat catcaccacc   9540
```

| | |
|---|---:|
| accactaagg cgcgccctcg agagcttttg attaagcctt ctagtccaaa aaacacgttt | 9600 |
| ttttgtcatt tatttcattt tcttagaata gttttagttta ttcattttat agtcacgaat | 9660 |
| gttttatgat tctatatagg gttgcaaaca agcattttttc attttatgtt aaaacaattt | 9720 |
| caggtttacc ttttattctg cttgtggtga cgcgtgtatc cgcccgctct tttggtcacc | 9780 |
| catgtattta attgcataaa taattcttaa aagtggagct agtctatttc tatttacata | 9840 |
| cctctcattt ctcatttcct cctaatgtgt caatgatcat attcttaact ggaccgatct | 9900 |
| tattcgtcag attcaaacca aaagttctta gggctaccac aggaggaaaa ttagtgtgat | 9960 |
| ataatttaaa taatttatcc gccattccta atagaacgtt gttcgacgga tatctttctg | 10020 |
| cccaaaaggg ttctaagctc aatgaagagc caatgtctaa acctctttgc | 10070 |

<210> SEQ ID NO 36
<211> LENGTH: 10100
<212> TYPE: DNA
<213> ORGANISM: Chaetomium globosum
<220> FEATURE:
<221> NAME/KEY: misc_feature
<222> LOCATION: (1)..(10100)
<223> OTHER INFORMATION: plasmid pMU3562

<400> SEQUENCE: 36

| | |
|---|---:|
| ggccgcaagc taattcgcgc gaagctagct tggcactggc cgtcgtttta caacgtcgtg | 60 |
| actgggaaaa ccctggcgtt acccaactta atcgccttgc agcacatccc ccttcgcca | 120 |
| gctggcgtaa tagcgaagag gcccgcaccg atcgcccttc ccaacagttg cgcagcctga | 180 |
| atggcgaatg cgcctgatg cggtattttc tccttacgca tctgtgcggt atttcacacc | 240 |
| gcataggaga tctaagctct ggcgtaatag cgaagaggcc cgcaccgatc gcccttccca | 300 |
| acagttgcgc agcctgaatg gcgaatggcg cctgatgcgg tattttctcc ttacgcatct | 360 |
| gtgcggtatt tcacaccgca tagggtaata actgatataa ttaaattgaa gctctaattt | 420 |
| gtgagtttag tatacatgca tttacttata atacagtttt ttagttttgc tggccgcatc | 480 |
| ttctcaaata tgcttcccag cctgcttttc tgtaacgttc accctctacc ttagcatccc | 540 |
| ttcccttttgc aaatagtcct cttccaacaa taataatgtc agatcctgta gagaccacat | 600 |
| catccacggt tctatactgt tgacccaatg cgtctccctt gtcatctaaa cccacaccgg | 660 |
| gtgtcataat caaccaatcg taaccttcat ctccttccacc catgtctctt tgagcaataa | 720 |
| agccgataac aaaatctttg tcgctcttcg caatgtcaac agtacccctta gtatattctc | 780 |
| cagtagatag ggagcccttg catgacaatt ctgctaacat caaaaggcct ctaggttcct | 840 |
| ttgttacttc ttctgccgcc tgcttcaaac cgctaacaat acctgggccc accacaccgt | 900 |
| gtgcattcgt aatgtctgcc cattctgcta ttctgtatac acccgcagag tactgcaatt | 960 |
| tgactgtatt accaatgtca gcaaattttc tgtcttcgaa gagtaaaaaa ttgtacttgg | 1020 |
| cggataatgc ctttagcggc ttaactgtgc cctccatgga aaaatcagtc aagatatcca | 1080 |
| catgtgtttt tagtaaacaa atttttggac ctaatgcttc aactaactcc agtaattcct | 1140 |
| tggtggtacg aacatccaat gaagcacaca agtttgtttg cttttcgtgc atgatattaa | 1200 |
| atagcttggc agcaacagga ctaggatgag tagcagcacg ttccttatat gtagctttcg | 1260 |
| acatgattta tcttcgtttc ggttttttgtt ctgtgcagtt gggttaagaa tactgggcaa | 1320 |
| tttcatgttt cttcaacact acatatgcgt atatatacca atctaagtct gtgctccttc | 1380 |
| cttcgttctt ccttctgttc ggagattacc gaatcaaaaa aatttcaaag aaaccgaaat | 1440 |
| caaaaaaaag aataaaaaaa aaatgatgaa ttgaaaagct cttgttaccc atcattgaat | 1500 |

```
tttgaacatc cgaacctggg agttttccct gaaacagata gtatatttga acctgtataa   1560
taatatatag tctagcgctt tacggaagac aatgtatgta tttcggttcc tggagaaact   1620
attgcatcta ttgcataggt aatcttgcac gtcgcatccc cggttcattt tctgcgtttc   1680
catcttgcac ttcaatagca tatctttgtt aacgaagcat ctgtgcttca ttttgtagaa   1740
caaaaatgca acgcgagagc gctaattttt caaacaaaga atctgagctg cattttttaca  1800
gaacagaaat gcaacgcgaa agcgctattt taccaacgaa gaatctgtgc ttcattttg    1860
taaaacaaaa atgcaacgcg agagcgctaa ttttcaaac aaagaatctg agctgcattt    1920
ttacagaaca gaaatgcaac gcgagagcgc tattttacca caaagaatc tatacttctt    1980
ttttgttcta caaaaatgca tcccgagagc gctattttc taacaaagca tcttagatta   2040
ctttttttct cctttgtgcg ctctataatg cagtctcttg ataacttttt gcactgtagg   2100
tccgttaagg ttagaagaag gctactttgg tgtctatttt ctcttccata aaaaaagcct   2160
gactccactt cccgcgttta ctgattacta gcgaagctgc gggtgcattt ttcaagata    2220
aaggcatccc cgattatatt ctataccgat gtggattgcg catactttgt gaacagaaag   2280
tgatagcgtt gatgattctt cattggtcag aaaattatga acggtttctt ctattttgtc   2340
tctatatact acgtatagga aatgtttaca ttttcgtatt gttttcgatt cactctatga   2400
atagttctta ctacaatttt tttgtctaaa gagtaatact agagataaac ataaaaaatg   2460
tagaggtcga gtttagatgc aagttcaagg agcgaaaggt ggatgggtag gttatatagg   2520
gatatagcac agagatatat agcaaagaga tactttttgag caatgtttgt ggaagcggta   2580
ttcgcaatat tttagtagct cgttacagtc cggtgcgttt ttggttttt gaaagtgcgt    2640
cttcagagcg ctttttgggttt tcaaaagcgc tctgaagttc ctatactttc tagctagaga  2700
ataggaactt cggaatagga acttcaaagc gttccgaaa acgagcgctt ccgaaaatgc    2760
aacgcgagct gcgcacatac agctcactgt tcacgtcgca cctatatctg cgtgttgcct   2820
gtatatatat atacatgaga gaacggcat agtgcgtgtt tatgcttaaa tgcgttatgg    2880
tgcactctca gtacaatctg ctctgatgcc gcatagttaa gccagccccg acacccgcca   2940
acaccgctg acgcgccctg acgggcttgt ctgctcccgg catccgctta cagacaagct   3000
gtgaccgtct ccgggagctg catgtgtcag aggttttcac cgtcatcacc gaaacgcgcg   3060
agacgaaagg gcctcgtgat acgcctattt ttataggtta atgtcatgat aataatggtt   3120
tcttagacgt caggtggcac ttttcgggga atgtgcgcg gaaccctat ttgtttattt      3180
ttctaaatac attcaaatat gtatccgctc atgagacaat aaccctgata aatgcttcaa   3240
taatattgaa aaggaagag tatgagtatt caacatttcc gtgtcgccct tattcccttt    3300
tttgcggcat tttgccttcc tgtttttgct cacccagaaa cgctggtgaa agtaaaagat   3360
gctgaagatc agttgggtgc acgagtgggt tacatcgaac tggatctcaa cagcggtaag   3420
atccttgaga gttttcgccc cgaagaacgt tttccaatga tgagcacttt taaagttctg   3480
ctatgtggcg cggtattatc ccgtattgac gccgggcaag agcaactcgg tcgccgcata   3540
cactattctc agaatgactt ggttgagtac tcaccagtca cagaaaagca tcttacggat   3600
ggcatgacag taagagaatt atgcagtgct gccataacca tgagtgataa cactgcggcc   3660
aacttacttc tgacaacgat cggaggaccg aaggagctaa ccgcttttttt gcacaacatg   3720
ggggatcatg taactcgcct tgatcgttgg gaaccggagc tgaatgaagc cataccaaac   3780
gacgagcgtg acaccacgat gcctgtagca atggcaacaa cgttgcgcaa actattaact   3840
```

```
ggcgaactac ttactctagc ttcccggcaa caattaatag actggatgga ggcggataaa    3900
gttgcaggac cacttctgcg ctcggccctt ccggctggct ggtttattgc tgataaatct    3960
ggagccggtg agcgtgggtc tcgcggtatc attgcagcac tggggccaga tggtaagccc    4020
tcccgtatcg tagttatcta cacgacgggg agtcaggcaa ctatggatga acgaaataga    4080
cagatcgctg agataggtgc ctcactgatt aagcattggt aactgtcaga ccaagtttac    4140
tcatatatac tttagattga tttaaaactt cattttttaat ttaaaaggat ctaggtgaag    4200
atcctttttg ataatctcat gaccaaaatc ccttaacgtg agttttcgtt ccactgagcg    4260
tcagaccccg tagaaaagat caaaggatct tcttgagatc cttttttttct gcgcgtaatc    4320 tgctgcttgc aaacaaaaaa accaccgcta ccagcggtgg tttgtttgcc ggatcaagag    4380
ctaccaactc tttttccgaa ggtaactggc ttcagcagag cgcagatacc aaatactgtc    4440
cttctagtgt agccgtagtt aggccaccac ttcaagaact ctgtagcacc gcctacatac    4500
ctcgctctgc taatcctgtt accagtggct gctgccagtg gcgataagtc gtgtcttacc    4560
gggttggact caagacgata gttaccggat aaggcgcagc ggtcgggctg aacggggggt    4620
tcgtgcacac agcccagctt ggagcgaacg acctacaccg aactgagata cctacagcgt    4680
gagcattgag aaagcgccac gcttcccgaa gggagaaagg cggacaggta tccggtaagc    4740
ggcagggtcg gaacaggaga gcgcacgagg gagcttccag ggggaaacgc ctggtatctt    4800
tatagtcctg tcgggtttcg ccacctctga cttgagcgtc gatttttgtg atgctcgtca    4860
ggggggcgga gcctatggaa aaacgccagc aacgcggcct ttttacggtt cctggccttt    4920
tgctggcctt ttgctcacat gttctttcct gcgttatccc ctgattctgt ggataaccgt    4980
attaccgcct ttgagtgagc tgataccgct cgccgcagcc gaacgaccga gcgcagcgag    5040
tcagtgagcg aggaagcgga agagcgccca atacgcaaac cgcctctccc cgcgcgttgg    5100
ccgattcatt aatccaggat cccaattaat gtgagttacc tcactcatta ggcacccag    5160 gctttacact ttatgcttcc ggctcgtatg ttgtgtggaa ttgtgagcgg ataacaattt    5220
cacacaggaa acagctatga ccatgattac gaattaattc gagctcggta cccggggatc    5280
gatccactag agatctgttt agcttgcctc gtccccgccg ggtcacccgg ccagcgacat    5340
ggaggcccag aatacccctcc ttgacagtct tgacgtgcgc agctcagggg catgatgtga    5400
ctgtcgcccg tacatttagc ccatacatcc ccatgtataa tcatttgcat ccatacattt    5460
tgatggccgc acggcgcgaa gcaaaaatta cggctcctcg ctgcagacct gcgagcaggg    5520
aaacgctccc ctcacagacg cgttgaattg tccccacgcc gcgcccctgt agagaaatat    5580
aaaaggttag gatttgccac tgaggttctt cttcatata cttccttta aaatcttgct    5640 aggatacagt tctcacatca catccgaaca taaacaacca tggccgacca agcgacgccc    5700
aacctgccat cacgagattt cgattccacg gccgccttct atgaaaggtt gggcttcgga    5760
atcgttttcc gggacgccgg ctggatgatc ctccagcgcg gggatctcaa gctggagttc    5820
ttcgcccacc ccgggctcga tccctcgcg agttggttca gctgctgcct gaggctggac    5880
gacctcgcgg agttctaccg gcagtgcaaa tccgtcggca tccaggaaac cagcagcggc    5940
tatccgcgca tccatgcccc cgaactgcag gagtggggag gcacgatggc cgctttggtc    6000
gacccggacg ggacgctcct gcgcctgata cagaacgaat tgcttgcagg catctcatga    6060
tcagtactga caataaaaag attcttgttt tcaagaactt gtcatttgta tagtttttt    6120 atattgtagt tgttctattt taatcaaatg ttagcgtgat ttatattttt tttcgcctcg    6180
acatcatctg cccagatgcg aagttaagtg cgcagaaagt aatatcatgc gtcaatcgta    6240
```

```
tgtgaatgct ggtcgctata ctgctgtcga ttcgatacta acgccgccat ccagtgtcga    6300
aaacgagctc tcgagaaccc ttaatataac ttcgtataat gtatgctata cgaagttatt    6360
aggtgatatc agatccacta gtcttctagg cgggttatct actgatccga gcttccacta    6420
ggatagcacc caaacacctg catatttgga cgacctttac ttacaccacc aaaaaccact    6480
ttcgcctctc ccgcccctga taacgtccac taattgagcg attacctgag cggtcctctt    6540
ttgtttgcag catgagactt gcatactgca aatcgtaagt agcaacgtct caaggtcaaa    6600
actgtatgga aaccttgtca cctcacttaa ttctagctag cctaccctgc aagtcaagag    6660
gtctccgtga ttcctagcca cctcaaggta tgcctctccc cggaaactgt ggccttttct    6720
ggcacacatg atctccacga tttcaacata taaatagctt ttgataatgg caatattaat    6780
caaatttatt ttacttcttt cttgtaacat ctctcttgta atcccttatt ccttctagct    6840 attttcata aaaaccaag caactgctta tcaacacaca aacactaaat caagaattc     6900 ttaattaaac aatgaaagct gctactgcgc tttcctgcct cgctggcggc agtcttgctg    6960
ctgctgggac cattaatcca gctaacaaga tacagaaaag ggctttgcaa acctcagatc    7020
cacactaccc atctccttgg atgaaccctg acgcagacgg atgggctgag gcttatgccc    7080
aagcaagaga ctttgtgtca caattaacat taccagagaa agtgaacttg actactggtg    7140
ttggctggca aggtgaacaa tgtgtcggcc aaacaggtgc aatcccaaga tttggccttc    7200
gttctctgtg tatgcatgat gctccattgg gcattagggg ttctgactac aactcagctt    7260
tcccttctgg acaaacagct gcagccactt gggatagagg cctaatgtat agacgagggt    7320
acgctatggg caaggaggct aaaggtaagg gtattaatgt cttattggga ccagtagcag    7380
gtccactggg acgaatgcca gctgcaggta gaaatttggga aggatttgca cctgatccag    7440
tgcttacagg cgttggcatg tctgagactg ttaagggtac acaagatgcc ggagtagtcg    7500
cctgtgccaa acactttatc ggtaacgagc aagagaattt cagacaagtg ggcgaagctc    7560
aaggatacgg gcataacatt tcagaaaccc taagctctaa tatcgatgat aagaccatgc    7620
atgaactata cttgtggcca tttgctgacg cagtacgagc gggtgttgga tctgttatgt    7680
gcagttatca acaggttaat aactcctatg gatgtcaaaa ttcaaaactt ttgaatgatt    7740
tgctcaaaaa tgaactgggc tttcaaggtt tcgtgatgag cgattggcaa gctcaacaca    7800
caggtgctgc atctgcggtc gctggtttgg atatgacgat gcctggtgac acatctttca    7860
acacaggtct ttcctttggg ggtacaaatc tgactttggc agtcttaaac ggaacagttc    7920
cagcataccg tgttgacgat atggccatga gaattatggc ctctattttc aaagtaagta    7980
agactacgga tttcgaccct atcaacttct cttttggac cctagatact tatggtccag    8040
tccattgggt ggccaaggag ggttaccagg aaattaactc tcatgttgac gttagagaag    8100
atcacggcaa actcataaga gaaatcgctg caaagggtac agtgttactt aaaaactcag    8160
gtgccctgcc attgcagaaa ccaaaatttg tggccgtcat tggtgaggac gctggtggta    8220
atccaaatgg tcctaacggt tgttctgaca gaggttgcga tgatggaaca ttagcaatgg    8280 ggtgggctc tggaactgca aactttcctt acctagtgac tcctgatgca gcattgcaag    8340
ctagagcaat agaagatgga tctaggtacg aaagtatctt atcaaattac gctcatgata    8400
aaacagacgc tctagtttca caagccaatg ttacggctat tgtatttgtt aatgccgaca    8460
gcggtgaagg ttcatcaat gtagatggaa atatgggcga cagaaagaat cttaccctat    8520
ggaaaaatgg cgacgatcta gttaaaagag tgtctggggc gtgttctaat accattgttg    8580
```

```
ttattcattc aacaggacct gtgctgctaa ccgaatggta tgaatcacca aacataactg    8640
ccatcttgtg ggcaggactc cctggtcagg aatcaggtaa ctcaatagct gatgtacttt    8700
acggcgatgt gaaccctgca gctaggagtc cttttacttg gggaaaaact agagaatcct    8760
acggtgccga tgtgctttat gagcctaata atggtaacgg tgccccctcaa caagatttct    8820 ctgaaggtgt tttcatcgat tacagatact ttgataaaca aaatagtagc gtaatctacg    8880
aatttgggca tggcctgagt tacacaacat ttgaatatag caatatcaga gtagaaaaat    8940
ctaatgcggg tgaatacaaa ccaactactg gttcaactgc tgctgcccct acattcggaa    9000
acttctcaac tgatttgaaa gactacttat tcccaaagga agattttttcc tatatctacc    9060 agtacattta tccatacgtc aacacaactg acgccaaaaa ggcatccgcc gatccacatt    9120
acggtcaaac tgcggaagag tttctccctc cacatgtctt ggatgcggat gcacaaccac    9180
ttttaagatc atccggtggg aactctccag ggggtaacag acaattgtac gatataatgt    9240
acacgatcac agctgatatc actaatacag gagccatagt cggcgaagag gttccacagc    9300
tatatgtttc cttgggcggt ccagaagatc caaaggttca acttagagat tttgatagaa    9360
tgagaatcga cccaggggaa actaaacaat tcacaggaag attaacacgt agagatttgt    9420
ctaattggga tattgaagta caggattggg tagtttcaga gcataagaaa acagcttttg    9480
tcggcaagtc cagcagaaag ttggacttaa agatcgaatt gccagatgat gatgacaaag    9540
gtggttctcc tccttctcat catcaccacc accactaagg cgcgcccctcg agagcttttg    9600 attaagcctt ctagtccaaa aaacacgttt ttttgtcatt tatttcattt tcttagaata    9660
gtttagttta ttcattttat agtcacgaat gttttatgat tctatatagg gttgcaaaca    9720 agcattttttc attttatgtt aaaacaattt caggtttacc ttttattctg cttgtggtga    9780
cgcgtgtatc cgcccgctct tttggtcacc catgtattta attgcataaa taattcttaa    9840
aagtggagct agtctatttc tatttacata cctctcattt ctcatttcct cctaatgtgt    9900
caatgatcat attcttaact ggaccgatct tattcgtcag attcaaacca aaagttctta    9960
gggctaccac aggaggaaaa ttagtgtgat ataatttaaa taatttatcc gccattccta    10020
atagaacgtt gttcgacgga tatctttctg cccaaaaggg ttctaagctc aatgaagagc    10080
caatgtctaa acctctttgc                                                10100
```

<210> SEQ ID NO 37
<211> LENGTH: 10253
<212> TYPE: DNA
<213> ORGANISM: Neocallimastix frontalis
<220> FEATURE:
<221> NAME/KEY: misc_feature
<222> LOCATION: (1)..(10253)
<223> OTHER INFORMATION: plasmid pMU3563

<400> SEQUENCE: 37

```
ggccgcaagc taattcgcgc gaagctagct tggcactggc cgtcgtttta caacgtcgtg      60
actgggaaaa ccctggcgtt acccaactta atcgccttgc agcacatccc ccttcgcca     120 gctggcgtaa tagcgaagag gcccgcaccg atcgcccttc ccaacagttg cgcagcctga    180
atggcgaatg gcgcctgatg cggtattttc tccttacgca tctgtgcggt atttcacacc    240
gcataggaga tctaagctct ggcgtaatag cgaagaggcc cgcaccgatc gcccttccca    300
acagttgcgc agcctgaatg gcgaatggcg cctgatgcgg tatttttctcc ttacgcatct    360 gtgcggtatt tcacaccgca tagggtaata actgatataa ttaaattgaa gctctaattt    420
gtgagtttag tatacatgca tttacttata atacagtttt ttagttttgc tggccgcatc    480
```

```
ttctcaaata tgcttcccag cctgcttttc tgtaacgttc accctctacc ttagcatccc      540
ttccctttgc aaatagtcct cttccaacaa taataatgtc agatcctgta gagaccacat      600
catccacggt tctatactgt tgacccaatg cgtctccctt gtcatctaaa cccacaccgg      660
gtgtcataat caaccaatcg taaccttcat ctcttccacc catgtctctt tgagcaataa      720
agccgataac aaaatctttg tcgctcttcg caatgtcaac agtacccttg gtatattctc      780
cagtagatag ggagcccttg catgacaatt ctgctaacat caaaaggcct ctaggttcct      840
ttgttacttc ttctgccgcc tgcttcaaac cgctaacaat acctgggccc accacaccgt      900
gtgcattcgt aatgtctgcc cattctgcta ttctgtatac acccgcagag tactgcaatt      960
tgactgtatt accaatgtca gcaaattttc tgtcttcgaa gagtaaaaaa ttgtacttgg     1020
cggataatgc cttagcggc ttaactgtgc cctccatgga aaaatcagtc aagatatcca     1080
catgtgtttt tagtaaacaa attttgggac ctaatgcttc aactaactcc agtaattcct     1140
tggtggtacg aacatccaat gaagcacaca agtttgtttg cttttcgtgc atgatattaa     1200
atagcttggc agcaacagga ctaggatgag tagcagcacg ttccttatat gtagctttcg     1260
acatgattta tcttcgtttc ggttttttgtt ctgtgcagtt gggttaagaa tactgggcaa     1320
tttcatgttt cttcaacact acatatgcgt atatatacca atctaagtct gtgctccttc     1380
cttcgttctt ccttctgttc ggagattacc gaatcaaaaa aatttcaaag aaaccgaaat     1440
caaaaaaaag aataaaaaaa aaatgatgaa ttgaaaagct cttgttaccc atcattgaat     1500
tttgaacatc cgaacctggg agttttccct gaaacagata gtatatttga acctgtataa     1560
taatatatag tctagcgctt tacggaagac aatgtatgta tttcggttcc tggagaaact     1620
attgcatcta ttgcataggt aatcttgcac gtcgcatccc cggttcattt tctgcgtttc     1680
catcttgcac ttcaatagca tatctttgtt aacgaagcat ctgtgcttca ttttgtagaa     1740
caaaaatgca acgcgagagc gctaattttt caaacaaaga atctgagctg cattttaca     1800
gaacagaaat gcaacgcgaa agcgctattt taccaacgaa gaatctgtgc ttcatttttg     1860
taaaacaaaa atgcaacgcg agagcgctaa ttttttcaaac aaagaatctg agctgcattt     1920
ttacagaaca gaaatgcaac gcgagagcgc tattttacca caaagaatc tatacttctt     1980
ttttgttcta caaaaatgca tcccgagagc gctatttttc taacaaagca tcttagatta     2040
cttttttttct cctttgtgcg ctctataatg cagtctcttg ataactttt gcactgtagg     2100
tccgttaagg ttagaagaag gctactttgg tgtctatttt ctcttccata aaaaaagcct     2160
gactccactc cccgcgttta ctgattacta gcgaagctgc gggtgcattt tttcaagata     2220
aaggcatccc cgattatatt ctataccgat gtggattgcg catactttgt gaacagaaag     2280
tgatagcgtt gatgattctt cattggtcag aaaattatga acgtttctt ctattttgtc     2340
tctatatact acgtatagga aatgtttaca ttttcgtatt gttttcgatt cactctatga     2400
atagttctta ctacaatttt tttgtctaaa gagtaatact agagataaac ataaaaatg     2460
tagaggtcga gtttagatgc aagttcaagg agcgaaaggt ggatgggtag gttatatagg     2520
gatatagcac agagatatat agcaaagaga tacttttgag caatgtttgt ggaagcggta     2580
ttcgcaatat tttagtagct cgttacagtc cggtgcgttt ttggtttttt gaaagtgcgt     2640
cttcagagcg cttttggttt tcaaaagcgc tctgaagttc ctatactttc tagctagaga     2700
ataggaactt cggaatagga acttcaaagc gtttccgaaa acgagcgctt ccgaaaatgc     2760
aacgcgagct gcgcacatac agctcactgt tcacgtcgca cctatatctg cgtgttgcct     2820
```

```
gtatatatat atacatgaga agaacggcat agtgcgtgtt tatgcttaaa tgcgttatgg   2880
tgcactctca gtacaatctg ctctgatgcc gcatagttaa gccagccccg acacccgcca   2940
acacccgctg acgcgccctg acgggcttgt ctgctcccgg catccgctta cagacaagct   3000
gtgaccgtct ccgggagctg catgtgtcag aggttttcac cgtcatcacc gaaacgcgcg   3060
agacgaaagg gcctcgtgat acgcctattt ttataggtta atgtcatgat aataatggtt   3120
tcttagacgt caggtggcac ttttcgggga atgtgcgcg gaaccccta ttgtttattt   3180
ttctaaatac attcaaatat gtatccgctc atgagacaat aaccctgata atgcttcaa   3240
taatattgaa aaaggaagag tatgagtatt caacatttcc gtgtcgccct tattcccttt   3300
tttgcggcat tttgccttcc tgttttgct cacccagaaa cgctggtgaa agtaaaagat   3360
gctgaagatc agttgggtgc acgagtgggt tacatcgaac tggatctcaa cagcggtaag   3420
atccttgaga gttttcgccc cgaagaacgt tttccaatga tgagcacttt taaagttctg   3480
ctatgtggcg cggtattatc ccgtattgac gccgggcaag agcaactcgg tcgccgcata   3540
cactattctc agaatgactt ggttgagtac tcaccagtca cagaaaagca tcttacggat   3600
ggcatgacag taagagaatt atgcagtgct gccataacca tgagtgataa cactgcggcc   3660
aacttacttc tgacaacgat cggaggaccg aaggagctaa ccgcttttt gcacaacatg   3720
ggggatcatg taactcgcct tgatcgttgg gaaccggagc tgaatgaagc cataccaaac   3780
gacgagcgtg acaccacgat gcctgtagca atggcaacaa cgttgcgcaa actattaact   3840
ggcgaactac ttactctagc ttcccggcaa caattaatag actggatgga ggcggataaa   3900
gttgcaggac cacttctgcg ctcggccctt ccggctggct ggtttattgc tgataaatct   3960
ggagccggtg agcgtgggtc tcgcggtatc attgcagcac tggggccaga tggtaagccc   4020
tcccgtatcg tagttatcta cacgacgggg agtcaggcaa ctatggatga acgaaataga   4080
cagatcgctg agataggtgc ctcactgatt aagcattggt aactgtcaga ccaagtttac   4140
tcatatatac tttagattga tttaaaactt cattttaat ttaaaaggat ctaggtgaag   4200
atccttttg ataatctcat gaccaaaatc ccttaacgtg agttttcgtt ccactgagcg   4260
tcagacccg tagaaaagat caaaggatct tcttgagatc cttttttct gcgcgtaatc   4320
tgctgcttgc aaacaaaaaa accaccgcta ccagcggtgg tttgtttgcc ggatcaagag   4380
ctaccaactc ttttccgaa ggtaactggc ttcagcagag cgcagatacc aaatactgtc   4440
cttctagtgt agccgtagtt aggccaccac ttcaagaact ctgtagcacc gcctacatac   4500
ctcgctctgc taatcctgtt accagtggct gctgccagtg gcgataagtc gtgtcttacc   4560
gggttggact caagacgata gttaccggat aaggcgcagc ggtcgggctg aacggggggt   4620
tcgtgcacac agcccagctt ggagcgaacg acctacaccg aactgagata cctacagcgt   4680
gagcattgag aaagcgccac gcttcccgaa gggagaaagg cggacaggta tccggtaagc   4740
ggcagggtcg gaacaggaga gcgcacgagg gagcttccag ggggaaacgc ctggtatctt   4800
tatagtcctg tcgggtttcg ccacctctga cttgagcgtc gatttttgtg atgctcgtca   4860
ggggggcgga gcctatggaa aaacgccagc aacgcggcct ttttacggtt cctggccttt   4920
tgctggcctt ttgctcacat gttctttcct gcgttatccc ctgattctgt ggataaccgt   4980
attaccgcct ttgagtgagc tgataccgct cgccgcagcc gaacgaccga gcgcagcgag   5040
tcagtgagcg aggaagcgga agagcgccca atacgcaaac cgcctctccc cgcgcgttgg   5100
ccgattcatt aatccaggat cccaattaat gtgagttacc tcactcatta ggcacccag   5160
gctttacact ttatgcttcc ggctcgtatg ttgtgtggaa ttgtgagcgg ataacaattt   5220
```

```
cacacaggaa acagctatga ccatgattac gaattaattc gagctcggta cccggggatc   5280
gatccactag agatctgttt agcttgcctc gtccccgccg ggtcacccgg ccagcgacat   5340
ggaggcccag aataccctcc ttgacagtct tgacgtgcgc agctcagggg catgatgtga   5400
ctgtcgcccg tacatttagc ccatacatcc ccatgtataa tcatttgcat ccatacattt   5460
tgatggccgc acggcgcgaa gcaaaaatta cggctcctcg ctgcagacct gcgagcaggg   5520
aaacgctccc ctcacagacg cgttgaattg tccccacgcc gcgcccctgt agagaaatat   5580
aaaaggttag gatttgccac tgaggttctt ctttcatata cttcctttta aaatcttgct   5640
aggatacagt tctcacatca catccgaaca taaacaacca tggccgacca agcgacgccc   5700
aacctgccat cacgagattt cgattccacg gccgccttct atgaaaggtt gggcttcgga   5760
atcgttttcc gggacgccgg ctggatgatc ctccagcgcg gggatctcaa gctggagttc   5820
ttcgcccacc ccgggctcga tcccctcgcg agttggttca gctgctgcct gaggctggac   5880
gacctcgcgg agttctaccg gcagtgcaaa tccgtcggca tccaggaaac cagcagcggc   5940
tatccgcgca tccatgcccc cgaactgcag gagtggggag gcacgatggc cgctttggtc   6000
gacccggacg ggacgctcct gcgcctgata cagaacgaat tgcttgcagg catctcatga   6060
tcagtactga caataaaaag attcttgttt tcaagaactt gtcatttgta tagttttttt   6120
atattgtagt tgttctattt taatcaaatg ttagcgtgat ttatatttt tttcgcctcg   6180 acatcatctg cccagatgcg aagttaagtg cgcagaaagt aatatcatgc gtcaatcgta   6240
tgtgaatgct ggtcgctata ctgctgtcga ttcgatacta acgccgccat ccagtgtcga   6300
aaacgagctc tcgagaaccc ttaatataac ttcgtataat gtatgctata cgaagttatt   6360
aggtgatatc agatccacta gtcttctagg cgggttatct actgatccga gcttccacta   6420
ggatagcacc caaacacctg catatttgga cgacctttac ttacaccacc aaaaaccact   6480
ttcgcctctc ccgcccctga taacgtccac taattgagcg attacctgag cggtcctctt   6540
ttgtttgcag catgagactt gcatactgca atcgtaagt agcaacgtct caaggtcaaa   6600
actgtatgga aaccttgtca cctcacttaa ttctagctag cctaccctgc aagtcaagag   6660
gtctccgtga ttcctagcca cctcaaggta tgcctctccc cggaaactgt ggccttttct   6720
ggcacacatg atctccacga tttcaacata taaatagctt ttgataatgg caatattaat   6780
caaatttatt ttacttcttt cttgtaacat ctctcttgta atcccttatt ccttctagct   6840 attttcata aaaaccaag caactgctta tcaacacaca aacactaaat caaagaattc   6900
ttaattaaac aatgcttttg caagcttcc ttttccttt ggctggtttt gcagccaaaa   6960
tatctgcaat cactaaaagg tgcttgcata tcttgaacag aaaatgtaca cgtatccatt   7020
tttcctctgt gtctttcctc aatatggaat ttgatccaga tcataattac ttagtatttg   7080
tcgatatcaa aggtggccca tcttgcaagt caaccaataa ctgtaagaaa actacgggtt   7140
attatcacat tgttcaattg cttattatgt ctgagttcaa tatagagagc acactggctc   7200
aacttacatt acaggaaaag attggcttac ttgctgggat cgattttggg cataccttcg   7260
ctgttgaaag attgaatatt ccatccctga gattttccga tggccctaat ggcttgagag   7320
ggacaaagtt tttcgactcc gtgccttcag cctgtttccc atgtggtacg gctttggctg   7380
ccacttttga taagagttg ttatttgagg caggtcgatt gatgggcgac gaagctaaac   7440
ataagggcgc acaagttgtc ttgggaccaa caatgaatat ccaaagaggg cctttgggtg   7500
gaagaggctt cgagtctttc tctgaagatg cgcacttaac aggtcaatca gctgcctcaa   7560
```

```
ttatcaatgg catacaagac aagggaattg ctgctacaat taaacatttt gtctgcaatg   7620
acttagagga tcaacgtaac tcttcagata gcattttaac ggaaagagcg ctcagagaaa   7680
tctacctaga gccattcaga ttagcaatca acattcaaa  cccagttgca cttatgacag   7740
gttacaacaa ggttaatgga gagcacgtga gccaatctga aagacttatc caagatatcc   7800
tgagaaaaga gtgggactgg gatggtacaa caatgtccga ctggtacgga acttacactt   7860
ctaaagaggc tatagaaaat ggacttgaca tagaaatgcc aggtccatcc atctttagaa   7920
atcagtccga agtagccgct atggtaacca ccaaagagtt gcacatcaaa aagattgatg   7980
aaagagttac taatgtctta aagttgatca aatacgctct gaagtctgga gtgccagaaa   8040
atgctccaga aactagcaac ggcaatacac cagagactgc agccctactg agaaagctgg   8100
ctcatgattc tgtcgttcta ttgaaaaacg acaataatgt tctgccttta tctaaagacg   8160
acaaaattgc cgtaatcggt ccaaatgcaa aattcgccgc atattgtggt ggaggctctg   8220
catctctgag agcgtactac acgacaaccc catttgattc aatctctaaa aagctcaata   8280
aggacccaga atacactatt ggtgcatacg gtcacagatt gctacctgcc ttgggcccac   8340
aactggttaa tcctaaaacg ggcaacgccg gttataactt gaaatactac ttggaaccaa   8400
aatccacaag cgagagaacc ttaattgatg aacgtgatct tgacctgtct aacatctttc   8460
tcgttgacta ctacaataag aaaatcaagg atgatttgtt tttcatcgat tttgatgggc   8520
aattcactcc agaagagaca gctgattacg agtttggcct ggcagtcttg gaaccgctc   8580 aattgtttgt tgatggtaag ttggttgtag ataacaaaac agtccagcag agaggtaata   8640 gtttcttaa  ctcaggtagt aacgaggtta ggaactctat tagtcttgag aagggaaaaa   8700
catattctat aaagatagaa tttggctcag ctccaacatt cacagttcca tctcatgact   8760
cagtgtcatt tggaggaggt ggaggtatta atcttggatt agctaaagtg atcaatccta   8820
aggacgaaat tgctaaagcc gcagaacttg cgaagaaagt tgacaaagta gtcctgaaca   8880
taggtttgaa ccaggaatgg gaaagtgaag gtttcgatag accagatatg aaattgatag   8940
gccatatcaa tgaacttgtt gatgctgtct tggacgcaaa tccaaatacg gtagtcgtta   9000
atcaatctgg aactccagtt gagttcccct ggatcaaaaa ggctaatgcg ctcgttcaag   9060
catggtacgg tggtaatgaa ttaggtaatg gaatagcaga cgtgttgttc ggcgatgtga   9120
acccttcagg caaactatct ctctcatttc ctgtcaaaaa tgtggataac cctgcatacc   9180
ttaactttaa aactgagaag ggcagagttt tgtacggtga ggacatcttc gttggctata   9240
agtattatga aaagctagaa cgtgaagttg cctttccttt cggattcggc ttgagttata   9300
caaagtttga tatatccggt agtaaagtct ccgtggatga aaaggatgat aacttgactg   9360
tgtcagtgaa cgtgaaaaac acaggtaaaa tcgacggatc agaggtagtt cagttttaca   9420
tctccaaaga tgaatctgat gtaattagac cagtgaagga actaaaagga tttgaaaagg   9480
tacatctcaa ggctggagct gattctactg tttcactgaa attaagcctc aaggattcta   9540
tttcattttt cgatgaatac caagacgaat ggtcagttga gaaaggtgat tacaaagtgc   9600
atgtaggtaa ttcaagcgat aatatcactt caactttgcc ttttaagatc gaaaaggact   9660
tcctctggtc tggtatggat gatgatgaca aaggtggttc tcctccttct catcatcacc   9720
accaccacta aggcgcgccc tcgagagctt tgattaagc  cttctagtcc aaaaaacacg   9780 ttttttttgtc atttatttca ttttcttaga atagttagt  ttattcattt tatagtcacg   9840
aatgttttat gattctatat aggggttgcaa acaagcattt ttcatttat  gttaaaacaa   9900 tttcaggttt accttttatt ctgcttgtgg tgacgcgtgt atccgcccgc tcttttggtc   9960
```

```
acccatgtat ttaattgcat aaataattct taaaagtgga gctagtctat ttctatttac    10020
atacctctca tttctcattt cctcctaatg tgtcaatgat catattctta actggaccga    10080
tcttattcgt cagattcaaa ccaaaagttc ttagggctac cacaggagga aaattagtgt    10140
gatataattt aaataattta tccgccattc ctaatagaac gttgttcgac ggatatcttt    10200
ctgcccaaaa gggttctaag ctcaatgaag agccaatgtc taaacctctt tgc           10253
```

<210> SEQ ID NO 38
<211> LENGTH: 10253
<212> TYPE: DNA
<213> ORGANISM: Debaryomyces hansenii
<220> FEATURE:
<221> NAME/KEY: misc_feature
<222> LOCATION: (1)..(10253)
<223> OTHER INFORMATION: plasmid pMU3564

<400> SEQUENCE: 38

```
ggccgcaagc taattcgcgc gaagctagct tggcactggc cgtcgtttta caacgtcgtg      60
actgggaaaa ccctggcgtt acccaactta atcgccttgc agcacatccc cccttcgcca     120
gctggcgtaa tagcgaagag gcccgcaccg atcgcccttc ccaacagttg cgcagcctga     180
atggcgaatg gcgcctgatg cggtattttc tccttacgca tctgtgcggt atttcacacc     240
gcataggaga tctaagctct ggcgtaatag cgaagaggcc cgcaccgatc gcccttccca     300
acagttgcgc agcctgaatg gcgaatggcg cctgatgcgg tattttctcc ttacgcatct     360
gtgcggtatt tcacaccgca tagggtaata actgatataa ttaaattgaa gctctaattt     420
gtgagtttag tatacatgca tttacttata atacagtttt ttagttttgc tggccgcatc     480
ttctcaaata tgcttcccag cctgcttttc tgtaacgttc accctctacc ttagcatccc     540
ttccctttgc aaatagtcct cttccaacaa taataatgtc agatcctgta gagaccacat     600
catccacggt tctatactgt tgacccaatg cgtctccctt gtcatctaaa cccacaccgg     660
gtgtcataat caaccaatcg taaccttcat ctcttccacc catgtctctt tgagcaataa     720
agccgataac aaaatctttg tcgctcttcg caatgtcaac agtaccctta gtatattctc     780
cagtagatag ggagcccttg catgacaatt ctgctaacat caaaaggcct ctaggttcct     840
ttgttacttc ttctgccgcc tgcttcaaac cgctaacaat acctgggccc accacaccgt     900
gtgcattcgt aatgtctgcc cattctgcta ttctgtatac cccgcagag tactgcaatt      960 tgactgtatt accaatgtca gcaaattttc tgtcttcgaa gagtaaaaaa ttgtacttgg    1020
cggataatgc ctttagcggc ttaactgtgc cctccatgaa aaatcagtc aagatatcca    1080 catgtgtttt tagtaaacaa attttgggac ctaatgcttc aactaactcc agtaattcct    1140
tggtggtacg aacatccaat gaagcacaca agtttgtttg cttttcgtgc atgatattaa    1200
atagcttggc agcaacagga ctaggatgag tagcagcacg ttccttatat gtagctttcg    1260
acatgattta tcttcgtttc ggttttttgtt ctgtgcagtt gggttaagaa tactgggcaa    1320
tttcatgttt cttcaacact acatatgcgt atatatacca atctaagtct gtgctccttc    1380
cttcgttctt ccttctgttc ggagattacc gaatcaaaaa aatttcaaag aaaccgaaat    1440
caaaaaaaag aataaaaaaa aaatgatgaa ttgaaaagct cttgttaccc atcattgaat    1500
tttgaacatc cgaacctggg agttttccct gaaacagata gtatatttga acctgtataa    1560
taatatatag tctagcgctt tacggaagac aatgtatgta tttcggttcc tggagaaact    1620
attgcatcta ttgcataggt aatcttgcac gtcgcatccc cggttcattt tctgcgtttc    1680
```

```
catcttgcac ttcaatagca tatctttgtt aacgaagcat ctgtgcttca ttttgtagaa    1740
caaaaatgca acgcgagagc gctaattttt caaacaaaga atctgagctg cattttaca     1800 gaacagaaat gcaacgcgaa agcgctattt taccaacgaa gaatctgtgc ttcattttg     1860 taaaacaaaa atgcaacgcg agagcgctaa tttttcaaac aaagaatctg agctgcattt    1920
ttacagaaca gaaatgcaac gcgagagcgc tattttacca acaaagaatc tatacttctt    1980
ttttgttcta caaaaatgca tcccgagagc gctattttc taacaaagca tcttagatta    2040
ctttttttct cctttgtgcg ctctataatg cagtctcttg ataactttt gcactgtagg    2100 tccgttaagg ttagaagaag gctactttgg tgtctatttt ctcttccata aaaaagcct     2160 gactccactt cccgcgttta ctgattacta gcgaagctgc gggtgcattt tttcaagata    2220
aaggcatccc cgattatatt ctataccgat gtggattgcg catactttgt gaacagaaag    2280
tgatagcgtt gatgattctt cattggtcag aaaattatga acggtttctt ctattttgtc    2340
tctatatact acgtatagga aatgtttaca ttttcgtatt gttttcgatt cactctatga    2400
atagttctta ctacaatttt tttgtctaaa gagtaatact agagataaac ataaaaaatg    2460
tagaggtcga gtttagatgc aagttcaagg agcgaaaggt ggatgggtag gttatatagg    2520
gatatagcac agagatatat agcaaagaga tacttttgag caatgtttgt ggaagcggta    2580
ttcgcaatat tttagtagct cgttacagtc cggtgcgttt ttggttttt gaaagtgcgt     2640 cttcagagcg ctttggttt tcaaaagcgc tctgaagttc ctatactttc tagctagaga    2700
ataggaactt cggaatagga acttcaaagc gtttccgaaa acgagcgctt ccgaaaatgc    2760
aacgcgagct gcgcacatac agctcactgt tcacgtcgca cctatatctg cgtgttgcct    2820
gtatatatat atacatgaga agaacggcat agtgcgtgtt tatgcttaaa tgcgttatgg    2880
tgcactctca gtacaatctg ctctgatgcc gcatagttaa gccagccccg cacccgcca     2940 acaccgctg acgcgccctg acgggcttgt ctgctcccgg catccgctta cagacaagct     3000
gtgaccgtct ccgggagctg catgtgtcag aggttttcac cgtcatcacc gaaacgcgcg    3060
agacgaaagg gcctcgtgat acgcctattt ttataggtta atgtcatgat aataatggtt    3120
tcttagacgt caggtggcac ttttcgggga aatgtgcgcg gaacccctat tgtttattt     3180 ttctaaatac attcaaatat gtatccgctc atgagacaat aaccctgata aatgcttcaa    3240
taatattgaa aaaggaagag tatgagtatt caacatttcc gtgtcgccct tattcccttt    3300
tttgcggcat tttgccttcc tgttttgct cacccagaaa cgctggtgaa agtaaaagat      3360
gctgaagatc agttgggtgc acgagtgggt tacatcgaac tggatctcaa cagcggtaag    3420
atccttgaga gttttcgccc cgaagaacgt tttccaatga tgagcacttt taaagttctg    3480
ctatgtggcg cggtattatc ccgtattgac gccgggcaag agcaactcgg tcgccgcata    3540
cactattctc agaatgactt ggttgagtac tcaccagtca cagaaaagca tcttacggat    3600
ggcatgacag taagagaatt atgcagtgct gccataacca tgagtgataa cactgcggcc    3660
aacttacttc tgacaacgat cggaggaccg aaggagctaa ccgcttttt gcacaacatg    3720 ggggatcatg taactcgcct tgatcgttgg gaaccggagc tgaatgaagc cataccaaac    3780
gacgagcgtg acaccacgat gcctgtagca atggcaacaa cgttgcgcaa actattaact    3840
ggcgaactac ttactctagc ttcccggcaa caattaatag actggatgga ggcggataaa    3900
gttgcaggac cacttctgcg ctcggccctt ccggctggct ggtttattgc tgataaatct    3960
ggagccggtg agcgtgggtc tcgcggtatc attgcagcac tggggccaga tggtaagccc    4020
tcccgtatcg tagttatcta cacgacgggg agtcaggcaa ctatggatga acgaaataga    4080
```

```
cagatcgctg agataggtgc ctcactgatt aagcattggt aactgtcaga ccaagtttac   4140
tcatatatac tttagattga tttaaaactt cattttaat ttaaaaggat ctaggtgaag    4200 atccttttg ataatctcat gaccaaaatc ccttaacgtg agttttcgtt ccactgagcg    4260
tcagaccccg tagaaaagat caaaggatct tcttgagatc ctttttttct gcgcgtaatc   4320
tgctgcttgc aaacaaaaaa accaccgcta ccagcggtgg tttgtttgcc ggatcaagag   4380
ctaccaactc tttttccgaa ggtaactggc ttcagcagag cgcagatacc aaatactgtc   4440
cttctagtgt agccgtagtt aggccaccac ttcaagaact ctgtagcacc gcctacatac   4500
ctcgctctgc taatcctgtt accagtggct gctgccagtg cgataagtc gtgtcttacc    4560 gggttggact caagacgata gttaccggat aaggcgcagc ggtcgggctg aacggggggt   4620
tcgtgcacac agcccagctt ggagcgaacg acctacaccg aactgagata cctacagcgt   4680
gagcattgag aaagcgccac gcttcccgaa gggagaaagg cggacaggta tccggtaagc   4740
ggcagggtcg gaacaggaga gcgcacgagg agcttccag ggggaaacgc ctggtatctt    4800
tatagtcctg tcgggtttcg ccacctctga cttgagcgtc gatttttgtg atgctcgtca   4860 gggggggcgga gcctatggaa aaacgccagc aacgcggcct ttttacggtt cctggccttt   4920
tgctggcctt ttgctcacat gttctttcct gcgttatccc ctgattctgt ggataaccgt   4980
attaccgcct ttgagtgagc tgataccgct cgccgcagcc gaacgaccga gcgcagcgag   5040
tcagtgagcg aggaagcgga agagcgccca atacgcaaac cgcctctccc cgcgcgttgg   5100
ccgattcatt aatccaggat cccaattaat gtgagttacc tcactcatta ggcaccccag   5160
gctttacact ttatgcttcc ggctcgtatg ttgtgtggaa ttgtgagcgg ataacaattt   5220
cacacaggaa acagctatga ccatgattac gaattaattc gagctcggta cccggggatc   5280
gatccactag agatctgttt agcttgcctc gtccccgccg ggtcacccgg ccagcgacat   5340
ggaggcccag aataccctcc ttgacagtct tgacgtgcgc agctcagggg catgatgtga   5400
ctgtcgcccg tacatttagc ccatacatcc ccatgtataa tcatttgcat ccatacattt   5460
tgatggccgc acggcgcgaa gcaaaaatta cggctcctcg ctgcagacct gcgagcaggg   5520
aaacgctccc ctcacagacg cgttgaattg tccccacgcc gcgcccctgt agagaaatat   5580
aaaaggttag gatttgccac tgaggttctt ctttcatata cttcctttta aaatcttgct   5640
aggatacagt tctcacatca catccgaaca taaacaacca tggccgacca agcgacgccc   5700
aacctgccat cacgagattt cgattccacg ccgccttct atgaaaggtt gggcttcgga   5760
atcgttttcc gggacgccgg ctggatgatc ctccagcgcg ggatctcaa gctggagttc    5820 ttcgcccacc ccgggctcga tcccctcgcg agttggttca gctgctgcct gaggctggac   5880 gacctcgcg agttctaccg gcagtgcaaa tccgtcggca tccaggaaac cagcagcggc    5940
tatccgcgca tccatgcccc cgaactgcag gagtggggag gcacgatggc cgctttggtc   6000
gacccggacg gacgctcct gcgcctgata cagaacgaat tgcttgcagg catctcatga    6060
tcagtactga caataaaaag attcttgttt tcaagaactt gtcatttgta gtttttttt    6120 atattgtagt tgttctattt taatcaaatg ttagcgtgat ttatatttt ttcgcctcg     6180 acatcatctg cccagatgcg aagttaagtg cgcagaaagt aatatcatgc gtcaatcgta   6240
tgtgaatgct ggtcgctata ctgctgtcga ttcgatacta acgccgccat ccagtgtcga   6300
aaacgagctc tcgagaaccc ttaatataac ttcgtataat gtatgctata cgaagttatt   6360
aggtgatatc agatccacta gtcttctagg cgggttatct actgatccga gcttccacta   6420
```

```
ggatagcacc caaacacctg catatttgga cgacctttac ttacaccacc aaaaaccact   6480
ttcgcctctc ccgcccctga taacgtccac taattgagcg attacctgag cggtcctctt   6540
ttgtttgcag catgagactt gcatactgca aatcgtaagt agcaacgtct caaggtcaaa   6600
actgtatgga aaccttgtca cctcacttaa ttctagctag cctaccctgc aagtcaagag   6660
gtctccgtga ttcctagcca cctcaaggta tgcctctccc cggaaactgt ggcctttcct   6720
ggcacacatg atctccacga tttcaacata taaatagctt ttgataatgg caatattaat   6780
caaatttatt ttacttcttt cttgtaacat ctctcttgta atcccttatt ccttctagct   6840
attttcata aaaaccaag caactgctta tcaacacaca aacactaaat caagaattc   6900
ttaattaaac aatgcttttg caagctttcc ttttccttt ggctggtttt gcagccaaaa   6960
tatctgcaat cactaaaagg tgcttgcata tcttgaacag aaaatgtaca cgtatccatt   7020
tttcctctgt gtcttcctc aatatggaat ttgatccaga tcataattac ttagtatttg   7080
tcgatatcaa aggtggccca tcttgcaagt caaccaataa ctgtaagaaa actacgggtt   7140
attatcacat tgttcaattg cttattatgt ctgagttcaa tatagagagc acactggctc   7200
aacttacatt acaggaaaag attggcttac ttgctgggat cgattttgg cataccttcg   7260
ctgttgaaag attgaatatt ccatccctga gattttccga tggccctaat ggcttgagag   7320
ggacaaagtt tttcgactcc gtgccttcag cctgtttccc atgtggtacg gctttggctg   7380
ccacttttga taaagagttg ttatttgagg caggtcgatt gatgggcgac gaagctaaac   7440
ataagggcgc acaagttgtc ttgggaccaa caatgaatat ccaaagaggg cctttgggtg   7500
gaagaggctt cgagtctttc tctgaagatg cgcacttaac aggtcaatca gctgcctcaa   7560
ttatcaatgg catacaagac aagggaattg ctgctacaat taaacatttt gtctgcaatg   7620
acttagagga tcaacgtaac tcttcagata gcattttaac ggaaagagcg ctcagagaaa   7680
tctacctaga gccattcaga ttagcaatca acattcaaa cccagttgca cttatgacag   7740
gttacaacaa ggttaatgga gagcacgtga gccaatctga aagacttatc caagatatcc   7800
tgagaaaaga gtgggactgg gatggtacaa caatgtccga ctggtacgga acttacactt   7860
ctaaagaggc tatagaaaat ggacttgaca tagaaatgcc aggtccatcc atctttagaa   7920
atcagtccga agtagccgct atggtaacca ccaaagagtt gcacatcaaa aagattgatg   7980
aaagagttac taatgtctta aagttgatca aatacgctct gaagtctgga gtgccagaaa   8040
atgctccaga aactagcaac ggcaatacac cagagactgc agccctactg agaaagctgg   8100
ctcatgattc tgtcgttcta ttgaaaaacg acaataatgt tctgccttta tctaaagacg   8160
acaaaattgc cgtaatcggt ccaaatgcaa aattcgccgc atattgtggt ggaggctctg   8220
catctctgag agcgtactac acgacaaccc catttgattc aatctctaaa aagctcaata   8280
aggacccaga atacactatt ggtgcatacg gtcacagatt gctacctgcc ttgggcccac   8340
aactggttaa tcctaaaacg ggcaacgccg gttataactt gaaatactac ttggaaccaa   8400
aatccacaag cgagagaacc ttaattgatg aacgtgatct tgacctgtct aacatctttc   8460
tcgttgacta ctacaataag aaaatcaagg atgatttgtt tttcatcgat tttgatgggc   8520
aattcactcc agaagagaca gctgattacg agtttggcct ggcagtcttg gaaccgctc   8580
aattgtttgt tgatggtaag ttggttgtag ataacaaaac agtccagcag agaggtaata   8640
gtttctttaa ctcaggtagt aacgaggtta ggaactctat tagtcttgag aagggaaaaa   8700
catattctat aaagatagaa tttggctcag ctccaacatt cacagttcca tctcatgact   8760
cagtgtcatt tggaggaggt ggaggtatta atcttggatt agctaaagtg atcaatccta   8820
```

```
aggacgaaat tgctaaagcc gcagaacttg cgaagaaagt tgacaaagta gtcctgaaca   8880
taggtttgaa ccaggaatgg gaaagtgaag gtttcgatag accagatatg aaattgatag   8940
gccatatcaa tgaacttgtt gatgctgtct tggacgcaaa tccaaatacg gtagtcgtta   9000
atcaatctgg aactccagtt gagttcccct tggatcaaaaa ggctaatgcg ctcgttcaag   9060
catggtacgg tggtaatgaa ttaggtaatg gaatagcaga cgtgttgttc ggcgatgtga   9120
acccttcagg caaactatct ctctcatttc ctgtcaaaaa tgtggataac cctgcatacc   9180
ttaactttaa aactgagaag ggcagagttt tgtacggtga ggacatcttc gttggctata   9240
agtattatga aaagctagaa cgtgaagttg cctttccttt cggattcggc ttgagttata   9300
caaagtttga tatatccggt agtaaagtct ccgtggatga aaaggatgat aacttgactg   9360
tgtcagtgaa cgtgaaaaac acaggtaaaa tcgacggatc agaggtagtt cagttttaca   9420
tctccaaaga tgaatctgat gtaattagac cagtgaagga actaaaagga tttgaaaagg   9480
tacatctcaa ggctggagct gattctactg tttcactgaa attaagcctc aaggattcta   9540
tttcattttt cgatgaatac caagacgaat ggtcagttga gaaaggtgat tacaaagtgc   9600
atgtaggtaa ttcaagcgat aatatcactt caactttgcc ttttaagatc gaaaaggact   9660
tcctctggtc tggtatggat gatgatgaca aaggtggttc tcctccttct catcatcacc   9720
accaccacta aggcgcgccc tcgagagctt ttgattaagc cttctagtcc aaaaaacacg   9780
tttttttgtc atttatttca ttttcttaga atagtttagt ttattcattt tatagtcacg   9840
aatgttttat gattctatat agggttgcaa acaagcattt ttcattttat gttaaaacaa   9900
tttcaggttt accttttatt ctgcttgtgg tgacgcgtgt atccgcccgc tcttttggtc   9960
acccatgtat ttaattgcat aaataattct taaaagtgga gctagtctat ttctatttac  10020
ataccctctca tttctcattt cctcctaatg tgtcaatgat catattctta actggaccga  10080
tcttattcgt cagattcaaa ccaaaagttc ttagggctac cacaggagga aaattagtgt  10140
gatataattt aaataattta tccgccattc ctaatagaac gttgttcgac ggatatcttt  10200
ctgcccaaaa gggttctaag ctcaatgaag agccaatgtc taaacctctt tgc          10253
```

<210> SEQ ID NO 39  
<211> LENGTH: 10076  
<212> TYPE: DNA  
<213> ORGANISM: Kluyveromyces marxianus  
<220> FEATURE:  
<221> NAME/KEY: misc_feature  
<222> LOCATION: (1)..(10076)  
<223> OTHER INFORMATION: plasmid pMU3565

<400> SEQUENCE: 39

```
ggccgcaagc taattcgcgc gaagctagct tggcactggc cgtcgtttta caacgtcgtg     60
actgggaaaa ccctggcgtt acccaactta atcgccttgc agcacatccc cccttcgcca    120
gctggcgtaa tagcgaagag gcccgcaccg atcgcccttc ccaacagttg cgcagcctga    180
atggcgaatg gcgcctgatg cggtattttc tccttacgca tctgtgcggt atttcacacc    240
gcataggaga tctaagctct ggcgtaatag cgaagaggcc cgcaccgatc gcccttccca    300
acagttgcgc agcctgaatg gcgaatggcg cctgatgcgg tattttctcc ttacgcatct    360
gtgcggtatt tcacaccgca tagggtaata actgatataa ttaaattgaa gctctaattt    420
gtgagtttag tatacatgca tttacttata atacagtttt ttagttttgc tggccgcatc    480
ttctcaaata tgcttcccag cctgcttttc tgtaacgttc accctctacc ttagcatccc    540
```

```
ttcccttttgc aaatagtcct cttccaacaa taataatgtc agatcctgta gagaccacat    600
catccacggt tctatactgt tgacccaatg cgtctcccctt gtcatctaaa cccacaccgg    660
gtgtcataat caaccaatcg taaccttcat ctcttccacc catgtctctt tgagcaataa    720
agccgataac aaaatctttg tcgctcttcg caatgtcaac agtaccctta gtatattctc    780
cagtagatag ggagcccttg catgacaatt ctgctaacat caaaaggcct ctaggttcct    840
ttgttacttc ttctgccgcc tgcttcaaac cgctaacaat acctgggccc accacaccgt    900
gtgcattcgt aatgtctgcc cattctgcta ttctgtatac cccgcagag tactgcaatt     960
tgactgtatt accaatgtca gcaaattttc tgtcttcgaa gagtaaaaaa ttgtacttgg    1020
cggataatgc ctttagcggc ttaactgtgc cctccatgga aaaatcagtc aagatatcca    1080
catgtgtttt tagtaaacaa attttgggac ctaatgcttc aactaactcc agtaattcct    1140
tggtggtacg aacatccaat gaagcacaca agtttgtttg cttttcgtgc atgatattaa    1200
atagcttggc agcaacagga ctaggatgag tagcagcacg ttccttatat gtagctttcg    1260
acatgattta tcttcgtttc ggttttttgtt ctgtgcagtt gggttaagaa tactgggcaa    1320
tttcatgttt cttcaacact acatatgcgt atatatacca atctaagtct gtgctccttc    1380
cttcgttctt ccttctgttc ggagattacc gaatcaaaaa aatttcaaag aaaccgaaat    1440
caaaaaaaag aataaaaaaa aaatgatgaa ttgaaaagct cttgttaccc atcattgaat    1500
tttgaacatc cgaacctggg agttttccct gaaacagata gtatatttga acctgtataa    1560
taatatatag tctagcgctt tacggaagac aatgtatgta tttcggttcc tggagaaact    1620
attgcatcta ttgcataggt aatcttgcac gtcgcatccc cggttcattt tctgcgtttc    1680
catcttgcac ttcaatagca tatctttgtt aacgaagcat ctgtgcttca ttttgtagaa    1740
caaaaatgca acgcgagagc gctaatttt caaacaaaga atctgagctg cattttttaca    1800
gaacagaaat gcaacgcgaa agcgctattt taccaacgaa gaatctgtgc ttcatttttg    1860
taaaacaaaa atgcaacgcg agagcgctaa tttttcaaac aaagaatctg agctgcatttt   1920
ttacagaaca gaaatgcaac gcgagagcgc tattttacca acaaagaatc tatacttctt   1980
ttttgttcta caaaaatgca tcccgagagc gctattttc taacaaagca tcttagatta   2040
cttttttttct cctttgtgcg ctctataatg cagtctcttg ataacttttt gcactgtagg    2100
tccgttaagg ttagaagaag gctactttgg tgtctatttt ctcttccata aaaaaagcct    2160
gactccactt cccgcgttta ctgattacta gcgaagctgc gggtgcattt tttcaagata    2220
aaggcatccc cgattatatt ctataccgat gtggattgcg catactttgt gaacagaaag    2280
tgatagcgtt gatgattctt cattggtcag aaaattatga acggtttctt ctattttgtc    2340
tctatatact acgtatagga aatgtttaca ttttcgtatt gttttcgatt cactctatga    2400
atagttctta ctacaatttt tttgtctaaa gagtaatact agagataaac ataaaaaatg    2460
tagaggtcga gttagatgc aagttcaagg agcgaaggt ggatgggtag gttatatagg      2520
gatatagcac agagatatat agcaaagaga tactttgag caatgtttgt ggaagcggta     2580
ttcgcaatat tttagtagct cgttacagtc cggtgcgttt ttggttttttt gaaagtgcgt    2640
cttcagagcg cttttggttt tcaaaagcgc tctgaagttc ctatactttc tagctagaga    2700
ataggaactt cggaatagga acttcaaagc gtttccgaaa acgagcgctt ccgaaaatgc    2760
aacgcgagct gcgcacatac agctcactgt tcacgtcgca cctatatctg cgtgttgcct    2820
gtatatatat atacatgaga agaacggcat agtgcgtgtt tatgcttaaa tgcgttatgg    2880
tgcactctca gtacaatctg ctctgatgcc gcatagttaa gccagccccg acacccgcca    2940
```

```
acaccogctg acgcgccctg acgggcttgt ctgctcccgg catccgctta cagacaagct    3000
gtgaccgtct ccgggagctg catgtgtcag aggttttcac cgtcatcacc gaaacgcgcg    3060
agacgaaagg gcctcgtgat acgcctattt ttataggtta atgtcatgat aataatggtt    3120
tcttagacgt caggtggcac ttttcgggga aatgtgcgcg gaaccccctat tgtttattt    3180
ttctaaatac attcaaatat gtatccgctc atgagacaat aaccctgata aatgcttcaa    3240
taatattgaa aaaggaagag tatgagtatt caacatttcc gtgtcgccct tattccttt    3300
tttgcggcat tttgccttcc tgttttgct cacccagaaa cgctggtgaa agtaaaagat    3360
gctgaagatc agttgggtgc acgagtgggt tacatcgaac tggatctcaa cagcggtaag    3420
atccttgaga gttttcgccc cgaagaacgt tttccaatga tgagcacttt taaagttctg    3480
ctatgtggcg cggtattatc ccgtattgac gccgggcaag agcaactcgg tcgccgcata    3540
cactattctc agaatgactt ggttgagtac tcaccagtca cagaaaagca tcttacggat    3600
ggcatgacag taagagaatt atgcagtgct gccataacca tgagtgataa cactgcggcc    3660
aacttacttc tgacaacgat cggaggaccg aaggagctaa ccgctttttt gcacaacatg    3720
ggggatcatg taactcgcct tgatcgttgg gaaccggagc tgaatgaagc cataccaaac    3780
gacgagcgtg acaccacgat gcctgtagca atggcaacaa cgttgcgcaa actattaact    3840
ggcgaactac ttactctagc ttcccggcaa caattaatag actggatgga ggcggataaa    3900
gttgcaggac cacttctgcg ctcggccctt ccggctggct ggtttattgc tgataaatct    3960
ggagccggtg agcgtgggtc tcgcggtatc attgcagcac tggggccaga tggtaagccc    4020
tcccgtatcg tagttatcta cacgacgggg agtcaggcaa ctatggatga acgaaataga    4080
cagatcgctg agataggtgc ctcactgatt aagcattggt aactgtcaga ccaagtttac    4140
tcatatatac tttagattga tttaaaactt catttttaat ttaaaaggat ctaggtgaag    4200
atcctttttg ataatctcat gaccaaaatc ccttaacgtg agttttcgtt ccactgagcg    4260
tcagaccccg tagaaaagat caaaggatct tcttgagatc ctttttttct gcgcgtaatc    4320
tgctgcttgc aaacaaaaaa accaccgcta ccagcggtgg tttgtttgcc ggatcaagag    4380
ctaccaactc tttttccgaa ggtaactggc ttcagcagag cgcagatacc aaatactgtc    4440
cttctagtgt agccgtagtt aggccaccac ttcaagaact ctgtagcacc gcctacatac    4500
ctcgctctgc taatcctgtt accagtggct gctgccagtg gcgataagtc gtgtcttacc    4560
gggttggact caagacgata gttaccggat aaggcgcagc ggtcgggctg aacggggggt    4620
tcgtgcacac agcccagctt ggagcgaacg acctacaccg aactgagata cctacagcgt    4680
gagcattgag aaagcgccac gcttcccgaa gggagaaagg cggacaggta tccggtaagc    4740
ggcagggtcg gaacaggaga gcgcacgagg gagcttccag ggggaaacgc ctggtatctt    4800
tatagtcctg tcgggtttcg ccacctctga cttgagcgtc gatttttgtg atgctcgtca    4860
ggggggcgga gcctatggaa aaacgccagc aacgcggcct ttttacggtt cctggccttt    4920
tgctggcctt ttgctcacat gttctttcct gcgttatccc ctgattctgt ggataaccgt    4980
attaccgcct ttgagtgagc tgataccgct cgccgcagcc gaacgaccga gcgcagcgag    5040
tcagtgagcg aggaagcgga agagcgccca atacgcaaac cgcctctccc cgcgcgttgg    5100
ccgattcatt aatccaggat cccaattaat gtgagttacc tcactcatta ggcaccccag    5160
gctttacact ttatgcttcc ggctcgtatg ttgtgtggaa ttgtgagcgg ataacaattt    5220
cacacaggaa acagctatga ccatgattac gaattaattc gagctcggta cccggggatc    5280
```

```
gatccactag agatctgttt agcttgcctc gtccccgccg ggtcacccgg ccagcgacat    5340
ggaggcccag aataccctcc ttgacagtct tgacgtgcgc agctcagggg catgatgtga    5400
ctgtcgcccg tacatttagc ccatacatcc ccatgtataa tcatttgcat ccatacattt    5460
tgatggccgc acggcgcgaa gcaaaaatta cggctcctcg ctgcagacct gcgagcaggg    5520
aaacgctccc ctcacagacg cgttgaattg tccccacgcc gcgccctgt agagaaatat     5580
aaaaggttag gatttgccac tgaggttctt ctttcatata cttccttta aaatcttgct     5640
aggatacagt tctcacatca catccgaaca taaacaacca tggccgacca agcgacgccc    5700
aacctgccat cacgagattt cgattccacg gccgccttct atgaaaggtt gggcttcgga    5760
atcgttttcc gggacgccgg ctggatgatc ctccagcgcg gggatctcaa gctggagttc    5820
ttcgcccacc ccgggctcga tcccctcgcg agttggttca gctgctgcct gaggctggac    5880
gacctcgcgg agttctaccg gcagtgcaaa tccgtcggca tccaggaaac cagcagcggc    5940
tatccgcgca tccatgcccc cgaactgcag gagtggggag gcacgatggc cgctttggtc    6000
gacccggacg ggacgctcct gcgcctgata cagaacgaat tgcttgcagg catctcatga    6060
tcagtactga caataaaaag attcttgttt tcaagaactt gtcatttgta tagttttttt    6120
atattgtagt tgttctattt taatcaaatg ttagcgtgat ttatatttt tttcgcctcg     6180
acatcatctg cccagatgcg aagttaagtg cgcagaaagt aatatcatgc gtcaatcgta    6240
tgtgaatgct ggtcgctata ctgctgtcga ttcgatacta acgccgccat ccagtgtcga    6300
aaacgagctc tcgagaaccc ttaatataac ttcgtataat gtatgctata cgaagttatt    6360
aggtgatatc agatccacta gtcttctagg cgggttatct actgatccga gcttccacta    6420
ggatagcacc caaacacctg catatttgga cgacctttac ttacaccacc aaaaaccact    6480
ttcgcctctc ccgcccctga taacgtccac taattgagcg attacctgag cggtcctctt    6540
ttgtttgcag catgagactt gcatactgca atcgtaagt agcaacgtct caaggtcaaa     6600
actgtatgga aaccttgtca cctcacttaa ttctagctag cctaccctgc aagtcaagag    6660
gtctccgtga ttcctagcca cctcaaggta tgcctctccc cggaaactgt ggcttttct     6720
ggcacacatg atctccacga tttcaacata taaatagctt ttgataatgg caatattaat    6780
caaatttatt ttacttcttt cttgtaacat ctctcttgta atcccttatt ccttctagct    6840
attttttcata aaaaaccaag caactgctta tcaacacaca aacactaaat caaagaattc    6900
ttaattaaac aatgcttttg caagctttcc ttttccttt ggctggtttt gcagccaaaa     6960
tatctgcatc aaaatttgat gtcgaacaac tcttatctga acttaatcag gatgaaagag    7020
tttctcttct gtctgccgtt gattttggc atactaaaaa gatagaacga ttaggtatcc     7080
ctgctgttag agtctctgat gggcctaatg ggatcagggg tacaaaattc tttgacggtg    7140
taccaagtgg ttgtttccct aacggtacag gtttggccag cacttttgac agagacttac    7200
tagaaactgc agggaagttg atggctaaag agtctatcgc taaaaatgcc gctgttatat    7260
tgggacctac aacaaatatg caaagaggtc cactaggtgg cagaggattt gagagctttt    7320
cagaagatcc atacttggct ggcatggcga cttcctcagt agttaaaggt atgcaaggcg    7380
agggtattgc agctacagta aagcactttg tttgcaatga cttagaagat caaagattca    7440
gctcaaatag tattgtctct gaaagagcgc taagagaaat ataccttgaa cctttagac    7500
tagctgttaa acatgctaat ccagtttgca tcatgacagc ttacaacaaa gttaatggcg    7560
atcactgttc acaatccaaa aagctcctta tcgatatctt gagagatgag tggaaatggg    7620
atggcatgtt gatgtcagat tggttcggca cttatacaac cgcagctgcc atcaaaaatg    7680
```

```
ggttagatat tgaatttcct ggacctactc gttggagaac aagggcattg gtttctcact    7740
ctttgaatag tagagaacaa atcactacgg aagatgttga tgatagggtg cgacaagttt    7800
tgaaaatgat caaatttgtg gtagataatt tggagaaaac cggtattgta gaaaacggtc    7860
ctgaatctac ttctaataac actaaggaga catctgactt gttgagagaa atagccgctg    7920
attcaatcgt ccttttgaaa aacaaaaaca attacctaac gagtaaagag aggaggcaat    7980
accatgtaat tggtccaaat gcgaaagcaa agacctcttc aggaggagga tctgcttcaa    8040
tgaactcata ctacgtggtt tctccatacg aaggtatcgt aaacaaactt ggtaaggagg    8100
ttgattacac cgtaggtgca tattcccaca aatcaattgg cggtcttgcc gaatcatctc    8160
tgattgacgc ggcaaagcca gcagacgctg agaacgctgg tttaattgcc aagttttact    8220
ccaatccagt cgaagagaga tccgaagatg aggagccatt ccatgttaca aaagttaata    8280
gaagtaatgt tcacctattc gactttaagc atgaaaaggt agatccaaag aatccttact    8340
ttttcgttac tttgaccgga caatacgtcc cacaggaaga tggggactat atcttctccc    8400
tccaagttta cggtagtggg ttgttttact tgaatgacga gttaatcatt gatcaaaagc    8460
ataatcaaga gagaggctcc ttctgtttcg gtgcaggaac aaaggagaga actaaaaagc    8520
taacgctcaa aaagggtcaa gtttacaacg ttagagttga gtatggcagt gggccaacat    8580
caggactggt cggtgaattt ggtgctggtg gttttcaggc aggcgtgatt aaggccatcg    8640
atgatgacga agagattaga aatgcagcag aactggctgc caagcatgat aaagcagtat    8700
tgataatagg tctgaacgga gaatgggaaa ccgaagggta tgaccgtgag aacatggatc    8760
tgccaaagag aactaacgaa ttagtcagag ccgttttgaa ggccaatcca aacacagtca    8820
tcgtaaacca gagcgggact ccagtagagt tcccttggtt ggaggaagct aatgcactcg    8880
tacaagcctg gtatggaggg aatgaattag gcaatgctat tgcagatgtg ctatacggcg    8940
acgttgttcc taacgaaaag ttatcactat cttggccatt caaattgcaa gacaatccag    9000
catttttgaa ctttaaaaca gagtttggca gagtagtgta tggtgaagat attttcgtcg    9060
gctacagata ttacgaaaag ctgcagagaa aagtcgcatt tccatttgga tatggtttgt    9120
cctacacgac tttcgaactg gatatttctg actttaaggt caccgatgac aaaatcgata    9180
tcagtgtgga cgttaaaaac actggtgata agtttgccgg atctgaagtt gtacaagttt    9240
acttctctgc gctgaactcc aaagtatctc gtcctgtgaa ggaattaaag ggattcgaaa    9300
aagtccatct tgaaccaggc gagaagaaaa cagtgaatat cgagctagag ttaaaagacg    9360
caatcagtta tttcaacgaa gagttaggaa atggcatgt ggaagcgggt gaatacttag    9420
tttcagttgg aacaagttct gatgatattc tatctgtaaa agagtttaaa gttgaaaaag    9480
atttgtactg gaagggtta gatgatgatg acaaaggtgg ttctcctcct tctcatcatc    9540
accaccacca ctaaggcgcg ccctcgagag cttttgatta agccttctag tccaaaaaac    9600 acgtttttt gtcatttatt tcattttctt agaatagttt agtttattca ttttatagtc    9660
acgaatgttt tatgattcta tatagggttg caaacaagca tttttcattt tatgttaaaa    9720
caatttcagg tttacctttt attctgcttg tggtgacgcg tgtatccgcc cgctctttg    9780 gtcacccatg tatttaattg cataaataat tcttaaagt ggagctagtc tatttctatt    9840 tacataccctc tcatttctca tttcctccta atgtgtcaat gatcatattc ttaactggac    9900
cgatcttatt cgtcagattc aaaccaaaag ttcttagggc taccacagga ggaaaattag    9960
tgtgatataa tttaaataat ttatccgcca ttcctaatag aacgttgttc gacggatatc  10020
```

| | | |
|---|---|---|
| tttctgccca | aaagggttct aagctcaatg aagagccaat gtctaaacct ctttgc | 10076 |

<210> SEQ ID NO 40
<211> LENGTH: 9203
<212> TYPE: DNA
<213> ORGANISM: Phytophthora infestans
<220> FEATURE:
<221> NAME/KEY: misc_feature
<222> LOCATION: (1)..(9203)
<223> OTHER INFORMATION: plasmid pMU3566

<400> SEQUENCE: 40
ggccgcaagc taattcgcgc gaagctagct tggcactggc cgtcgtttta caacgtcgtg 60
actgggaaaa ccctggcgtt acccaactta atcgccttgc agcacatccc cccttcgcca 120
gctggcgtaa tagcgaagag gcccgcaccg atcgcccttc ccaacagttg cgcagcctga 180
atggcgaatg gcgcctgatg cggtattttc tccttacgca tctgtgcggt atttcacacc 240
gcataggaga tctaagctct ggcgtaatag cgaagaggcc cgcaccgatc gcccttccca 300
acagttgcgc agcctgaatg gcgaatggcg cctgatgcgg tattttctcc ttacgcatct 360
gtgcggtatt tcacaccgca tagggtaata actgatataa ttaaattgaa gctctaattt 420
gtgagtttag tatacatgca tttacttata atacagtttt ttagttttgc tggccgcatc 480
ttctcaaata tgcttcccag cctgcttttc tgtaacgttc accctctacc ttagcatccc 540
ttccctttgc aaatagtcct cttccaacaa taataatgtc agatcctgta gagaccacat 600
catccacggt tctatactgt tgacccaatg cgtctccctt gtcatctaaa cccacaccgg 660
gtgtcataat caaccaatcg taaccttcat ctcttccacc catgtctctt tgagcaataa 720
agccgataac aaaatctttg tcgctcttcg caatgtcaac agtaccctta gtatattctc 780
cagtagatag ggagcccttg catgacaatt ctgctaacat caaaaggcct ctaggttcct 840
ttgttacttc ttctgccgcc tgcttcaaac cgctaacaat acctgggccc accacaccgt 900
gtgcattcgt aatgtctgcc cattctgcta ttctgtatac acccgcagag tactgcaatt 960
tgactgtatt accaatgtca gcaaattttc tgtcttcgaa gagtaaaaaa ttgtacttgg 1020
cggataatgc ctttagcggc ttaactgtgc cctccatgga aaaatcagtc aagatatcca 1080
catgtgtttt tagtaaacaa attttgggac ctaatgcttc aactaactcc agtaattcct 1140
tggtggtacg aacatccaat gaagcacaca agtttgtttg cttttcgtgc atgatattaa 1200
atagcttggc agcaacagga ctaggatgag tagcagcacg ttccttatat gtagctttcg 1260
acatgattta tcttcgtttc ggtttttgtt ctgtgcagtt gggttaagaa tactgggcaa 1320
tttcatgttt cttcaacact acatatgcgt atatatacca atctaagtct gtgctccttc 1380
cttcgttctt ccttctgttc ggagattacc gaatcaaaaa aatttcaaag aaaccgaaat 1440
caaaaaaaag aataaaaaaa aaatgatgaa ttgaaaagct cttgttaccc atcattgaat 1500
tttgaacatc cgaacctggg agttttccct gaaacagata gtatatttga acctgtataa 1560
taatatatag tctagcgctt tacggaagac aatgtatgta tttcggttcc tggagaaact 1620
attgcatcta ttgcataggt aatcttgcac gtcgcatccc cggttcattt tctgcgtttc 1680
catcttgcac ttcaatagca tatctttgtt aacgaagcat ctgtgcttca ttttgtagaa 1740
caaaaatgca acgcgagagc gctaattttt caaacaaaga atctgagctg catttttaca 1800
gaacagaaat gcaacgcgaa agcgctattt taccaacgaa gaatctgtgc ttcatttttg 1860
taaaacaaaa atgcaacgcg agagcgctaa tttttcaaac aaagaatctg agctgcattt 1920
ttacagaaca gaaatgcaac gcgagagcgc tattttacca acaaagaatc tatacttctt 1980

```
ttttgttcta caaaaatgca tcccgagagc gctattttc taacaaagca tcttagatta    2040
cttttttct cctttgtgcg ctctataatg cagtctcttg ataactttt gcactgtagg      2100
tccgttaagg ttagaagaag gctactttgg tgtctatttt ctcttccata aaaaagcct    2160
gactccactt cccgcgttta ctgattacta gcgaagctgc gggtgcattt ttcaagata    2220
aaggcatccc cgattatatt ctataccgat gtggattgcg catactttgt gaacagaaag   2280
tgatagcgtt gatgattctt cattggtcag aaaattatga acggtttctt ctattttgtc   2340
tctatatact acgtatagga aatgtttaca ttttcgtatt gttttcgatt cactctatga   2400
atagttctta ctacaatttt tttgtctaaa gagtaatact agagataaac ataaaaaatg   2460
tagaggtcga gtttagatgc aagttcaagg agcgaaaggt ggatgggtag gttatatagg   2520
gatatagcac agagatatat agcaaagaga tacttttgag caatgtttgt ggaagcggta   2580
ttcgcaatat tttagtagct cgttacagtc cggtgcgttt ttggtttttt gaaagtgcgt   2640
cttcagagcg cttttggttt tcaaaagcgc tctgaagttc ctatactttc tagctagaga   2700
ataggaactt cggaatagga acttcaaagc gtttccgaaa acgagcgctt ccgaaaatgc   2760
aacgcgagct gcgcacatac agctcactgt tcacgtcgca cctatatctg cgtgttgcct   2820
gtatatatat atacatgaga agaacggcat agtgcgtgtt tatgcttaaa tgcgttatgg   2880
tgcactctca gtacaatctg ctctgatgcc gcatagttaa gccagccccg acacccgcca   2940
acacccgctg acgcgccctg acgggcttgt ctgctcccgg catccgctta cagacaagct   3000
gtgaccgtct ccgggagctg catgtgtcag aggttttcac cgtcatcacc gaaacgcgcg   3060
agacgaaagg gcctcgtgat acgcctattt ttataggtta atgtcatgat aataatggtt   3120
tcttagacgt caggtggcac ttttcgggga aatgtgcgcg gaacccctat tgtttattt    3180
ttctaaatac attcaaatat gtatccgctc atgagacaat aaccctgata aatgcttcaa   3240
taatattgaa aaaggaagag tatgagtatt caacatttcc gtgtcgccct tattcccttt    3300
tttgcggcat tttgccttcc tgttttgct cacccagaaa cgctggtgaa agtaaaagat    3360
gctgaagatc agttgggtgc acgagtgggt tacatcgaac tggatctcaa cagcggtaag   3420
atccttgaga gttttcgccc cgaagaacgt tttccaatga tgagcacttt taaagttctg    3480
ctatgtggcg cggtattatc ccgtattgac gccgggcaag agcaactcgg tcgccgcata   3540
cactattctc agaatgactt ggttgagtac tcaccagtca cagaaaagca tcttacggat   3600
ggcatgacag taagagaatt atgcagtgct gccataacca tgagtgataa cactgcggcc   3660
aacttacttc tgacaacgat cggaggaccg aaggagctaa ccgcttttt gcacaacatg    3720
ggggatcatg taactcgcct tgatcgttgg gaaccggagc tgaatgaagc cataccaaac   3780
gacgagcgtg acaccacgat gcctgtagca atggcaacaa cgttgcgcaa actattaact   3840
ggcgaactac ttactctagc ttcccggcaa caattaatag actggatgga ggcggataaa   3900
gttgcaggac cacttctgcg ctcggccctt ccggctggct ggtttattgc tgataaatct   3960
ggagccggtg agcgtgggtc tcgcggtatc attgcagcac tggggccaga tggtaagccc   4020
tcccgtatcg tagttatcta cacgacgggg agtcaggcaa ctatggatga acgaaataga   4080
cagatcgctg agataggtgc ctcactgatt aagcattggt aactgtcaga ccaagtttac   4140
tcatatatac tttagattga tttaaaactt cattttaat ttaaaggat ctaggtgaag      4200
atccttttg ataatctcat gaccaaaatc ccttaacgtg agttttcgtt ccactgagcg    4260
tcagacccg tagaaaagat caaaggatct tcttgagatc ctttttttct gcgcgtaatc     4320
```

```
tgctgcttgc aaacaaaaaa accaccgcta ccagcggtgg tttgtttgcc ggatcaagag    4380
ctaccaactc tttttccgaa ggtaactggc ttcagcagag cgcagatacc aaatactgtc    4440
cttctagtgt agccgtagtt aggccaccac ttcaagaact ctgtagcacc gcctacatac    4500
ctcgctctgc taatcctgtt accagtggct gctgccagtg gcgataagtc gtgtcttacc    4560
gggttggact caagacgata gttaccggat aaggcgcagc ggtcgggctg aacgggggt     4620
tcgtgcacac agcccagctt ggagcgaacg acctacaccg aactgagata cctacagcgt    4680
gagcattgag aaagcgccac gcttcccgaa gggagaaagg cggacaggta tccggtaagc    4740
ggcagggtcg gaacaggaga gcgcacgagg gagcttccag ggggaaacgc ctggtatctt    4800
tatagtcctg tcgggtttcg ccacctctga cttgagcgtc gatttttgtg atgctcgtca    4860
gggggggcgga gcctatggaa aaacgccagc aacgcggcct ttttacggtt cctggccttt    4920
tgctggcctt ttgctcacat gttctttcct gcgttatccc ctgattctgt ggataaccgt    4980
attaccgcct ttgagtgagc tgataccgct cgccgcagcc gaacgaccga gcgcagcgag    5040
tcagtgagcg aggaagcgga agagcgccca atacgcaaac cgcctctccc cgcgcgttgg    5100
ccgattcatt aatccaggat cccaattaat gtgagttacc tcactcatta ggcaccccag    5160
gctttacact ttatgcttcc ggctcgtatg ttgtgtggaa ttgtgagcgg ataacaattt    5220
cacacaggaa acagctatga ccatgattac gaattaattc gagctcggta cccggggatc    5280
gatccactag agatctgttt agcttgcctc gtccccgccg ggtcacccgg ccagcgacat    5340
ggaggcccag aatacccctcc ttgacagtct tgacgtgcgc agctcagggg catgatgtga    5400
ctgtcgcccg tacatttagc ccatacatcc ccatgtataa tcatttgcat ccatacattt    5460
tgatggccgc acggcgcgaa gcaaaaatta cggctcctcg ctgcagacct gcgagcaggg    5520
aaacgctccc ctcacagacg cgttgaattg tccccacgcc gcgcccctgt agagaaatat    5580
aaaaggttag gatttgccac tgaggttctt ctttcatata cttccttta aaatcttgct     5640
aggatacagt tctcacatca catccgaaca taaacaacca tggccgacca agcgacgccc    5700
aacctgccat cacgagattt cgattccacg gccgccttct atgaaaggtt gggcttcgga    5760
atcgttttcc gggacgccgg ctggatgatc ctccagcgcg ggatctcaa gctggagttc    5820
ttcgcccacc ccgggctcga tcccctcgcg agttggttca gctgctgcct gaggctggac    5880
gacctcgcgg agttctaccg gcagtgcaaa tccgtcggca tccaggaaac cagcagcggc    5940
tatccgcgca tccatgcccc cgaactgcag gagtggggag gcacgatggc cgctttggtc    6000
gacccggacg ggacgctcct gcgcctgata cagaacgaat tgcttgcagg catctcatga    6060
tcagtactga caataaaaag attcttgttt tcaagaactt gtcatttgta tagtttttt     6120
atattgtagt tgttctattt taatcaaatg ttagcgtgat ttatatttt tttcgcctcg     6180
acatcatctg cccagatgcg aagttaagtg cgcagaaagt aatatcatgc gtcaatcgta    6240
tgtgaatgct ggtcgctata ctgctgtcga ttcgatacta acgccgccat ccagtgtcga    6300
aaacgagctc tcgagaaccc ttaatataac ttcgtataat gtatgctata cgaagttatt    6360
aggtgatatc agatccacta gtcttctagg cgggttatct actgatccga gcttccacta    6420
ggatagcacc caaacacctg catatttgga cgacctttac ttacaccacc aaaaaccact    6480
ttcgcctctc ccgcccctga taacgtccac taattgagcg attacctgag cggtcctctt    6540
ttgtttgcag catgagactt gcatactgca aatcgtaagt agcaacgtct caaggtcaaa    6600
actgtatgga aaccttgtca cctcacttaa ttctagctag cctaccctgc aagtcaagag    6660
gtctccgtga ttcctagcca cctcaaggta tgcctctccc cggaaactgt ggcctttcct    6720
```

```
ggcacacatg atctccacga tttcaacata taaatagctt ttgataatgg caatattaat    6780
caaatttatt ttacttcttt cttgtaacat ctctcttgta atcccttatt ccttctagct    6840 attttcata aaaaccaag caactgctta tcaacacaca aacactaaat caaagaattc      6900
ttaattaaac aatgcaggtg atcaagccct tgaactacgt gctggcattg ctggcgatgc    6960
aggttgtgag cgctgctaca aacagttgca catcttggtc tgaaagattt cagaaaaatc   7020
tggaaggcgt gtgcgtttgt tcagaagcta cttgtgatac aatcgataat ggttcaagtc   7080
atttgtcagg ctccgaagca ggcgttttta ccacttctaa agctggagat agactaacat   7140
tttcaacagt agacatggag gcaacagcaa atgaagctgc cgactttgtc attgacacaa   7200
caaagactta tcaatcaatt atagggtttg gtggcgcctt cactgattct agtgctatca   7260
acttgcacat gctcaattct aagttgcaag agcattccag aactacttac tttgagatg    7320 atggattaca atacacgatt ggtagaatac caattggctc tacggatttc tctttaacca   7380
tctacagcta taatgatgtg aaggggatt tggctatgga aaacttctct attgatatgg    7440
ataaggataa aaagattcca ttcattcata gagcaatggg caaatcttca agaggttga    7500 aattgtacgc gtcatcttgg gcacctcctg cctggatgac aactgaaaat acgactataa   7560
actgtgcagt tcaaggttac ccaggtggag aatactggaa ggctttagct ttgtactatt   7620
ccaaatttgt ttccgcctat gaggctgagg gaatcccaat ctgggcgatg actactcaaa   7680
acgagcctac acaacaattc gccttcaaat actggcaaag tctgagattc aatgttacca   7740
cagaacgaga tttcataaag agagatttgg gtccacaaat gaaaactgac catccagact   7800
tgaagatcat aatgatggac gatcaaaaag acctttgct agattgggac gcaaccctac    7860
tggatgccga atcagcacag tacgtttctg gtgctggtgt tcattggtac aaaaacttgg   7920
atttccttgt ggatactgcc ggtaattttg cggacctcga aacttttcac gaaaaatacc   7980
cagacttatt cattctggcc accgaggctt gtgaaggcta cctacttgac ggtatcgtaa   8040
ctggagcagg ccctacgctt caaaatccta catttgcctg gcaaagagca caaatctacg   8100
ctagggatat cattggtgat cttgcacatt acgccgcagg ttggaccgat tggaacttag   8160
tacttaatac aacaggcggt ccaacatgga tcgacaactt gattgattca cctatactta   8220
tcgatgaagc tgggggagct gaattttaca agcaaccaat gtattatgct atgggtcatt   8280
tttctaagtt tttgccagct gacagtgtca gagtttctct atctactagc tcctcagctt   8340
cctcaaccct cgcaaaagtt gattctgtcg cattttgac accagataat caagtagtcc    8400
taattctctc caatcgtgat acttctgccc atgacatcac tttatcatta agctcacaac   8460
agctttcaac atcagttaca ttggaagcct taagtatcaa aactctagtc attggagagc   8520
tagaggaaac agcggttcca gctagagtga aaggcaagc actccaacca gttccaccat   8580
cccgtagacc agtcagacct gacccaccac ttgcggtatt agcattggat gatgatgaca   8640
aaggtggttc tcctccttct catcatcacc accaccacta aggcgcgccc tcgagagctt   8700
ttgattaagc cttctagtcc aaaaaacacg ttttttgtc atttatttca ttttcttaga    8760
atagtttagt ttattcattt tatagtcacg aatgttttat gattctatat agggttgcaa   8820
acaagcattt ttcatttat gttaaaacaa tttcaggttt accttttatt ctgcttgtgg    8880
tgacgcgtgt atccgcccgc tcttttggtc acccatgtat ttaattgcat aaataattct   8940
taaaagtgga gctagtctat ttctatttac atacctctca tttctcattt cctcctaatg   9000
tgtcaatgat catattctta actggaccga tcttattcgt cagattcaaa ccaaaagttc   9060
```

```
ttagggctac cacaggagga aaattagtgt gatataattt aaataattta tccgccattc    9120
ctaatagaac gttgttcgac ggatatcttt ctgcccaaaa gggttctaag ctcaatgaag    9180
agccaatgtc taaacctctt tgc                                            9203
```

<210> SEQ ID NO 41
<211> LENGTH: 6
<212> TYPE: PRT
<213> ORGANISM: Artificial sequence
<220> FEATURE:
<223> OTHER INFORMATION: linker sequence

<400> SEQUENCE: 41

```
Gly Gly Ser Pro Pro Ser
1               5
```